United States Patent
Stuyver et al.

(10) Patent No.: US 6,709,812 B1
(45) Date of Patent: Mar. 23, 2004

(54) METHOD FOR TYPING AND DETECTING HBV

(75) Inventors: Lieven Stuyver, Herzele (BE); Rudi Rossau, Ekeran (BE); Geert Maertens, Bruges (BE)

(73) Assignee: Innogenetics N.V., Ghent (BE)

( * ) Notice: Subject to any disclaimer, the term of this patent is extended or adjusted under 35 U.S.C. 154(b) by 0 days.

(21) Appl. No.: 09/155,885

(22) PCT Filed: Apr. 21, 1997

(86) PCT No.: PCT/EP97/02002

§ 371 (c)(1),
(2), (4) Date: Oct. 8, 1998

(87) PCT Pub. No.: WO97/40193

PCT Pub. Date: Oct. 30, 1997

(30) Foreign Application Priority Data

Apr. 19, 1996 (EP) .............................. 96870053

(51) Int. Cl.⁷ .............................. C12Q 1/70; C12Q 1/68; C12N 15/36; C07H 21/04

(52) U.S. Cl. .............................. 435/5; 435/6; 536/24.32; 536/23.72

(58) Field of Search ................... 435/5, 6; 536/23.72, 536/24.32

(56) References Cited

U.S. PATENT DOCUMENTS 6,228,575 B1 * 5/2001 Gingeras et al. ................ 435/5

FOREIGN PATENT DOCUMENTS

| EP | 0 229 701 A | 7/1987 | |
|----|-------------|--------|---|
| EP | 0 569 237 A | 11/1993 | |
| WO | WO 91 10746 A | 7/1991 | |
| WO | 90 13667 | 7/1993 | |
| WO | WO 93 13120 A | 7/1993 | |
| WO | WO 95 02690 A | 1/1995 | |
| WO | 95/11995 | * 5/1995 | C12Q/1/68 |

OTHER PUBLICATIONS

Norder et al (Journal of General Virology 73:1201–1208, 1992).*
Ni et al (Res. Virol. 146:397–407, 1995).*
Zhang et al (Journal of Medical Virology 48:8–16, 1996).*
Rodriguez–Frias et al (Hepatology 22(6):1641–1647, 1995).*
Blum, H.E. Digestion 56:85–95, 1995.*
Harrison, T.J. European Journal of Gastroenterolgy & Hepatology 8(4): 306–311, 1996.*
Carman et al. Hepatitis and Chronic Liver Disease. 16(2): 407–428, Jun. 1996.*
Ling et al. Hepatology 24(3): 711–713, Sep. 1996.*
Norder et al. Virology 198:489–503, 1994.*

G.A. Tipples et al.: "Mutation in HBV RNA–dependent DNA polymerase confers resistance to lamivu vitro" Hepatology, vol. 24, No. 3, Sep. 1996, Philadelphia US, pp. 714–717, XP0020442 cited in the application see the whole document.
R. Ling et al.: "Selection of mutations in the hepatitis B virus polymerase during therapy of transplant recipients with lamivudine" Hepatology, vol. 24, No. 3, Sep. 1996, Philadelphia US, pp. 713, XP002044247 cited in the application see the whole document.
A. Bartholomeusz et al.: "Mutations in the hepatitis B virus polymerase gene that are associated resistance to famciclovir and lamivudine" International Antiviral News, vol. 5, No. 8, 1997, Lo GB, pp. 123–124, XP002044248 see the whole document.
Grandjacques et al, "Rapid detection of genotypes and mutations in the pre–core promoter and the pre–core region of hepatitis B virus genome: correlation with viral persistence and disease diverity", Journal of Hepatology 2000; 33:430–439.
Lau et al, "Features of response and resistance to lamivudine in patients with chronic hepatitis B with and without HbeAg", AASLD Abstract, Hepatology Oct. 1998, p. 318A.
Stuyver et al, "A new genotype of hepatitis B virus: complete genome and phylogenetic relatedness", Journal of General Virology (2000) 81, 67–74.
Magnius, et al., "Subtypes, Genotypes and Molecular Epidemiology of the Hepatitis B Virus as Reflected by Sequence Variability of the S–Gene", Intervirology 1995, 38:24–34.
Database Strand, Acc. Nr. Q69847, "Hepatitis B virus subtype . . . ", Mar. 6, 1995, B.M. Andrews, et al., XP002034142.

* cited by examiner

Primary Examiner—Mary E Mosher
(74) Attorney, Agent, or Firm—Nixon & Vanderhye, P.C.

(57) ABSTRACT

The present invention relates to a method for detection and/or genetic analysis of HBV in a biological sample, comprising hybridizing the polynucleic acids of the sample with a combination of at least two nucleotide probes, with said combination hybridizing specifically to a mutant target sequence chosen from the HBV RT pol gene region and/or to a mutant target sequence chosen from the HBV preCore region and/or to a mutant target sequence chosen from the HBsAg region of HBV and/or to a HBV genotype-specific target sequence, with said target sequences being chosen from FIG. 1, and with said probes being applied to known locations on a solid support and with said probes being capable of hybridizing to the polynucleic acids of the sample under the same hybridization and wash conditions, or with said probes hybridizing specifically with a sequence complementary to any of said target sequences, or a sequence wherein T of said target sequence is replaced by U; and detecting the hybrids formed; and inferring the HBV genotype and/or mutants present in said sample from the differential hybridization signal(s) obtained. The invention further relates to sets of nucleotide probes and possibly primers useful in said methods as well as to their use in a method for typing and/or detecting HBV and to assay kits using the same.

30 Claims, 28 Drawing Sheets

Figure 1D:
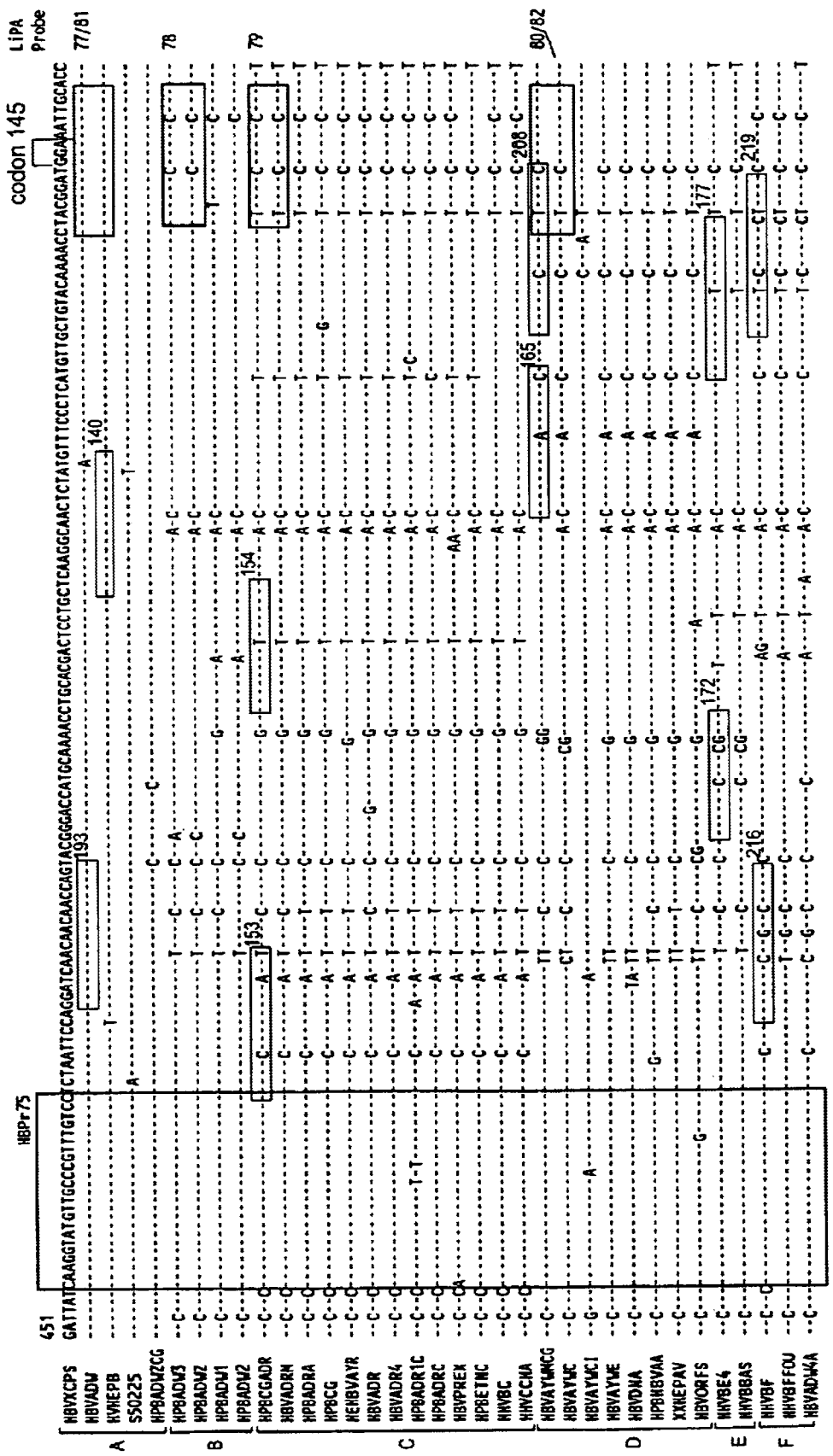
Figure 1E:
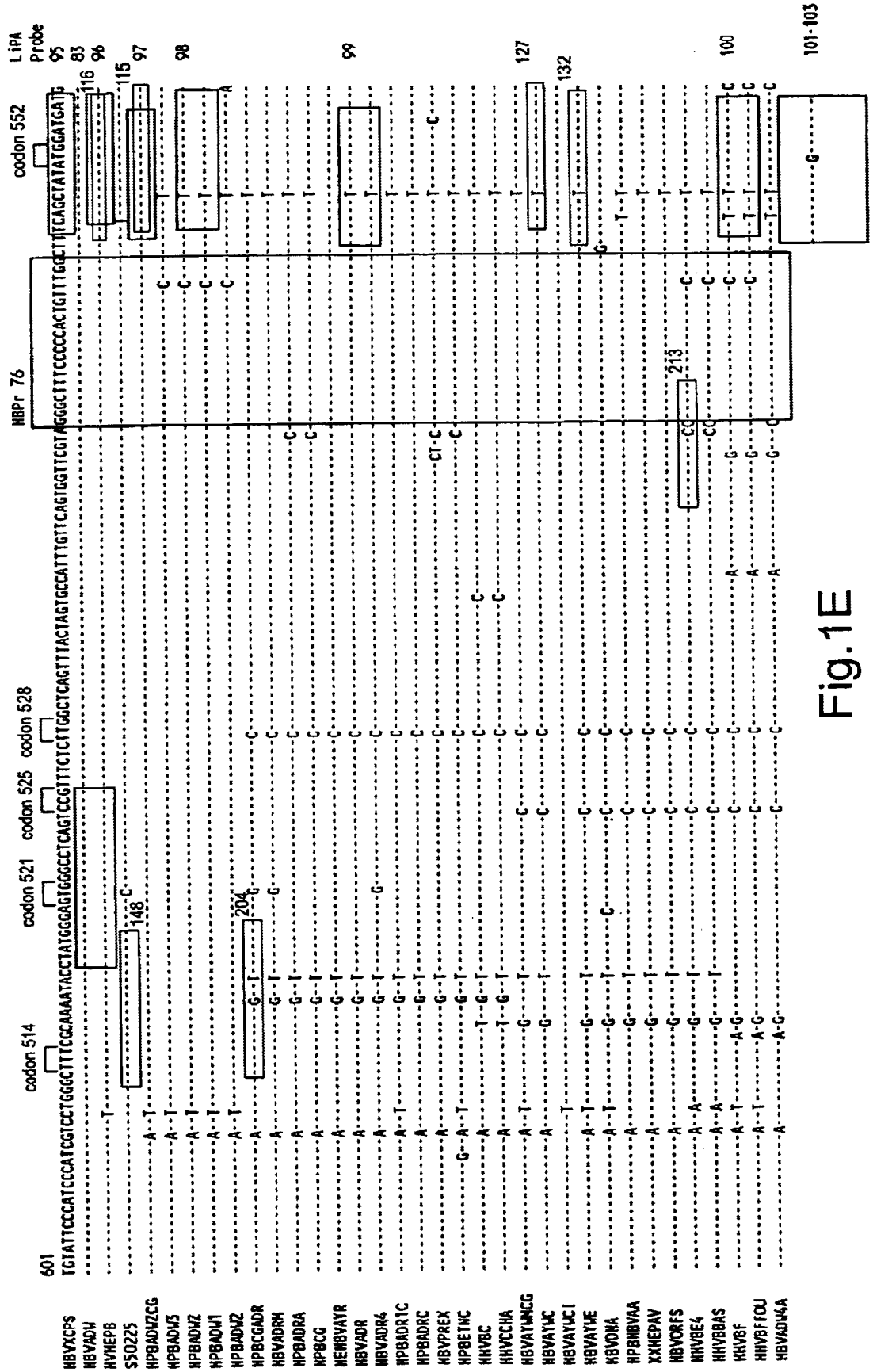
Figure 1F:
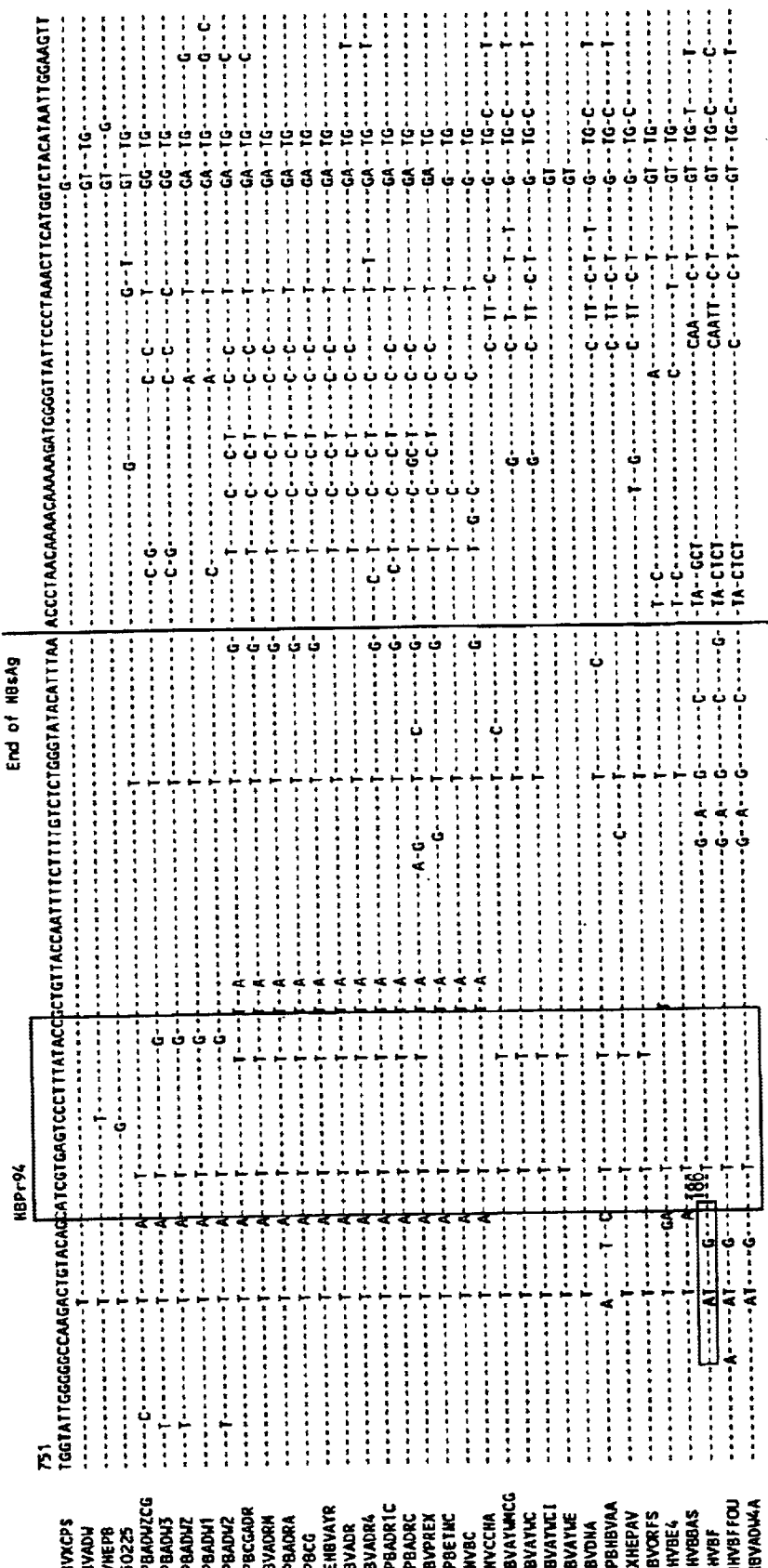
Figure 1L:
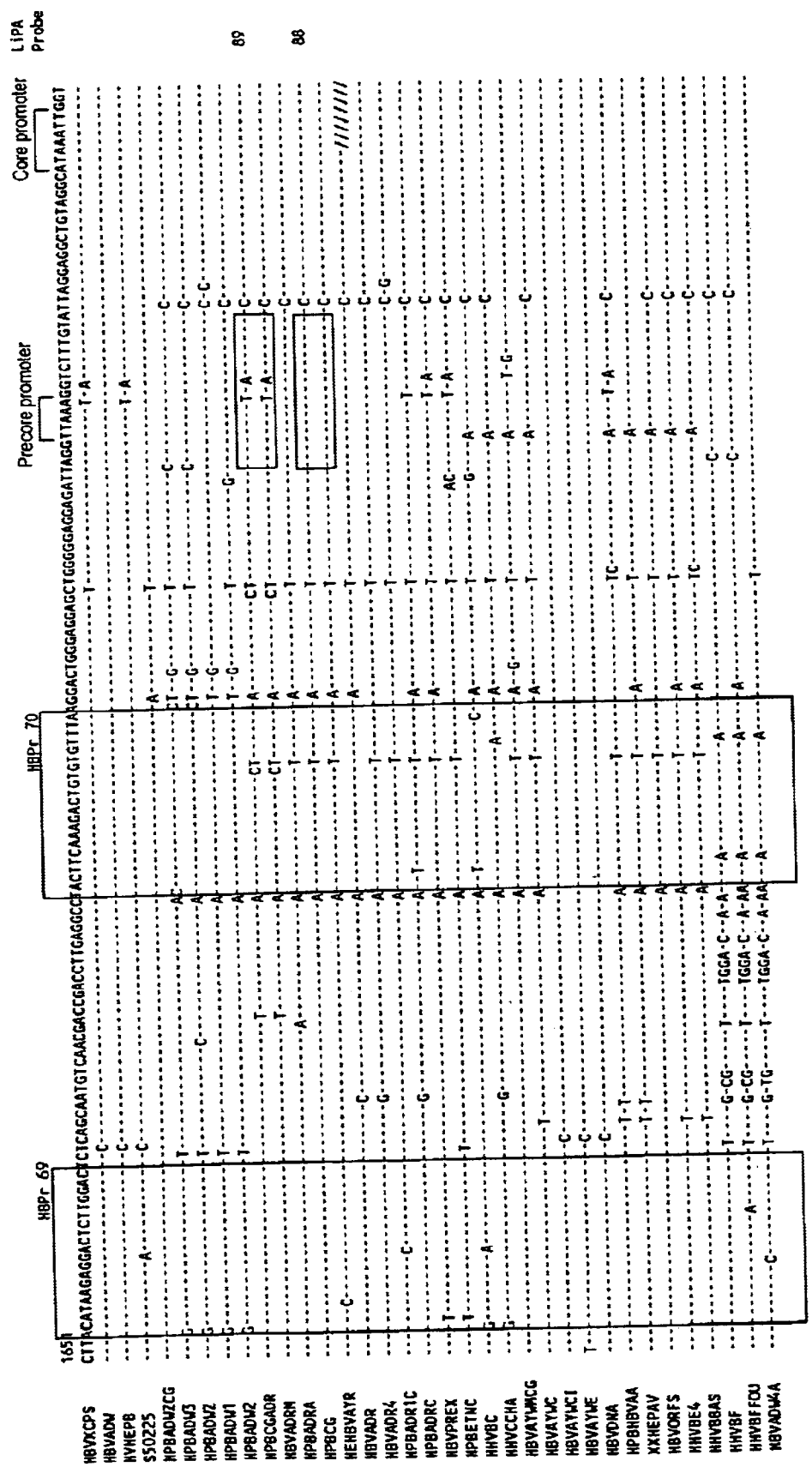
Figure 1M:
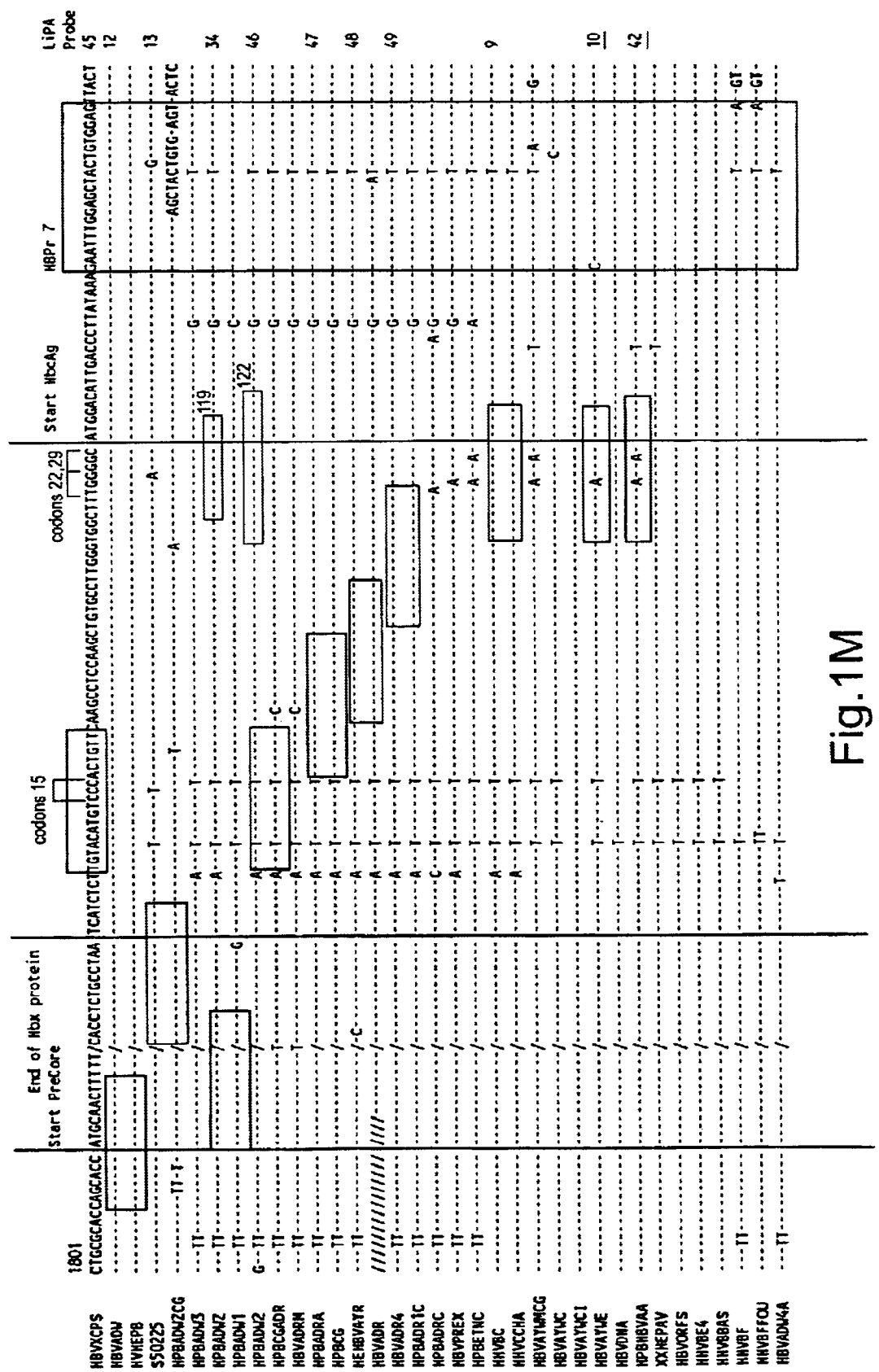
Figure 1T:
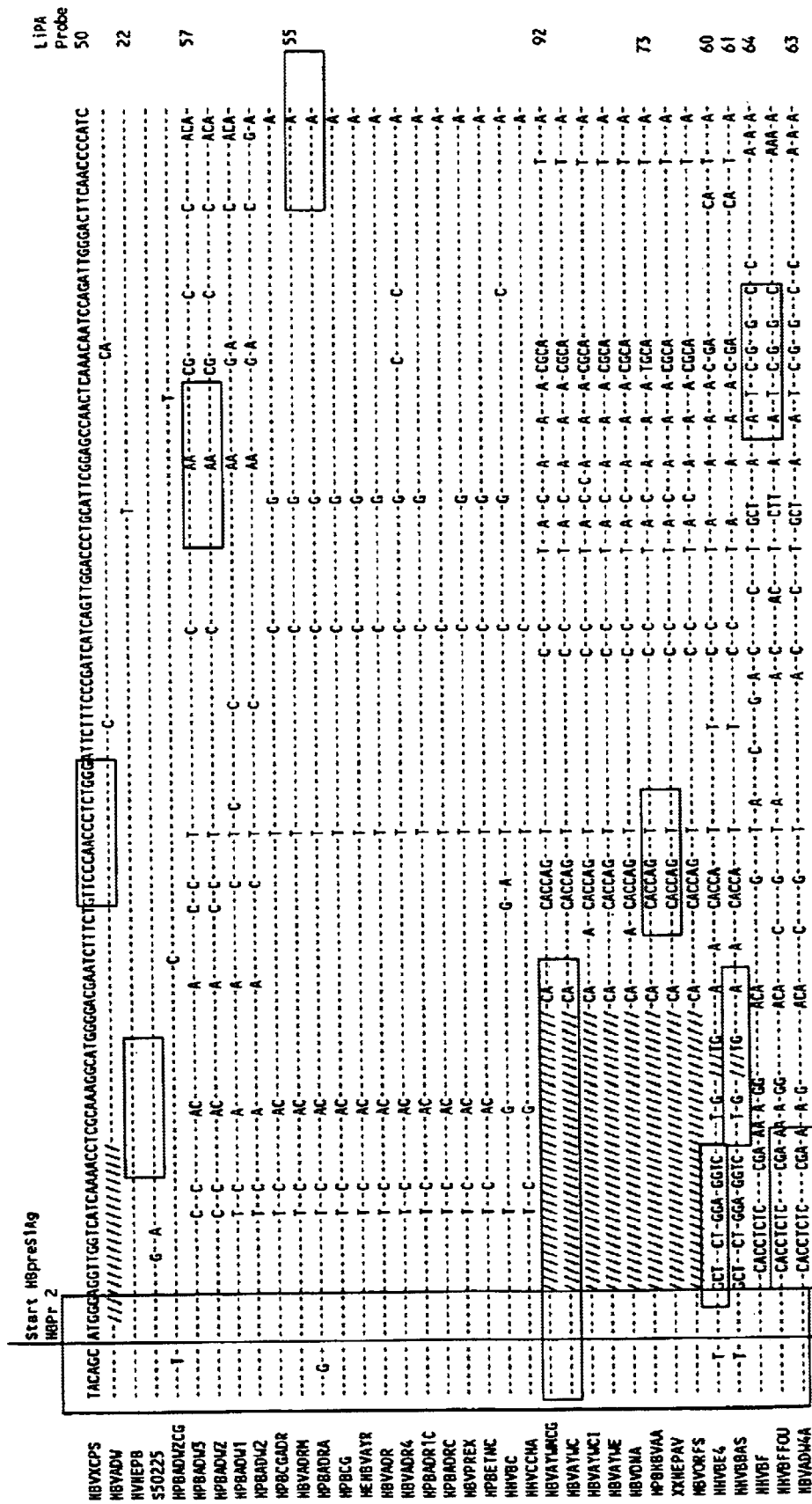
Figure 1V:
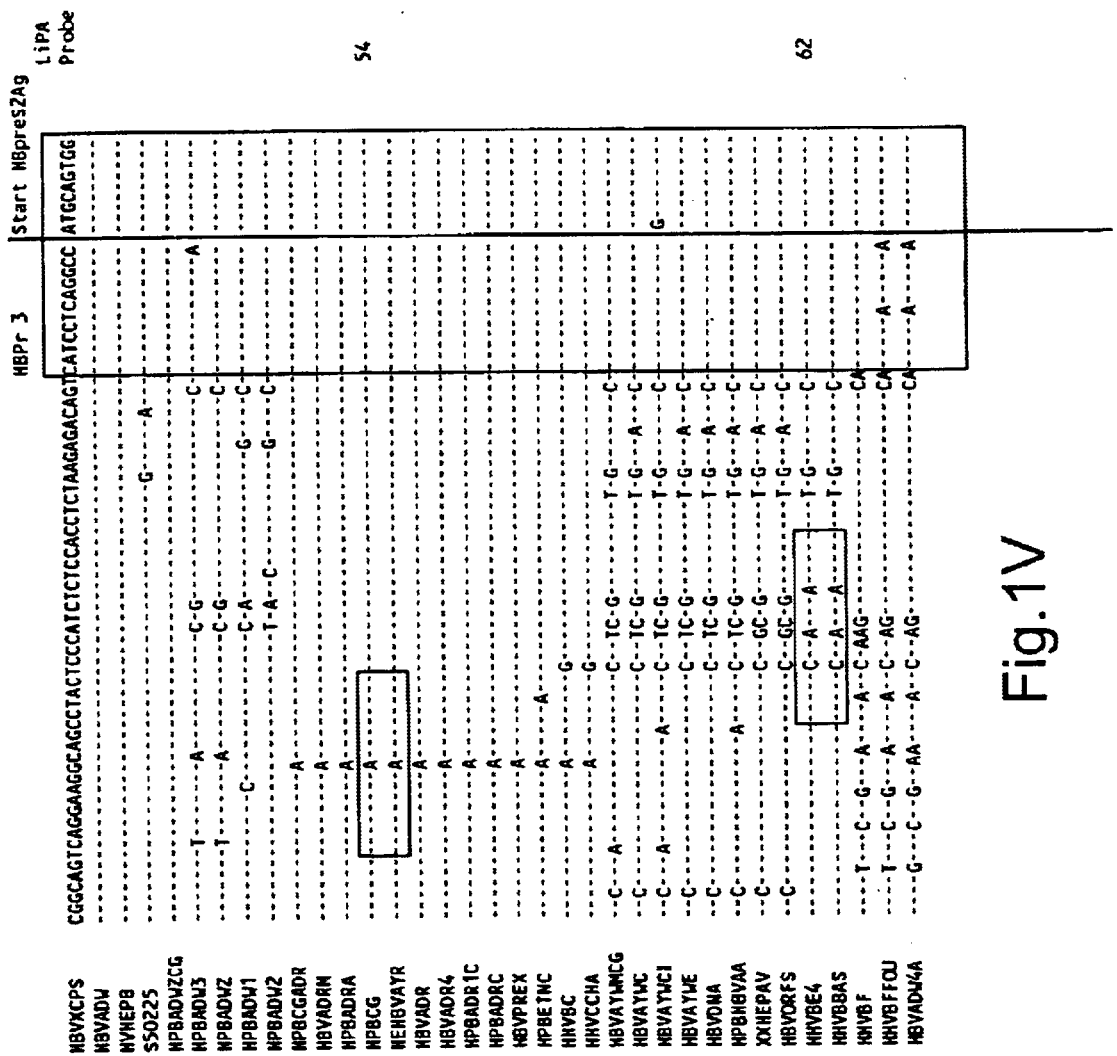

| LiPA line | LiPA HBV design Region | Purpose | HBPr Probe number/SEQ ID NO | sequence |
|---|---|---|---|---|
| 0 | | Pencil line | | |
| 1 | | biotinylated DNA | | |
| 2 | PreS1 | ampl. contr. | 33 | CTGAGGGCTCCACCCCA |
| 3 | PreS1 | Genotype A | 22 | AACCTCGCAAAGGCAT |
| 4 | PreS1 | Genotype A | 50 | CCCAGAGGGTTGGGAAC |
| | PreS1 | Genotype A | 15 | GCCAGCAGCCAACCAG |
| 5 | PreS1 | Genotype B | 57 | CTGCATTCAAAGCCAACT |
| | PreS1 | Genotype B | 58 | CCCCATGGGGACTGTTG |
| 6 | PreS1 | Genotype B | 59 | CATACTCACAACTGTGCCA |
| 7 | PreS1 | Genotype C | 55 | TTCAACCCCAACAAGGATC |
| 8 | PreS1 | Genotype C | 54 | TCAGGAAGACAGCCTAC |
| 9 | PreS1 | Genotype D | 92 | TTCTGCCCCATGCTGTA |
| 10 | PreS1 | Genotype D | 56 | AATGCTCCAGCTCCTAC |
| 11 | PreS1 | Genotype D | 73 | TTCCACCAGCAATCCTC |
| 12 | PreS1 | Genotype E | 60 | GGGCTTTCTTGGACGGTCC |
| | PreS1 | Genotype E | 61 | CTCTCGAATGGGGGAAGA |
| | PreS1 | Genotype E | 62 | CCTACCCCAATCACTCCA |
| 13 | PreS1 | Genotype F | 63 | AGCACCTCTCTCAACGACA |
| 14 | PreS1 | Genotype F | 64 | GCAAATTCCAGCAGTCCCG |
| | PreS1 | Genotype F | 65 | GCCAATGGCAAACAAGGTA |
| 15 | preCore | promotor | 88 | TAGGTTAAAGGTCTTTGT |
| 16 | preCore | promotor | 89 | TAGGTTAATGATCTTTGT |
| 17 | preCore | scan codon -2 to +3 | 12 | AAGTTGCATGGTGCTG |
| 18 | preCore | scan codon 1 to 5 | 34 | ATGCAACTTTTTCACC |
| 19 | preCore | scan codon 5 to 9 | 13 | CACCTCTGCCTAATCAT |
| 20 | preCore | scan codon 12 to 17 | 45 | TGTACATGTCCCACTGTT |
| 21 | preCore | scan codon 12 to 17 | 46 | TGTTCATGTCCTACTGTT |
| 22 | preCore | scan codon 16 to 20 | 47 | ACTGTTCAAGCCTCCAAG |
| 23 | preCore | scan codon 19 to 23 | 48 | GGCACAGCTTGGAGGCTT |
| 24 | preCore | scan codon 23 to 27 | 49 | AAAGCCACCCAAGGCACA |
| 25 | preCore | codon 28 wt | 9 | TGGCTTTGGGGCATGG |
| 26 | preCore | codon 28 mt | 10 | TGGCTTTAGGGCATGG |
| 27 | preCore | codon 28+29 mt | 42 | TGGCTTTAGGACATGGA |

Fig. 2

Genotyping in HBsAg

| Genotype | Oligo | Sequence |
|---|---|---|
| A | HBPr 193 | GGA TCA ACA ACA ACC AGT |
|  | HBPr 140 | CT CAA GGC AAC TCT ATG GG |
|  | HBPr 77 | CTA CGG ATG GAA ATT GC |
| B | HBPr 78 | TAC GGA CGG AAA CTG C |
| C | HBPr 153 | CT CTA CTT CCA GGA ACA G |
|  | HBPr 154 | C TGC ACG ATT CCT GCT |
|  | HBPr 204 | CT TTC GCA AGA TTC CTA TGG G |
| D | HBPr 165 | AC TCT ATG TAT CCC TCC T |
|  | HBPr 208 | GC TGT ACC AAA CCT TCG GAT |
| E | HBPr 172 | G GGA CCC TGC CGA AC |
|  | HBPr 213 | AG TGG TTC GCC GGG CTG G |
| F | HBPr 216 | CA GGA TCC ACG ACC ACC AGG |
|  | HBPr 219 | GC TGT TCC AAA CCC TCG GAG |
|  | HBPr 186 | G CCA AAT CTG TGC AGC |
| A/B | HBPr 148 | CT TTC GCA AAA TAC CTA TG |
| C/D/E | HBPr 80 | CTT CGG ACG GAA ATT GC |
| E/F | HBPr 177 | ATG TTG CTG TTC AAA ACC TG |

Drug resistance in RT pol gene

| Genotype | Oligo | Sequence | |
|---|---|---|---|
| A | HBPr 115 | TCA GCT ATA TGG ATG ATG | wild type |
|  | HBPr 116 | TTC AGC TAT GTG GAT GAT | mutant |
| D | HBPr 127 | TC AGT TAT ATG GAT GAT G | wild type |
|  | HBPr 132 | T TTC AGT TAT GTG GAT GAT | mutant |

PreCore region

| Genotype | Oligo | Sequence | |
|---|---|---|---|
|  | HBPr 88 | TAG GTT AAA GGT CTT TGT | promoter wild type |
|  | HBPr 89 | TAG GTT AAT GAT CTT TGT | promoter mutant |
|  | HBPr 119 | TGG CTT TGG GGC ATG | wild type codon 28 |
|  | HBPr 10 | TGG CTT TAG GGC ATG G | mutant M2 codon 28 |
|  | HBPr 122 | TGG CTT TGG GAC ATG G | mutant M4 codon 29 |
|  | HBPr 42 | TGG CTT TAG GAC ATG GA | mutant M2/M4 codo |

Fig. 4

METHOD FOR TYPING AND DETECTING HBV

The present invention relates to the field of Hepatitis B virus (HBV) diagnosis. More particularly, the present invention relates to the field of HBV genotyping and/or determination of the presence of HBV mutants in test samples.

The present invention relates particularly to a method for the rapid and reliable detection of HBV mutants and/or genotypes occuring in a test sample using specific sets of probes optimized to function together in a reverse-hybridisation assay.

Hepatitis B virus is a small enveloped DNA virus of approximately 3200 bp long. Historically it has been characterized on the basis of immunological reaction of the HBsAg with sets of monoclonal antibodies. Isolates were described as a, indicating the common determinant for all different subtypes, followed by subtype-specific combinations: dw, dr, yw, or yr. The latter are mutually exlusive pairs of determinants, covering the HBsAg amino acids 122 (d=lys, y=arg) and 160 (w=lys, r=arg). Several subdeterminants for w exist and can be ascribed to the appeareance of certain amino acid variants at codon 127. More recently, a genetic classification has been proposed, based on molecular analysis of the virus. This kind of analysis showed that in total six different genotypes exist, indicated from A to F, with a maximum genetic divergence of 8% when comparing complete genomes (reviewed by Magnius and Norder, 1995).

The genetic variability of HBV might be clinically important. Indeed, the genome variability might include some mechanisms by which HBV avoids immune clearance, and hence induces chronic infection. An important protein marker in inducing immune tolerance, virus elimination, and chronic infection, is HBeAg. The expression of this protein is strictly controled both at the transcriptional and translational level (Li et al., 1993; Okamoto et al., 1990; Yuan et al., 1995; Sato et al., 1995). Therefore, in the natural course of HBV infection, a well characterized stage of the disease is indicated as HBe-negative chronic hepatitis B (reviewed by Hadziyannis S. J., 1995). This phase is mostly due to the appeareance of preCore translational stop codon mutations. The overal genetic variability determines the frequency and physical location on the viral genome where these translational stop-codon mutations appear. The transcriptional regulation was proposed to be the mechanism for genotype A (and possibly also F), whereas the translational control was more likely to be found in the other genotypes (Li et al.; 1993; Sato et al., 1995). Contradictory to the translational regulation, it was shown that the transcriptional regulation was unable to block the HBeAg expression completely and was therefore proposed to categorize the phenotype of this mutant as HBe-suppressed, rather than as HBe-negative (Takahashi et al., 1995). In any case, these preCore mutants would lead to a destruction of the preexisting balance between HBeAg in circulation and the HBc-derived peptides presented by class I HLA molecules on the surface of infected hepatocytes, thereby diminishing the supressive effect of HBeAg on T cells, finally resulting in partial liberation of core-specific CTLs and leading to apoptosis of the infected hepatocytes. In general, after the emergence of the HBe-minus variants, the course of the viral infection is characterized by the progression of chronic hepatitis, which may lead to the development of cirrhosis and hepatocellular carcinoma (Hadziyannis, 1995).

Another issue for which the genetic variability or genotyping of the virus might be of relevance is in the development of vaccines where the response may be mediated by the virus type. Protection against HBV infection of all subtypes is conferred by antibodies to the common 'a' determinant of the HB surface antigen (HBsAg). It has been shown that this 'a' determinant presents a number of epitopes, and that its tertiary structure is most important for its antigenicity. The most important region lies between amino acid 124 and 147, but can be extended from amino acid 114 to 150. An adequate anti-HBs response, built up after vaccination, is in principle fully protective infection with a HBV strain harboring mutations in the 'a' determinant region might result in vaccine failure, because the vaccine-induced humoral immune response does not recognize the mutant HBsAg. The most common vaccine-associated escape mutants are the substitutions of a glycine at position 145 to an arginine (G145R), K141E, and T126N. But a 2-aa insertion between aa position 122 and 123, and 8-aa insertion between aa 123 and 124 have also been found (Carman et al., 1990, 1995; Crawford, 1990; Waters et al., 1992).

Lamivudine is a (−) enantiomer of 3' thiacytidine, a 2'3'-dideoxynucleoside analogue, and is known to be a potent inhibitor of HBV replication through inhibition of the reverse transcriptase (RT) activity of the HBV polymerase. Lamivudine treatment can result in histological improvements in chronic hepatitis patients, and when given pre- and post-liver transplantation, it can prevent graft reinfection (Honkoop et al., 1995; Naoumov et al., 1995). However, after treatment, a hepatitis flare-up can be observed in most patients, with ALT elevations and HBV DNA that becomes detectable again. This HBV DNA rebound is associated with a new quasi species equilibrium. In a few cases, virus breakthrough during therapy was observed, due to the selection of lamivudine resistant HBV strains. The exact nature of this breakthrough has been ascribed to the accumulation of mutations in the RT part of the Polymerase. A similar mechanism in the HIV RT polymerase has been found, where upon lamivudine treatment, mutations accumulate in the YMDD motif (Gao et al., 1993). This YMDD motif is also present in the RT part of the HBV polymerase, and lamivudine-selected mutations in HBV have been found in this region (Tipples et al., 1996), as well as in other regions of the RT part of the polymerase (Ling et al., 1996). Penciclovir is another drug that has been shown to inhibit the reverse transcriptase activity of the HBV polymerase (Shaw et al., 1996), and mutations in the HBV polymerase may also be detected upon treatment with this drug.

From all this it can be concluded that the information on the following issues is essential for proper in vitro diagnosis, monitoring and follow-up of HBV infections:

genotype;

preCore mutations;

vaccine escape mutations;

RT gene mutations selected by treatment with drugs such as lamivudune and penciclovir.

To obtain all this information using existing technologies is compilcated, time-consuming, and requires highly-skilled and experienced personel.

It is thus an aim of the present invention to develop a rapid and reliable detection method for determination of the presence or absence of one or more HBV genotypes possibly present in a biological sample.

More particularly, it is an aim of the present invention to develop a rapid and reliable detection method for determination of the presence or absence of one or more variations in the HBV preS1 region and/or in the HBsAg region representing one or more HBV genotypes possibly present in a biological sample in one single experiment.

More particularly, it is an aim of the present invention to develop a rapid and reliable detection method for determination of the presence or absence of one or more HBV mutants possibly present in a biological sample in one single experiment.

More particularly, it is an aim of the present invention to develop a rapid and reliable detection method for determination of one or more mutations in the preCore region of HBV possibly present in a biological sample in one single experiment.

More particularly, it is an aim of the present invention to develop a rapid and reliable detection method for determination of one or more mutations in the HBsAg region of HBV possibly present in a biological sample in one single experiment.

More particularly, it is an aim of the present invention to develop a rapid and reliable detection method for determination of one or more mutations in the polymerase (pol) gene region of HBV possibly present in a biological sample in one single experiment.

More particularly, it is an aim of the present invention to develop a rapid and reliable detection method for the simultaneous determination of one Dr several HBV Genotypes in combination with one or several HBV mutants possibly present in a biological sample in one single experiment.

It is also an aim of the present invention to provide a genotyping assay or method which allows to infer the nucleotide sequence at codons of interest and/or the HBV mutants of interest, and/or infer the HBV genotype possibly present in a biological sample.

Even more particularly it is also an aim of the present invention to provide a genotyping assay allowing the detection of the different HBV mutants and genotypes in one single experimental setup.

It is another aim of the present invention to select particular probes able to discriminate one or more HBV mutations in one of the above mentioned regions of the HBV genome and/or able to discriminate one or more HBV genotypes.

It is more particularly an aim of the present invention to select particular probes able to discriminate wild-type HBV from mutant HBV sequences.

It is also an aim of the present invention to select particular probes able to discriminate wild-type and polymorphic variants of HBV from mutant HBV sequences.

It is also an aim of the present invention to select particular probes able to discriminate HBV genotype sequences.

It is moreover an aim of the present invention to combine a set of selected probes able to genotype HBV and/or discriminate different HBV mutants possibly present in a biological sample, whereby all probes can be used under the same hybridisation and wash conditions.

It is also an aim of the present invention to select primers enabling the amplification of the gene fragment(s) determining the HBV genomic mutations or variations of interest as discussed above.

The present invention also aims at diagnostic kits comprising said probes useful for developing such a genotyping assay and/or assays for detecting, monitoring or following-up HBV infection and/or assays for detecting HBV mutations.

All the aims of the present invention have been met by the following specific embodiments.

As a solution to the above-mentioned problem that it is essential for proper diagnosis, monitoring and follow-up of HBV infection to have information on the genotype of HBV present, the present invention provides an elegant way to tackle problems of such complexity which involves residing to a reverse hybridization approach (particularly on Line Probe Assays strips, as described by Stuyver et al., 1993). Using this technology it is possible to conveniently obtain all essential data in one test run. To achieve this goal, a set of probes needs to be designed and assembled which can detect all relevant polymorphisms in the HBV gene regions of interest.

The present invention thus particularly relates to a method for determining the presence or absence of one or more HBV genotypes in a biological sample, comprising:

(i) if need be releasing, isolating or concentrating the polynucleic acids present in the sample;

(ii) if need be amplifying the relevant part of a suitable HBV gene present in said sample with at least one suitable primer pair;

(iii) hybridizing the polynucleic acids of step (i) or (ii) with at least two nucleotide probes hybridizing specifically to a HBV genotype specific target sequence chosen from FIG. 1; with said probes being applied to known locations on a solid support and with said probes being capable of hybridizing to polynucleic acids of step (i) or (ii) under the same hybridization and wash conditions or with said probes hybridizing specifically with a sequence complementary to any of said target sequences, or a sequence wherein T of said target sequence is replaced by U;

(iv) detecting the hybrids formed in step (iii);

(v) inferring the HBV genotype present in said sample from the differential hybridization signal(s) obtained in step (iv).

The genotype specific target sequences can be any nucieotide variation appearing upon alignment of the different HBV genomes that permits classification of a certain HBV isolate as a certain genotype (see FIG. 1).

The expression "relevant part of a suitable HBV gene" refers to the part of the HBV gene encompassing the HBV genotype specific target sequence chosen from FIG. 1 to be detected.

According to a preferred embodiment of the present invention, step (iii) is performed using a set of at least 2, preferably at least 3, more preferably at least 4 and most preferably at least 5 probes all meticulously designed such that they show the desired hybridization results, when used in a reverse hybridisation assay format, more particularly under the same hybridization and wash conditions implying that each of said probes is able to form a complex upon hybridisation with its target sequence present in the polynucleic acids of the sample as obtained after step (i) or (ii).

The numbering of the HBV gene encoded amino acids and nucleotides is as generally accepted in literature.

More particularly, the present invention relates to a set of at least 2 probes allowing the detection of a genotype specific variation, possibly also including one or more probes allowing the detection of a wild-type sequence, a polymorphic or a mutated sequence at any one of the nucleotide positions showing a sequence diversity upon alignment of all known or yet to be discovered HBV sequences as represented in FIG. 1 for all complete HBV genomes found in the EMBL/NCBI/DDBJ/Genbank.

The sets of probes according to the present invention have as a common characteristic that all the probes in said set are designed so that they can be used together in a reverse-hybridization assay, more particularly under similar or identical hybridization and wash conditions as indicated above and below.

Selected sets of probes according to the present invention include probes which allow to differentiate any of the HBV genotype specific nucleotide changes as represented in FIG. 1, preferably in the preS1 or HBsAg region of HBV. Said probes being characterized in that they can function in a method as set out above.

In order to solve the above-mentioned problem of obtaining information or, the possible presence of HBV mutants in a given sample, the present invention provides an elegant way to tackle this problem which involves residing to a reverse hybridisation approach (particularly on Line Probe Assays strips, as described by Stuyver et al., 1993). Using this technology it is possible to conveniently obtain all essential data in one test run. To achieve this goal, a set of probes needs to be designed and assembled which can detect all relevant mutations and possibly also wild-type sequences or polymorphisms in the HBV gene regions of interest.

Another particularly preferred embodiment of the present invention thus is a method for determining the presence or absence of one or more HBV mutants in a biological sample, comprising:

(i) if need be releasing, isolating or concentrating the polynucleic acids present in the sample;

(ii) if need be amplifying the relevant part of a suitable HBV gene present in said sample with at least one suitable primer pair;

(iii) hybridizing the polynucleic acids of step (i) or (ii) with at least two nucleotide probes hybridizing specifically to a HBV mutant target sequence chosen from FIG. 1, with said probes being applied to known locations on a solid support and with said probes being capable of hybridizing to the polynucleic acids of step (i) or (ii) under the same hybridization and wash conditions, or with said probes hybridizing specifically with a sequence complementary to any of said target sequences, or a sequence wherein T of said target sequence is replaced by U and with said set or probes possibly also comprising one or more wild-type HBV probes corresponding with the respective mutated HBV target sequence;

(iv) detecting the hybrids formed in step (iii);

(v) inferring the HBV mutant(s) present in said sample from the differential hybridization signal(s) obtained in step (iv).

It is to be understood that the term "mutant target sequence" not only covers the sequence containing a mutation, but also the corresponding wild-type sequence. The HBV mutant target sequence according to the present invention can be any sequence including a HBV mutated codon known in the art or yet to be discovered. Particularly preferred HBV mutant target regions are set out below.

In order to solve the problem as referred to above of obtaining information on the essential issues for proper diagnosis of HBV (namely genotype and different mutations particularly mutations in the preCore region, vaccine escape mutations and RT gene mutations selected by treatment with drugs such as lamivudine and penciclovir), the present invention provides a particularly elegant way to obtain such complex information.

Moreover, careful analysis of the data obtained by the present inventors clearly revealed that combining the information concerning the preCore and escape mutants with data on the genotype is essential to allow adequate interpretation of the results. Hence it is highly advantageous to be able to produce all relevant data simultaneously.

In this method for diagnosing HBV mutants, preferably in combination with HBV genotyping, a set of probes selected as defined above may be used, wherein said set of probes is characterized as being chosen such that for a given HBV mutation, the following probes are included in said set.

at least one probe for detecting the presence of the mutated nucleotide(s) at said position;

at least one probe for detecting the presence of the wild-type nucleotide(s) at said position;

possibly also (an) additional probe(s) for detecting wild-type polymorphisms at positions surrounding the mutation position.

Inclusion of the latter two types of probes greatly contributes to increasing the sensitivity of said assays as demonstrated in the examples section.

Selected sets of probes according to the present invention include at least one probe, preferably at least two probes, characterizing the presence of a HBV mutation at nucleotide positions chosen from the preCore region of HBV, more particularly from the following list of codons susceptible to mutations in the HBV preCore region, such as codon 15 in genotype A, and for all genotypes: codon 28, codon 29, and codon 28 and 29, or in the preCore promoter region (see FIG. 1).

Said probes being characterized in that they can function in a method as set out above.

An additional embodiment of the present invention includes at least one probe, preferably at least two probes, characterizing the presence of a vaccine escape mutation in codon positions chosen from the HBsAg region of HBV, more particularly from the list of codons susceptible to mutations in the HBV HBsAg region, such as at codons 122, 126, 141, 143, 144 or 145 (see FIG. 1).

An additional embodiment of the present invention includes at least one probe, preferably at least two probes, characterizing the presence of a mutation in the RT pol gene region of HBV, that gives rise to resistance to drugs such as lamivudine and penciclovir, for instance mutation of M to V or to I at position 552 (in the YMDD motif), mutation of V to I at position 555, mutation of F to L at position 514, mutation of V to L at position 521, mutation of P to L at position 525 and mutation of L to M at position 528 (see FIG. 1).

In a selected embodiment, a combination of at least two oligonucleotide probes is used and said combination of probes hybridizes specifically to at least two of the following groups of target sequences:

a mutant target sequence chosen from the HBV RT pol gene region, a mutant target sequence chosen from the HBV preCore region, a mutant target sequence chosen from the HBsAg region of HBV, a HBV genotype-specific target sequence.

For instance, an embodiment involves hybridizing with at least one nucleotide probe hybridizing specifically to a genotype specific target sequence chosen from FIG. 1 and at least one nucleotide probe hybridizing specifically to a HBV mutant target sequence chosen from FIG. 1.

Another selected embodiment involves, for instance, hybridizing with at least one nucleotide probe hybridizing specifically to a genotype specific target sequence chosen from FIG. 1 and at least one nucleotide probe hybridizing specifically to a HBV mutant target sequence chosen from the RT pol gene region as represented in FIG. 1.

Another selected embodiment involves, for instance, hybridizing with at least one nucleotide probe hybridizing specifically to a genotype specific target sequence chosen from FIG. 1 and at least one nucieotide probe hybridizing specifically to a HBV mutant target sequence chosen from the preCore region as represented in FIG. 1.

Another selected embodiment involves, for instance, hybridizing with at least one nucieotide probe hybridizing specifically to a genotype specific target sequence chosen from FIG. 1 and at least one nucleotide probe hybridizing specifically to a HBV vaccine escape mutant target sequence within the HBsAg region as represented in FIG. 1.

In a selected embodiment, a combination of at least three oligonucleotide probes is used and said combination of probes hybridizes specifically to at least three of the following groups of target sequences:

a mutant target sequence chosen from the HBV RT pol gene region, a mutant target sequence chosen from the HBV preCore region, a mutant target sequence chosen from the HBsAg region of HBV, a HBV genotype-specific target sequence.

For instance, an embodiment involves hybridizing with at least one nucleotide probe hybridizing specifically to a genotype specific target sequence chosen from FIG. 1, and at least one nucleotide probe hybridizing specifically to a HBV mutant target sequence chosen from the preCore region as represented in FIG. 1, and at least one nucleotide probe hybridizing specifically to a HBV vaccine escape mutant target sequence chosen from the HBsAg region as represented in FIG. 1.

For instance, another embodiment involves hybridizing with at least one probe hybridizing specifically to a mutant target sequence from the HBV RT pol gene region of HBV, and at least one probe hybridizing specifically to a mutant target sequence from the HBsAg region of HBV, and at least one probe hybridizing specifically to a genotype-specific target sequence from the HBsAg region of HBV. According to this embodiment, the relevant part of the HBV genome can be amplified by use of one primer pair, for instance HBPr 75 and HBPr 94.

In a selected embodiment, a combination of at least four oligonucleotide probes is used and said combination of probes hybridizes specifically to all of the following groups of target sequences:

a mutant target sequence chosen from the HBV RT pol gene region, a mutant target sequence chosen from the HBV preCore region, a mutant target sequence chosen from the HBsAg region of HBV, a HBV genotype-specific target sequence.

Particularly preferred embodiments of the invention thus include a set of probes as set out above comprising at least one, preferably at least two, at least three, at least four or more probe(s) for targeting one, preferably two, three or more nucieotide changes appearing in the alignment of HBV genomes as represented in FIG. 1.

Even more preferred selected sets of probes according to the present invention include probes derived from two of the same or different regions of HBV bearing HBV mutated nucleotides, or in addition also a third (set of) probe(s) characterizing the presence of a third HBV mutation at any of the positions shown in FIG. 1, or particular combinations thereof.

Particularly preferred is also a set of probes which allows simultaneous detection of HBV mutations at codons 15, 28 and 29 in the preCore region, possibly in combination with mutations in the preCore promoter regions, in combination with mutations at codons 122, 126, 141, 143, 144, 145 in the HBsAg region, possibly also in combination with mutations in the HBV pol gene at codons 514, 521, 525, 528, 552 or 555.

In the instances where the alignment of HBV genomes of FIG. 1 is referred to in this invention, it should be construed as referring to an alignment of all existing and future HBV genomes. The existing HBV genome sequences can be deduced from any database, such as the EMBL/NCBI/DDBJ/GENBANK database.

A preferred set of preCore, preS1, HBsAg and RT pol gene probes of this invention are the probes with SEQ ID NO 1 to 278 of Table 1 (see also FIG. 1).

Particularly preferred sets of probes in this respect are shown in FIG. 2 and in FIG. 4. The probes in FIG. 2 and in FIG. 4 were withheld after a first selection for preCore, preS1, HBsAg and RT pol probes.

The probes of the invention are designed for obtaining optimal performance under the same hybridization conditions so that they can be used in sets of at least 2 probes for simultaneous hybridization. This highly increases the usefulness of these Probes and results in a significant gain in time and labour. Evidently, when other hybridization conditions would be preferred, all probes should be adapted accordingly by adding or deleting a number of nucleotides at their extremities. It should be understood that these concomitant adaptations should give rise to essentially the same result, namely that the respective probes still hybridize specifically with the defined target. Such adaptations might also be necessary if the amplified material should be RNA in nature and not DNA as in the case for the NASBA system.

The selection of the preferred probes of the present invention is based on a reverse hybridization assay format using immobilized oligonucleotide probes present at distinct locations on a solid support. More particularly the selection of preferred probes of the present invention is based on the use of the Line Probe Assay (LiPA) principle which is a reverse hybridization assay using oligonucleotide probes immobilized as parallel lines on a solid support strip (Stuyver et al. 1993; international application WO 94/12670). This approach is particularly advantageous since it is fast and simple to perform. The reverse hybridization format and more particularly the LiPA approach has many practical advantages as compared to other DNA techniques or hybridization formats, especially when the use of a combination of probes is preferable or unavoidable to obtain the relevant information sought.

It is to be understood, however, that any other type of hybridization assay or format using any of the selected probes as described further in the invention, is also covered by the present invention.

The reverse hybridization approach implies that the probes are immobilized to certain locations on a solid support and that the target DNA is labelled in order to enable the detection of the hybrids formed.

The following definitions serve to illustrate the terms and expressions used in the present invention.

The term "genetic analysis" refers to the study of the nucleotide_sequence of the genome of HBV by any appropriate technique.

The term "HBV mutant" refers to any HBV strain harbouring genomic variations with serological, genetical or clinical consequences.

The term "vaccine escape mutant" is reviewed in the introduction section and in example 7. The most important region lies between amino acid 124 and 147 of the HBsAg region, but can be extended from amino acid 114 to 150.

The term "mutant resistant to drugs such as lamivudine and penciclovir" is reviewed in the introduction section and in Example 8.

The term "HBV genotype" refers to HBV strains with an intergenotype variation of 8% or more based on a comparison of complete genomes.

The target material in the samples to be analyzed may either be DNA or RNA, e.g. genomic DNA, messenger RNA, viral RNA or amplified versions thereof. These molecules are also termed polynucleic acids.

It is possible to use genomic DNA or RNA molecules from samples susceptible of containing HBV in the methods according to the present invention.

Well-known extraction and purification procedures are available for the isolation of RNA or DNA from a sample (f.i. in Maniatis et al., Molecular Cloning: A Laboratory Manual, 2nd Edition, Cold Spring Harbour Laboratory Press (1989)).

The term "probe" refers to single stranded sequence-specific oligonucleotides which have a sequence which is complementary to the target sequence to be detected.

The term "target sequence" as referred to in the present invention describes the nucieotide sequence of a part of wild-type, polymorphic or mutant HBV gene sequence to be specifically detected by a probe according to the present invention. The polymorphic sequence may encompass one or more polymorphic nucleotides; the mutant sequence may encompass one or more nucleotides that are different from the wild-type sequence. It is to be understood that the term "mutant target sequence" not only covers the sequence containing a mutation, but also the corresponding wild-type sequence. Target sequences may generally refer to single nucleotide positions, codon positions, nucleotides encoding amino acids or to sequences spanning any of the foregoing positions. In the present invention said target sequence often includes one, two or more variable nucleotide positions. In the present invention polynucleic acids detected by the probes of the invention will comprise the target sequence against which the probe is detected.

It is to be understood that the complement of said target sequence is also a suitable target sequence in some cases. The target sequences as defined in the present invention provide sequences which should at least be complementary to the central part of the probe which is designed to hybridize specifically to said target region. In most cases the target sequence is completely complementary to the sequence of the probe.

The term "complementary" as used herein means that the sequence of the single stranded probe is exactly the (inverse) complement of the sequence of the single stranded target, with the target being further defined as the sequence where the mutation to be detected is located.

Since the current application requires the detection of single basepair mismatches, stringent conditions for hybridization are required, allowing in principle only hybridization of exactly complementary sequences. However, variations are possible in the length of the probes (see below). It should also be noted that, since the central part of the probe is essential for its hybridization characteristics, possible deviations of the probe sequence versus the target sequence may be allowable towards head and tail of the probe when longer probe sequences are used. These variations, which may be conceived from the common knowledge in the art, should however always be evaluated experimentally, in order to check if they result in equivalent hybridization characteristics as the exactly complementary probes.

Preferably, the probes of the invention are about 5 to 50 nucleotides long, more preferably from about 10 to 25 nucleotides. Particularly preferred lengths of probes include 10, 11, 12, 13, 14, 15, 16, 17, 18, 19, 20, 21, 22, 23, 24 or 25 nucleotides. The nucleotides as used in the present invention may be ribonucleotides, deoxyribonucleotides and modified nucleotides such as inosine or nucleotides containing modified groups which do not essentially alter their hybridisation characteristics.

Probe sequences are represented throughout the specification as single stranded DNA oligonucleotides from the 5' to the 3' end. It is obvious to the man skilled in the art that any of the below-specified probes can be used as such, or in their complementary form, or in their RNA form (wherein T is replaced by U).

The probes according to the invention can be prepared by cloning of recombinant plasmids containing inserts including the corresponding nucleotide sequences, if need be by cleaving the latter out from the cloned plasmids upon using the adequate nucleases and recovering them, e.g. by fractionation according to molecular weight. The probes according to the present invention can also be synthesized chemically, for instance by the conventional phosphotriester method.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead) or a chip. Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin, haptens or proteins.

The term "labelled" refers to the use of labelled nucleic acids. Labelling may be carried out by the use of labelled nucleotides incorporated during the polymerase step of the amplification such as illustrated by Saiki et al. (1988) or Bej et al. (1990) or labelled primers, or by any other method known to the person skilled in the art. The nature of the label may be isotopic ($^{32}P$, $^{35}S$, etc.) or non-isotopic (biotin, digoxigenin, etc.).

The term "primer" refers to a single stranded oligonucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5–50 nucleotides long. Specific length and sequence will depend on the complexity of the required DNA or RNA targets, as well as on the conditions of primer use such as temperature and ionic strength.

The expression "suitable primer pair" in this invention refers to a pair of primers allowing the amplification of part or all of the HBV gene for which probes are immobilized.

The fact that amplification primers do not have to match exactly with the corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990; Walker et al., 1992) or amplification by means of Qβ replicase (Lizardi et al. 1988; Lomeli et al., 1989) or any other suitable method to amplify nucleic acid molecules known in the art.

The oligonucleotides used as primers or probes may also comprise nucleotide analogues such as phosphorothiates (Matsukura et al., 1987), alkylphosphorothiates (Miller et al., 1979) or peptide nucleic acids (Nielsen et al., 1991; Nielsen et al., 1993) or may contain intercalating agents (Asseline et al., 1984).

As most other variations or modifications introduced into the original DNA sequences of the invention these variations will necessitate adaptions with respect to the conditions under which the oligonucleotide should be used to obtain the required specificity and sensitivity. However the eventual results of hybridisation will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The "sample" may be any biological material taken either directly from the infected human being (or animal), or after culturing (enrichment). Biological material may be e.g. expectorations of any kind, broncheolavages, blood, skin tissue, biopsies, sperm, lymphocyte blood culture material, colonies, liquid cultures, faecal samples, urine etc.

The sets of probes of the present invention will include at least 2, 3, 4, 5, 6, 7, 8, 9, 10, 11, 12, 13, 14, 15, 16, 17, 18, 19, 20, 21, 22, 23, 24, 25, 26, 27, 28, 29, 30 or more probes. Said probes may be applied in two or more (possibly as many as there are probes) distinct and known positions on a solid substrate. Often it is preferable to apply two or more probes together in one and the same position of said solid support.

For designing probes with desired characteristics, the following useful guidelines known to the person skilled in the art can be applied.

Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

The stability of the [probe: target] nucleic acid hybrid should be chosen to be compatible with the assay conditions. This may be accomplished by avoiding long AT-rich sequences, by terminating the hybrids with G:C base pairs, and by designing the probe with an appropriate Tm. The beginning and end points of the probe should be chosen so that the length and % GC result in a Tm about 2–10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account when designing a probe. It is known that hybridization will increase as the ionic strength of the reaction mixture increases, and that the thermal stability of the hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. The degree of stringency is chosen such as to maximize the difference in stability between the hybrid formed with the target and the nontarget nucleic acid. In the present case, single base pair changes need to be detected, which requires conditions of very high stringency.

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly complementary base sequence will normally primarily determine hybrid stability. While oligonucleotide probes of different lengths and base composition may be used, preferred oligonucleotide probes of this invention are between about 5 to 50 (more particularly 10–25) bases in length and have a sufficient stretch in the sequence which is perfectly complementary to the target nucleic acid sequence.

Regions in the target DNA or RNA which are known to form strong internal structures inhibitory to hybridization are less preferred. Likewise, probes with extensive self-complementarity should be avoided. As explained above, hybridization is the association of two single strands of complementary nucleic acids to form a hydrogen bonded double strand. It is implicit that if one of the two strands is wholly or partially involved in a hybrid that it will be less able to participate in formation of a new hybrid. There can be intramolecular and intermolecular hybrids formed within the molecules of one type of probe if there is sufficient self complementarity. Such structures can be avoided through careful probe design. By designing a probe so that a substantial portion of the sequence of interest is single stranded, the rate and extent of hybridization may be greatly increased. Computer programs are available to search for this type of interaction. However, in certain instances, it may not be possible to avoid this type of interaction.

Standard hybridization and wash conditions are disclosed in the Materials & Methods section of the Examples. Other conditions are for instance 3×SSC (Sodium Saline Citrate), 20% deionized FA (Formamide) at 50° C.

Other solutions (SSPE (Sodium saline phosphate EDTA), TMACI (Tetramethyl ammonium Chloride), etc.) and temperatures can also be used provided that the specificity and sensitivity of the probes is maintained. If need be, slight modifications of the probes in length or in sequence have to be carried out to maintain the specificity and sensitivity required under the given circumstances.

In a more preferential embodiment, the above-mentioned polynucleic acids from step (i) or (ii) are hybridized with at least two, three, four, five, six, seven, eight, nine, ten, eleven, twelve, thirteen, fourteen, fifteen, sixteen, seventeen, eighteen, nineteen, twenty, or more of the above-mentioned target region specific probes, preferably with 5 or 6 probes, which, taken together, cover the "mutation region" of the relevant HBV gene.

The term "mutation region" means the region in the relevant HBV gene sequence where at least one mutation encoding a HBV mutant is located in a preferred parts of this mutation region is represented in FIG. 1.

Apart from mutation regions as defined above the HBV wild-type or mutant genomes may also show polymorphic nucleotide variations at positions other than those referred to as genotype specific or mutant specific variated positions as shown in FIG. 1.

Since some mutations may be more frequently occurring than others, e.g. in certain geographic areas or in specific circumstances (e.g. rather closed communities) it may be appropriate to screen only for specific mutations, using a selected set of probes as indicated above. This would result in a more simple test, which would cover the needs under certain circumstances.

In order to detect HBV genotypes and/or HBV mutants with the selected set of oligonucleotide probes, any hybridization method known in the art can be used (conventional dot-blot, Southern blot, sandwich, etc.).

However, in order to obtain fast and easy results if a multitude of probes are involved, a reverse hybridization format may be most convenient.

In a preferred embodiment the selected set of probes are immobilized to a solid support in known distinct locations (dots, lines or other figures). In another preferred embodiment the selected set of probes are immobilized to a membrane strip in a line fashion. Said probes may be immobilized individually or as mixtures to delineated locations on the solid support.

A specific and very user-friendly embodiment of the above-mentioned preferential method is the LiPA method, where the above-mentioned set of probes is immobilized in parallel lines on a membrane, as further described in the examples.

The invention also provides for a set of primers allowing amplification of the region of the respective HBV gene to be detected by means of probes. Examples of such primers of the invention are given in Table 1 and FIG. 1.

Primers may be labelled with a label of choice (e.g. biotine). Different primer-based target amplification systems may be used, and preferably PCR-amplification, as set out in the examples. Single-round or nested PCR may be used.

The invention also provides a kit for detection and/or genetic analysis of HBV genotypes and/or HBV mutants present in a biological sample comprising the following components:

(i) when appropriate, a means for releasing, isolating or concentrating the polynucleic acids present in said sample;
(ii) when appropriate, at least one suitable primer pair;
(iii) at least two of the probes as defined above, possibly fixed to a solid support;
(iv) a hybridization buffer, or components necessary for producing said buffer;
(v) a wash solution, or components necessary for producing said solution;
(vi) when appropriate, a means for detecting the hybrids resulting from the preceding hybridization.
(vii) when appropriate, a means for attaching said probe to a known location on solid support.

The term "hybridization buffer" means a buffer enabling a hybridization reaction to occur between the probes and the polynucleic acids present in the sample, or the amplified products, under the appropriate stringency conditions.

The term "wash solution" means a solution enabling washing of the hybrids formed under the appropriate stringency conditions.

As illustrated in the Examples section, a line probe assay (LiPA) was designed for screening for HBV genotypes and/or HBV mutants. The principle of the assay is based on reverse hybridization of an amplified polynucleic acid fragment such as a biotinylated PCR fragment of the HBV gene onto short oligonucleotides. The latter hybrid can then, via a biotine-streptavidine coupling, be detected with a non-radioactive colour developing system.

The following examples only serve to illustrate the present invention. These examples are in no way intended to limit the scope of the present invention.

FIGURE AND TABLE LEGENDS

FIG. 1: Alignment of 35 complete HBV genomes. Isolates belonging to genotype A are: HBVXCPS, HBVADW, HVHEPB, S50225, HPBADWZCG; genotype B: HPBADW3, HPBADWZ, HPBADW1, HPBADW2; genotype C: HPBCGADR, HBVADRM, HPBADRA, HPBCG, HEHBVAYR, HBVADR, HBVADR4, HPBADR1C, HPBADRC, HBVPREX, HPBETNC, HHVBC, HHVC-CHA; genotype D: HBVAYWMCG, HBVAYWC, HBVAYWCI, HBVAYWE, HBVDNA, HPBHBVAA, XXHEPAV, HBVORFS; genotype E: HHVBE4, HHVB-BAS; and genotype F: HHBF, HHVBFFOU, HBVADW4A. To preserve alignment, several gaps were created in the alignment and are indicated with/. Positions of start and end of the different HBV encoded genes is indicated: HBsAg: hepatitis B surface antigen (small surface antigen); HBx: hepatitis B X protein; HB Pol: hepatitis B polymerase protein, encoding a terminal protein, a spacer, a RT/DNA polymerase region, and an RNAse H activity; HBcAg: hepatitis B Core antigen; HBpreS1Ag: hepatitis B preS1 antigen (large surface antigen); HBpreS2Ag: hepatitis B preS2 antigen (middle surface antigen). The position of the PCR primers is indicated with a large box over all 35 sequences. The polarity of the PCR primer can be deduced from the position of the name above these boxes: left= antisense primer; right=sense primer. LiPA probes are indicated with small boxes, the numbers of the probes are indicated next to the probes or to the right of the alignment, and correspond to the probe numbers in Table 1.

FIG. 2: LiPA HBV design. The content of a HBV LiPA strip is detailed. For each line number, the region on the viral genome is indicated, Together with the genotype that is detected, the probe number that corresponds with the boxes from the alignment in FIG. 1, and the sequence of the probe.

Figure 3:
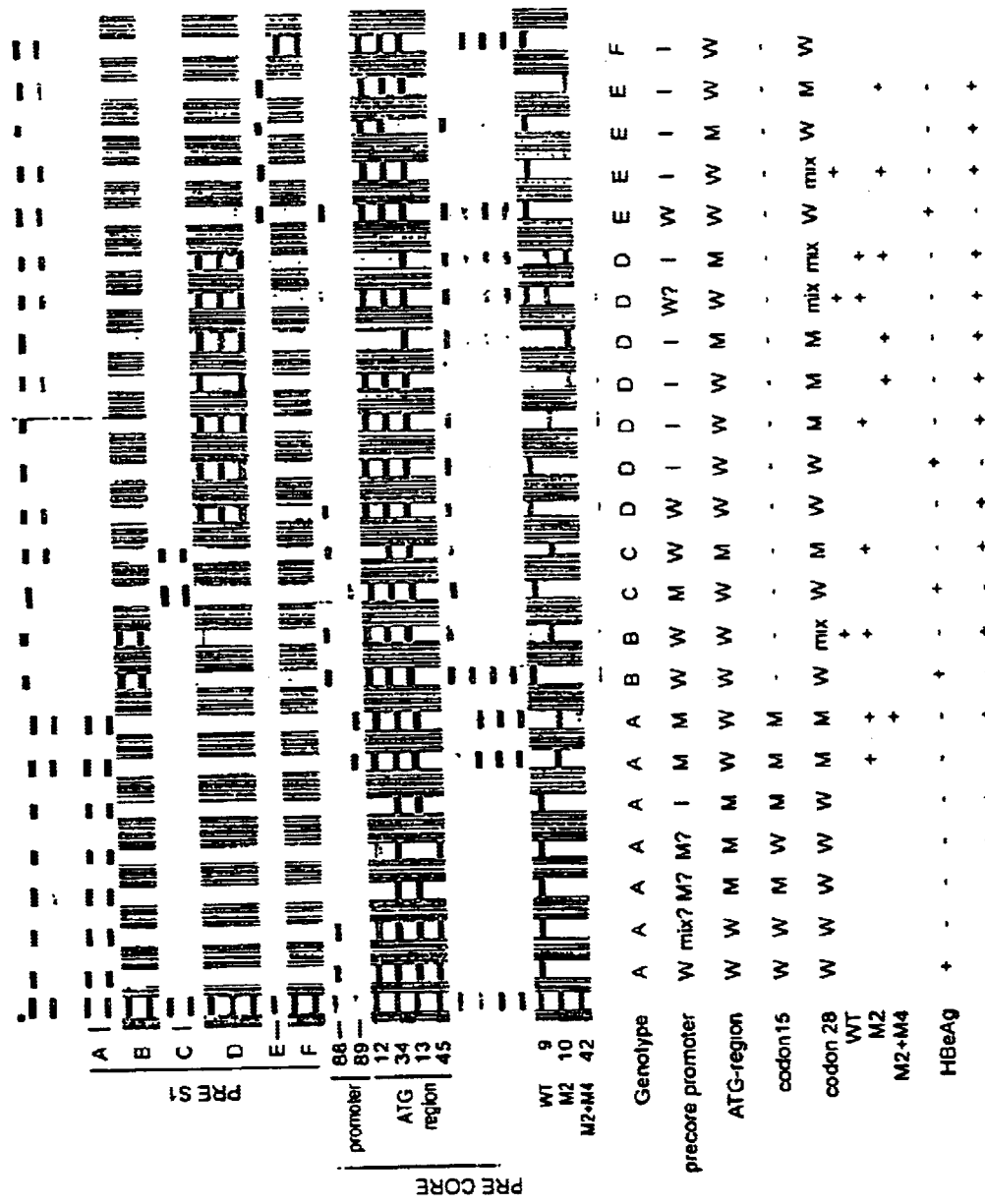

FIG. 3: Combined result of genotype determination in the preS1 region and preCore scanning on 24 samples. The interpretation of each sample is given under each strip. Probe reactivities on lines 3 to 14 are obtained from the preS1 PCR fragment, probe reactivities on lines 15 to 27 are due to the preCore PCR fragment. Genotypes are indicated from A to F. The interpretation for the preCore region is as follows: W=wild type; M=mutant; I=indeterminate, meaning that no reactivity is observed, which is due to mutations that could not yet be detected with the selected probes; mix=mixture of wild type and mutant; interpretation of codon 15 is only relevant for genotype A, the absence of reactivity on HBPr 45 for genotypes B to F is of no use as is indicated with—(not applicable). Since the presence or absence of preCore mutations has effect on the serological HBeAg status, this is also indicated.

FIG. 4: Probes used in HBV LiPA. Probes were designed for genotyping in the HBsAg region and for detection of drug resistance mutations in the YMDD motif (see also FIG. 5), as well as for detection of mutations in the pre Core region (see also FIG. 6).

Figure 5:
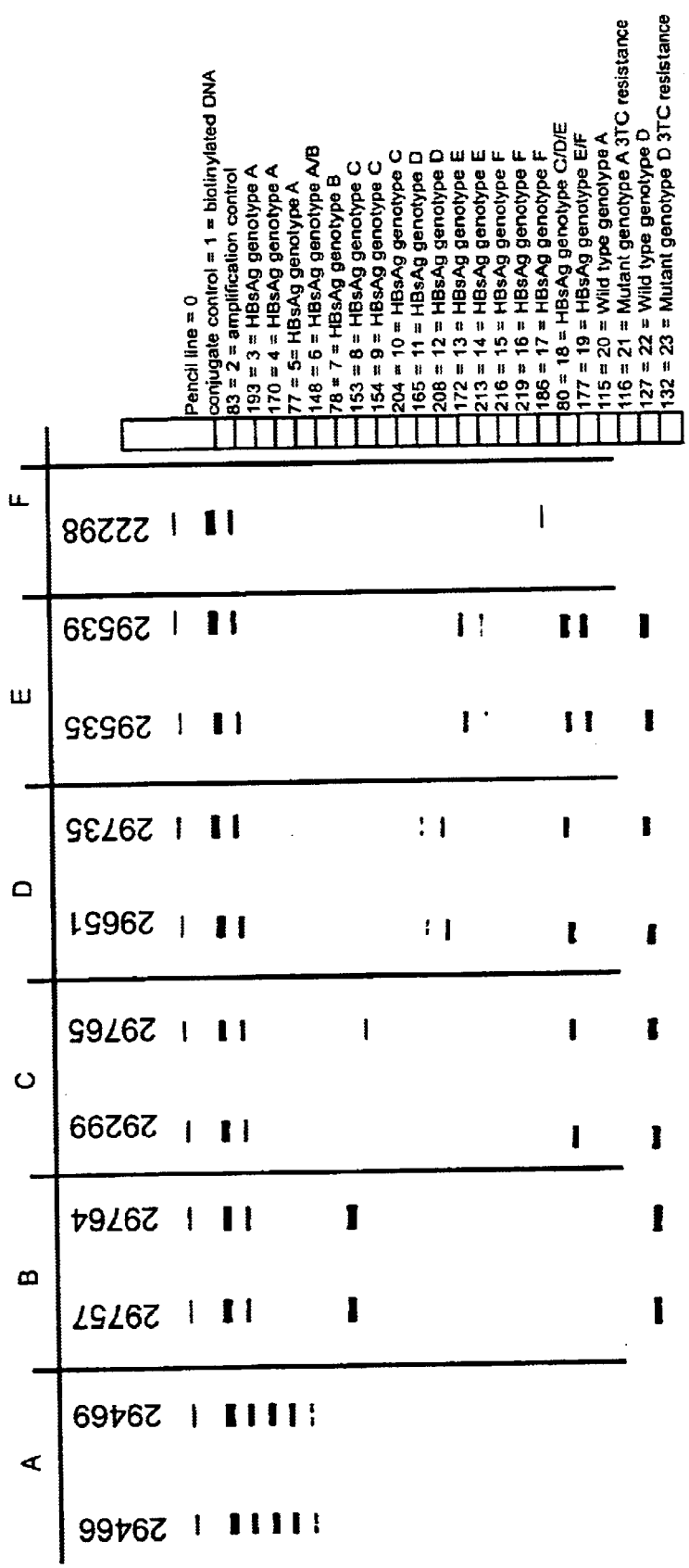

FIG. 5: Example of a LiPA assay combining HBV genotyping in the HBsAg region and detection of drug resistance mutations in the YMDD motif. Genotypes are indicated from A to F. The design of the strip is shown to the right, with the numbers of the probes corresponding to the numbers in Table 1 and in FIG. 4. The genotypes and mutant motifs to which each probe hybridizes are written to the outer right. The combination of reactive probes allows the determination of a unique genotype.

Figure 6:
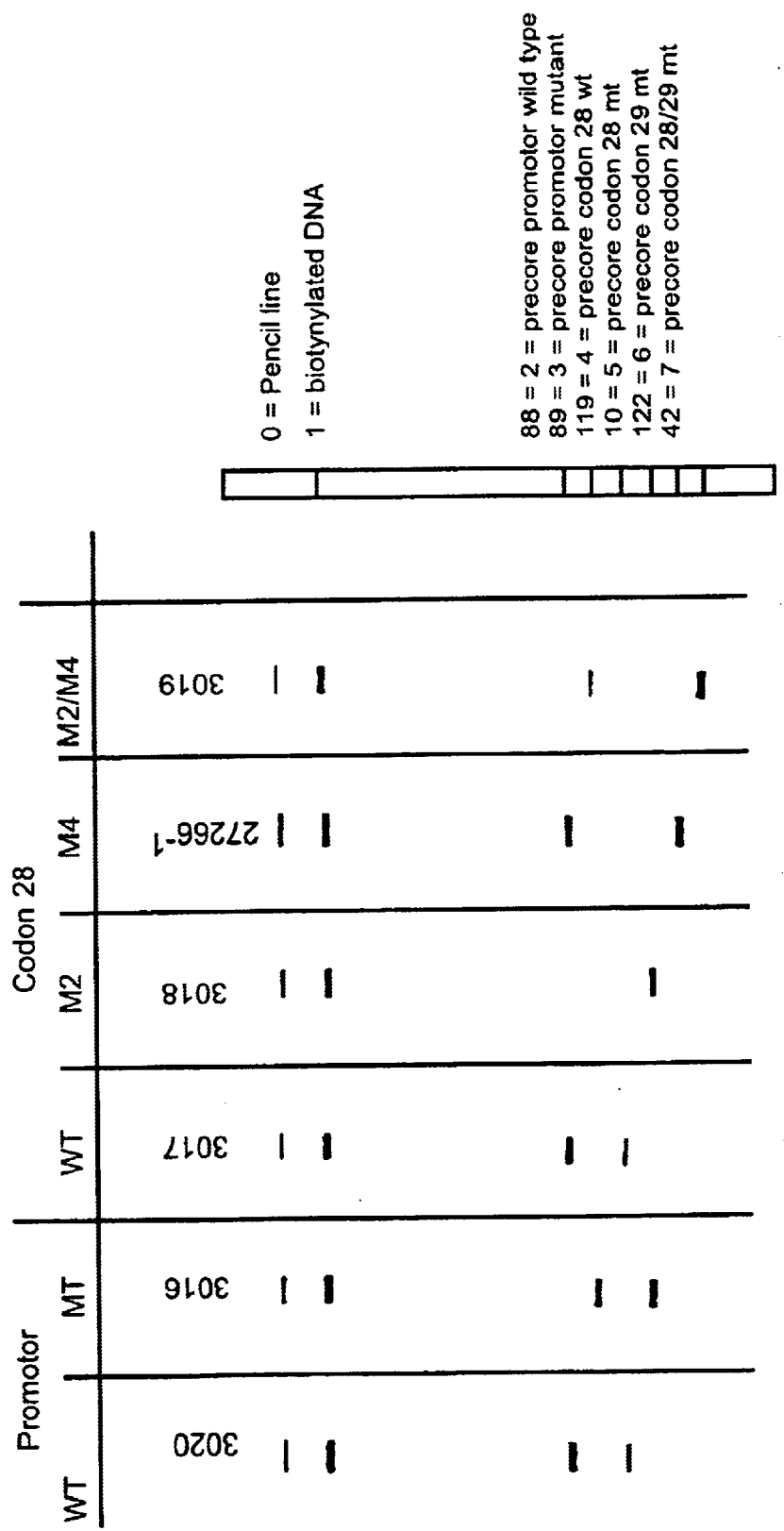

FIG. 6: Example of the determination of preCore mutations by the LiPA technique. The design of the strip is shown to the right, with the numbers of the probes corresponding to the numbers in Table 1. The mutant target sequences to which the probes hybridize are indicated to the outer right. Motif M2 corresponds to a mutation in codon 28, M4 corresponds to a mutation in codon 29. M2/M4 has mutations in both 28 and 29.

Figure 7:
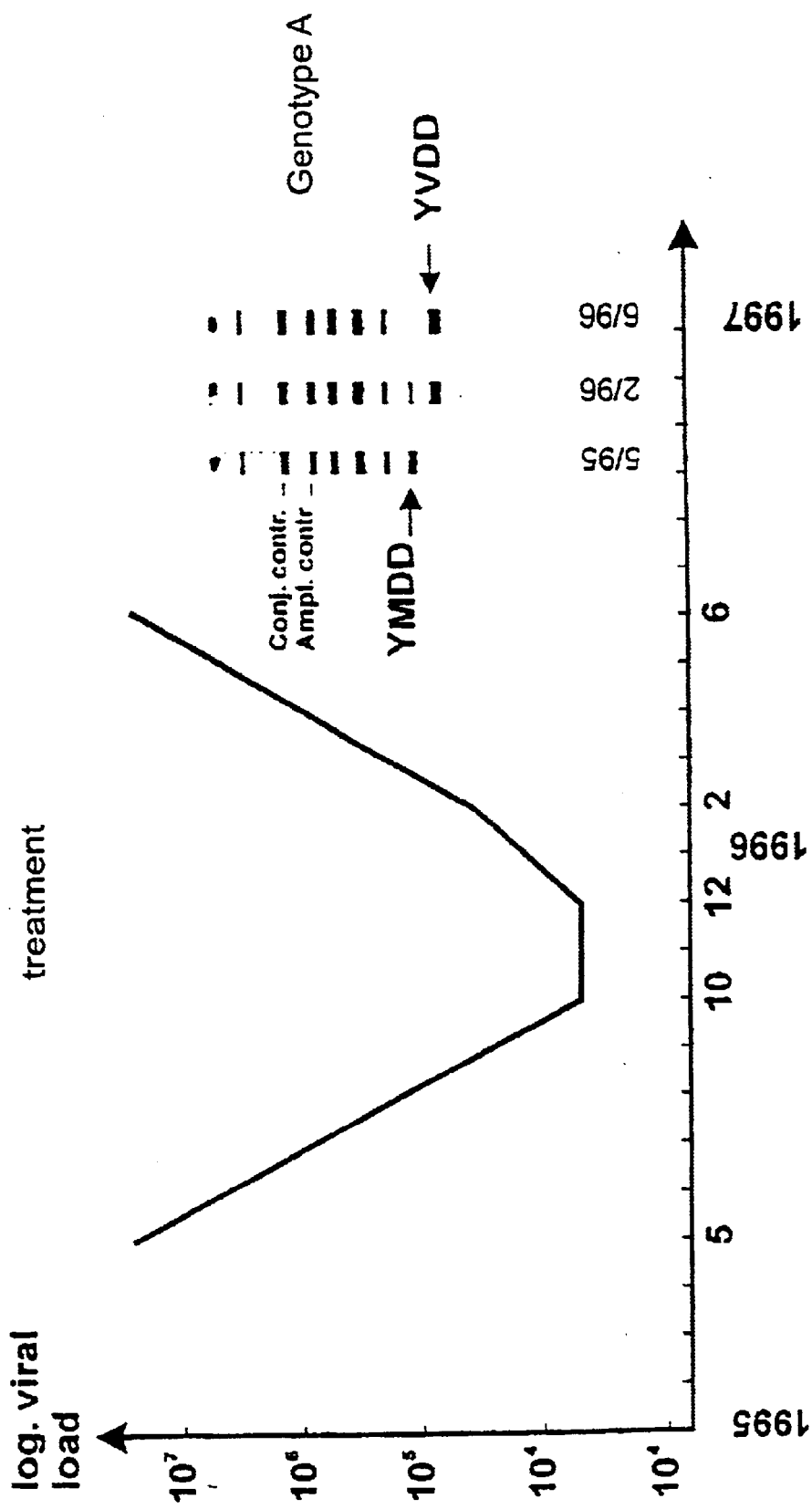

FIG. 7: Detection of a mutation in the YMDD motif of HBV pol upon treatment with lamivudine. The graph shows a time course of the viral load during lamivudine treatment. To the right LiPA strips are shown, corresponding to assays at the beginning of the treatment (5/95), 10 months of treatment (2/96) and 14 months of treatment (6/96). The assay shows that during treatment the YMDD motif mutates to YVDD.

Table 1: Overview of all primers and probes referred to in the Figures with an indication of their respective SEQ ID NO and the region of the HBV genome they are designed for. Primers from the PreS1 region include 1, 106, 2 (sense primers) and 4, 107 and 3 (antisense primers). Primers from the HBsAg region include 75 and 104 (sense primers) and 76, 94 and 105 (antisense primers). Primers from the Pre-Core region include 5, 6, 69, 70, 84, 86, 87 and 108 (sense primers) and 7, 8, 85 and 109 (antisense primers). The remaining oligonucleotides are probes from the PreCore, PreS1, HBsAg and RT pol gene regions of HBV as indicated. The YMDDV motif and its mutants consist of amino acids 551 to 555 of the RT pol protein; the sequence MGVGL and its mutant consist of amino acids 519 to 523 of the RT pol protein; the sequence SPFLL and its mutants and genotypic variants consist of amino acids 524 to 528 of the RT pol protein.

TABLE 1

HBV probe and primer design

| Name | Sequence | SEQ ID NO | Region |
|---|---|---|---|
| HBPr1 | GGGTCACCATATTCTTGGG | 1 | preS1 primer sense |
| HBPr2 | GAACAAGAGCTACAGCATGGG | 2 | preS1 primer sense |
| HBPr3 | CCACTGCATGGCCTGAGGATG | 3 | preS1 primer anti-sense |
| HBPr4 | GTTCCT/GGAACTGGAGCCACCAG | 4 | preS1 primer anti-sense |
| HBPr5 | TCTTTGTATTAGGAGGCTGTAG | 5 | preCore primer sense |
| HBPr6 | GCTGTAGGCATAAATTGGTCTG | 6 | preCore primer sense |
| HBPr7 | CTCCACAGT/AAGCTCCAAATTC | 7 | preCore primer anti-sense |
| HBPr8 | GAAGGAAAGAAGTCAGAAGGC | 8 | preCore primer anti-sense |
| HBPr9 | TGGCTTTGGGGCATGG | 9 | preCore |
| HBPr10 | TGGCTTTAGGGCATGG | 10 | preCore |
| HBPr11 | TGGCTTTAGGACATGG | 11 | preCore |
| HBPr12 | AAGTTGCATGGTGCTG | 12 | preCore |
| HBPr13 | CACCTCTGCCTAATCAT | 13 | preCore |
| HBPr14 | TGGGGTGGAGCCCTCAG | 14 | preS1 |
| HBPr15 | GCCAGCAGCCAACCAG | 15 | preS1 |
| HBPr16 | CCCATGGGGGACTGT | 16 | preS1 |
| HBPr17 | AACCCCAACAAGGATG | 17 | preS1 |
| HBPr18 | TCCACCAGCAATCCT | 18 | preS1 |
| HBPr19 | TGGGGGAAGAATATTT | 19 | preS1 |
| HBPr20 | AAATTCCAGCAGTCCC | 20 | preS1 |
| HBPr21 | GTTCCCAACCCTCTGG | 21 | preS1 |
| HBPr22 | AACCTCGCAAAGGCAT | 22 | preS1 |
| HBPr23 | TGCATTCAAAGCCAAC | 23 | preS1 |
| HBPr24 | TACTCACAACTGTGCC | 24 | preS1 |
| HBPr25 | ACCCTGCGTTCGGAGC | 25 | preS1 |
| HBPr26 | CAGGAAGACAGCCTAC | 26 | preS1 |
| HBPr27 | GATCCAGCCTTCAGAG | 27 | preS1 |
| HBPr28 | ATGCTCCAGCTCCTAC | 28 | preS1 |
| HBPr29 | GCTTTCTTGGACGGTC | 29 | preS1 |
| HBPr30 | CTACCCCAATCACTCC | 30 | preS1 |
| HBPr31 | AGCACCTCTCTCAACG | 31 | preS1 |
| HBPr32 | CCAATGGCAAACAAGG | 32 | preS1 |
| HBPr33 | CTGAGGGCTCCACCCCA | 33 | preS1 |
| HBPr34 | ATGCAACTTTTTCACC | 34 | preCore |
| HBPr35 | ATCTCTTGTACATGTC | 35 | preCore |
| HBPr36 | ATCTCATGTTCATGTC | 36 | preCore |
| HBPr37 | CAGTGGGACATGTACA | 37 | preCore |
| HBPr38 | CAGTAGGACATGAACA | 38 | preCore |
| HBPr39 | CTGTTCAAGCCTCCAA | 39 | preCore |
| HBPr40 | AGCCTCCAAGCTGTGC | 40 | preCore |
| HBPr41 | AAAGCCACCCAAGGCA | 41 | preCore |
| HBPr42 | TGGCTTTAGGACATGGA | 42 | preCore |
| HBPr43 | GACATGTACAAGAGATGA | 43 | preCore |
| HBPr44 | GACATGAACATGAGATGA | 44 | preCore |
| HBPr45 | TGTACATGTCCCACTGTT | 45 | preCore |

TABLE 1-continued

HBV probe and primer design

| Name | Sequence | SEQ ID NO | Region |
|---|---|---|---|
| HBPr46 | TGTTCATGTCCTACTGTT | 46 | preCore |
| HBPr47 | ACTGTTCAAGCCTCCAAG | 47 | preCore |
| HBPr48 | GGCACAGGCTTGGAGGCTT | 48 | preCore |
| HBPr49 | AAAGCCACCCAAGGCACA | 49 | preCore |
| HBPr50 | CCCAGAGGGTTGGGAAC | 50 | preS1 |
| HBPr51 | CAGCATGGGGCAGAATCT | 51 | preS1 |
| HBPr52 | TCCACCAGCAATCCTCTG | 52 | preS1 |
| HBPr53 | GGATCCAGCCTTCAGAGC | 53 | preS1 |
| HBPr54 | TCAGGAAGACAGCCTAC | 54 | preS1 |
| HBPr55 | TTCAACCCCAACAAGGATC | 55 | preS1 |
| HBPr56 | AATGCTCCAGCTCCTAC | 56 | preS1 |
| HBPr57 | CTGCATTCAAAGCCAACT | 57 | preS1 |
| HBPr58 | CCCCATGGGGGACTGTTG | 58 | preS1 |
| HBPr59 | CATACTCACAACTGTGCCA | 59 | preS1 |
| HBPr60 | GGGCTTTCTTGGACGGTCC | 60 | preS1 |
| HBPr61 | CTCTCGAATGGGGGAAGA | 61 | preS1 |
| HBPr62 | CCTACCCCAATCACTCCA | 62 | preS1 |
| HBPr63 | AGCACCTCTCTCAACGACA | 63 | preS1 |
| HBPr64 | GCAAATTCCAGCAGTCCCG | 64 | preS1 |
| HBPr65 | GCCAATGGCAAACAAGGTA | 65 | preS1 |
| HBPr66 | GACATGAACATGAGATG | 66 | preCore |
| HBPr67 | GGACATGAACAAGAGAT | 67 | preCore |
| HBPr68 | GACATGTACAAGAGATG | 68 | preCore |
| HBPr69 | ACATAAGAGGACTCTTGGAC | 69 | preCore primer sense |
| HBPr70 | TACTTCAAAGACTGTGTGTTTA | 70 | preCore primer sense |
| HBPr71 | ACAAAGACCTTTAAC/TCT | 71 | preCore promoter |
| HBPr72 | ACAAAGATCATTAAC/TCT | 72 | preCore promoter |
| HBPr73 | TTCCACCAGCAATCCTC | 73 | preS1 |
| HBPr74 | GATCCAGCCTTCAGAGC | 74 | preS1 |
| HBPr75 | CAAGGTATGTTGCCCGTTTGTCC | 75 | HBsAg primer sense |
| HBPr76 | CCAAACAGTGGGGGAAAGCCC | 76 | HBsAg primer anti-sense |
| HBPr77 | CTACGGATGGAAATTGC | 77 | HBsAg codon 145 wild type |
| HBPr78 | TACGGACGGAAACTGC | 78 | HBsAg codon 145 wild type |
| HBPr79 | TTCGGACGGAAACTGC | 79 | HBsAg codon 145 wild type |
| HBPr80 | CTTCGGACGGAAATTGC | 80 | HBsAg codon 145 wild type |
| HBPr81 | CTACGGATAGAAATTGC | 81 | HBsAg codon 145 mutant |
| HBPr82 | CTTCGGACAGAAATTGC | 82 | HBsAg codon 145 mutant |
| HBPr83 | CTATGGGAGTGGGCCTCAGT/CC | 83 | HB Pol |
| HBPr84 | GCTGTAGGCATAAATTGGTCTG | 84 | preCore primer sense |
| HBPr85 | CTCCACAGT/AAGCTCCAAATTC | 85 | preCore primer anti-sense |
| HBPr86 | ACATAAGAGGACTCTTGGAC | 86 | preCore primer sense |
| HBPr87 | TACTTCAAAGACTGTGTGTTTA | 87 | preCore primer sense |
| HBPr88 | TAGGTTAAAGGTCTTTGT | 88 | preCore promoter |
| HBPr89 | TAGGTTAATGATCTTTGT | 89 | preCore promoter |
| HBPr90 | CATGTCCCACTGTTCAA | 90 | preCore |
| HBPr91 | CATGTCCTACTGTTCAA | 91 | preCore |
| HBPr92 | TTCTGCCCCATGCTGTA | 92 | preS1 |
| HBPr93 | TTCTGCCCCATGCTGTAG | 93 | preS1 |
| HBPr94 | GGTAA/TAAAGGGACTCAC/AGATG | 94 | HBsAg primer anti-sense |
| HBPr95 | TCAGCTATATGGATGAT | 95 | HB Pol |
| HBPr96 | CAGCTATATGGATGAT | 96 | HB Pol |
| HBPr97 | TTCAGCTATATGGATG | 97 | HB Pol |
| HBPr98 | TCAGTTATATGGATGAT | 98 | HB Pol |
| HBPr99 | TTTCAGTTATATGGATG | 99 | HB Pol |
| HBPr100 | TTTAGTTATATGGATGA | 100 | HB Pol |
| HBPr101 | TCAGCTATGTGGATGAT | 101 | HB Pol |
| HBPr102 | TCAGTTATGTGGATGAT | 102 | HB Pol |
| HBPr103 | TTTCAGCTATGTGGATG | 103 | HB Pol |
| HBPr104 | CAAGGTATGTTGCCCGTTTGTCC | 104 | HBsAg primer sense |
| HBPr105 | GGT/CAA/TAAAGGGACTCAC/AGATG | 105 | HBsAg primer anti-sense |
| HBPr106 | GGGTCACCATATTCTTGGG | 106 | preS1 primer sense |
| HBPr107 | GTTCCT/GGAACTGGAGCCACCAG | 107 | preS1 primer anti-sense |
| HBPr108 | CCGGAAAGCTTGAGCTCTTCTTTTTCACCTCTGCCTAATC | 108 | preCore primer sense |
| HBPr109 | CCGGAAAGCTTGAGCTCTTCAAAAAGTTGCATGGTGCTGG | 109 | preCore primer anti-sense |
| HBPr110 | CCTCTGCCGATCCATACTGCGGAAC | 110 | preX primer sense |
| HBPr111 | CTGCGAGGCGAGGGAGTTCTTCTTC | 111 | HB Core primer anti-sense |
| HBPr112 | TGCCATTTGTTCAGTGGTTCGTAGGGC | 112 | HBsAg primer sense |
| HBPr113 | CCGGCAGATGAGAAGGCACAGACGG | 113 | HBX primer antisense |
| HBPr114 | TTCAGCTATATGGATGAT | 114 | YMDD motif |
| HBPr115 | TCAGCTATATGGATGATG | 115 | YMDD motif |
| HBPr116 | TTCAGCTATGTGGATGAT | 116 | YMDD motif |
| HBPr117 | TCAGCTATGTGGATGATG | 117 | YMDD motif |
| HBPr118 | GGCTTTGGGGCATGG | 118 | preCore codon 28 wild type |
| HBPr119 | TGGCTTTGGGGCATG | 119 | preCore codon 28 wild type |
| HBPr120 | GTGGCTTTGGGGCATG | 120 | preCore codon 28 wild type |

TABLE 1-continued

HBV probe and primer design

| Name | Sequence | SEQ ID NO | Region |
|---|---|---|---|
| HBPr121 | GGCTTTGGGGCATGGA | 121 | preCore codon 28 wild type |
| HBPr122 | TGGCTTTGGGACATGG | 122 | preCore codon 28 wild type, codon 29 mutant |
| HBPr123 | GGCTTTGGGACATGG | 123 | preCore codon 28 wild type, codon 29 mutant |
| HBPr124 | TGGCTTTGGGACATG | 124 | preCore codon 28 wild type, codon 29 mutant |
| HBPr125 | GTGGCTTTGGGACATG | 125 | preCore codon 28 wild type, codon 29 mutant |
| HBPr126 | GGCTTTGGGACATGGA | 126 | preCore codon 28 wild type, codon 29 mutant |
| HBPr127 | TCAGTTATATGGATGATG | 127 | YMDD genotype D, wild type |
| HBPr128 | TTCAGTTATATGGATGAT | 128 | YMDD genotype D, wild type |
| HBPr129 | TTTCAGTTATATGGATGAT | 129 | YMDD genotype D, wild type |
| HBPr130 | TCAGTTATGTGGATGATG | 130 | YMDD genotype D, mutant |
| HBPr131 | TTCAGTTATGTGGATGAT | 131 | YMDD genotype D, mutant |
| HBPr132 | TTTCAGTTATGTGGATGAT | 132 | YMDD genotype D, mutant |
| HBPr133 | TTTCAGTTATGTGGATGA | 133 | YMDD genotype D, mutant |
| HBPr134 | TGCTGCTATGCCTCATCTTC | 134 | outer HBsAg primer sense |
| HBPr135 | CA(G/A)AGACAAAAGAAAATTGG | 135 | outer HBsAg primer anti-sense |
| HBPr136 | CTATGGATGGAAATTGC | 136 | HBsAg mutant codon 143 |
| HBPr137 | CCTATGGATGGAAATTG | 137 | HBsAg mutant codon 143 |
| HBPR138 | ACCTATGGATGGAAATT | 138 | HBsAg mutant codon 143 |
| HBPr139 | CT CAA GGC AAC TCT ATG TGG | 139 | HBsAg, genotype A |
| HBPr140 | CT CAA GGC AAC TCT ATG GG | 140 | HBsAg, genotype A |
| HBPr141 | T CAA GGC AAC TCT ATG TTG | 141 | HBsAg, genotype A |
| HBPr142 | ATC CCA TCA TCT TGG G | 142 | HBsAg, genotype B |
| HBPr143 | ATC CCA TCA TCT TGG GCG G | 143 | HBsAg, genotype B |
| HBPr144 | TC CCA TCA TCT TGG GCG G | 144 | HBsAg, genotype B |
| HBPr145 | C CCA TCA TCT TGG GCT GG | 145 | HBsAg, genotype B |
| HBPr146 | TTC GCA AAA TAC CTA TGG | 146 | HBsAg, genotype B |
| HBPr147 | T TTC GCA AAA TAC CTA TG | 147 | HBsAg, genotype B |
| HBPr148 | CT TTC GCA AAA TAC CTA TG | 148 | HBsAg, genotype B |
| HBPr149 | TC GCA AAA TAC CTA TGG G | 149 | HBsAg, genotype B |
| HBPr150 | T CTA CTT CCA GGA ACA T | 150 | HBsAg, genotype C |
| HBPr151 | T CTA CTT CCA GGA ACA TC | 151 | HBsAg, genotype C |
| HBPr152 | CT CTA CTT CCA GGA ACA T | 152 | HBsAg, genotype C |
| HBPr153 | CT CTA CTT CCA GGA ACA G | 153 | HBsAg, genotype C |
| HBPr154 | C TGC ACG ATT CCT GCT | 154 | HBsAg, genotype C |
| HBPr155 | TGC ACG ATT CCT GCT CA | 155 | HBsAg, genotype C |
| HBPr156 | C TGC ACG ATT CCT GCT C | 156 | HBsAg, genotype C |
| HBPr157 | TGC ACG ATT CCT GCT CAA | 157 | HBsAg, genotype C |
| HBPr158 | TTC GCA AGA TTC CTA TG | 158 | HBsAg, genotype C |
| HBPr159 | CT TTC GCA AGA TTC CTA T | 159 | HBsAg, genotype C |
| HBPr160 | CT TTC GCA AGA TTC CTA | 160 | HBsAg, genotype C |
| HBPr161 | CT TTC GCA AGA TTC CTA TG | 161 | HBsAg, genotype C |
| HBPr162 | C TCT ATG TAT CCC TCC T | 162 | HBsAg, genotype D |
| HBPr163 | TCT ATG TAT CCC TCC TG | 163 | HBsAg, genotype D |
| HBPr164 | C TCT ATG TAT CCC TCC TGG | 164 | HBsAg, genotype D |
| HBPr165 | CC TCT ATG TAT CCC TCC T | 165 | HBsAg, genotype D |
| HBPr166 | C TGT ACC AAA CCT TCG G | 166 | HBsAg, genotype D |
| HBPr167 | C TGT ACC AAA CCT TCG | 167 | HBsAg, genotype D |
| HBPr168 | GC TGT ACC AAA CCT TCG G | 168 | HBsAg, genotype D |
| HBPr169 | TGT ACC AAA CCT TCG GAG | 169 | HBsAg, genotype D |
| HBPr170 | GGA CCC TGC CGA ACC T | 170 | HBsAg, genotype E |
| HBPr171 | GGA CCC TGC CGA ACC G | 171 | HBsAg, genotype E |
| HBPr172 | G GGA CCC TGC CGA AC | 172 | HBsAg, genotype E |
| HBPr173 | GGA CCC TGC CGA AC | 173 | HBsAg, genotype E |
| HBPr174 | GT TGC TGT TCA AAA CCT T | 174 | HBsAg, genotype E |
| HBPr175 | GT TGC TGT TCA AAA CCT G | 175 | HBsAg, genotype E |
| HBPr176 | TGT TGC TGT TCA AAA CCT G | 176 | HBsAg, genotype E |
| HBPr177 | A TGT TGC TGT TCA AAA CCT G | 177 | HBsAg, genotype E |
| HBPr178 | GA TCC ACG ACC ACC A | 178 | HBsAg, genotype F |
| HBPr179 | GGA TCC ACG ACC ACC A | 179 | HBsAg, genotype F |
| HBPr180 | GGA TCC ACG ACC ACC | 180 | HBsAg, genotype F |
| HBPr181 | GA TCC ACG ACC ACC AGG | 181 | HBsAg, genotype F |
| HBPr182 | TGT TCC AAA CCC TCG G | 182 | HBsAg, genotype F |
| HBPr183 | C TGT TCC AAA CCC TCG | 183 | HBsAg, genotype F |
| HBPr184 | C TGT TCC AAA CCC TCG G | 184 | HBsAg, genotype F |
| HBPr185 | GT TCC AAA CCC TCG GAT | 185 | HBsAg, genotype F |
| HBPr186 | G CCA AAT CTG TGC AGC | 186 | HBsAg, genotype F |
| HBPr187 | CCA AAT CTG TGC AGC AT | 187 | HBsAg, genotype F |
| HBPr188 | G CCA AAT CTG TGC AGC AG | 188 | HBsAg, genotype F |
| HBPr189 | GG CCA AAT CTG TGC AGC | 189 | HBsAg, genotype F |
| HBPr190 | A TCA ACA ACA ACC AGT A | 190 | HBsAg, genotype A |
| HBPr191 | GA TCA ACA ACA ACC AGT | 191 | HBsAg, genotype A |
| HBPr192 | GA TCA ACA ACA ACC AGT A | 192 | HBsAg, genotype A |
| HBPr193 | GGA TCA ACA ACA ACC AGT | 193 | HBsAg, genotype A |
| HBPr194 | T CAA GGC AAC TCT ATG TGG | 194 | HBsAg, genotype A |
| HBPr195 | AGG TTA AAG GTC TTT GT | 195 | promoter genotype A wild type |

TABLE 1-continued

HBV probe and primer design

| Name | Sequence | SEQ ID NO | Region |
|---|---|---|---|
| HBPr196 | T AGG TTA AAG GTC TTT GG | 196 | promoter genotype A wild type |
| HBPr197 | TT AGG TTA AAG GTC TTT | 197 | promoter genotype A wild type |
| HBPr198 | GG TTA AAG GTC TTT GTA GG | 198 | promoter genotype A wild type |
| HBPr199 | AGG TTA ATG ATC TTT GT | 199 | promoter genotype A mutant |
| HBPr200 | T AGG TTA ATG ATC TTT GG | 200 | promoter genotype A mutant |
| HBPr201 | CT TTC GCA AGA TTC CTA TGG | 201 | HBsAg genotype C codon 160 |
| HBPr202 | GCT TTC GCA AGA TTC CTA TG | 202 | HBsAg genotype C codon 160 |
| HBPr203 | GCT TTC GCA AGA TTC CTA TGG | 203 | HBsAg genotype C codon 160 |
| HBPr204 | CT TTC GCA AGA TTC CTA TGG G | 204 | HBsAg genotype C codon 160 |
| HBPr205 | GC TGT ACC AAA CCT TCG GAG | 205 | HBsAg genotype D codon 140 |
| HBPr206 | TGC TGT ACC AAA CCT TCG G | 206 | HBsAg genotype D codon 140 |
| HBPr207 | TGC TGT ACC AAA CCT TCG GAG | 207 | HBsAg genotype D codon 140 |
| HBPr208 | GC TGT ACC AAA CCT TCG GAT | 208 | HBsAg genotype D codon 140 |
| HBPr209 | TGG TTC GCC GGG CTT T | 209 | HBsAg genotype E codon 184 |
| HBPr210 | G TGG TTC GCC GGG CTT G | 210 | HBsAg genotype E codon 184 |
| HBPr211 | GG TTC GCC GGG CTT TC | 211 | HBsAg genotype E codon 184 |
| HBPr212 | TGG TTC GCC GGG CTT TC | 212 | HBsAg genotype E codon 184 |
| HBPr213 | AG TGG TTC GCC GGG CTG G | 213 | HBsAg genotype E codon 184 |
| HBPr214 | A GGA TCC ACG ACC ACC AGG | 214 | HBsAg genotype F |
| HBPr215 | A GGA TCC ACG ACC ACC AGT | 215 | HBsAg genotype F |
| HBPr216 | CA GGA TCC ACG ACC ACC AGG | 216 | HBsAg genotype F |
| HBPr217 | C TGT TCC AAA CCC TCG GAG | 217 | HBsAg genotype F |
| HBPr218 | C TGT TCC AAA CCC TCG GAT | 218 | HBsAg genotype F |
| HBPr219 | GC TGT TCC AAA CCC TCG GAG | 219 | HBsAg genotype F |
| HBPr220 | CTGAACCTTTACCCCGTTGC | 220 | enhancer primer |
| HBPr221 | CTCGCCAACTTACAAGGCCTTTC | 221 | enhancer primer |
| HBPr222 | AGAATGGCTTGCCTGAGTGC | 222 | Core primer anti-sense |
| HBPr223 | GCT TTC GCA AGA TTC CTA TGG G | 223 | HBsAg genotype C codon 160 |
| HBPr224 | G GCT TTC GCA AGA TTC CTA TGG | 224 | HBsAg genotype C codon 160 |
| HBPr225 | G GCT TTC GCA AGA TTC CTA TGG G | 225 | HBsAg genotype C codon 160 |
| HBPr226 | G GCT TTC GCA AGA TTC CTA TGG GA | 226 | HBsAg genotype C codon 160 |
| HBPr227 | C AGC TAT ATG GAT GAT GTG | 227 | YMDDV motif |
| HBPr228 | AGC TAT ATG GAT GAT GTG GG | 228 | YMDDV motif |
| HBPr229 | GC TAT ATG GAT GAT GTG GT | 229 | YMDDV motif |
| HBPr230 | AGC TAT ATG GAT GAT GTG GT | 230 | YMDDV motif |
| HBPr231 | C AGC TAT ATG GAT GAT ATA | 231 | YMDDI motif |
| HBPr232 | AGC TAT ATG GAT GAT ATA GG | 232 | YMDDI motif |
| HBPr233 | GC TAT ATG GAT GAT ATA GT | 233 | YMDDI motif |
| HBPr234 | AGC TAT ATG GAT GAT ATA GT | 234 | YMDDI motif |
| HBPr235 | CCA TCA TCT TGG GCT TG | 235 | HBSAg GENOTYPE B CODON 155 |
| HBPr236 | CA TCA TCT TGG GCT TT | 236 | HBSAg GENOTYPE B CODON 155 |
| HBPr237 | CCA TCA TCT TGG GCT TT | 237 | HBSAg GENOTYPE B CODON 155 |
| HBPr238 | CCA TCA TCT TGG GCT TTC | 238 | HBSAg GENOTYPE B CODON 155 |
| HBPr239 | CCC ACT GTC TGG CTT TC | 239 | HBSAg GENOTYPE B CODON 190 |
| HBPr240 | CC ACT GTC TGG CTT TC | 240 | HBSAg GENOTYPE B CODON 190 |
| HBPr241 | CC ACT GTC TGG CTT T | 241 | HBSAg GENOTYPE B CODON 190 |
| HBPr242 | CCC ACT GTC TGG CTT G | 242 | HBSAg GENOTYPE B CODON 190 |
| HBPr243 | TAT ATG GAT GAT GTG GTA | 243 | YMDDV MOTIF |
| HBPr244 | TAT GTG GAT GAT GTG GTA | 244 | YVDDV MOTIF |
| HBPr245 | TAT ATA GAT GAT GTG GTA | 245 | YIDDV MOTIF |
| HBPr246 | TAT ATT GAT GAT GTG GTA | 246 | YIDDV MOTIF |
| HBPr247 | TAT GTA GAT GAT GTG GTA | 247 | YIDDV MOTIF |
| HBPr248 | TAT GTT GAT GAT GTG GTA | 248 | YVDDV MOTIF |
| HBPr249 | TAT ATG GAT GAT ATA GTA | 249 | YMDDI MOTIF |
| HBPr250 | TAT ATG GAT GAT ATC GTA | 250 | YMDDI MOTIF |
| HBPr251 | TAT GTG GAT GAT ATA GTA | 251 | YVDDI MOTIF |
| HBPr252 | TAT GTG GAT GAT ATC GTA | 252 | YVDDI MOTIF |
| HBPr253 | TAT ATA GAT GAT ATA GTA | 253 | YIDDI MOTIF |
| HBPr254 | TAT ATA GAT GAT ATC GTA | 254 | YIDDI MOTIF |
| HBPr255 | TAT ATT GAT GAT ATA GTA | 255 | YIDDI MOTIF |
| HBPr256 | TAT ATT GAT GAT ATC GTA | 256 | YIDDI MOTIF |
| HBPr257 | TAT GTA GAT GAT ATA GTA | 257 | YVDDI MOTIF |
| HBPr258 | TAT GTA GAT GAT ATC GTA | 258 | YVDDI MOTIF |
| HBPr259 | TAT GTT GAT GAT ATA GTA | 259 | YVDDI MOTIF |
| HBPr260 | TAT GTT GAT GAT ATC GTA | 260 | YVDDI MOTIF |
| HBPr261 | TAT ATG GAT GAT CTG GTA | 261 | YMDDL MOTIF |
| HBPr262 | TAT GTG GAT GAT CTG GTA | 262 | YVDDL MOTIF |
| HBPr263 | TAT ATA GAT GAT CTG GTA | 263 | YIDDL MOTIF |
| HBPr264 | TAT ATT GAT GAT CTG GTA | 264 | YIDDL MOTIF |
| HBPr265 | TAT GTA GAT GAT CTG GTA | 265 | YVDDL MOTIF |
| HBPr266 | TAT GTT GAT GAT CTG GTA | 266 | YVDDL MOTIF |
| HBPr267 | T ATG GGA GTG GGC CTC AG | 267 | MGVGL |
| HBPr268 | T ATG GGA TTG GGC CTC AG | 268 | MGLGL |
| HBPr269 | C AGT CCG TTT CTC TTG GC | 269 | SPFLL |

EXAMPLES

Example 1
HBV DNA Preparation and PCR Amplification

Serum samples were collected from HBsAg-positive individuals and stored at minus 20° C. until use in 0.5 ml aliquots. To prepare the viral genome, 18 µl serum was mixed with 2 µl 1 N NaOH and incubated at 37° C. for 60 minutes. The denaturation was stopped and neutralized by adding 20 µl of 0.1N HCl. After a 15 minutes centrifugation step, the supernatant was collected and the pellet discarded. PCR was carried out on this lysate as follows: 32 µl $H_2O$ was mixed with 5 µl of 10×PCR buffer, 1 µl 10 mM dXTPs, 1 µl of each biotinylated primer (10 pmol/µl), 10 µl of serum lysate, and 2 U Taq enzyme. The amplification scheme contained 40 cycles of 95° C. 1 min, annealing at 45° C. for 1 min, and extension at 72° C. for 1 min. Amplification products were visualized on 3% agarose gel.

The outer primer set for preS1 has the following sequence:

outer sense: HBPr 1: 5'-bio-GGGTCACCATATTCTTGGG-3' (SEQ ID NO:1)

outer antisense HBPr 4: 5'-bio-GTTCC(T/G)GAACTGGAGCCACCAG-3' (SEQ ID NO:4)

The outer primer set for preCore has the following sequence:

outer sense: HBPr 69: 5'-bio-ACATAAGGACTCTTGGAC-3' (SEQ ID NO:69)

outer antisense: HBPr 8: 5'-bio-GAAGGAAAGAAGTCAGAAGGC-3' (SEQ ID NO:8)

The outer primer set for HBsAg has the following sequence:

outer sense: HBPr 134: 5'-bio-TGCTGCTATGCCTCATCTTC-3' (SEQ ID NO:134)

outer antisense: HBPr 135: 5'-bio-CA(G/A)AGACAAAAGAAAATTGG-3'.(SEQ ID NO:135)

Samples that were negative in the first round PCR were retested in a nested reaction composed of the following: µl $H_2O$, 5 µl 10×Taq buffer, 1 µl 10 mM dXTPs, 1 µl of each nested primer (10 pmol/µl), 1 µl of the first round PCR product, and 2 U Taq polymerase. The amplification scheme was identical as for the first round PCR. The sequence of the nested primers were as follows, for the preS1 region:

nested sense HBPr 2: 5'-bio-GAACAAGAGCTACAGCATGGG-3' (SEQ ID NO:2)

nested antisense HBPr 3: 5'-bio-CCACTGCATGGCCTGAGGATG-3' (SEQ ID NO:3)

and for the preCore region:

nested sense HBPr 70: 5'-bio-TACTTCAAAGACTGTGTGTTTA-3' (SEQ ID NO:70)

nested antisense HBPr 7: 5'-bio-CTCCACAG(T/A)AGCTCCAAATTC-3' (SEQ ID NO:7)

In a second reaction the HBsAg region can be amplified in a similar protocol by using the following primers: HBPr 75: 5'-bio-CAAGGTATGTTGCCCGTTTGTCC-3' (SEQ ID NO:75) in combination with either HBPr 76: 5'-bio-CCAAACAGTGGGGGAAAGCCC-3' (SEQ ID NO:76); or with HBPr 94: 5'-bio-GGTA(A/T)AAAGGGACTCA(C/A)GATG-3' (SEQ ID NO:94).

Example 2
Preparation of the Line Probe Assays

Probes were designed to cover the universal, genotypic and mutant motifs. In principle only probes that discriminate between one single nucleotide variation were retained. However, for certain polymorphisms at the extreme ends of the probe, cross-reactivity was tolerated. Specificity was reached experimentally for each probe individually after considering the % (G+C), the probe length, the final concentration, and hybridization temperature. Optimized probes were provided enzymatically with a poly-T-tail using the TdT (Pharmacia) in a standard reaction condition. Briefly, 400 pmol probe was incubated at 37° C. in a 30 µl reaction mix containing 5.3 mM dTTP, 25 mM Tris.HCL pH 7.5, 0.1 M sodium cacodylate, 1 mM $CoCl_2$, 0.1 M DTT and 170 U terminal deoxynucleotidyl transferase (Pharmacia). After one hour incubation, the reaction was stopped and the tailed probes were precipitated and washed with ice-cold ethanol. Probes were dissolved in 6×SSC at their respectively specific concentrations and applied as horizontal lines on membrane strips in concentrations between 0.2 and 2.5 pM/ml. Biotinylated DNA was applied alongside as positive control (LiPA line 1). The oligonucleotides were fixed to the membrane by baking at 80° C. for 12 hours. The membrane was than sliced into 4 mm strips. The design of this strip is indicated in FIG. 2.

Example 3
LiPA Test Performance

Equal volumes (10 µl each) of the biotinylated PCR fragment and of the denaturation solution (DS; 400 mM NaOH/10 mM EDTA) were mixed in test troughs and incubated at room temperature for 5 minutes. Then, 2 ml of the 37° C. prewarmed hybridization solution (HS, 3×SSC/0.1% SDS) was added, followed by the addition of one strip per test trough. Hybridisation occured for 1 hour at 50±0.5° C. in a closed shaking water bath. The strips were washed twice with 2 ml of stringent wash solution (3×SSC/0.1% SDS) at room temperature for 20 seconds, and once at 50° C. for 30 minutes. Following this stringent wash, strips were rinsed two times with 2 ml of the Innogenetics standard Rinse Solution (RS). Strips were incubated on a rotating platform with the alkaline phosphatase-labelled streptavidin conjugate, diluted in standard Conjugate Solution for 30 minutes at room temperature (20 to 25° C.). Strips were than washed twice with 2 ml of RS and once with standard Substrate Buffer (SB), and the colour reaction was started by adding BCIP and NBT to the SB. After maximum 30 minutes at room temperature, the colour reaction was stopped by replacing the colour compounds by distilled water. Immediately after drying, the strips were interpreted. Reactivities were considered positive whenever the reactivity was stronger than the reaction on the negative control. Strips can be stored on a dry dark place. The complete procedure described above can also be replaced by the standardized Inno-LiPA automation device (auto-LiPA).

Example 4
Selection of Reference Material.

PCR fragments were prepared, derived from members of the different genotypes, the different preCore wild type and mutant sequences, drug resistant motifs and vaccine escape mutants. The PCR fragments were amplified with primers lacking the biotine group at their 5'-end and cloned into the pretreated EcoRV site of the pGEMT vector (Promega). Recombinant clones were selected after α-complementation and restriction fragment length analysis, and sequenced with plasmid primers. Other biotinylated fragments were directly sequenced with a dye-terminator protocol (Applied Biosystems) using the amplification primers. Alternatively, nested PCR was carried out with analogs of the primers, in which the biotine group was replaced with the T7- and SP6-primer sequence, respectively. These amplicons were than sequenced with an SP6- and T7-dye-primer procedure. By doing so, a reference panel of recombinant clones was prepared, which is necessary for optimizing LiPA probes.

Example 5

Genotyping HBV-infected Serum Samples.

Only after creating a sequence alignment as shown in FIG. 1, it became clear which regions could be useful for HBV genotyping. The preS1 region seems to be suitable because of the high degree of variability. Probes were therefore designed to cover most of these variable regions as shown in Table 1. Only a limited selection of probes was retained because of their specific reaction with the reference panel. The most important ones are indicated as boxed regions in FIG. 1. These selected probes were then applied in a LiPA format indicated in FIG. 2, as line number 2 to 14. Some of the probes could be applied together in one line, because of their universal character, while others need to be applied separately. With the selection of probes thus obtained, serum samples collected in different parts of the world (Europe, South-America, Africa, Middle-East) were tested. The upper part of FIG. 3 shows the reactivity of a selection of samples on these probes. Genotyping of these samples is straightforward, with samples 2 to 8 belonging to genotype A, samples 9 and 10 belonging to genotype B, samples 11 and 12 belonging To genotype C, samples 3 to 19 belonging to genotype D, samples 20 to 23 belonging to genotype E, and sample 24 belonging to genotype F.

Genotyping can also be performed in the HBsAg region. Again, probes were designed to cover most of the variable regions shown in FIG. 1. Only a limited selection of probes were retained. These probes are boxed in FIG. 1 and are listed in FIG. 4. A LiPA strip was prepared carrying these probes and samples belonging to the different genotypes were characterized, as shown in FIG. 5.

Example 6

Scanning The PreCore Region for Mutations.

HBeAg expression can be regulated at the transcriptional and translational level. It is postulated that a transcriptional regulation exists due to the presence of a dinucleotide variation in the promoter region of the preCore mRNA. Probes covering the wild type (e.g. probe HBPr 88) and the mutant (e.g. HBPr 89) motif were selected and their positions are indicated in the alignment shown in FIG. 1, and applied on the LiPA strip as line 15 and 16 (FIG. 2).

At the translational level, much more mutations might arise, all possibly resulting in abrogation of the HBeAg expression: any mutations at codon 1 (ATG) destroying translation initiation, codon 2 (CAA to TAA), codon 7 (TGC to TGA), codon 12 (TGT to TGA), codon 13 in genotype B, C, D, E, F (TCA to TGA or TAA), codon 14 (TGT to TGA), codon 18 (CAA to TAA), codon 21 (AAG to TAG), codon 23 (TGC to TGA), codon 26 (TGG to TAG or TGA), codon 28 (TGG to TAG or TGA). However, due to secondary contrain of the encapsidation signal, most of the mutations occur at codon 28 (TGG to TAG). Along with the mutation at codon 28, a second mutation at codon 29 (GGC to GAC) is often observed. In the case of genotype A and again as a consequence of the secondary constrain, stop codon mutations at codon 28 are only likely to occur after selection of a codon 15 mutation (CCC to CCT). Hence, correct interpretation of preCore mutations is genotype dependent. In addition to the above mentioned stop codons, a huge amount of different deletion- or insertion-mutations in the preCore open reading frame might give essentially the same result.

In order to develop a sensitive assay to detect the relevant mutations and the hypothetical mutations, a probe scanning procedure was developed. Partially overlapping probes were designed and applied in a LiPA format (FIG. 2, line 17 To 27). In this assay format, wild type sequences over the complete preCore region, together with the codon 15 variation for genotype A versus non-A genotypes, and the most common mutations at codon 28 (TAG), at codon 29 (GAC) and the combination of codon 28 and 29 (TAGGAC) are positively recognized. Absence of reactivity at one of the other probes is always indicative for the presence of a variation. The exact nature of this variation can then be revealed by sequence analysis or with further designed LiPA probes.

FIG. 3 shows the reactivity of the selected genotyped samples on the probes for the preCore region. Samples were previously tested for the presence of HBeAg or for anti-HBe. The interpretation of the reactivity on the LiPA probes for each sample is indicated below each strip. This approach allowed for the simultaneous screening of a sample for preCore mutations and the characterization of the viral genotype.

FIG. 6 also shows a panel of samples with mutations in the preCore region, as well as wild type samples. The probes used in this assay are listed in FIG. 4. This assay includes a codon 29 mutant (M4 motif), which was not present in the experiment in FIG. 3.

Example 7

Detection of Mutants in the HBsAg Region.

Vaccine escape mutants have been described. The most commonly found mutant is the variation at codon 145 of HBsAg (G145R or GGA to AGA). LiPA probes are designed to detect wild type and mutant probes. Genotypic variations are present in the vicinity of codon 145. Therefore, genotype A is covered by probe 77, genotype B by probe 78, genotype C by probe 79, and genotype D/E by probe 80. Hence, in principle, it is possible to genotype and detect the wild type strains of the virus in one single experiment. Mutant target sequences are covered by probe 81 and 82 for genotype A and D, respectively. Probe 83 can be used as a positive control in these experiments. Further detection of mutants in the a determinant region is possible by means of a probe scanning approach. Herefore, probes are designed to cover the wild type sequence of the different genotypes over the HBsAg epitope region and applied in a LiPA format. Again here, absence of staining at one of these probes is indicative for the presence of a mutant strain. The exact nature of, this variant is then determined by sequencing analysis.

Example 8

Detection of HBV Strains Resistant to Lamivudine.

Through analogy with HIV and the resistance against the anti-viral compound 3TC (lamivudine or (−)-β-1-2',3'-dideoxy-3'-thiacytidine), it was predicted that upon treatment of HBV-infected patients with 3TC, viral strains would be selected showing resistance at the YMDD motif in the HB pol gene. The YMDD motif is physically located in the HBsAg region, but is encoded in another reading frame. Hence, this part of the HBV pol region is amplified with the primer combination HBPr 74-HBr 94, but not with the combination HBPr 74-HBr 76. Probes covering the wild type YMDD motif and YVDD mutant motif are indicated in FIG. 1, respectively probes 95 to 100 and 101 to 103, as well as probes 115, 116, 127 and 132, the latter probes yielding the best results in the LiPA assay. Such an assay was used to determine the presence of mutations in the YMDD motif in serum of a HBV-infected patient during treatment with lamivudine. FIG. 7 shows that in the first phase of the treatment (May 1995) no mutations were detected. During the treatment, the viral load decreased, reaching a level of approximately 10⁴ during November and December 1995, whereafter a breakthrough was 10 observed, resulting in a level as high as during the first months of the treatment by June 1996. Interestingly, a LiPA assay performed in February 1996 indicated that the majority of virus present, possessed a mutation in the YMDD motif, which had changed to YVDD. In June 1996, no more wild type motif, but only mutant YVDD could be detected. With this assay, resistant HBV strains can thus easily be detected. Furthermore, the combined detection of the YMDD motif and preCore mutants might be clinically important in prediction and prognosis of further treatment.

REFERENCES.

Asseline U, Delarue M, Lancelot G, Toulme F, Thuong N (1984) Nucleic acid-binding molecules with high affinity and base sequence specificity: intercalating agents covalently linked to oligodeoxynucleotides. Proc. Natl. Acad. Sci. USA 81(11):3297–301.

Barany F. Genetic disease detection and DNA amplification using cloned thermostable ligase. Proc Natl Acad Sci USA 1991; 88: 189–193.

Bej A, Mahbubani M, Miller R, Di Cesare J, Haff L, Atlas R. Mutiplex PCR amplification and immobilized capture probes for detection of bacterial pathogens and indicators in water. Mol Cell Probes 1990; 4:353–365.

Boom R., Sol C. J. A., Salimans M. M. M., et al. Rapid and simple method for purification of nucleic acids. J Clin Microbiol 1990; 28: 495–503.

Carman W, Zanetti A, Karayiannis P, Waters J, Manzillo G, Tanzi E, Zuckerman A, and Thomas H. Vaccine induced escape mutants. Lancet 1990; 336:325–329.

Carman W, Koruia J, Wallace L, MacPhee R, Mimms L, and Decker R. Fulminant reactivation of hepatitis B due to envelope protein mutant that escaped detection by monoclonal HBsAG ELISA. Lancet 1995; 345: 1406–1407.

Compton J. Nucleic acid sequence-based amplification. Nature 1991; 350: 91–92.

Crawford D. Hepatitis B virus 'escape' mutants: Arare event which causes vaccinationfailare. British Med. J. 1990; 301: 1058–1059.

Duck P. Probe amplifier system based on chimeric cycling oligonucleotides. Biotechniques 1990; 9: 142–147.

Gao Q, Gu Z, Parniak M, Cameron I, Cammack N, Boucher C, and Wainberg M. The same mutation that encodes low-level human immunodeficiency virus type-1 resistance to 2',3'-dideoxyinosine and 2',3'-dideoxycytidine confers high level resistance to the (−) enantiomer of 2',3'-dideoxy-3'-thiacytidine. Antimicrob. Agents Chemother. 1993; 37: 1390–1392.

Guatelli J, Whitfield K, Kwoh D, Barringer K, Richman D, Gengeras T. Isothermal, in vitro amplification of nucleic acids by a multienzyme reaction modeled after retroviral replication. Proc Natl Acad Sci USA 1990; 87: 1874–1878.

Hadziyannis S. Hepaptis B e antigen negative chronic hepatitis B: from clinical recognitionto pathogenesis and treatment. Viral Hepatitis 1995; 1: 7–36.

Honkoop P, de Man R, Zondervan P, Niesters H, and Schalm S. Histological improvement in patients with chronic hepatitis B virus infection treated with lavimudine is associated with a decrease in HBV-DNA by PCR. Hepatol. 1995; 22: abstract 887.

Kwoh D, Davis G, Whitfield K, Chappelle H, Dimichele L, Gingeras T. Transcription-based amplification system and detection of amplified human immunodeficiency virus type 1 with a bead-based sandwich hybridization format. Proc Natl Acad Sci USA 1989; 86: 1173–1177.

Kwok S, Kellogg D, McKinney N, Spasic D, Gode L, Levenson C, Sinisky J. Effects of primer-template mismatches on the polymerase chain reaction: Human immunodeficiency views type 1 model studies. Nucl. Acids Res. 1990; 18: 999.

Landgren U, Kaiser R, Sanders J, Hood L. A ligase-mediated gene detection technique. Science 1988; 241:1077–1080.

Li J-S, Tong S-P, Wen Y-M, Vivitski L, Zhang Q, and Trépo C. Hepatitis B virus genotype A rarely circulates as an Hbe-minus mutant: possible contribution of a single nucieotide in the preCore region. J. Virol. 1993; 67: 5402–5410.

Ling, R., Mutimer, D., Ahmed, M., Boxall, E. H., Elias, E., Dusheiko, G. M. and Harrison, T. J. Selection of mutations in the Hepatitis B Virus polymerase during therapy of transplant recipients with lamivudine. Hepatology 1996; 24: 711–713.

Lok A, Akarca U, and Greene S. Mutations in the precore region of hepatitis B virus serve to enhance of the secondary structure of the pre-genome encapsidation signal. Proc. Natl. Acad. Sci. USA 1994; 91: 4077–4081.

Lomeli H, Tyagi S, Printchard C, Lisardi P, Kramer F. Quantitative assays based on the use of replicatable hybridization probes. Clin Chem 1989; 35: 1826–1831.

Magnius L, and Norder H. Subtypes, genotypes and molecular epidemiology of the hepatitis B virus as reflected by sequence variability of the S-gene. Intervirology 1995; 38: 24–34.

Matsukura M, Shinozuka K, Zon G, Mitsuya H, Reitz M, Cohen J, Broder S (1987) Phosphorothioate analogs of oligodeoxynucleotides: inhibitors of replication and cytopathic effects of human immunodeficiency virus. Proc. Natl. Acad. Sci. USA 84(21):7706–10.

Miller P, Yano J, Yano E, Carroll C, Jayaram K, Ts'o P (1979) Nonionic nucleic acid analogues. Synthesis and characterization of dideoxyribonucleoside methylphosphonates. Biochemistry 18(23):5134–43.

Naoumov N, Perllio R, Chokshi S, Dienstag J, Vicary C, Brown N, and Williams R. Reduction in hepatitis B virus quasispecies during lamivudine treatment is associated with enhanced virus repilication and hepatocytolisis. Hepatol. 1995; 22: abstract 885.

Nielsen P, Egholm M, Berg R, Buchardt O (1991) Sequence-selective recognition of DNA by strand displacement with a thymine-substituted polyamide. Science 254(5037):1497–500.

Nielsen P, Egholm M, Berg R, Buchardt O (1993) Sequence specific inhibition of DNA restriction enzyme cleavage by PNA. Nucleic-Acids-Res. 21(2):197–200.

Okamoto H, Yotsumoto S, Akahane Y, Yamanaka T, Miyazaki Y, Sugai Y, Tsuda F, Tanaka T, Miyakawa Y, and Mayumi M. Hepatitis B virus with precore region defects prevail in persistently infected hosts along with seroconversion to the antibody against e antigen. J. Virol. 1990; 64: 1298–1303.

Saiki R, Walsh P, Levenson C, Erlich H. Genetic analysis of amplified DNA with immobilized sequence-specific oligonucleotide probes Proc Natl Acad Sci USA 1989; 86:6230–6234.

Sato S, Suzuki K, Akahane Y, Akamatsu K, Akiyama K, Yunomura K, Tsuda F, Tanaka T, Okamoto H, Miyakawa Y, Mayumi M. Hepatitis B virus strains with mutations in the core promoter in patients with fulminant hepatitis. Ann. Intern. Medicine 1995; 122: 241–248.

Shaw, T., Mok, S. S., Locarnini, S. A. Inhibition of hepatitis B virus DNA polymerase by enantiomers of penciclovir triphosphate and metabolic basis for selective inhibition of HBV replication by penciclovir. Hepatology 1996; 24: 996–1002.

Stuyver L, Rossau R, Wyseur A, et al. Typing of hepatitis C virus isolates and characterization of new subtypes using a line probe assay. J. Gen. Virol. 1993; 74: 1093–1102.

Takahashi K, Aoyama K, Onhno N, Iwata K, Akahane Y, Baba K, Yoshizawa H, and Mishiro S. The precore/core promoter mutant (T1762A1764) of hepatitis B virus: clinical significance and an easy method for detection. J. Gen. Virol. 1995; 76: 3159–3164.

Tipples, G. A., Ma, M. M., Fischer, K. P., Bain, V. G., Kneteman, N. M. and Tyrell, D. L. J. Mutation in HBV RNA-dependent DNA polymerase confers resistance to lamivudine in vivo. Hepatology 1996; 24: 714–717.

Waters J, Kennedy M, Voet P, Hauser P., Petre J, Carman W, and Thomas H. Loss of the common 'a' determinant of hepatitis B surface antigen by vaccine-induced escape mutants. J. Clin. Invest. 1992; 90: 2543–2547.

Wu D, Wallace B. The ligation amplification reaction (LAR)—amplification of specific DNA sequences using sequential rounds of template-dependent ligation. Genomics 1989; 4:560–569.

Yuan T, Faruqi A, Shih J, and Shih C. The mechanism of natural occurrence of two closely linked HBV precore predominant mutations. Virol. 1995; 211: 144–156.

Zhang X, Zoulim F, Habersetzer F, Xiong S, and Trépo C. Analysis of hepatitis B virus genotypes and preCore region variability during interferon treatment of Hbe antigen negative chronic hepatitis B. J. Med. Virol. 1996; xxx—xxx.

What is claimed is:

1. A method for identifying HBV drug resistant strains in a sample, comprising:
(i) hybridizing polynucleic acids present in said sample, with a combination of at least a first probe and a second probe, wherein said first probe hybridizes specifically to a mutant HBV RT pol gene target sequence present in said sample, wherein said mutant target sequence comprises at least one codon selected from the group consisting of codons 514, 519–528 and 551–555; and wherein said second probe hybridizes specifically to HBV genotype-specific target nucleic acid sequences in said sample;
(ii) detecting the hybrids formed in step (i);
(iii) inferring the identity of HBV drug resistant strains in said sample from the differential hybridization signal(s) obtained in step (ii), through discrimination between wild-type and drug resistant HBV strains and through determination of the genotype.

2. A method according to claim 1 wherein said first probe is a mutant probe identifying a drug resistant HBV strain.

3. A method according to claim 1 wherein said first probe is a wild-type probe identifying a wild-type HBV strain.

4. A method according to claim 1 wherein said sample is a biological sample.

5. A method according to claim 4 wherein said biological sample is a sample from a patient.

6. A method according to claim 1 wherein steps (i) to (iii) are repeated on at least two samples from a patient such that the presence of said HBV mutant strains may be monitored as a function of time.

7. A method according to claim 1 wherein the genotype of said HBV strain is determined from said inferring step (iii).

8. A method according to claim 7 wherein said genotyping is performed in a HBV region selected from the groups consisting of preS1 and HBsAg.

9. A method according to claim 7 wherein detection of the presence of a HBV strain resistant to drugs and inferring of the genotype of said strain are done in one single experimental setup.

10. A method according to claim 1 wherein said probes hybridize under the same hybridization and wash conditions.

11. A method according to claim 1 wherein said polynucleic acids in said sample are released, isolated, concentrated and/or amplified prior to the hybridizing of step (i).

12. A method according to claim 1 wherein said hybridization assay is a reverse hybridization assay.

13. A method according to claim 1 wherein said hybridization assay is a line probe assay.

14. A method according to claim 1 wherein the resistance of HBV strains to lamivudine or penciclovir is inferred from step (iii).

15. A method according to claim 1, wherein the presence or absence of a mutation in the YMDD motif of said HBV RT pol is detected.

16. A method according to claim 1, wherein said mutant HBV RT pol gene target sequence comprises at least codon 552.

17. A method according to claim 16, wherein said mutant HBV RT pol gene target sequence further comprises at least one codon selected from the group consisting of codon 514, 521, 525, 528, and 555.

18. A method according to claim 1, wherein said mutant HBV RT pol gene target sequence comprises at least one codon selected from the group consisting of codon 514, 521, 525, 528, 552 and 555.

19. A method according to claim 3, wherein said first probe hybridizes specifically to SEQ ID NO: 115 or the complement thereof.

20. A method according to claim 1, wherein said second probe hybridizes specifically to of a sequence selected from the group consisting SEQ ID NOs: 22, 58, 63, 148, 193 and 219 or the complements thereof.

21. A method according to claim 3, wherein said first probe hybridizes specifically to SEQ ID NO: 115 or the complement thereof; and wherein said second probe hybridizes specifically to a sequence selected from the group consisting of SEQ ID NOs: 22, 58, 63, 148, 193 and 219 or the complements thereof.

22. A combination comprising at least a combination of a first probe and a second probe, wherein said first probe hybridizes specifically to a mutant HBV RT pol gene target sequence and identifies drug resistant HBV strains, said target sequence comprising at least one codon selected from the group consisting of codons 514, 519–528 and 551–555; and wherein said second probe hybridizes specifically to an HBV genotype-specific target nucleic acid sequence.

23. A combination according to claim 22 further comprising a third probe which is a wild-type probe identifying wild-type HBV strains.

24. A combination according to claim 23 wherein said third probe hybridizes specifically to SEQ ID NO: 115 or the complement thereof.

25. A combination according to claim 22 wherein said second probe hybridizes specifically to a sequence selected from the group consisting of SEQ ID NOs: 22, 58, 63, 148, 193 and 219 or the complements thereof.

26. A method according to claim 1 wherein in step (i) said nucleic acids in said sample are further hybridized with a third probe which hybridizes specifically to a nucleic acid sequence selected from the group consisting of a mutant HBV preCore gene target sequence, a mutant HBsAg gene target sequence, a mutant HBV RT pol gene target sequence and a HBV genotype-specific target sequence.

27. A method according to claim 26 wherein the first probe is a wild-type probe identifying wild-type HBV strains.

28. A method according to claim 27 wherein said probe hybridizing specifically to a mutant HBV preCore gene target is selected from the group consisting of SEQ ID NOs: 88 and 119, wherein said probe hybridizing specifically to a mutant HBsAg gene target is SEQ ID NO: 78, wherein said probe hybridizing specifically to a mutant HBV RT pol gene target is SEQ ID NO: 115 and wherein said probe hybridizing specifically to a HBV genotype-specific target sequence is selected from the group consisting of SEQ ID NOs: 22, 58, 63, 148, 193 and 219; or wherein said probe hybridizes specifically to the complements thereof.

29. A method according to claim 1 or 26 wherein at least one mutation selected from the list consisting of a mutation of F to L at position 514, a mutation of V to L at position 521, a mutation of P to L at position 525, a mutation of L to M at position 528, a mutation of M to V or I at position 552, a mutation of V or L to I at position 555, is detected in said HBV RT.

30. A method according to claim 1 or 26 further wherein the presence of wild-type polymorphisms at positions surrounding the mutation position is detected.

* * * * *

SEQUENCE LISTING (1) GENERAL INFORMATION:

(iii) NUMBER OF SEQUENCES: 313

(2) INFORMATION FOR SEQ ID NO: 1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 1:

GGGTCACCAT ATTCTTGGG           19

(2) INFORMATION FOR SEQ ID NO: 2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

GAACAAGAGC TACAGCATGG G          21

(2) INFORMATION FOR SEQ ID NO: 3:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO

```
        (xi) SEQUENCE DESCRIPTION: SEQ ID NO: 3:

CCACTGCATG GCCTGAGGAT G                                              21

(2) INFORMATION FOR SEQ ID NO: 4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

GTTCCKGAAC TGGAGCCACC AG                                             22

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 5:

TCTTTGTATT AGGAGGCTGT AG                                             22

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 6:

GCTGTAGGCA TAAATTGGTC TG                                             22

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 7:

CTCCACAGWA GCTCCAAATT C                                              21
```

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 8:

GAAGGAAAGA AGTCAGAAGG C                          21

(2) INFORMATION FOR SEQ ID NO: 9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 9:

TGGCTTTGGG GCATGG                              16

(2) INFORMATION FOR SEQ ID NO: 10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 10:

TGGCTTTAGG GCATGG                              16

(2) INFORMATION FOR SEQ ID NO: 11:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 11:

TGGCTTTAGG ACATGG                              16

(2) INFORMATION FOR SEQ ID NO: 12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 12:

AAGTTGCATG GTGCTG                                                      16

(2) INFORMATION FOR SEQ ID NO: 13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 13:

CACCTCTGCC TAATCAT                                                     17

(2) INFORMATION FOR SEQ ID NO: 14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 14:

TGGGGTGGAG CCCTCAG                                                     17

(2) INFORMATION FOR SEQ ID NO: 15:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 15:

GCCAGCAGCC AACCAG                                                      16

(2) INFORMATION FOR SEQ ID NO: 16:

(i) SEQUENCE CHARACTERISTICS:
        (A) LENGTH: 15 base pairs

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 16:

CCCATGGGGG ACTGT                                                          15

(2) INFORMATION FOR SEQ ID NO: 17:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 17:

AACCCCAACA AGGATG                                                         16

(2) INFORMATION FOR SEQ ID NO: 18:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 18:

TCCACCAGCA ATCCT                                                          15

(2) INFORMATION FOR SEQ ID NO: 19:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 19:

TGGGGGAAGA ATATTT                                                         16

(2) INFORMATION FOR SEQ ID NO: 20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 20:

AAATTCCAGC AGTCCC                                                      16

(2) INFORMATION FOR SEQ ID NO: 21:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 21:

GTTCCCAACC CTCTGG                                                          16

(2) INFORMATION FOR SEQ ID NO: 22:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 22:

AACCTCGCAA AGGCAT                                                          16

(2) INFORMATION FOR SEQ ID NO: 23:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 23:

TGCATTCAAA GCCAAC                                                          16

(2) INFORMATION FOR SEQ ID NO: 24:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 24:

TACTCACAAC TGTGCC                                                           16

(2) INFORMATION FOR SEQ ID NO: 25:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 25:

ACCCTGCGTT CGGAGC                                                           16

(2) INFORMATION FOR SEQ ID NO: 26:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 26:

CAGGAAGACA GCCTAC                                                           16

(2) INFORMATION FOR SEQ ID NO: 27:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 27:

GATCCAGCCT TCAGAG                                                           16

(2) INFORMATION FOR SEQ ID NO: 28:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 28:

ATGCTCCAGC TCCTAC                                                  16

(2) INFORMATION FOR SEQ ID NO: 29:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 29:

GCTTTCTTGG ACGGTC                                                  16

(2) INFORMATION FOR SEQ ID NO: 30:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 30:

CTACCCCAAT CACTCC                                                  16

(2) INFORMATION FOR SEQ ID NO: 31:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 31:

AGCACCTCTC TCAACG                                                  16

(2) INFORMATION FOR SEQ ID NO: 32:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 32:

```
CCAATGGCAA ACAAGG                                                  16

(2) INFORMATION FOR SEQ ID NO: 33:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 33:

CTGAGGGCTC CACCCCA                                                 17

(2) INFORMATION FOR SEQ ID NO: 34:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 34:

ATCTCTTGTA CATGTC                                                  16

(2) INFORMATION FOR SEQ ID NO: 35:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 35:

ATCTCTTGTA CATGTC                                                  16

(2) INFORMATION FOR SEQ ID NO: 36:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 36:

ATCTCATGTT CATGTC                                                  16
```

(2) INFORMATION FOR SEQ ID NO: 37:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 37:

CAGTGGGACA TGTACA                                                                 16

(2) INFORMATION FOR SEQ ID NO: 38:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 38:

CAGTAGGACA TGAACA                                                                 16

(2) INFORMATION FOR SEQ ID NO: 39:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 39:

CTGTTCAAGC CTCCAA                                                                 16

(2) INFORMATION FOR SEQ ID NO: 40:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 40:

AGCCTCCAAG CTGTGC                                                                 16

(2) INFORMATION FOR SEQ ID NO: 41:

(i) SEQUENCE CHARACTERISTICS:

(A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 41:

AAAGCCACCC AAGGCA                                                     16

(2) INFORMATION FOR SEQ ID NO: 42:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 42:

TGGCTTTAGG ACATGGA                                                    17

(2) INFORMATION FOR SEQ ID NO: 43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 43:

GACATGTACA AGAGATGA                                                   18

(2) INFORMATION FOR SEQ ID NO: 44:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 44:

GACATGAACA TGAGATGA                                                   18

(2) INFORMATION FOR SEQ ID NO: 45:

(i) SEQUENCE CHARACTERISTICS:
        (A) LENGTH: 18 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 45:

TGTACATGTC CCACTGTT                                                     18

(2) INFORMATION FOR SEQ ID NO: 46:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 46:

TGTTCATGTC CTACTGTT                                                     18

(2) INFORMATION FOR SEQ ID NO: 47:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 47:

ACTGTTCAAG CCTCCAAG                                                     18

(2) INFORMATION FOR SEQ ID NO: 48:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 48:

GGCACAGGCT TGGAGGCTT                                                    19

(2) INFORMATION FOR SEQ ID NO: 49:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 49:

AAAGCCACCC AAGGCACA                                                          18

(2) INFORMATION FOR SEQ ID NO: 50:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 50:

CCCAGAGGGT TGGGAAC                                                           17

(2) INFORMATION FOR SEQ ID NO: 51:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 51:

CAGCATGGGG CAGAATCT                                                          18

(2) INFORMATION FOR SEQ ID NO: 52:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 52:

TCCACCAGCA ATCCTCTG                                                          18

(2) INFORMATION FOR SEQ ID NO: 53:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 53:

GGATCCAGCC TTCAGAGC                                                  18

(2) INFORMATION FOR SEQ ID NO: 54:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 54:

TCAGGAAGAC AGCCTAC                                                   17

(2) INFORMATION FOR SEQ ID NO: 55:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 55:

TTCAACCCCA ACAAGGATC                                                 19

(2) INFORMATION FOR SEQ ID NO: 56:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 56:

AATGCTCCAG CTCCTAC                                                   17

(2) INFORMATION FOR SEQ ID NO: 57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 57:

CTGCATTCAA AGCCAACT                         18

(2) INFORMATION FOR SEQ ID NO: 58:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 58:

CCCCATGGGG GACTGTTG                         18

(2) INFORMATION FOR SEQ ID NO: 59:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 59:

CATACTCACA ACTGTGCCA            19

(2) INFORMATION FOR SEQ ID NO: 60:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 60:

GGGCTTTCTT GGACGGTCC            19

(2) INFORMATION FOR SEQ ID NO: 61:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 61:

CTCTCGAATG GGGAAGA                          18

(2) INFORMATION FOR SEQ ID NO: 62:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 62:

CCTACCCCAA TCACTCCA                                            18

(2) INFORMATION FOR SEQ ID NO: 63:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 63:

AGCACCTCTC TCAACGACA                                          19

(2) INFORMATION FOR SEQ ID NO: 64:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 64:

GCAAATTCCA GCAGTCCCG                                          19

(2) INFORMATION FOR SEQ ID NO: 65:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 65:

GCCAATGGCA AACAAGGTA                                          19

(2) INFORMATION FOR SEQ ID NO: 66:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 66:

GACATGAACA TGAGATG                                                              17

(2) INFORMATION FOR SEQ ID NO: 67:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 67:

GGACATGAAC AAGAGAT                                                              17

(2) INFORMATION FOR SEQ ID NO: 68:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 68:

GACATGTACA AGAGATG                                                              17

(2) INFORMATION FOR SEQ ID NO: 69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 69:

ACATAAGAGG ACTCTTGGAC                                                           20

(2) INFORMATION FOR SEQ ID NO: 70:

(i) SEQUENCE CHARACTERISTICS:
        (A) LENGTH: 22 base pairs
        (B) TYPE: nucleic acid

```
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 70:

TACTTCAAAG ACTGTGTGTT TA                                              22

(2) INFORMATION FOR SEQ ID NO: 71:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 71:

ACAAAGACCT TTAAYCT                                                    17

(2) INFORMATION FOR SEQ ID NO: 72:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 72:

ACAAAGATCA TTAAYCT                                                    17

(2) INFORMATION FOR SEQ ID NO: 73:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 73:

TTCCACCAGC AATCCTC                                                    17

(2) INFORMATION FOR SEQ ID NO: 74:

(i) SEQUENCE CHARACTERISTICS:
            (A) LENGTH: 17 base pairs
            (B) TYPE: nucleic acid
            (C) STRANDEDNESS: single
            (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 74:

GATCCAGCCT TCAGAGC                                                         17

(2) INFORMATION FOR SEQ ID NO: 75:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 75:

CAAGGTATGT TGCCCGTTTG TCC                                                  23

(2) INFORMATION FOR SEQ ID NO: 76:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 76:

CCAAACAGTG GGGAAAGCC C                                                     21

(2) INFORMATION FOR SEQ ID NO: 77:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 77:

CTACGGATGG AAATTGC                                                         17

(2) INFORMATION FOR SEQ ID NO: 78:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 78:

TACGGACGGA AACTGC                                                               16

(2) INFORMATION FOR SEQ ID NO: 79:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 79:

TTCGGACGGA AACTGC                                                               16

(2) INFORMATION FOR SEQ ID NO: 80:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 80:

CTTCGGACGG AAATTGC                                                              17

(2) INFORMATION FOR SEQ ID NO: 81:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 81:

CTACGGATAG AAATTGC                                                              17

(2) INFORMATION FOR SEQ ID NO: 82:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 82:

CTTCGGACAG AAATTGC                                                        17

(2) INFORMATION FOR SEQ ID NO: 83:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 83:

CTATGGGAGT GGGCCTCAGY C                                                   21

(2) INFORMATION FOR SEQ ID NO: 84:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 84:

GCTGTAGGCA TAAATTGGTC TG                                                  22

(2) INFORMATION FOR SEQ ID NO: 85:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 85:

CTCCACAGWA GCTCCAAATT C                                              21

(2) INFORMATION FOR SEQ ID NO: 86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 86:

ACATAAGAGG ACTCTTGGAC                                                 20

(2) INFORMATION FOR SEQ ID NO: 87:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 87:

TACTTCAAAG ACTGTGTGTT TA                          22

(2) INFORMATION FOR SEQ ID NO: 88:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 88:

TAGGTTAAAG GTCTTTGT                             18

(2) INFORMATION FOR SEQ ID NO: 89:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 89:

TAGGTTAATG ATCTTTGT                             18

(2) INFORMATION FOR SEQ ID NO: 90:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 90:

CATGTCCCAC TGTTCAA                              17

(2) INFORMATION FOR SEQ ID NO: 91:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 91:

CATGTCCTAC TGTTCAA                                                    17

(2) INFORMATION FOR SEQ ID NO: 92:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 92:

TTCTGCCCCA TGCTGTA                                                    17

(2) INFORMATION FOR SEQ ID NO: 93:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 93:

TTCTGCCCCA TGCTGTAG                                                   18

(2) INFORMATION FOR SEQ ID NO: 94:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 94:

GGTAWAAAGG GACTCAMGAT G                                               21

(2) INFORMATION FOR SEQ ID NO: 95:

(i) SEQUENCE CHARACTERISTICS:
            (A) LENGTH: 17 base pairs (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 95:

TCAGCTATAT GGATGAT                                                      17

(2) INFORMATION FOR SEQ ID NO: 96:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 96:

CAGCTATATG GATGAT                                                       16

(2) INFORMATION FOR SEQ ID NO: 97:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 97:

TTCAGCTATA TGGATG                                                       16

(2) INFORMATION FOR SEQ ID NO: 98:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 98:

TCAGTTATAT GGATGAT                                                      17

(2) INFORMATION FOR SEQ ID NO: 99:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 99:

TTTCAGTTAT ATGGATG                                                              17

(2) INFORMATION FOR SEQ ID NO: 100:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 100:

TTTAGTTATA TGGATGA                                                              17

(2) INFORMATION FOR SEQ ID NO: 101:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 101:

TCAGCTATGT GGATGAT                                                              17

(2) INFORMATION FOR SEQ ID NO: 102:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 102:

TCAGTTATGT GGATGAT                                                              17

(2) INFORMATION FOR SEQ ID NO: 103:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 103:

TTTCAGCTAT GTGGATG                                                          17

(2) INFORMATION FOR SEQ ID NO: 104:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 104:

CAAGGTATGT TGCCCGTTTG TCC                                                   23

(2) INFORMATION FOR SEQ ID NO: 105:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 105:

GGYAWAAAGG GACTCAMGAT G                                                     21

(2) INFORMATION FOR SEQ ID NO: 106:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 106:

GGGTCACCAT ATTCTTGGG                                                        19

(2) INFORMATION FOR SEQ ID NO: 107:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 107:

GTTCCKGAAC TGGAGCCACC AG                                                   22

(2) INFORMATION FOR SEQ ID NO: 108:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 108:

CCGGAAAGCT TGAGCTCTTC TTTTTCACCT CTGCCTAATC                                  40

(2) INFORMATION FOR SEQ ID NO: 109:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 109:

CCGGAAAGCT TGAGCTCTTC AAAAAGTTGC ATGGTGCTGG                              40

(2) INFORMATION FOR SEQ ID NO: 110:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 110:

GTGGTTCGCC GGGCTTG                                                          17

(2) INFORMATION FOR SEQ ID NO: 111:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 111:

```
CTGCGAGGCG AGGGAGTTCT TCTTC                                              25
```

(2) INFORMATION FOR SEQ ID NO: 112:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 112:

```
TGCCATTTGT TCAGTGGTTC GTAGGGC                                            27
```

(2) INFORMATION FOR SEQ ID NO: 113:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 113:

```
CCGGCAGATG AGAAGGCACA GACGG                                              25
```

(2) INFORMATION FOR SEQ ID NO: 114:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 114:

```
TTCAGCTATA TGGATGAT                                                      18
```

(2) INFORMATION FOR SEQ ID NO: 115:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 115:

```
TCAGCTATAT GGATGATG                                                      18
```

(2) INFORMATION FOR SEQ ID NO: 116:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 116:

TTCAGCTATG TGGATGAT                                            18

(2) INFORMATION FOR SEQ ID NO: 117:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 117:

TCAGCTATGT GGATGATG                                            18

(2) INFORMATION FOR SEQ ID NO: 118:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 118:

GGCTTTGGGG CATGG                                                  15

(2) INFORMATION FOR SEQ ID NO: 119:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 119:

TGGCTTTGGG GCATG                                                  15

(2) INFORMATION FOR SEQ ID NO: 120:

(i) SEQUENCE CHARACTERISTICS:

(A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 120:

GTGGCTTTGG GGCATG                                                    16

(2) INFORMATION FOR SEQ ID NO: 121:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 121:

GGCTTTGGGG CATGGA                                                    16

(2) INFORMATION FOR SEQ ID NO: 122:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 122:

TGGCTTTGGG ACATGG                                                    16

(2) INFORMATION FOR SEQ ID NO: 123:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 123:

GGCTTTGGGA CATGG                                                     15

(2) INFORMATION FOR SEQ ID NO: 124:

(i) SEQUENCE CHARACTERISTICS:
            (A) LENGTH: 15 base pairs
            (B) TYPE: nucleic acid
            (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 124:

TGGCTTTGGG ACATG                                                    15

(2) INFORMATION FOR SEQ ID NO: 125:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 125:

GTGGCTTTGG GACATG                                                   16

(2) INFORMATION FOR SEQ ID NO: 126:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 126:

GGCTTTGGGA CATGGA                                                   16

(2) INFORMATION FOR SEQ ID NO: 127:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 127:

TCAGTTATAT GGATGATG                                                 18

(2) INFORMATION FOR SEQ ID NO: 128:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 128:

TTCAGTTATA TGGATGAT                                                 18

(2) INFORMATION FOR SEQ ID NO: 129:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 129:

TTTCAGTTAT ATGGATGAT                                                19

(2) INFORMATION FOR SEQ ID NO: 130:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 130:

TCAGTTATGT GGATGATG                                                 18

(2) INFORMATION FOR SEQ ID NO: 131:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 131:

TTCAGTTATG TGGATGAT                                                 18

(2) INFORMATION FOR SEQ ID NO: 132:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 132:

TTTCAGTTAT GTGGATGAT                                                    19

(2) INFORMATION FOR SEQ ID NO: 133:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 133:

TTTCAGTTAT GTGGATGA                                                     18

(2) INFORMATION FOR SEQ ID NO: 134:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 134:

TGCTGCTATG CCTCATCTTC                                                   20

(2) INFORMATION FOR SEQ ID NO: 135:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 135:

CARAGACAAA AGAAAATTGG                                                   20

(2) INFORMATION FOR SEQ ID NO: 136:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 136:

CTATGGATGG AAATTGC                                                    17

(2) INFORMATION FOR SEQ ID NO: 137:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 137:

CCTATGGATG GAAATTG                                                    17

(2) INFORMATION FOR SEQ ID NO: 138:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 138:

ACCTATGGAT GGAAATT                                                    17

(2) INFORMATION FOR SEQ ID NO: 139:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 139:

CTCAAGGCAA CTCTATGTGG                                                 20

(2) INFORMATION FOR SEQ ID NO: 140:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 140:

CTCAAGGCAA CTCTATGGG                                                  19

(2) INFORMATION FOR SEQ ID NO: 141:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 141:

TCAAGGCAAC TCTATGTTG                                              19

(2) INFORMATION FOR SEQ ID NO: 142:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 142:

ATCCCATCAT CTTGGG                                                16

(2) INFORMATION FOR SEQ ID NO: 143:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 143:

ATCCCATCAT CTTGGGCGG                                           19

(2) INFORMATION FOR SEQ ID NO: 144:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 144:

TCCCATCATC TTGGGCGG                                           18

(2) INFORMATION FOR SEQ ID NO: 145:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 145:

CCCATCATCT TGGGCTGG                                              18

(2) INFORMATION FOR SEQ ID NO: 146:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 146:

TTCGCAAAAT ACCTATGG                                              18

(2) INFORMATION FOR SEQ ID NO: 147:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 147:

TTTCGCAAAA TACCTATG                                              18

(2) INFORMATION FOR SEQ ID NO: 148:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 148:

CTTTCGCAAA ATACCTATG                                             19

(2) INFORMATION FOR SEQ ID NO: 149:

(i) SEQUENCE CHARACTERISTICS:
        (A) LENGTH: 18 base pairs
        (B) TYPE: nucleic acid

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 149:

TCGCAAAATA CCTATGGG                                                    18

(2) INFORMATION FOR SEQ ID NO: 150:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 150:

TCTACTTCCA GGAACAT                                                     17

(2) INFORMATION FOR SEQ ID NO: 151:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 151:

TCTACTTCCA GGAACATC                                                    18

(2) INFORMATION FOR SEQ ID NO: 152:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 152:

CTCTACTTCC AGGAACAT                                                    18

(2) INFORMATION FOR SEQ ID NO: 153:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 153:

CTCTACTTCC AGGAACAG                                                      18

(2) INFORMATION FOR SEQ ID NO: 154:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 154:

CTGCACGATT CCTGCT                                                        16

(2) INFORMATION FOR SEQ ID NO: 155:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 155:

TGCACGATTC CTGCTCA                                                       17

(2) INFORMATION FOR SEQ ID NO: 156:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 156:

CTGCACGATT CCTGCTC                                                       17

(2) INFORMATION FOR SEQ ID NO: 157:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 157:

TGCACGATTC CTGCTCAA                                                    18

(2) INFORMATION FOR SEQ ID NO: 158:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 158:

TTCGCAAGAT TCCTATG                                                     17

(2) INFORMATION FOR SEQ ID NO: 159:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 159:

CTTTCGCAAG ATTCCTAT                                                    18

(2) INFORMATION FOR SEQ ID NO: 160:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 160:

CTTTCGCAAG ATTCCTA                                                     17

(2) INFORMATION FOR SEQ ID NO: 161:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 161:

CTTTCGCAAG ATTCCTATG                                                                19

(2) INFORMATION FOR SEQ ID NO: 162:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 162:

CTCTATGTAT CCCTCCT                                                                  17

(2) INFORMATION FOR SEQ ID NO: 163:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 163:

TCTATGTATC CCTCCTG                                                                  17

(2) INFORMATION FOR SEQ ID NO: 164:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 164:

CTCTATGTAT CCCTCCTGG                                                                19

(2) INFORMATION FOR SEQ ID NO: 165:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 165:

CCTCTATGTA TCCCTCCT                                                                 18

(2) INFORMATION FOR SEQ ID NO: 166:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 166:

CTGTACCAAA CCTTCGG                                                      17

(2) INFORMATION FOR SEQ ID NO: 167:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 167:

CTGTACCAAA CCTTCG                                                       16

(2) INFORMATION FOR SEQ ID NO: 168:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 168:

GCTGTACCAA ACCTTCGG                                                     18

(2) INFORMATION FOR SEQ ID NO: 169:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 169:

TGTACCAAAC CTTCGGAG                                                     18

(2) INFORMATION FOR SEQ ID NO: 170:

```
    (i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 170:

GGACCCTGCC GAACCT                                                     16

(2) INFORMATION FOR SEQ ID NO: 171:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 171:

GGACCCTGCC GAACCG                                                     16

(2) INFORMATION FOR SEQ ID NO: 172:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 172:

GGGACCCTGC CGAAC                                                      15

(2) INFORMATION FOR SEQ ID NO: 173:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 173:

GGACCCTGCC GAAC                                                       14

(2) INFORMATION FOR SEQ ID NO: 174:

(i) SEQUENCE CHARACTERISTICS:
        (A) LENGTH: 18 base pairs
```

(B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 174:

GTTGCTGTTC AAAACCTT                                                         18

(2) INFORMATION FOR SEQ ID NO: 175:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 175:

GTTGCTGTTC AAAACCTG                                                         18

(2) INFORMATION FOR SEQ ID NO: 176:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 176:

TGTTGCTGTT CAAAACCTG                                                        19

(2) INFORMATION FOR SEQ ID NO: 177:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 177:

ATGTTGCTGT TCAAAACCTG                                                       20

(2) INFORMATION FOR SEQ ID NO: 178:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 178:

GATCCACGAC CACCA                                                        15

(2) INFORMATION FOR SEQ ID NO: 179:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 179:

GGATCCACGA CCACCA                                                       16

(2) INFORMATION FOR SEQ ID NO: 180:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 180:

GGATCCACGA CCACC                                                        15

(2) INFORMATION FOR SEQ ID NO: 181:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 181:

GATCCACGAC CACCAGG                                                      17

(2) INFORMATION FOR SEQ ID NO: 182:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 182:

TGTTCCAAAC CCTCGG                                                    16

(2) INFORMATION FOR SEQ ID NO: 183:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 183:

CTGTTCCAAA CCCTCG                                                    16

(2) INFORMATION FOR SEQ ID NO: 184:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 184:

CTGTTCCAAA CCCTCGG                                                   17

(2) INFORMATION FOR SEQ ID NO: 185:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 185:

GTTCCAAACC CTCGGAT                                                   17

(2) INFORMATION FOR SEQ ID NO: 186:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 186:

GCCAAATCTG TGCAGC                                                    16

(2) INFORMATION FOR SEQ ID NO: 187:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 187:

CCAAATCTGT GCAGCAT                                                   17

(2) INFORMATION FOR SEQ ID NO: 188:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 188:

GCCAAATCTG TGCAGCAG                                                  18

(2) INFORMATION FOR SEQ ID NO: 189:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 189:

GGCCAAATCT GTGCAGC                                                   17

(2) INFORMATION FOR SEQ ID NO: 190:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 190:

ATCAACAACA ACCAGTA                                              17

(2) INFORMATION FOR SEQ ID NO: 191:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 191:

GATCAACAAC AACCAGT                                              17

(2) INFORMATION FOR SEQ ID NO: 192:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 192:

GATCAACAAC AACCAGTA                                             18

(2) INFORMATION FOR SEQ ID NO: 193:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 193:

GGATCAACAA CAACCAGT                                             18

(2) INFORMATION FOR SEQ ID NO: 194:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 194:

TCAAGGCAAC TCTATGTGG                                            19

(2) INFORMATION FOR SEQ ID NO: 195:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 195:

AGGTTAAAGG TCTTTGT                        17

(2) INFORMATION FOR SEQ ID NO: 196:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 196:

TAGGTTAAAG GTCTTTGG                        18

(2) INFORMATION FOR SEQ ID NO: 197:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 197:

TTAGGTTAAA GGTCTTT                        17

(2) INFORMATION FOR SEQ ID NO: 198:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 198:

GGTTAAAGGT CTTTGTAGG                      19

(2) INFORMATION FOR SEQ ID NO: 199:

(i) SEQUENCE CHARACTERISTICS:

(A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 199:

AGGTTAATGA TCTTTGT                                                  17

(2) INFORMATION FOR SEQ ID NO: 200:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 200:

TAGGTTAATG ATCTTTGG                                                 18

(2) INFORMATION FOR SEQ ID NO: 201:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 201:

CTTTCGCAAG ATTCCTATGG                                               20

(2) INFORMATION FOR SEQ ID NO: 202:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 202:

GCTTTCGCAA GATTCCTATG                                               20

(2) INFORMATION FOR SEQ ID NO: 203:

(i) SEQUENCE CHARACTERISTICS:
            (A) LENGTH: 21 base pairs
            (B) TYPE: nucleic acid
            (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 203:

GCTTTCGCAA GATTCCTATG G                                            21

(2) INFORMATION FOR SEQ ID NO: 204:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 204:

CTTTCGCAAG ATTCCTATGG G                                            21

(2) INFORMATION FOR SEQ ID NO: 205:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 205:

GCTGTACCAA ACCTTCGGAG                                              20

(2) INFORMATION FOR SEQ ID NO: 206:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 206:

TGCTGTACCA AACCTTCGG                                               19

(2) INFORMATION FOR SEQ ID NO: 207:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 207:

TGCTGTACCA AACCTTCGGA G                                        21

(2) INFORMATION FOR SEQ ID NO: 208:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 208:

GCTGTACCAA ACCTTCGGAT                                          20

(2) INFORMATION FOR SEQ ID NO: 209:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 209:

TGGTTCGCCG GGCTTT                                              16

(2) INFORMATION FOR SEQ ID NO: 210:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 210:

GTGGTTCGCC GGGCTTG                                             17

(2) INFORMATION FOR SEQ ID NO: 211:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 211:

GGTTCGCCGG GCTTTC                                                          16

(2) INFORMATION FOR SEQ ID NO: 212:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 212:

TGGTTCGCCG GGCTTTC                                                         17

(2) INFORMATION FOR SEQ ID NO: 213:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 213:

AGTGGTTCGC CGGGCTGG                                                        18

(2) INFORMATION FOR SEQ ID NO: 214:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 214:

AGGATCCACG ACCACCAGG                                                       19

(2) INFORMATION FOR SEQ ID NO: 215:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 215:

AGGATCCACG ACCACCAGT                                    19

(2) INFORMATION FOR SEQ ID NO: 216:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 216:

CAGGATCCAC GACCACCAGG                                   20

(2) INFORMATION FOR SEQ ID NO: 217:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 217:

CTGTTCCAAA CCCTCGGAG                                    19

(2) INFORMATION FOR SEQ ID NO: 218:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 218:

CTGTTCCAAA CCCTCGGAT                                    19

(2) INFORMATION FOR SEQ ID NO: 219:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 219:

GCTGTTCCAA ACCCTCGGAG                                   20

(2) INFORMATION FOR SEQ ID NO: 220:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 220:

CTGAACCTTT ACCCCGTTGC                                                20

(2) INFORMATION FOR SEQ ID NO: 221:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 221:

CTCGCCAACT TACAAGGCCT TTC                                          23

(2) INFORMATION FOR SEQ ID NO: 222:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 222:

AGAATGGCTT GCCTGAGTGC                                                20

(2) INFORMATION FOR SEQ ID NO: 223:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 223:

GCTTTCGCAA GATTCCTATG GG                                           22

(2) INFORMATION FOR SEQ ID NO: 224:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 224:

GGCTTTCGCA AGATTCCTAT GG                                          22

(2) INFORMATION FOR SEQ ID NO: 225:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 225:

GGCTTTCGCA AGATTCCTAT GGG                                         23

(2) INFORMATION FOR SEQ ID NO: 226:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 226:

GGCTTTCGCA AGATTCCTAT GGGA                                        24

(2) INFORMATION FOR SEQ ID NO: 227:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 227:

CAGCTATATG GATGATGTG                                              19

(2) INFORMATION FOR SEQ ID NO: 228:

(i) SEQUENCE CHARACTERISTICS:
            (A) LENGTH: 20 base pairs
            (B) TYPE: nucleic acid

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 228:

AGCTATATGG ATGATGTGGG                                               20

(2) INFORMATION FOR SEQ ID NO: 229:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 229:

GCTATATGGA TGATGTGGT                                                19

(2) INFORMATION FOR SEQ ID NO: 230:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 230:

AGCTATATGG ATGATGTGGT                                               20

(2) INFORMATION FOR SEQ ID NO: 231:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 231:

CAGCTATATG GATGATATA                                            19

(2) INFORMATION FOR SEQ ID NO: 232:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 232:

AGCTATATGG ATGATATAGG                                                        20

(2) INFORMATION FOR SEQ ID NO: 233:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 233:

GCTATATGGA TGATATAGT                                                         19

(2) INFORMATION FOR SEQ ID NO: 234:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 234:

AGCTATATGG ATGATATAGT                                                        20

(2) INFORMATION FOR SEQ ID NO: 235:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 235:

CCATCATCTT GGGCTTG                                                           17

(2) INFORMATION FOR SEQ ID NO: 236:

(i) SEQUENCE CHARACTERISTICS:
                (A) LENGTH: 16 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 236:

CATCATCTTG GGCTTT                                                                16

(2) INFORMATION FOR SEQ ID NO: 237:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 237:

CCATCATCTT GGGCTTT                                                                17

(2) INFORMATION FOR SEQ ID NO: 238:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 238:

CCATCATCTT GGGCTTTC                                                               18

(2) INFORMATION FOR SEQ ID NO: 239:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 239:

CCCACTGTCT GGCTTTC                                                                17

(2) INFORMATION FOR SEQ ID NO: 240:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 240:

CCACTGTCTG GCTTTC                                                            16

(2) INFORMATION FOR SEQ ID NO: 241:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 241:

CCACTGTCTG GCTTT                                                             15

(2) INFORMATION FOR SEQ ID NO: 242:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 242:

CCCACTGTCT GGCTTG                                                            16

(2) INFORMATION FOR SEQ ID NO: 243:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 243:

TATATGGATG ATGTGGTA                                                          18

(2) INFORMATION FOR SEQ ID NO: 244:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 244:

TATGTGGATG ATGTGGTA                                                          18

(2) INFORMATION FOR SEQ ID NO: 245:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 245:

TATATAGATG ATGTGGTA                                                        18

(2) INFORMATION FOR SEQ ID NO: 246:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 246:

TATATTGATG ATGTGGTA                                                        18

(2) INFORMATION FOR SEQ ID NO: 247:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 247:

TATGTAGATG ATGTGGTA                                                    18

(2) INFORMATION FOR SEQ ID NO: 248:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 248:

TATGTTGATG ATGTGGTA                                                   18

(2) INFORMATION FOR SEQ ID NO: 249:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 249:

TATATGGATG ATATAGTA                                              18

(2) INFORMATION FOR SEQ ID NO: 250:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 250:

TATATGGATG ATATCGTA                                                  18

(2) INFORMATION FOR SEQ ID NO: 251:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 251:

TATGTGGATG ATATAGTA                                                  18

(2) INFORMATION FOR SEQ ID NO: 252:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 252:

TATGTGGATG ATATCGTA                                                  18

(2) INFORMATION FOR SEQ ID NO: 253:

(i) SEQUENCE CHARACTERISTICS:
        (A) LENGTH: 18 base pairs
```

(B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 253:

TATATAGATG ATATAGTA                                             18

(2) INFORMATION FOR SEQ ID NO: 254:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 254:

TATATAGATG ATATCGTA                                             18

(2) INFORMATION FOR SEQ ID NO: 255:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 255:

TATATTGATG ATATAGTA                                             18

(2) INFORMATION FOR SEQ ID NO: 256:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 256:

TATATTGATG ATATCGTA                                             18

(2) INFORMATION FOR SEQ ID NO: 257:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 257:

TATGTAGATG ATATAGTA                                                            18

(2) INFORMATION FOR SEQ ID NO: 258:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 258:

TATGTAGATG ATATCGTA                                                            18

(2) INFORMATION FOR SEQ ID NO: 259:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 259:

TATGTTGATG ATATAGTA                                                            18

(2) INFORMATION FOR SEQ ID NO: 260:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 260:

TATGTTGATG ATATCGTA                                                            18

(2) INFORMATION FOR SEQ ID NO: 261:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 261:

TATATGGATG ATCTGGTA                                                                18

(2) INFORMATION FOR SEQ ID NO: 262:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 262:

TATGTGGATG ATCTGGTA                                                                18

(2) INFORMATION FOR SEQ ID NO: 263:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 263:

TATATAGATG ATCTGGTA                                                                18

(2) INFORMATION FOR SEQ ID NO: 264:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 264:

TATATTGATG ATCTGGTA                                                                18

(2) INFORMATION FOR SEQ ID NO: 265:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 265:

TATGTAGATG ATCTGGTA                                                      18

(2) INFORMATION FOR SEQ ID NO: 266:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 266:

TATGTTGATG ATCTGGTA                                                      18

(2) INFORMATION FOR SEQ ID NO: 267:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 267:

TATGGGAGTG GGCCTCAG                                                      18

(2) INFORMATION FOR SEQ ID NO: 268:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 268:

TATGGGATTG GGCCTCAG                                                      18

(2) INFORMATION FOR SEQ ID NO: 269:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 269:

```
CAGTCCGTTT CTCTTGGC                                                        18

(2) INFORMATION FOR SEQ ID NO: 270:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 270:

CAGTCTGTTT CTCTTGGC                                                        18

(2) INFORMATION FOR SEQ ID NO: 271:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 271:

CAGTCCGTTT CTCATGGC                                                        18

(2) INFORMATION FOR SEQ ID NO: 272:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 272:

CAGTCTGTTT CTCATGGC                                                        18

(2) INFORMATION FOR SEQ ID NO: 273:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 273:

CAGTCCGTTT CTCCTGGC                                                        18
```

(2) INFORMATION FOR SEQ ID NO: 274:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 274:

CAGTCTGTTT CTCCTGGC                                              18

(2) INFORMATION FOR SEQ ID NO: 275:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 275:

CAGCCCGTTT CTCCTGGC                                              18

(2) INFORMATION FOR SEQ ID NO: 276:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 276:

CAGCCTGTTT CTCCTGGC                                              18

(2) INFORMATION FOR SEQ ID NO: 277:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 277:

CAGCCCGTTT CTCATGGC                                              18

(2) INFORMATION FOR SEQ ID NO: 278:

(i) SEQUENCE CHARACTERISTICS:

(A) LENGTH: 18 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 278:

```
CAGCCTGTTT CTCATGGC                                                    18
```

(2) INFORMATION FOR SEQ ID NO: 279:

(i) SEQUENCE CHARACTERISTICS:
(A) LENGTH: 3221 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 279:

```
AATTCCACTG CCTTCCACCA AGCTCTGCAG GATCCCAAAG TCAGGGGTCT GTATCTTCCT      60
GCTGGTGGCT CCAGTTCAGG AACAGTAAAC CCTGCTCCGA ATATTGCCTC TCACATCTCG     120
TCAATCTCCG CGAGGACTGG GGACCCTGTG ACGAACATGG AGAACATCAC ATCAGGATTC     180
CTAGGACCCC TGCTCGTGTT ACAGGCGGGG TTTTTCTTGT TGACAAGAAT CCTCACAATA     240
CCGCAGAGTC TAGACTCGTG GTGGACTTCT CTCAATTTTC TAGGGGGTC ACCCGTGTGT      300
CTTGGCCAAA ATTCGCAGTC CCCAACCTCC AATCACTCAC CAACCTCCTG TCCTCCAATT     360
TGTCCTGGTT ATCGCTGGAT GTGTCTGCGG CGTTTTATCA TATTCCTCTT CATCCTGCTG     420
CTATGCCTCA TCTTCTTGTT GGTTCTTCTG GATTATCAAG GTATGTTGCC CGTTTGTCCT     480
CTAATTCCAG GATCAACAAC AACCAGTACG GGACCATGCA AAACCTGCAC GACTCCTGCT     540
CAAGGCAACT CTATGTTTCC CTCATGTTGC TGTACAAAAC CTACGGATGG AAATTGCACC     600
TGTATTCCCA TCCCATCGTC CTGGGCTTTC GCAAAATACC TATGGGAGTG GGCCTCAGTC     660
CGTTTCTCTT GGCTCAGTTT ACTAGTGCCA TTTGTTCAGT GGTTCGTAGG GCTTTCCCCC     720
ACTGTTTGGC TTTCAGCTAT ATGGATGATG TGGTATTGGG GGCCAAGACT GTACAGCATC     780
GTGAGTCCCT TTATACCGCT GTTACCAATT TTCTTTTGTC TCTGGGTATA CATTTAAACC     840
CTAACAAAAC AAAAAGATGG GGTTATTCCC TAAACTTCAT GGTCTACATA ATTGGAAGTT     900
GGGGAACATT GCCACAGGAT CATATTGTAC AAAAGATCAA ACACTGTTTT AGAAAACTTC     960
CTGTTAACAG GCCTATTGAT TGGAAAGTAT GTCAAAGAAT TGTGGGTCTT TTGGGCTTTG    1020
CTGCTCCATT TACTCAATGT GGATATCCTG CCTTAATGCC TTTGTATGCA TGTATACAAG    1080
CTAAACAGGC TTTCACTTTC TCGCCAACTT ACAAGGCCTT TCTAAGTAAA CAGTACATGA    1140
ACCTTTACCC CGTTGCTCGG CAACGGCCTG GTCTGTGCCA AGTGTTTGCT GACGCAACCC    1200
CCACTGGCTG GGGCTTGGCC ATAGGCCATC AGCGCATGCG TGGAACCTTT GTGGCTCCTC    1260
TGCCGATCCA TACTCGGGAA CTCCTAGCCG CTTGTTTTGC TCGCAGCCGG TCTGGAGCAA    1320
AGCTCATCGG AACTGACAAT TCTGTCGTCC TCTCGCGGAA ATATACATCG TTTCCATGGC    1380
TGCTAGGCTG TACTGCCAAC TGGATCCTTC GCGGGACGTC CTTTGTTTAC GTCCCGTCGG    1440
```

```
CGCTGAATCC CGCGGACGAC CCCTCTCGGG GCCGCTTGGG AGTCTCTCGT CCCCTTCTCC    1500

GTCTGCCGTT CCAGCCGACC ACGGGGCGCA CCTCTCTTTA CGCGGTCTCC CCGTCTGTGC    1560

CTTCTCATCT GCCGGTCCGT GTGCACTTCG CTTCACCTCT GCACGTTGCA TGGAGACCAC    1620

CGTGAACGCC CATCAGATCC TGCCCAAGGT CTTACATAAG AGGACTCTTG GACTCTCAGC    1680

AATGTCAACG ACCGACCTTG AGGCCTACTT CAAAGACTGT GTGTTTAAGG ACTGGGAGGA    1740

GCTGGGGGAG GAGATTAGGT TAAAGGTCTT TGTATTAGGA GGCTGTAGGC ATAAATTGGT    1800

CTGCGCACCA GCACCATGCA ACTTTTTCAC CTCTGCCTAA TCATCTCTTG TACATGTCCC    1860

ACTGTTCAAG CCTCCAAGCT GTGCCTTGGG TGGCTTTGGG GCATGGACAT TGACCCTTAT    1920

AAAGAATTTG GAGCTACTGT GGAGTTACTC TCGTTTTTGC CTTCTGACTT CTTTCCTTCC    1980

GTCAGAGATC TCCTAGACAC CGCCTCAGCT CTGTATCGAG AAGCCTTAGA GTCTCCTGAG    2040

CATTGCTCAC CTCACCATAC TGCACTCAGG CAAGCCATTC TCTGCTGGGT GGAATTGATG    2100

ACTCTAGCTA CCTGGGTGGG TAATAATTTG GAAGATCCAG CATCCAGGGA TCTAGTAGTC    2160

AATTATGTTA ATACTAACAT GGGTTTAAAG ATCAGGCAAC TATTGTGGTT TCATATATCT    2220

TGCCTTACTT TTGGAAGAGA GACTGTGCTT GAATATTTGG TCTCTTTCGG AGTGTGGATT    2280

CGCACTCCTC CAGCCTATAG ACCACCAAAT GCCCCTATCT TATCAACACT TCCGAAAACT    2340

ACTGTTGTTA GACGACGGGA CCGAGGCAGG TCCCCTAGAA GAAGAACTCC CTCGCCTCGC    2400

AGACGCAGAT CTCAATCGCC GCGTCGCAGA AGATCTCAAT CTCGGGAATC TCAATGTTAG    2460

TATTCCTTGG ACTCATAAGG TGGGAAACTT TACTGGGCTT TATTCCTCTA CAGTACCTAT    2520

CTTTAATCCT GAATGGCAAA CTCCTTCCTT TCCTAAGATT CATTTACAAG AGGACATTAT    2580

TAATAGGTGT CAACAATTTG TGGGCCCTCT CACTGTAAAT GAAAAGAGAA GATTGAAATT    2640

AATTATGCCT GCCAGATTCT ATCCTACCCA CACTAAATAT TTGCCCTTAG ACAAAGGAAT    2700

TAAACCTTAT TATCCAGATC AGGTAGTTAA TCATTACTTC CAAACCAGAC ATTATTTACA    2760

TACTCTTTGG AAGGCTGGTA TTCTATATAA GAGGGAAACC ACACGTAGCG CATCATTTTG    2820

CGGGTCACCA TATTCTTGGG AACAAGAGCT ACAGCATGGG AGGTTGGTCA TCAAAACCTC    2880

GCAAAGGCAT GGGGACGAAT CTTTCTGTTC CCAACCCTCT GGGATTCTTT CCCGATCATC    2940

AGTTGGACCC TGCATTCGGA GCCAACTCAA ACAATCCAGA TTGGGACTTC AACCCCATCA    3000

AGGACCACTG GCCAGCAGCC AACCAGGTAG GAGTGGGAGC ATTCGGGCCA AGGCTCACCC    3060

CTCCACACGG CGGTATTTTG GGGTGGAGCC CTCAGGCTCA GGGCATATTG ACCACAGTGT    3120

CAACAATTCC TCCTCCTGCC TCCACCAATC GGCAGTCAGG AAGGCAGCCT ACTCCCATCT    3180

CTCCACCTCT AAGAGACAGT CATCCTCAGG CCATGCAGTG G                        3221
```

(2) INFORMATION FOR SEQ ID NO: 280:

(i) SEQUENCE CHARACTERISTICS:
        (A) LENGTH: 3200 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 280:

```
AATTCCACTG CCTTGCACCA AGCTCTGCAG GATCCCAGAG TCAGGGGTCT GTATCTTCCT      60
```

-continued

| | |
|---|---|
| GCTGGTGGCT CCAGTTCAGG AACAGTAAAC CCTGCTCCGA ATATTGCCTC TCACATCTCC | 120 |
| TCAATCTCCG CGAGGACTGG GGACCCTGTG ACGATCATGG AGAACATCAC ATCAGGATTA | 180 |
| CTAGGACCCC TGCTCGTGTT ACAGGCGGGG TTTTTCTTGT TGACAAGAAT CCTCACAATT | 240 |
| CCGCAGAGTC TAGACTCGTG GTGGACTTCT CTCAATTTTC TAGGGGGATC ACCCGTGTGT | 300 |
| CTTGGCCAAA ATTCGCAGTC CCCAACCTCC AATCACTCAC CAACCTCCTG TCCTCCAATT | 360 |
| TGTCCTGGTT ATCGCTGGAT GTGTCTGCGG CGTTTTATCA TATTCCTCTT CATCCTGCTG | 420 |
| CTATGCCTCA TCTTCTTATT GGTTCTTCTG GATTATCAAG GTATGTTGCC CGTTTGTCCT | 480 |
| CTAATTCCAG GATCAACAAC AACCAGTACG GGACCATGCA AAACCTGCAC GACTCCTGCT | 540 |
| CAAGGCAACT CTAAGTTTCC CTCATGTTGC TGTACAAAAC CTACGGATGG AAATTGCACC | 600 |
| TGTATTCCCA TCCCATCGTC CTGGGCTTTC GCAAAATACC TATGGGAGTG GCCTCAGTC | 660 |
| CGTTTCTCTT GGCTCAGTTT ACTAGTGCCA TTTGTTCAGT GGTTCGTAGG GCTTTCCCCC | 720 |
| ACTGTTTGGC TTTCAGCTAT ATGGATGATG TGGTATTGGG GGCCAAGTCT GTACAGCATC | 780 |
| GTGAGTCCCT TTATACCGCT GTTACCAATT TTCTTTTGTC TCTGGGTATA CATTTAAACC | 840 |
| CTAACAAAAC AAAAGATGG GGTTATTCCC TAAACTTCAT GGGCTACATA ATTGGAAGTT | 900 |
| GGGGAACTTT GCCACAGGAT CATATTGTAC AAAAGATCAA ACACTGTTTT AGAAAACTTC | 960 |
| CTGTTAACAG GCCTATTGAT TGGAAAGTAT GTCAAAGAAT TGTGGGTCTT TTGGGCTTTG | 1020 |
| CTGCTCCATT TACACAATGT GGATATCCTG CCTTAATGCC TTTGTATGCA TGTATACAAG | 1080 |
| CTAAACAGGC TTTCACTTTC TCGCCAACTT ACAAGGCCTT TCTAAGTAAA CAGTACATGA | 1140 |
| ACCTTTACCC CGTTGCTCGG CAACGGCCTG GTCTGTGCCA AGTGTTTGCT GACGCAACCC | 1200 |
| CCACTGGCTG GGGCTTAGCC ATAGGCCATC AGCGCATGCG TGGAACCTTT GTGGCTCCTC | 1260 |
| TGCCGATCCA TACTGCGGAA CTCCTAGCCG CTTGTTTTGC TCGCAGCCGG TCTGGAGCAA | 1320 |
| AGCTCATCGG AACTGACAAT TCTGTCGTCC TCTCGCGGAA ATATACATCA TTTCCATGGC | 1380 |
| TGCTAGGCTG TACTGCCAAC TGGATCCTTC GCGGGACGTC CTTTGTTTAC GTCCCGTCGG | 1440 |
| CGCTGAATCC CGCGGACGAC CCCTCTCGGG GCCGCTTGGG ACTCTCTCGT CCCCTTCTCC | 1500 |
| GTCTGCCGTT CCAGCCGACC ACGGGGCGCA CCTCTCTTTA CGCGGTCTCC CCGTCTGTGC | 1560 |
| CTTCTCATCT GCCGGTCCGT GTGCACTTCG CTTCACCTCT GCACGTTGCA TGGCGACCAC | 1620 |
| CGTGAACGCC CATCAGATCC TGCCCAAGGT CTTACATAAG AGGACTCTTG GACTCCCAGC | 1680 |
| AATGTCAACG ACCGACCTTG AGGCCTACTT CAAAGACTGT GTGTTAAGG ACTGGGAGGA | 1740 |
| GTTGGGGGAG GAGATTAGGT TAATGATCTT TGTATTAGGA GGCTGTAGGC ATAAATTGGT | 1800 |
| CTGCGCACCA GCACCATGCA ACTTTTTCAC CTCTGCCTAA TCATCTCTTG TACATGTCCC | 1860 |
| ACTGTTCAAG CCTCCAAGCT GTGCCTTGGG TGGCTTTGGG GCATGGACAT TGACCCTTAT | 1920 |
| AAAGAATTTG GAGCTACTGT GGAGTTACTC TCGTTTTTGC CTTCTGACTT CTTTCCTTCC | 1980 |
| GTACGAGATC TCCTAGACAC CGCCTCAGCT CTGTATCGAG AAGCCTTAGA GTCTCCTGAG | 2040 |
| CATTGCTCAC CTCACCATAC TGCACTCAGG CAAGCCATTC TCTGCTGGGG GAATTGATG | 2100 |
| ACTCTAGCTA CCTGGGTGGG TAATAATTTG CAAGATCCAG CATCCAGAGA TCTAGTAGTG | 2160 |
| AATTATGTTA ATACTAACAT GGGTTTAAAG ATCAGGCAAC TATTGTGGTT TCATATATCT | 2220 |
| TGCCTTACTT TTGAAGAGA GACTGTACTT GAATATTTGG TCTCTTTCGG AGTGTGGATT | 2280 |
| CGCACTCCTC CAGCCTATAG ACCACCAAAT GCCCCTATCT TATCAACACT TCCGGAAACT | 2340 |
| ACTGTTGTTA GACGACGGGA CCGAGGCAGG TCCCCTAGAA GAAGAACTCC CTCGCCTCGC | 2400 |

-continued

| | |
|---|---|
| AGACGCAGAT CTCAATCGCC GCGTCGCAGA AGATCTCAAT CTCGGGAATC TCAATGTTAG | 2460 |
| TATTCCTTGG ACTCATAAGG TCGGAAACTT TACGGGCTT TATTCCTCTA CAGTACCTAT | 2520 |
| CTTTAATCCT GAATGGCAAA CTCCTTCCTT TCCTAAGATT CATTTACAAG AGGACATTAT | 2580 |
| TAATAGGTGT CAACAATTTG TGGGCCCTCT CACTGTAAAT GAAAAGAGAA GATTGAAATT | 2640 |
| AATTATGCCT GCTAGATTCT ATCCTACCCA CACTAAATAT TTGCCCTTAG ACAAAGGAAT | 2700 |
| TAAACCTTAT TATCCAGATC AGGTAGTTAA TCATTACTTC CAAACCAGAC ATTATTTACA | 2760 |
| TACTCTTTGG AAGGCTGGTA TTCTATATAA GAGGGAAACC ACACGTAGCG CATCATTTTG | 2820 |
| CGGGTCACCA TATTCTTGGG AACAAGAGCT ACAGCATTCG CAAAGGCATG GGACGAATC | 2880 |
| TTTCTGTTCC CAACCCTCTG GGATTCCTTC CCGATCATCA GTTGGACCCT GCATTCGGAG | 2940 |
| CCAACTCAAC AAATCCAGAT TGGGACTTCA ACCCCATCAA GGACCACTGG CCAGCAGCCA | 3000 |
| ACCAGGTAGG AGTGGGAGCA TTCGGGCCAG GGCTCACCCC TCCACACGGC GGTATTTTGG | 3060 |
| GGTGGAGCCC TCAGGCTCAG GGCATATTGA CCACAGTGTC AACAATTCCT CCTCCTGCCT | 3120 |
| CCACCAATCG GCAGTCAGGA AGGCAGCCTA CTCCCATCTC TCCACCTCTA AGAGACAGTC | 3180 |
| ATCCTCAGGC CATGCAGTGG | 3200 |

(2) INFORMATION FOR SEQ ID NO: 281:

(i) SEQUENCE CHARACTERISTICS:
        (A) LENGTH: 3221 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 281:

| | |
|---|---|
| AATTCCACTG CCTTCCACCA AGCTCTGCAA GACCCCAGAG TCAGGGGTCT GTATTTTCCT | 60 |
| GCTGGTGGCT CCAGTTCAGG AACAGTAAAC CCTGCTCCGA ATATTGCCTC TCACATCTCG | 120 |
| TCAATCTCCG CGAGGACCGG GGACCCTGTG ACGAACATGG AGAACATCAC ATCAGGATTC | 180 |
| CTAGGACCCC TGCCCGTGTT ACAGGCGGGG TTTTTCTTGT TGACAAGAAT CCTCACAATA | 240 |
| CCGCAGAGTC TAGACTCGTG GTGGACTTCT CTCAATTTTC TAGGGGGATC ACCCGTGTGT | 300 |
| CTTGGCCAAA ATTCGCGATC CCCAACCTCC AATCACTCAC CAACCTCCTG TCCTCCAATT | 360 |
| TGTCCTGGTT ATCGCTGGAT GTGTCTGCGG CGTTTTATCA TATTCCTCTT CATCCTGCTG | 420 |
| CTATGCCTCA TCTTCTTATT GGTTCTTCTG GATTATCAAG GTATGTTGCC CGTTTGTCCT | 480 |
| CTAATTCTAG GATCAACAAC AACCAGTACG GGACCATGCA AAACCTGCAC GACTCCTGCT | 540 |
| CAAGGCAACT CTATGTTTCC CTCATGTTGC TGTACAAAAC CTACGATGG AAATTGCACC | 600 |
| TGTATTCCCA TCCCATCGTC TTGGGCTTTC GCAAAATACC TATGGGAGTG GCCTCAGTC | 660 |
| CGTTTCTCTT GGCTCAGTTT ACTAGTGCCA TTTGTTCAGT GGTTCGTAGG GCTTTCCCCC | 720 |
| ACTGTTTGGC TTTCAGCTAT ATGGATGATG TGGTATTGGG GGCCAAGTCT GTACAGCATC | 780 |
| GTGAGTTCCT TTATACCGCT GTTACCAATT TTCTTTTGTC TCTGGGTATA CATTTAAACC | 840 |
| CTAACAAAAC AAAAAGATGG GGTTATTCCC TAAACTTCAT GGGTTATGTA ATTGGAAGTT | 900 |
| GGGGAACATT GCCACAGGAT CATATTGTAC AAAAAATCAA ACACTGTTTT AGAAAAACTTC | 960 |
| CTGTTAACAG GCCTATTGAT TGGAAAGTAT GTCAAAGAAT TGTGGGTCTT TTGGGCTTTG | 1020 |

-continued

```
CTGCTCCTTT TACACAATGT GGATATCCTG CCTTAATGCC CTTGTATGCA TGTATACAAG     1080

CTAAACAGGC TTTCACTTTC TCGCCAACTT ACAAGGCCTT TCTAAGTAAA CAGTACATGA     1140

ACCTTTACCC CGTTGCTCGG CAACGGCCTG GTCTGTGCCA AGTATTTGCT GATGCAACCC     1200

CCACTGGCTG GGGCTTGGCC ATAGGCCATC AGCGCATGCG CGGAACCTTT GTGGCTCCTC     1260

TGCCGATCCA TACTGCGGAA CTCCTAGCCG CTTGTTTTGC TCGCAGCCGG TCTGGAGCGA     1320

AACTCATCGG AACTGACAAT TCTGTCGTCC TCTCGCGGAA ATATACCTCG TTTCCATGGC     1380

TACTAGGCTG TGCTGCCAAC TGGATCCTTC GCGGGACGTC CTTTGTTTAC GTCCCGTCGG     1440

CGCTGAATCC CGCGGACGAC CCCTCTCGGG GCCGCTTGGG ACTCTCTCGT CCCCTTCTCC     1500

GTCTGCCGTT CCAGCCGACC ACGGGCGCA CCTCTCTTTA CGCGGTCTCC CCGTCTGTGC     1560

CTTCTCATCT GCCGGTCCGT GTGCACTTCG CTTCACCTCT GCACGTTGCA TGGAGACCAC     1620

CGTGAACGCC CATCAGATCC TGCCCAAGGT CTTACATAAG AGGACTCTTG GACTCCCAGC     1680

AATGTCAACG ACCGACCTTG AGGCCTACTT CAAAGACTGT GTGTTTAAGG ACTGGGAGGA     1740

GCTGGGGGAG GAGATTAGGT TAAAGGTCTT TGTATTAGGA GGCTGTAGGC ATAAATTGGT     1800

CTGCGCACCA GCACCATGCA ACTTTTTCAC CTCTGCCTAA TCATCTCTTG TACATGTCCC     1860

ACTGTTCAAG CCTCCAAGCT GTGCCTTGGG TGGCTTTGGG GCATGGACAT TGACCCTTAT     1920

AAAGAATTTG GAGCTACTGT GGAGTTACTC TCGTTTTTGC CTTCTGACTT CTTTCCTTCC     1980

GTCAGAGATC TCCTAGACAC CGCCTCGGCT CTGTATCGGG AAGCCTTAGA GTCTCCTGAG     2040

CATTGCTCAC CTCACCATAC CGCACTCAGG CAAGCCATTC TCTGCTGGGG GGAATTGATG     2100

ACTCTAGCTA CCTGGGTGGG TAATAATTTG GAAGATCCAG CATCCAGGGA TCTAGTAGTC     2160

AATTATGTTA ATACTAACAT GGGATTAAAG ATCAGGCAAC TCTTGTGGTT TCATATCTCT     2220

TGCCTTACTT TTGGAAGAGA AACTGTACTT GAATATTTGG TCTCTTTCGG AGTGTGGATT     2280

CGCACTCCTC CAGCCTATAG ACCACCAAAT GCCCCTATCT TATCAACACT TCCGGAAACT     2340

ACTGTTGTTA GACGACGGGA CCGAGGCAGG TCCCCTAGAA GAAGAACTCC CTCGCCTCGC     2400

AGACGCAGAT CTCAATCGCC GCGTCGCAGA AGATCTCAAT CTCGGGAATC TCAATGTTAG     2460

TATTCCTTGG ACTCATAAGG TGGGAAACTT CACTGGGCTT TATTCCTCTA CAGCACCTAT     2520

CTTTAATCCT GAATGGCAAA CTCCTTCCTT TCCTAAAATT CATTTACAAG AGGACATTAT     2580

TAATAGGTGT CAACAATTTG TGGGCCCTCT CACTGTAAAT GAAAAGAGAA GATTGAAATT     2640

AATTATGCCT GCTAGATTCT ATCCTACCCA CACTAAATAT TTGCCCTTAG ACAAAGGAAT     2700

TAAACCTTAT TATCCAGATC AGGTAGTTAA TCATTACTTC CAAACCAGAC ATTATTTACA     2760

TACTCTTTGG AAGGCGGGTA TTCTATATAA GAGAGAAACC ACACGTAGCG CATCATTTTG     2820

CGGGTCACCA TATTCTTGGG AACAAGAGCT ACAGCATGGG AGGTTGGTCA TCAAAACCTC     2880

GCAAAGGCAT GGGGACGAAT CTTTCTGTTC CCAACCCTCT GGGATTCTTT CCCGATCACA     2940

AGTTGGACCC TGTATTCGGA GCCAACTCAA ACAATCCAGA TTGGGACTTC AACCCCATCA     3000

AGGACCACTG GCCAGCAGCC AACCAGGTAG GAGTGGGAGC ATTCGGGCCA GGGTTCACCC     3060

CTCCACACGG CGGTGTTTTG GGGTGGAGCC CTCAGGCTCA GGGCATGTTG ACCCCAGTGT     3120

CAACAATTCC TCCTCCTGCC TCCGCCAATC GGCAGTCAGG AAGGCAGCCT ACTCCCATCT     3180

CTCCACCTCT AAGAGACAGT CATCCTCAGG CCATGCAGTG G                        3221
```

(2) INFORMATION FOR SEQ ID NO: 282:

(i) SEQUENCE CHARACTERISTICS:
        (A) LENGTH: 3221 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 282:

```
AATTCCACTG CCTTCCACCA AGCTCTGCAG GATCCCAGAG TCAGGGGTCT GTATCTTCCT      60
GCTGGTGGCT CCAGTTCAGG AACAGTAAAC CCTGCTCCGA ATATTGCCTC TCACATCTCG     120
TCAATCTCCG CGAGGACTGG GGACCCTGTG ACGAACATGG AGAACATCAC ATCAGGATTC     180
CTAGGACCCC TGCTCGTGTT ACAGGCGGGG TTTTCCTTGT TGACAAGAAT CCTCACAATA     240
CCGCAGAGTC TAGACTCGTG GTGGACTTCT CTCAATTTTC TAGGGGGGTC ACCCGTGTGC     300
CTTGGCCAAA ATTCGCAGTC CCCAACCTCC AATCACTCAC CAACCTCCTG TCCTCCAATT     360
TGTCCTGGTT ATCGCTGGAT GTGTCTGCGG CGTTTTATCA TATTCCTCTT CATCCTGCTG     420
CTATGCCTCA TCTTCTTATT GGTTCTTCTG GATTATCAAG GTATGTTGCC CGTTTGTCCT     480
ATAATTCCAG GATCAACAAC AACCAGTACG GGACCATGCA AAACCTGCAC GACTCCTGCT     540
CAAGGCAACT CTTTGTTTCC CTCATGTTGC TGTACAAAAC CTACGGATGG AAATTGCACC     600
TGTATTCCCA TCCCATCGTC CTGGGCTTTC GCAAAATACC TATGGGAGCG GGCCTCAGTC     660
CGTTTCTCTT GGCTCAGTTT ACTAGTGCCA TTTGTTCAGT GGTTCGTAGG GCTTTCCCCC     720
ACTGTTTGGC TTTTAGCTAT ATGGATGATG TGGTATTGGG GGCCAAGTCT GTACAGCATC     780
GTGAGGCCCT TTATACCGCT GTTACCAATT TTCTTTTGTC TCTGGGTATA CATTTAAACC     840
CTAACAAAAC AAAAAGATGG GGTTATTCCC TAAACTTCAT GGGTTACAGA ATTGGAAGTT     900
GGGGAACATT GCCACAGGAT CACATTGTAC AAAAGATCAA ACACTGTTTT AGAAAACTTC     960
CTGTTAACAG GCCTATTGAT TGGAAGGTAT GTCAAAGAAT TGTGGGTCTT TTGGGCTTTG    1020
CTGCTCCTTT TACACAATGT GGATATCCTG CCTTAATGCC TTTGTATGCA TGTATACAAG    1080
CTAAACAGGC TTTCTCTTTC TCGCCAACTT ACAAGGCCTT TCTAAGTAAA CAGTACCTGA    1140
ACCTTTACCC CGTTGCTCGG CAACGGCCTG GTCTGTGCCA AGTGTTTGCT GACGCAACCC    1200
CCACTGGCTG GGGCTTAGCC ATAGGCCATC AGCGCATGCG TGGAACCTTT GTGGCTCCTC    1260
TGCCGATCCA TACTGCGGAA CTCCTAGCCG CTTGTTTTGC TCGCAGCCGG TCTGGAGCAA    1320
AGCTCATCGG AACTGACAAT TCTGTCGTCC TCTCGCGGAA ATATACATCG TTTCCATGGC    1380
TGCTAGGCTG TGCTGCCAAC TGGATCCTTC GCGGGACGTC CTTTGTTTAC GTCCCGTCGG    1440
CGCTGAATCC CGCGGACGAC CCCTCTCGGG GCCGCTTGGG ACTCTATCGT CCCCTTCTCC    1500
GTCTGCCGTT CCAGCCGACC ACGGGGCGCA CCTCTCTTTA CGCGGTCTCC CCGTCTGTGC    1560
CTTCTCATCT GCCGGTCCGT GTGCACTTCG CTTCACCTCT GCACGTTGCA TGGAGACCAC    1620
CGTGAACGCC CATCAGAGCC TGCCCAAGGT CTTACATAAG AGAACTCTTG GACTCCCAGC    1680
AATGTCAACG ACCGACCTTG AGGCCTACTT CAAAGACTGT GTGTTAAGG ACTGGGAGGA    1740
GCTGGGGGAG GAGATTAGGT TAATGATCTT TGTATTAGGA GGCTGTAGGC ATAAATTGGT    1800
CTGCGCACCA GCACCATGCA ACTTTTTCAC CTCTGCCTAA TCATCTCTTG TTCATGTCTC    1860
ACTGTTCAAG CCTCCAAGCT GTGCCTTGGG TGGCTTTGAG GCATGGACAT TGACCCTTAT    1920
AAAGAATTTG GAGCTAGTGT GGAGTTACTC TCGTTTTTGC CTCATGACTT CTTTCCTTCC    1980
GTCAGAGATC TCCTAGACAC CGCCTCAGCT CTGTATCGAG AAGCCTTAGA GTCTCCTGAG    2040
```

```
CATTGCTCAC CTCACCATAC TGCACTCAGG CAAGCCGTTC TCTGCTGGGG GGAATTAATG      2100

ACTCTAGCTA CCTGGGTGGG TAATAATTTG CAAGATCCAG CATCCAGGGA TCAAGTAGTC      2160

AATTATGTTA ATACTAACAT GGGTTTAAAG ATCAGGCAAC TATTGTGGTT TCATATATCT      2220

TGTCTTATGT TTGGAAGAGA CACTGTACTT GAATATTTGG TCTCTTTCGG AGTGTGGATT      2280

CGCACTCCTC CAGCCTATAG ACCACCAAAT GCCCCTATCT TATCAACACT TCCGGAAACT      2340

ACTGTTGTTA GATGTCGGGA CCGACGCAGG TCCCCTAGAA GAAGAACTCC CTCGCCTCGC      2400

AGACGCAGAT CTCAATCGCC GCGTCGCAGA AGATCTCAAT CTCGGGAATC TCAATGTTAG      2460

TATTCCTTGG ACTCATAAGG TGGGAAACTT TACTGGGCTT TATTCCTCTA CAGTACCTAT      2520

CTTTAATCCT GAATGGCAAA CTCCTTCCTT TCCTAAGATT CATTTACAAG AGGACATTAT      2580

TAATAGGTGT CAACAATTTG TGGGCCCTCT TACTGTAAAT GAAAGAGAA GATTGAAATT       2640

AATTATGCCT GCTAGATTCT ATCCTACCCA CACAAAATAT TTGCCCTTAG ACAAAGGAAT      2700

TAAACCTTAT TATCCAGATC AGGTAGTTAA TCATTACTTC CAAACCAGAC ACTATTTACA      2760

TACTCTTTGG AAGGCTGGTA TTCTATATAA GAGGGAACCC ACACGTAGCG CATCATTTTC      2820

CCGGTCACCA TATTCTTGGG AACAAGAGCT ACAGCATGGG AGGTGGGACA TCAAAACCTC      2880

GCAAAGGCAT GGGGACGAAT CTTTCTGTTC CCAACCCTCT GGGATTCTTT CCCGATCATC      2940

AGTTGGACCC TGCATTCGGA GCCAACTCAA ACAATCCAGA TTGGGACTTC AACCCCATCA      3000

AGGACCACTG GCCAGCAGCC AACCAGGTGG GAGTGGGAGC ATTCGGGCCA GGGCTCACCC      3060

CTCCACACGG CGGTATTTTG GGGTGGAGCC CTCAGGCTCA AGGCATATTG ACCACAGTGT      3120

CAACAATTCC TCCTCCTGCC TCCACCAATC GGCAGTCAGG AAGGCAGCCT ACTCCCATCT      3180

CTCCACCTCT GAGAGAAAGT CATCCTCAGG CCATGCAGTG G                         3221

(2) INFORMATION FOR SEQ ID NO: 283:

(i) SEQUENCE CHARACTERISTICS:
        (A) LENGTH: 3221 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 283:

AATTCCACAG CTTTCCACCA AGCTCTGCAA GATCCCAGAG TCAGGGGCCT GTATTTTCCT        60

GCTGGTGGCT CCAGTTCAGG AACACTCAAC CCTGTTCCAA CTATTGCCTC TCACATCTCG       120

TCAATCTCCT CGAGGATTGG GGACCCTGCA CCGAACATGG AGAACATCAC ATCAGGATTC       180

CTAGGACCCC TGCTCGTGTT ACAGGCGGGG TTTTTCTTGT TGACAAGAAT CCTCACAATA       240

CCGCAGAGTC TAGACTCGTG GTGGACTTCT CTCAATTTTC TAGGGGAGC ACCCGTGTGT        300

CTTGGCCAAA ATTCGCAGTC CCCAACCTCC AATCACTCAC CAACCTCCTG TCCTCCAATT       360

TGTCCTGGTT ATCGCTGGAT GTGTCTGCGG CGTTTTATCA TATTCCTCTT CATCCTGCTG       420

CTATGCCTCA TCTTCTTATT GGTTCTTCTG GATTATCAAG GTATGTTGCC CGTTTGTCCT       480

CTAATTCCAG GATCAACAAC AACCAGCACG GGACCCTGCA AAACCTGCAC GACTCCTGCT       540

CAAGGCAACT CTATGTTTCC CTCATGTTGC TGTACAAAAC CTACGGATGG AAATTGCACC       600

TGTATTCCCA TCCCATCATC TTGGGCTTTC GCAAAATACC TATGGGAGTG GGCCTCAGTC       660
```

-continued

```
CGTTTCTCTT GGCTCAGTTT ACTAGTGCCA TTTGTTCAGT GGTTCGTAGG GCTTTCCCCC      720

ACTGTTTGGC TTTCAGCTAT ATGGATGATG TGGTACTGGG GGCCAAGTCT GTACAACATC      780

TTGAGTCCCT TTATACCGCT GTTACCAATT TTCTTTTGTC TTTGGGTATA CATTTAAACC      840

CTAACAAAAC AAAGAGATGG GGTTATTCCC TGAATTTCAT GGGTTATGTA ATTGGAAGTT      900

GGGGTACATT GCCACAGGAT CATATTGTAC AAAAAATCAA ACACTGTTTT AGAAAACTTC      960

CTGTTAATCG ACCTATTGAT TGGAAAGTAT GTCAGAGACT TGTAGGTCTT TTAGGCTTTG     1020

CCGCTCCATT TACACAATGT GGTTACCCTG CATTAATGCC TTTGTATGCA TGTATACAAG     1080

CGAAACAGGC TTTTACTTTC TCGCCAACTT ACAAGGCCTT TCTAAGTAAA CAGTATATGA     1140

ACCTTTACCC CGTTGCCCGG CAACGGCCTG GTCTGTGCCA AGTGTTTGCT GACGCAACCC     1200

CCACTGGCTG GGGCTTGGCC ATCGGCCATC AGCGCATGCG TGAAACCTTT GTGGCTCCTC     1260

TGCCGATCCA TACTGCAGAA CTCCTAGCCG CTTGTTTTGC TCGCAGCCGG TCTGGAGCAA     1320

AACTCATCGG GACTGACAAT TCTGTCGTCC TTTCTCAGAA ATATACATCC TTTCCATAGC     1380

TGCTAGGTTG TACTGCCAAC TAGATTCTTC GCGGGACGTC CTTTGTCTAC GTCCCGTCGG     1440

CGCTGAATCC CGCGGACGAC CCCTCGCGAG GCCGCTTGGG ACTGTATCGT CCCCTTCTCC     1500

GTCTGCCGTA CCGTCCGACC ACGGGGCGCA CCTCTCTTTA CGCGGTCTCC CCGTCTGTGC     1560

CTTCTCATCT GCCGGTCCGT GTGCACTTCG CTTCACCTCT GCACGTTGCA TGGAGACCAC     1620

CGTGAACGCC CATCAGGTCC TGCCCAAGGT CTTACATAAG AGGACTCTTG GACTCTCAGC     1680

AATGTCAACG ACCGACCTTG AGGCCTACTT CAAAGACTGT GTGTTTAAAG ACTGGGAGGA     1740

GTTGGGGGAG GAGATTAGGT TAAAGGTCTT TGTATTAGGA GGCTGTAGGC ATAAATTGGT     1800

CTGCGCACCA TTATCATGCA ACTTTTTCAC CTCTGCCTAA TCATCTCTTG TACATGTCCC     1860

ACTTTTCAAG CCTCCAAGCT GTGCCTTGGA TGGCTTTGGG GCATGGACAT TGACCCTTCG     1920

AAAGAATTTG AGCTACTGTG GAGTTACTCT CATTTTTGCC TTCTGACTTC TTTCCTTCCG     1980

TCCGGGATCT ACTAGAATAC AGCCTCAGCT CTATATCGGG AAGCCTTAGA GTCTCCTGAG     2040

CATTGCTCAC CTCACCATAC AGCACTCAGG CAAGCCATTC TCTGCTGGGG GAAATTAATG     2100

ACTCTAGCTA CCTGGGTGGG TAATAATTTG GAAGATCCAG CATCCAGGGA TCTAGTAGTC     2160

AATTATGTTA ATACTAACAT GGGCCTAAAG ATCAGGCAAT TATTGTGGTT TCATATTTCT     2220

TGCCTTACTT TTGGAAGAGA AACTGTCCTT GAGTATTTGG TCTCTTTCGG AGTGTGGATT     2280

CGCACTCCTC CAGCCTATAG ACCACCAAAT GCCCCTATCT TATCAACACT TCCGGAAACT     2340

ACTGTTGTTA GACGACGAGA CCGAGGCAGG TCCCCTAGAA GAAGAACTCC CTCGCCTCGC     2400

AGACGCAGAT CTCAATCGCC GCGTCGCAGA AGATCTCAAT CTCGGGAATC TCAATGTTAG     2460

TATTCCTTGG ACTCATAAGG TGGGAAATTT TACTGGGCTT TATTCTTCTA CTGTCCCTAT     2520

CTTTAATCCT GAATGGCAAA CACCTTCTTT TCCTAAAATT CATTTACATG AAGACATTGC     2580

TAATAGGTGT CAGCAATTTG TAGGCCCTCT CACTGTAAAT GAAAAAGAA GACTGAAATT      2640

AATTATGCCT GCTAGGTTTT ATCCTAACAG CACAAAATAT TTGCCCTTAG ACAAAGGGAG     2700

TAAAACTTAT TATCCTGATC ATGTAGTTAA TCATTACTTT CAAACCCGAC ATTATTTACA     2760

TACTCTTTGG AAGGCTGGGA TTCTATATAA GAGGGAAACT ACACGTAGCG CCTCATTTTG     2820

CGGGTCACCA TATTCTTGGG AACAAGAGCT ACATCATGGG AGGTTGGTCA TCAAAACCTC     2880

GCAAAGGCAT GGGGACGAAC CTTTCTGTTC CCAACCCTCT GGGATTCTTT CCCGATCATC     2940

AGTTGGACCC TGCATTCGGA GCCAATTCAA ACAATCCAGA TTGGGACTTC AACCCCATCA     3000
```

-continued

| | |
|---|---|
| AGGACCACTG GCCACAAGCC AACCAGGTAG GAGTGGGAGC ATTTGGGCCA GGGTTCACTC | 3060 |
| CCCCACACGG AGGTGTTTTG GGGTGGAGCC CTCAGGCTCA GGGCATATTG GCCACCGTGC | 3120 |
| CAGCGATGCC TCCTCCTGCC TCCACCAATC GGCAGTCAGG AAGGCAGCCT ACTCCCATCT | 3180 |
| CTCCACCTCT AAGAGACAGT CATCCTCAGG CCATGCAGTG G | 3221 |

(2) INFORMATION FOR SEQ ID NO: 284:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 284:

| | |
|---|---|
| AACTCCACCA CGTTCCACCA AACTCTTCAA GATCCCAGAG TCAGGGCTCT GTACTTTCCT | 60 |
| GCTGGTGGCT CCAGTTCAGG AACAGTAAAC CCTGTTCAGA ACACTGCCTC TTCCATATCG | 120 |
| TCAATCTTAT CGACGACTGG GGACCCTGTG CCGAACATGG AGAACATCGC ATCAGGACTC | 180 |
| CTAGGACCCC TGCTCGTGTT ACAGGCGGGG TTTTTCTCGT TGACAAAAAT CCTCACAATA | 240 |
| CCTCTGAGTC TAGACTCGTG GTGGACTTCT CTCAATTTTC TAGGGAAAC ACCCGTGTGT | 300 |
| CTTGGCCAAA ATTCGCAGTC CCAAATCTCC AGTCACTCAC CAACTTGTTG TCCTCCGATT | 360 |
| TGTCCTGGTT ATCGCTGGAT GTGTCTGCGG CGTTTTATCA TCTTCCTCTG CATCCTGCTG | 420 |
| CTATGCCTCA TCTTCTTGTT GGTTCTTCTG GACTATCAAG GTATGTTGCC CGTTTGTCCT | 480 |
| CTAATTCCAG GATCATCAAC CACCAGCACA GGACCATGCA AAACCTGCAC GACTCCTGCT | 540 |
| CAAGGAACCT CTATGTTTCC CTCATGTTGC TGTACAAAAC CTACGGACGG AAACTGCACC | 600 |
| TGTATTCCCA TCCCATCATC TTGGGCTTTC GCAAAATACC TATGGGAGTG GGCCTCAGTC | 660 |
| CGTTTCTCTT GGCTCAGTTT ACTAGTGCCA TTTGTTCAGT GGTTCGTAGG GCTTTCCCCC | 720 |
| ACTGTCTGGC TTTCAGTTAT ATGGATGATG TGGTTTTGGG GGCCAAGTCT GTACAACATC | 780 |
| TTGAGTCCCT TTATGCCGCT GTTACCAATT TTCTTTTGTC TTTGGGTATA CATTTAAACC | 840 |
| CTCAGAAAAC AAAAAGATGG GGCTACTCCC TTAACTTCAT GGGGTATGTA ATTGGAAGTT | 900 |
| GGGGGACCTT ACCCCAAGAA CATATTGTGT TGAAAATCAA ACAATGTTTT AGGAAACTTC | 960 |
| CTGTAAACAG GCCTATTGAT TGGAAAGTAT GTCAACGAAT TGTGGGTCTT TTGGGATTTG | 1020 |
| CTGCTCCTTT CACACAATGT GGATATCCTG CTTTAATGCC TTTATATGCA TGTATACAAG | 1080 |
| CTAAACAGGC TTTTACTTTT TCGCCAACGT ATAAGGCCTT TCTAAACAAA CAATATCTGA | 1140 |
| ACCTTTACCC CGTTGCTCGG CAACGGCCAG GTCTGTGCCA AGTGTTTGCT GACGCAACCC | 1200 |
| CCACTGGCTG GGGCTTGGCC ATAGGCCATC AGCGCATGCG TGGGACCTTT GTGTCTCCTC | 1260 |
| TGCCGATCCA TACTGTGGAA CTCCTAGCAG CTTGTTTTGC TCGCAGCAGG TCTGGAGCAA | 1320 |
| AACTTATCGG GACTGACAAT TCTGTCGTCC TTTCCCGCAA ATATACATCG TTTCCATGGC | 1380 |
| TGCTAGGCTG TGCTGCCAAC TGGATCCTGC GCGGGACGTC CTTTGTCTAC GTCCCGTCGG | 1440 |
| CGCTGAATCC CGCGGACGAC CCCTCCCGGG GCCGCTTGGG GCTCTACCGC CCGCTTCTCC | 1500 |
| GCCTGCCGTA CCGTCCGACC ACGGGGCGCA CCTCTCTTTA CGCGGACTCC CCGTCTGTGC | 1560 |
| CTTCTCATCT GCCGGACCGT GTGCACTTCG CTTCACCTCT GCACGTCGCA TGGAGACCAG | 1620 |

-continued

```
CGTGAACGCC CATCGGAACC TGCCCAAGGT CTTGCATAAG AGGACTCTTG GACTTTCAGC      1680

AATGTCAACG ACCGACCTTG AGGCACACTT CAAAGACTGT GTGTTACTG AGTGGGAGGA       1740

GTTGGGGGAG GAGATCAGGT TAAAGGTCTT TGTACTAGGA GGCTGTAGGC ATAAATTGGT      1800

CTGTTCACCA GCACCATGCA ACTTTTTCAC CTCTGCCTAA TCATCTCATG TTCATGTCCT      1860

ACTGTTCAAG CCTCCAAGCT GTGCCTTGGG TGGCTTTGGG GCATGGACAT TGACCCGTAT      1920

AAAGAATTTG GAGCTTCTGT GGAGTTACTC TCTTTTTTGC CTTCTGACTT CTTTCCTTCT      1980

ATTCGAGATC TTCTCGACAC CGCCTCTGCT CTGTATCGGG AGGCCTTAGA GTCTCCGGAA      2040

CATTGTTCAC CTCACCATAC GGCACTCAGG CAAGCTATTC TGTGTTGGGG TGAGTTGATG      2100

AATCTAGCCA CCTGGGTGGG AAGTAATTTG GAAGACCCAG CCTCCCGGGA ATTAGTAGTC      2160

AGTTATGTCA ATGTTAATAT GGGCCTAAAA ATCAGACAAC TATTGTGGTT TCACATTTCC      2220

TGTCTTACGT TTGGAAGAGA AACTGTTCTT GAATATTTGG TGTCTTTTGG AGTGTGGATT      2280

CGCACACCTC CAGCATATAG ACCACCAAAT GCCCCTATCT TATCAACACT TCCGGAAACT      2340

ACTGTTGTTA GACGACGAGG CAGGTCCCCT AGAAGAAGAA CTCCCTCGCC TCGCAGACGA      2400

AGGTCTCAAT CGCCGCGTCG CAGAAGATCT CAATCTCGGG AATCTCAATG TTAGTATTCC      2460

TTGGACTCAT AAGGTGGGAA ACTTTACGGG GCTTTATTCT TCTACGGTAC CTAGCTTTAA      2520

TCCTCAATGG CAAACTCCTT CATTTCCTGA CATTCATTTG CAGGAGGACA TCATTAATAA      2580

GTGTAAACAA TTTGTGGGAC CCCTTACAGT GAATGAAAAA AGGAGACTAA AATTGATTAT      2640

GCCTGCTAGG TTCTATCCCA ATGTTACTAA ATATTTGCCC TTAGATAAAG GAATTAAACC      2700

TTATTATCCA GAGCATGTAG TTAATCATTA CTTCCAGACG AGACATTATT TACATACTCT      2760

TTGGAAGGCG GGTATCTTAT ATAAAAGAGA GACAACACGT AGCGCCTCAT TTTGCGGGTC      2820

ACCATATTCT TGGGAACAAG AGCTACAGCA TGGGAGGTTG GTCCTCCAAA CCTCGACAAG      2880

GCATGGGGAC AAATCTTTCC GTCCCCAATC CTCTGGGATT CTTTCCCGAT CACCAGTTGG      2940

ACCCTGCATT CAAAGCCAAC TCCGACAATC CCGATTGGGA CCTCAACCCA CACAAGGACA      3000

ACTGGCCGGA CTCCAACAAG GTGGGAGTGG GAGCATTCGG GCCGGGATTC ACTCCACCCC      3060

ATGGGGGACT GTTGGGGTGG AGCCCTCAAG CTCAGGGCAT ACTCACAACT GTGCCAACAG      3120

CTCCTCCTCC TGCCTCCACC AATCGGCAGT TAGGAAGGAA GCCTACTCCC CTGTCTCCAC      3180

CTCTAAGAGA CACTCATCCT CAGGCAATGC AGTGG                                3215
```

(2) INFORMATION FOR SEQ ID NO: 285:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 285:

```
AACTCCACCA CGTTCCACCA AACTCTTCAA GATCCCAGAG TCAGGGCTCT GTACTTTCCT        60

GCTGGTGGCT CCAGTTCAGG AACAGTAAAC CCTGTTCAGA ACACTGTCTC TTCCATATCG       120

TCAATCTTAT CGAAGACTGG GGACCCTGTG CCGAACATGG AGAACATCGC ATCAGGACTG       180

CTAGGACCCC TGCTCGTGTT ACAGGCGGGG TTTTTCTTGT TGACAAAAAT CCTCACAATC       240
```

-continued

| | |
|---|---|
| CCACAGAGTC TAGACTCGTG GTGGACTTCT CTCAATTTTC TAGGGGGAAC ACCCGTGTGT | 300 |
| CTTGGCCAAA ATTCGCAGTC CCAAATCTCC AGTCACTCAC CAACTTGTTG TCCTCCGATT | 360 |
| TGTCCTGGTT ATCGCTGGAT GTGTCTGCGG CGTTTTATCA TCTTCCTCTG CATCCTGCTG | 420 |
| CTATGCCTCA TCTTCTTGTT GGTTCTTCTG GACTATCAAG GTATGTTGCC CGTTTGTCCT | 480 |
| CTAATTCCAG GATCATCAAC CACCAGCACC GGACCATGCA AAACCTGCAC GACTCCTGCT | 540 |
| CAAGGAACCT CTATGTTTCC CTCATGTTGC TGTACAAAAC CTACGGACGG AAACTGCACC | 600 |
| TGTATTCCCA TCCCATCATC TTGGGCTTTC GCAAAATACC TATGGGAGTG GGCCTCAGTC | 660 |
| CGTTTCTCTT GGCTCAGTTT ACTAGTGCCA TTTGTTCAGT GGTTCGTAGG GCTTTCCCCC | 720 |
| ACTGTCTGGC TTTCAGTTAT ATGGATGATG TGGTTTTGGG GGCCAAGTCT GTACAACATC | 780 |
| TTGAGTCCCT TTATGCCGCT GTTACCAATT TTCTTTTGTC TTTGGGTATA CATTTAAACC | 840 |
| CTCAGAAAAC AAAAAGATGG GGCTACTCCC TCAACTTCAT GGGGTATGTA ATTGGAAGTT | 900 |
| GGGGCACCTT ACCCCAAGAA CATATTGTGT TGAAACTCAA ACAATGCTTT AGAAAACTTC | 960 |
| CTGTAAACAG ACCTATTGAT TGGAAGGTGT GTCAACGAAT TGTGGGTCTT TTGGGATTTG | 1020 |
| CTGCTCCTTT CACACAATGT GGTTATCCTG CTTTAATGCC TTTATATGCA TGTATACAAG | 1080 |
| CTAAACAGGC TTTTACTTTT TCGCCAACGT ATAAGGCCTT TCTAACCAAA CAATATCTGA | 1140 |
| ACCTTTACCC CGTTGCTCGG CAACGGCCAG GTCTGTGCCA AGTGTTTGCT GACGCAACCC | 1200 |
| CCACTGGCTG GGGCTTGGCC ATAGGCCATC AGCGCATGCG TGGAACCTTT GTGTCTCCTC | 1260 |
| TGCCGATCCA TACTGCGGAA CTCCTAGCCG CTTGTTTTGC TCGCAGCAGG TCTGGAGCAA | 1320 |
| AACTTATCGG GACTGACAAT TCTGTTGTCC TTTCCCGCAA ATATACATCG TTTCCATGGC | 1380 |
| TGCTAGGCTG TGCTGCCAAC TGGATCCTGC GCGGACGTC CTTTGTCTAC GTTCCGTCGG | 1440 |
| CGCTGAATCC CGCGGACGAC CCCTCCCGGG GCCGCTTGGG GCTCTACCGC CCGCTTCTCC | 1500 |
| GTCTGCCGTA CCGACCGACC ACGGGGCGCA CCTCTCTTTA CGCGGACTCC CCGTCTGTGC | 1560 |
| CTTCTCGTCT GCCGGACCGT GTGCACTTCG CTTCACCTCT GCACGTCGCA TGGAGACCAC | 1620 |
| CGTGAACGCC CATCGGAACC TGCCCAAGGT CTTGCATAAG AGGACTCTTG ACTTTCAGC | 1680 |
| AATGTCACCG ACCGACCTTG AGGCATACTT CAAAGACTGT GTGTTACTG AGTGGGAGGA | 1740 |
| GTTGGGGGAG GAGATCAGGT TAAAGGTCTT TGTACTAGGA GGCTGTAGGC ATAAATTGGT | 1800 |
| CTGTTCACCA GCACCATGCA ACTTTTTCAC CTCTGCCTAA TCATCTCATG TTCATGTCCT | 1860 |
| ACTGTTCAAG CCTCCAAGCT GTGCCTTGGG TGGCTTTGGG GCATGGACAT TGACCCGTAT | 1920 |
| AAAGAATTTG GAGCTTCTGT GGAGTTACTC TCTTTTTTGC CTTCTGACTT CTTTCCTTCT | 1980 |
| ATTCGAGATC TTCTCGACAC CGCCTCTGCT CTGTATCGGG AGGCCTTAGA GTCTCCGGAA | 2040 |
| CATTGTTCAC CTCACCATAC GGCACTCAGG CAAGCTATTT TGTGTTGGGG TGAGTTGATG | 2100 |
| AATCTAGCCA CCTGGGTGGG AAGTAATTTG GAAGACCCAG CATCCCGGGA ATTAGTAGTC | 2160 |
| AGTTATGTCA ATGTTAATAT GGGCCTAAAA ATCAGACAAC TATTGTGGTT TCACATTTCC | 2220 |
| TGTCTTACTT TTGGAAGAGA AACTGTTCTT GAATATTTGG TGTCTTTTGG AGTGTGGATT | 2280 |
| CGCACACCTC CTGCATATAG ACCACCAAAT GCCCCTATCT TATCAACACT TCCGGAAACT | 2340 |
| ACTGTTGTTA GACGACGAGG CAGGTCCCCT AGAAGAAGAA CTCCCTCACC TCGCAGACGA | 2400 |
| AGGTCTCAAT CGCCCGGTCG CAGAAGATCT CAATCTCGGG AATCTCAATG TTAGTATCCC | 2460 |
| TTGGACTCAT AAGGTGGGAA ACTTTACGGG GCTTTATTCT TCTACGGTAC CTAGCTTTAA | 2520 |
| TCCTAAATGG CAAACTCCTT CCTTTCCTGA CATTCATTTG CAGGAGGATA TCATTAATAG | 2580 |
| GTGTGAACAA TTTGTGGGAC CCCTCACAGT GAATGAAAAC AGGAGACTAA AATTGATTAT | 2640 |

| | |
|---|---|
| GCCTGCTAGG TTCTATCCCA ATGTTACTAA ATATTTGCCC TTAGATAAAG GAATCAAACC | 2700 |
| TTATTATCCA GAGCATGTAG TTAATCATTA CTTCCAGACG AGACATTATT TACATACTCT | 2760 |
| TTGGAAGGCG GGTATCTTAT ATAAAAGAGA GACAACACGT AGCGCCTCAT TTTGCGGGTC | 2820 |
| ACCATATTCT TGGGAACAAG ATCTACAGCA TGGGAGGTTG GTCCTCCAAA CCTCGACAAG | 2880 |
| GCATGGGGAC AAATCTTTCC GTCCCCAATC CTCTGGGATT CTTTCCCGAT CACCAGTTGG | 2940 |
| ACCCTGCATT CAAAGCCAAC TCCGACAATC CCGATTGGGA CCTCAACCCA CACAAGGACA | 3000 |
| ACTGGCCGGA CTCCAACAAG GTGGGAGTGG GAGCATTCGG GCCGGGATTC ACTCCACCCC | 3060 |
| ATGGGGGACT GTTGGGGTGG AGCCCTCAAG CTCAGGGCAT ACTCACAACT GTGCCAACAG | 3120 |
| CTCCTCCTCC TGCCTCCACC AATCGGCAGT TAGGAAGGAA GCCTACTCCC CTGTCTCCAC | 3180 |
| CTCTAAGAGA CACTCATCCT CAGGCCATGC AGTGG | 3215 |

(2) INFORMATION FOR SEQ ID NO: 286:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 286:

| | |
|---|---|
| AACTCCACCA CTTTCCACCA AACTCTTCAA GATCCCAGAG TCAGGGCTCT GTACTTTCCT | 60 |
| GCTGGTGGCT CCAGTTCAGG AACAGTAAGC CCTGCTCAGA ATACTGTCTC AGCCATATCG | 120 |
| TCAATCTTAT CGAAGACTGG GGACCCTGTG CCGAACATGG AGAACATCGC ATCAGGACTC | 180 |
| CTAGGACCCC TGCTCGTGTT ACAGGCGGGG TTTTTCTTGT TGACAAAAAT CCTCACAATA | 240 |
| CCACAGAGTC TAGACTCGTG GTGGACTTCT CTCAATTTTC TAGGGGGAAC ACCCGTGTGT | 300 |
| CTTGGCCAAA ATTCGCAGTC CCAAATCTCC AGTCACTCAC CAACCTGTTG TCCTCCAATT | 360 |
| TGTCCTGGTT ATCGCTGGAT GTGTCTGCGG CGTTTTATCA TCTTCCTCTG CATCCTGCTG | 420 |
| CTATGCCTCA TCTTCTTGTT GGTTCTTCTG GACTATCAAG GTATGTTGCC CGTTTGTCCT | 480 |
| CTAATTCCAG GATCATCAAC CACCAGCACG GGACCATGCA AGACCTGCAC AACTCCTGCT | 540 |
| CAAGGAACCT CTATGTTTCC CTCATGTTGC TGTACAAAAC CTATGGATGG AAACTGCACC | 600 |
| TGTATTCCCA TCCCATCATC TTGGGCTTTC GCAAAATACC TATGGGAGTG GGCCTCAGTC | 660 |
| CGTTTCTCTT GGCTCAGTTT ACTAGTGCCA TTTGTTCAGT GGTTCGTAGG CTTTCCCCC | 720 |
| ACTGTCTGGC TTTCAGTTAT ATGGATGATG TGGTATTGGG GGCCAAGTCT GTACAACATC | 780 |
| TTGAGTCCCT TTATGCCGCT GTTACCAATT TTCTTTTGTC TTTGGGTATA CATTTAAACC | 840 |
| CTAACAAAAC AAAAAGATGG GGATATTCCC TTAACTTCAT GGGATATGTA ATTGGGAGTT | 900 |
| GGGGCACATG GCCACAGGAT CATATTGTAC AAAACTTCAA ACTATGTTTT AGAAAACTTC | 960 |
| CTGTAAACAG GCCTATTGAT TGGAAAGTTT GTCAACGAAT TGTGGGTCTT TTGGGGTTTG | 1020 |
| CTGCCCCTTT TACGCAATGT GGATATCCTG CTTTAATGCC TTTATATGCA TGTATACAAG | 1080 |
| CAAAACAGGC TTTTACTTTC TCGCCAACTT ACAAGGCCTT TCTCAGTAAA CAGTATATGA | 1140 |
| CCCTTTACCC CGTTGCTCGG CAACGGCCTG GTCTGTGCCA AGTGTTTGCT GACGCAACCC | 1200 |
| CCACTGGTTG GGGCTTGGCC ATAGGCCATC AGCGCATGCG TGGAACCTTT GTGTCTCCTC | 1260 |

```
TGCCGATCCA TACTGCGGAA CTCCTAGCCG CTTGTTTTGC TCGCAGCAGG TCTGGAGCAA      1320

ACCTCATCGG GACCGACAAT TCTGTCGTAC TCTCCCGCAA GTATACATCG TTTCCATGGC      1380

TGCTAGGCTG TGCTGCCAAC TGGATCCTGC GCGGGACGTC CTTTGTTTAC GTCCCGTCGG      1440

CGCTGAATCC CGCGGACGAC CCCTCCCGGG GCCGCTTGGG GCTCTACCGC CCGCTTCTCC      1500

GTCTGCCGTA CCGTCCGACC ACGGGGCGCA CCTCTCTTTA CGCGGACTCC CCGTCTGTGC      1560

CTTCTCATCT GCCGGACCGT GTGCACTTCG CTTCACCTCT GCACGTCGCA TGGAGACCAC      1620

CGTGAACGCC CACCGGAACC TGCCCAAGGT CTTGCATAAG AGGACTCTTG GACTTTCAGC      1680

AATGTCAACG ACCGACCTTG AGGCATACTT CAAAGACTGT GTGTTTAATG AGTGGGAGGA      1740

GCTGGGGGAG GAGATTAGGT TAAAGGTCTT TGTACTCGGA GGCTGTAGGC ATAAATTGGT      1800

CTGTTCACCA GCACCATGCA ACTTTTTCAC CTCTGCCTAG TCATCTCTTG TTCATGTCCT      1860

ACTGTTCAAG CCTCCAAGCT GTGCCTTGGG TGGCTTTGGG GCATGGACAT TGACCCCTAT      1920

AAAGAATTTG GAGCTACTGT GGAGTTACTC TCTTTTTTGC CTTCTGACTT CTTTCCGTCG      1980

GTGCGGGACC TCCTAGATAC CGTCTCTGCT CTGTATCGGG AAGCCTTAAA ATCTCCTGAG      2040

CATTGCTCAC CTCACCACAC AGCACTCAGG CAAGCTATTC TGTGCTGGGG GGAATTAATG      2100

ACTCTAGCTA CCTGGGTGGG TAATAATTTG GAAGATCCAG CATCCCGGGA TCTAGTAGTC      2160

AATTATGTTA ACACTAACAT GGGCCTAAAG ATCAGGCAAC TATGGTGGTT TCACATTTCC      2220

TGTCTTACTT TTGGAAGAGA AACTGTTCTG GAATATTTGG TATCTTTTGG AGTGTGGATT      2280

CGCACTCCTC CTGCCTACAG ACCACCAAAT GCCCCTATCT TATCAACACT TCCGGAAACT      2340

ACTGTTGTTA GACGACGAGG CAGGTCCCCT AGAAGAAGAA CTCCCTCGCC TCGCAGACAA      2400

AGGTCTCAAT CACCGCGTCG CAGAAGATCT CAATCTCGGG AATCCCAATG TTAGTATCAG      2460

TTGGACTCAT AAGGTGGGAA ACTTTACGGG GCTTTATTCT TCTACAGTAC CTGTCTTTAT      2520

TCCTGAATGG CAAACTCCTT CTTTTCCAGA CATTCATTTA CAGGAGGACA TTGTTGATAG      2580

ATGTAAGCAA TTTGTGGGAC CCCTTACAGT AAATGAAAAC AGGAGACTAA AATTAATACC      2640

GCCTGCTAGA TTTTATCCCA ATGTTACCAA ATATTTGCCC TTAGATAAAG GTATCAAACC      2700

TTATTATCCA GAGCATGTAG TTAATCATTA CTTCCAGACT AGACATTATT TGCATACTCT      2760

TTGGAAGGCG GGTATCTTAT ATAAAAGAGA GTCAACACAT AGCGCCTCAT TTTGCGGGAG      2820

ACCTTATTCT TGGGAACAAG ATCTACAGCA TGGGAGGTTG GTCTTCCAAA CCTCGAAAAG      2880

GCATGGGGAC AAATCTTTCT GTCCCCAATC CCCTGGGATT CTTCCCCGAT CATCAGTTGG      2940

ACCCTGCATT CAAAGCCAAC TCAGAAAATC CAGATTGGGA CCTCAACCCA CACAAGGACA      3000

ACTGGCCGGA CGCCCACAAG GTGGGAGTGG GAGCATTCGG GCCAGGATTC ACCCCTCCCC      3060

ATGGGGACT GTTGGGGTGG AGCCCTCAGG CTCAGGGCAT ACTCACATCT GTGCCAGCAG      3120

CTCCTCCTCC TGCCTCCACC AATCGGCAGT CAGGACGGCA GCCTACTCCC CTATCTCCAC      3180

CTCTAAGGGA CACTCATCCT CAGGCCATGC AGTGG                                3215
```

(2) INFORMATION FOR SEQ ID NO: 287:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 287:

```
AACTCCACCA CTTTCCACCA AACTCTTCAA GATCCCGGAG TCAGGGCCCT GTACTTTCCT      60
GCTGGTGGCT CCAGTTCAGG AACAGTGAGC CCTGCTCAGA ATACTGTCTC TGCCATATCG     120
TCAATCTTAT CGAAGACTGG GGACCCTGTA CCGAACATGG AGAACATCGC ATCAGGACTC     180
CTAGGACCCC TGCTCGTGTT ACAGGCGGGG TTTTTCTTGT TGACAAAAAT CCTCACAATA     240
CCACAGAGTC TAGACTCGTG GTGGACTTCT CTCAATTTTC TAGGGGGAAC ACCCGTGTGT     300
CTTGGCCAAA ATTCGCAGTC CCAAATCTCC AGTCACTCAC CAACCTGTTG TCCTCCAATT     360
TGTCCTGGTT ATCGCTGGAT GTGTCTGCGG CGTTTTATCA TCTTCCTCTG CATCCTGCTG     420
CTATGCCTCA TCTTCTTGTT GGTTCTTCTG GACTATCAAG GTATGTTGCC CGTTTGTCCT     480
CTAATTCCAG GATCATCAAC AACCAGCACC GGACCATGCA AAACCTGCAC AACTCCTGCT     540
CAAGGAACCT CTATGTTTCC CTCATGTTGC TGTACAAAAC CTACGGATGG AAACTGCACC     600
TGTATTCCCA TCCCATCATC TTGGGCTTTC GCAAAATACC TATGGGAGTG GGCCTCAGTC     660
CGTTTCTCTT GGCTCAGTTT ACTAGTGCCA TTTGTTCAGT GGTTCGTAGG GCTTTCCCCC     720
ACTGTCTGGC TTTCAGTTAT ATGGATGATA TGGTTTTGGG GGCCAAGTCT GTACAACATC     780
TTGAGTCCCT TTATGCCGCT GTTACCAATT TTCTTTTGTC TTTGGGTATA CATTTAAACC     840
CTCACAAAAC AAAAGATGG GGATATTCCC TTAACTTCAT GGGATATGTA ATTGGGAGCT      900
GGGGCACATT GCCACAGGAA CATATTGTAC AAAAAATCAA AATGTGGTTT AGGAAACTTC     960
CTGTAAACAG GCCTATTGAT TGGAAAGTAT GTCAACGAAT TGTGGGTCTT TTGGGGTTTG    1020
CCGCCCCTTT CACGCAATGT GGATATCCTG CTTTAATGCC TTTATATGCA TGTATACAAG    1080
CAAAACAGGC TTTTACTTTC TCGCCAACTT ACAAGGCCTT TCTAACTAAA CAGTATCTGA    1140
ACCTTTACCC CGTTGCTCGG CAACGGCCAG GTCTGTGCCA AGTGTTTGCT GACGCAACCC    1200
CCACTGGTTG GGGCTTGGCC ATAGGCCATC AGCGCATGCG TGGAACCTTT GTGTCTCCTC    1260
TGCCGATCCA TACTGCGGAA CTCCTAGCCG CTTGTTTTGC TCGCAGCCGG TCTGGGGCAA    1320
AACTCATCGG GACTGACAAT TCTGTCGTGC TCTCCCGCAA GTATACATCA TTTCCATGGC    1380
TGCTAGGCTG TGCTGCCAAC TGGATCCTGC GCGGGACGTC CTTTGTTTAC GTCCCGTCGG    1440
CGCTGAATCC CGCGGACGAC CCTTCCCGGG GCCGCTTGGG GCTCTACCGC CCGCTTCTCC    1500
GCCTGTTGTA CCGACCGACC ACGGGGCGCA CCTCTCTTTA CGCGGACTCC CCGTCTGTGC    1560
CTTCTCATCT GCCGGACCGT GTGCACTTCG CTTCACCTCT GCACGTCGCA TGGAGACCGC    1620
CGTGAACGCC CACGGGAACC TGCCCAAGGT CTTGCATAAG AGGACTCTTG GACTTTCAGC    1680
AATGTCAACG ACCGACCTTG AGGCATACTT CAAAGACTGT GTGTTTAATG AGTGGGAGGA    1740
GTTGGGGGAG GAGGTTAGGT TAAAGGTCTT TGTACTAGGA GGCTGTAGGC ATAAATTGGT    1800
GTGTTCACCA GCACCATGCA ACTTTTTCAC CTCTGCCTAA TCATCTCATG TTCATGTCCT    1860
ACTGTTCAAG CCTCCAAGCT GTGCCTTGGG TGGCTTTGGG GCATGGACAT TGACCCGTAT    1920
AAAGAATTTG GAGCTTCTGT GGAGTTACTC TCTTTTTTGC CTTCTGACTT CTTTCCGTCG    1980
GTGCGAGATC TCCTCGACAC CGCCTCTGCT TTGTATCGGG AGGCCTTAGA GTCTCCGGAA    2040
CATTGTTCAC CTCACCATAC GGCACTCAGG CAAGCTATTC TGTGTTGGGG TGAGTTAATG    2100
AATCTAGCCA CCTGGGTGGG AAGTAATTTG GAAGATCCGG CATCCAGGGA ATTAGTAGTC    2160
AGCTATGTCA ACGTTAATAT GGGCCTAAAA ATCAGACAAC TATTGTGGTT TCACATTTCC    2220
```

```
TGTCTTACTT TGGGAGAGA AACTGTTCTT GAATATTTGG TGTCTTTTGG AGTGTGGATT    2280

CGCACTCCTC CTGCATATAG ACCACCAAAT GCCCCTATCT TATCAACACT TCCGGAAACT    2340

ACTGTTGTTA GACGAAGAGG CAGGTCCCCT AGAAGAAGAA CTCCCTCGCC TCGCAGACGA    2400

AGGTCTCAAT CGCCGCGTCG CAGAAGATCT CAATCTCGGG AATCTCAATG TTAGTATTCC    2460

TTGGACACAT AAGGTGGGAA ACTTTACGGG GCTTTATTCT TCTACGGTAC CTTGCTTTAA    2520

TCCTAAATGG CAAACTCCTT CTTTTCCTGA CATTCATTTG CAGGAGGACA TTGTTGATAG    2580

ATGTAAGCAA TTTGTGGGGC CCCTTACAGT AAATGAAAAC AGGAGACTAA AATTAATTCC    2640

GCCCGCTAGG TTTTATCCCA ATGTTACTAA ATATTTGCCC TTAGATAAAG GGATCAAAAA    2700

GTATTATCCA GAGTATGTAG TTAATCATTA CTTCCAGACG CGACATTATT TACACACTCT    2760

TTGGAAGGCG GGGATCTTAT ATAAAAGAGA GTCCACACGT AGCGCCTCAT TTTGCGGGTC    2820

ACCATATTCT TGGGAACAAG ATCTACAGCA TGGGAGGTTG GTCTTCCAAA CCTCGAAAAG    2880

GCATGGGGAC AAATCTTTCT GTCCCCAATC CTCTGGGATT CTTCCCCGAT CATCAGTTGG    2940

ACCCTGCATT CAAAGCCAAC TCAGAAAATC CAGATTGGGA CCTCAACCCG AACAAGGACA    3000

ACTGGCCGGA CGCCAACAAG GTGGGAGTGG GAGCATTCGG GCCAGGGTTC ACCCCTCCCC    3060

ATGGGGGACT GTTGGGGTGG AGCCCTCAGG CTCAGGGCCT ACTCACAACT GTGCCAGCAG    3120

CTCCTCCTCC TGCCTCCACC AATCGGCAGT CAGGAAGGCA GCCTACTCCC TTATCCCCAC    3180

CTCTAAGGGA CACTCATCCT CAGGCCATGC AGTGG                              3215

(2) INFORMATION FOR SEQ ID NO: 288:

(i) SEQUENCE CHARACTERISTICS:
        (A) LENGTH: 3213 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 288:

AACTCCACCA CATTTCACCA AGTCCTGCTA GATCCCAGAG TGAGGGGCCT ATATTTTCCT      60

CCTGGTGGCT CCAGTTCCGG AACAGTAAAC CCTGTTGCGA CTACTGCCTC ACCCATATCT     120

TCAATCTCCT CGAGGACTGG GGACCCTGCA CCGAACATGG AGAGCACAAC ATCAGGATTG     180

CTAGGACCCC TGCTCGTGTT ACAGGCGGGG TTTTTCTTGT TGACAAGAAT CCTCACAATC     240

CCACAGAGTC TAGACTCGTG GTGGACTTCT CTCAATTTTC TAGGGGGAGC ACCCACGTGA     300

CCTGGCCAAA ATTCGCAGTC CCCAACCTCC AATCACTCAC CAACCTCTTG TCCTCCAATT     360

TGTCCTGGCT ATCGCTGGAT GTGTCTGCGG CGTTTTATCA TATTCCTCTT CATCCTGCTT     420

CTATGCCTCA TCTTCTTGTT GGTTCTTCTG GACTACCAAG GTATGTTGCC CGTTTGTCCG     480

CTACTTCCAG GAACATCAAC CACCAGCACG GGACCATGCA AGACCTGCAC GATTCCTGCT     540

CAAGGAACCT CTATGTTTCC CTCTTGTTGC TGTACAAAAC CTTCGGACGG AAACTGCACT     600

TGTATTCCCA TCCCATCATC CTGGGCTTTC GCAAGATTCC TATGGGAGGG GGCCTCAGTC     660

CGTTTCTCCT GGCTCAGTTT ACTAGTGCCA TTTGTTCAGT GGTTCGTAGG GCTTTCCCCC     720

ACTGTTTGGC TTTCAGTTAT ATGGATGATG TGGTATTGGG GGCCAAGTCT GTACAACATC     780

TTGAGTCCCT TTTTACCTCT ATTACCAATT TTCTTTTGTC TTTGGGTATA CATTTGAACC     840
```

```
CTAATAAAAC CAAACGTTGG GGCTACTCCC TTAACTTCAT GGGATATGTA ATTGGCAGTT      900
GGGGTACTTT ACCGCAAGAA CATATTGTAC TAAAAATCAA GCAATGTTTT CGGAAACTGC      960
CTGTAAATAG ACCTATTGAC TGGAAAGTAT GTCAAAGAAT TGTGGGTCTT TTGGGCTTTG     1020
CTGCCCCTTT TACACAATGT GGCTATCCTG CCTTAATGCC TTTATATGCA TGTATACAAT     1080
CTAAGCAGGC TTTCACTTTC TCGCCAACTT ACAAGGCCTT TCTGTGTAAA CAATATCTGC     1140
ACCTTTACCC CGTTGCCCGG CGAACGGCTC TCTGCCAAGT ATTTGCTGAC GCAACCCCCA     1200
CTGGATGGGG CTTGGCCATA GGCCATCGGC GCATGCGTGG AACCTTTGTG GCTCCTCTGC     1260
CGATCCATAC TGCGGAACTC CTAGCAGCTT GTTTTGCTCG CAGCCGGTCT GGAGCGAAAC     1320
TCATCGGGAC TGACAACTCG GTTGTTCTCT CTCGGAAATA CACCTCATTC CCATGGCTGC     1380
TCGGGTGTGC TGCCAACTGG ATCCTGCGCG GGACGTACTT TGTTTACGTC CCGTCGGCTC     1440
TGAATCCCGC GGACGACCCG TCTCGCGGCC GTTTGGGCCT CATCCGTCCC CTTCTTCATC     1500
TGCGGTTCCG GCCGACCACG GGGCGCACCT CTCTTTACGC GGTCTCCCCG TCTGTGCCTT     1560
CTCATCTGCC GGACCGTGTG CACTTCGCTT CACCTCTGCA CGTCGCATGG AGACCACCGT     1620
GAACGCCGAT CAGGTCTTGC CCAAGGTCTT ACATAAGAGG ACTCTTGGAC TCTCAGCAAT     1680
GTCAACGTCC GACCTTGAGG CATACTTCAA AGACTGCTTG TTTAAAGACT GGGAGGACTT     1740
GGGGGAGGAG ATTAGGTTAA TGATCTTTGT ACTAGGAGGC TGTAGGCATA AATTGGTCTG     1800
TTCACCAGCA CCATGCAACT TTTTTCACCT CTGCCTAATC ATCTCATGTT CATGTCCTAC     1860
TGTTCACGCC TCCAAGCTGT GCCTTGGGTG GCTTTGGGGC ATGGACATTG ACCCGTATAA     1920
AGAATTTGGA GCTTCTGTGG AGTTACTCTC TTTTTTGCCT TCTGATTTCT TTCCTTCCAT     1980
TCGAGATCTC CTCGACACCG CCTCTGCTCT GTATAGGGAG GCCTTAGAGT CTCCGGAACA     2040
TTGTTCACCT CATCATACAG CACTCAGGCA AGCTATTCTG TGTTGGGGTG AGTTGATGAA     2100
TCTGGCCACC TGGGTGGGAA GTAATTTGGA AGACCCAGCA TCCAGGGAAC TAGTAGTCAG     2160
CTATGTCAAT GTTAATATGG GCCTAAAAAT CAGACAACTA TTGTGGTTTC ACATTTCCTG     2220
CCTTACTTTT GGAAGAGAAA CTGTTTTGGA GTATTTGGTA TCTTTTGGAG TGTGGATTCG     2280
CACTCCTCCC GCTTACAGAC CACCAAATGC CCCTATCTTA TCAACACTTC CGGAAACTAC     2340
TGTTGTTAGA CGACGAGGCA GGTCCCCTAG AAGAAGAACT CCCTCGCCTC GCAGACGAAG     2400
ATCTGAATCG CCGCGTCGCA GAAGATCTCA ATCTCGGGAA TCTCAATGTT AGTATCCCTT     2460
GGACTCATAA GGTGGGAAAC TTTACTGGGC TTTATTCTTC TACTGTACCT GTCTTTAATC     2520
CTGAGTGGCA AACTCCCTCC TTTCCTCACA TTCATTTACA GGAGGACATT ATTAATAGAT     2580
GTCAACAATA TGTGGGCCCT CTTACAGTTA ATGAAAAAAG GAGATTAAAA TTAATTATGC     2640
CTGCTAGGTT TTATCCTAAA CTTACCAAAT ATTTGCCCTT GGATAAAGGC ATTAAACCTT     2700
ATTATCCTGA ACATGCAGTT AATCATTACT TCAAAACTAG GCATTATTTA CATACTCTGT     2760
GGAAGGCGGG CATTCTATAT AAGAGAGAAA CTACACGCAG CGCCTCATTT TGTGGGTCAC     2820
CATATTCTTG GGAACAAGAG CTACAGCATG GGAGGTTGGT CTTCCAAACC TCGACAAGGC     2880
ATGGGGACGA ATCTTTCTGT TCCCAATCCT CTGGGATTCT TTCCCGATCA CCAGTTGGAC     2940
CCTGCGTTCG GAGCCAACTC AAACAATCCA GATTGGGACT TCAACCCCAA CAAGGATCGT     3000
TGGCCAGAGG CAAATCAGGT AGGAGCGGGA GCATTCGGGC CAGGGTACCC CCCACCACAC     3060
GGCGGTCTTT TGGGGTGGAG CCCTCAGGCT CAGGGCATAT TGACAACCGT GCCAGCAGCA     3120
CCTCCTCCTG CCTCCACCAA TCGGCAGTCA GGAAGACAGC CTACTCCCAT CTCTCCACCT     3180
CTAAGAGACA GTCATCCTCA GGCCATGCAG TGG                                  3213
```

(2) INFORMATION FOR SEQ ID NO: 289:

(i) SEQUENCE CHARACTERISTICS:
        (A) LENGTH: 3213 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 289:

```
AACTCCACCA CATTTCACCA AGTCCTGCTA GATCCCAGAG TGAGGGGCCT ATATTTTCCT      60
CCTGGTGGCT CCAGTTCCGG AACAGTAAAC CCTGTTCCGA CTACTGCCTC ACCCATATCG     120
TCAATCTCCT CGAGGACTGG GGACCCTGCA CCGAACATGG AGAGCACAAC ATCAGGATTC     180
CTAGGACCCC TGCTCGTGTT ACAGGCGGGG TTTTTCTTGT TGACAAGAAT CCTCACAATA     240
CCACAGAGTC TAGACTCGTG GTGGACTTCT CTCAATTTTC TAGGGGAGC  ACCCACGTGT     300
CCTGGCCAAA ATTCGCAGTC CCCAACCTCC AATCACTCAC CAACCTCTTG TCCTCCAATT     360
TGTCCTGGCT ATCGCTGGAT GTGTCTGCGG CGTTTTATCA TATTCCTCTT CATCCTGCTG     420
CTATGCCTCA TCTTCTTGTT GGTTCTTCTG GACTACCAAG GTATGTTGCC CGTTTGTCCT     480
CTACTTCCAG GAACATCAAC CACCAGCACG GGACCATGCA AGACCTGCAC GATTCCTGCT     540
CAAGGAACCT CTATGTTTCC CTCTTGTTGC TGTACAAAAC CTTCGGACGG AAACTGCACT     600
TGTATTCCCA TCCCATCATC CTGGGCTTTC GCAAGATTCC TATGGGAGGG GGCCTCAGTC     660
CGTTTCTCCT GGCTCAGTTT ACTAGTGCCA TTTGTTCAGT GGTTCGTAGG GCTTTCCCCC     720
ACTGTTTGGC TTTCAGTTAT ATGGATGATG TGGTATTGGG GGCCAAGTCT GTACAACATC     780
TTGAGTCCCT TTTTACCTCT ATTACCAATT TTCTTTTGTC TTTGGGTATA CATTTGAACC     840
CTAATAAAAC CAAACGTTGG GGCTACTCCC TTAACTTCAT GGGATATGTA ATTGGCAGTT     900
GGGGTACTTT ACCGCAAGAA CATATTGTAC TAAAAATCAA GCAATGTTTT CGGAAACTGC     960
CTGTAAATAG ACCTATTGAC TGGAAAGTAT GTCAAAGAAT TGTGGGTCTT TTGGGCTTTG    1020
CTGCCCCTTT TACACAATGT GGCTATCCTG CCTTAATGCC TTTATATGCA TGTATACAAT    1080
CTAAGCAGGC TTTCACTTTC TCGCCAACTT ACAAGGCCTT TCTGTGTAAA CAATATCTGC    1140
ACCTTTACCC CGTTGCCCGG CGAACGGCTC TCTGCCAAGT ATTTGCTGAC GCAACCCCCA    1200
CTGGATGGGG CTTGGCCATA GGCCATCGGC GCATGCGTGG AACCTTTGTG GCTCCTCTGC    1260
CGATCCATAC TGCGGAACTC CTAGCAGCTT GTTTTGCTCG CAGCCGGTCT GGAGCGAAAC    1320
TCATCGGGAC TGACAACTCG GTTGTTCTCT CTCGGAAATA CACCTCATTC CCATGGCTGC    1380
TCGGGTGTGC TGCCAACTGG ATCCTGCGCG GGACGTACTT TGTTTACGTC CCGTCGGCGC    1440
TGAATCCCGC GGACGACCCG TCTCGCGGCC GTTTGGGCCT CATCCGTCCC CTTCTTCATC    1500
TGCGGTTCCG GCCGACCACG GGGCGCACCT CTCTTTACGC GGTCTCCCCG TCTGTGCCTT    1560
CTCATCTGCC GGACCGTGTG CACTTCGCTT CACCTCTGCA CGTCGCATGG AGACCACCGT    1620
GAACGCCGAT CAGGTCTTGC CCAAGGTCTT ACATAAGAGG ACTCTTGGAC TCTCAGCAAT    1680
GTCAACGTCC GACCTTGAGG CATACTTCAA AGACTGCTTG TTTAAAGACT GGGAGGACTT    1740
GGGGGAGGAG ATTAGGTTAA TGATCTTTGT ACTAGGAGGC TGTAGGCATA AATTGGTCGT    1800
TTCACCAGCA CCATGCAACT TTTTTCACCT CTGCCTAATC ATCTCATGTT CATGTCCTAC    1860
```

```
TGTTCACGCC TCCAAGCTGT GCCTTGGGTG GCTTTGGGGC ATGGACATTG ACCCGTATAA    1920

AGAATTTGGA GCTTCTGTGG AGTTACTCTC TTTTTTGCCT TCTGATTTCT TTCCTTCCAT    1980

TCGAGATCTC CTCGACACCG CCTCTGCTCT GTATAGGGAG GCCTTAGAGT CTCCGGAACA    2040

TTGTTCACCT CATCATACAG CACTCAGGCA AGCTATTCTG TGTTGGGGTG AGTTGATGAA    2100

TCTGGCCACC TGGGTGGGAA GTAATTTGGA AGACCCAGCA TCCAGGGAAC TAGTAGTCAG    2160

CTATGTCAAT GTTAATATGG GCCTAAAAAT CAGACAACTA TTGTGGTTTC ACATTTCCTG    2220

CCTTACTTTT GGAAGAGAAA CTGTTTTGGA GTATTTGGTA TCTTTTGGAG TGTGGATTCG    2280

CACTCCTCCC GCTTACAGAC CACCAAATGC CCCTATCTTA TCAACACTTC CGGAAACTAC    2340

TGTTGTTAGA CGACGAGGCA GGTCCCCTAG AAGAAGAACT CCCTCGCCTC GCAGACGAAG    2400

ATCTGAATCG CCGCGTCGCA GAAGATCTCA ATCTCGGGAA TCTCAATGTT AGTATCCCTT    2460

GGACTCATAA GGTGGGAAAC TTTACTGGGC TTTATTCTTC TACTGTACCT GTCTTTAATC    2520

CTGAGTGGCA AACTCCCTCC TTTCCTCACA TTCATTTACA GGAGGACATT ATTAATAGAT    2580

GTCAACAATA TGTGGGCCCT CTTACAGTTA ATGAAAAAAG GAGATTAAAA TTAATTATGC    2640

CTGCTAGGTT TTATCCTAAA CTTACCAAAT ATTTGCCCTT GGATAAAGGC ATTAAACCTT    2700

ATTATCCTGA ACATGCAGTT AATCATTACT TCAAAACTAG GCATTATTTA CATACTCTGT    2760

GGAAGGCGGG CATTCTATAT AAGAGAGAAA CTACACGCAG CGCCTCATTT TGTGGGTCAC    2820

CATATTCTTG GAACAAGAG CTACAGCATG GGAGGTTGGT CTTCCAAACC TCGACAAGCG    2880

ATGGGACGA ATCTTTCTGT TCCCAATCCT CTGGGATTCT TTCCCGATCA CCAGTTGGGT    2940

CCTGCGTTCG GAGCCAACTC AAACAATCCA GATTGGGACT TCAACCCCAA CAAGGATCAC    3000

TGGCCAGAGG CAAATCAGGT AGGAGCGGGA GCATTCGGGC CAGGGTACCC CCCACCACAC    3060

GGCGGTCTTT TGGGGTGGAG CCCTCAGGCT CAGGGCATAT TGACAACCGT GCCAGCAGCA    3120

CCTCCTCCTG CCTCCACCAA TCGGCAGTCA GGAAGACAGC CTACTCCCAT CTCTCCACCT    3180

CTAAGAGACA GTCATCCTCA GGCCATGCAG TGG                                 3213

(2) INFORMATION FOR SEQ ID NO: 290:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 290:

AACTCCACAA CATTCCACCA AGCTCTGCTA GATCCCAGAG TGAGGGGCCT ATATTTTCCT      60

GCTGGTGGCT CCAGTTCCGG AACAGTAAAC CCTGTTCCGA CTACTGTCTC ACCCATATCG     120

TCAATCTTCT CGAGGACTGG GGACCCTGCA CCGAACATGG AGAGCACAAC ATCAGGATTC     180

CTAGGACCCC TGCTCGTGTT ACAGGCGGGG TTTTTCTTGT TGACAAGAAT CCTCACAATA     240

CCACAGAGTC TAGACTCGTG GTGGACTTCT CTCAATTTTC TAGGGGAGC ACCCACGTGT      300

CCTGGCCAAA ATTCGCAGTC CCCAACCTCC AATCACTCAC CAACCTCTTG TCCTCCAATT     360

TGTCCTGGTT ATCGCTGGAT GTGTCTGCGG CGTTTTATCA TATTCCTCTT CATCCTGCTG     420

CTATGCCTCA TCTTCTTGTT GGTTCTTCTG GACTACCAAG GTATGTTGCC CGTTTGTCCT     480
```

```
                                                        -continued

CTACTTCCAG GAACATCAAC TACCAGCACG GGACCATGCA AGACCTGCAC GATTCCTGCT        540

CAAGGAACCT CTATGTTTCC CTCTTGTTGC TGTACAAAAC CTTCGGACGG AAACTGCACT        600

TGTATTCCCA TCCCATCATC CTGGGCTTTC GCAAGATTCC TATGGGAGTG GGCCTCAGTC        660

CGTTTCTCCT GGCTCAGTTT ACTAGTGCCA TTTGTTCAGT GGTTCGCAGG GCTTTCCCCC        720

ACTGTTTGGC TTTCAGTTAT ATGGATGATG TGGTATTGGG GGCCAAGTCT GTACAACATC        780

TTGAGTCCCT TTTTACCTCT ATTACCAATT TTCTTTTGTC TTTGGGTATA CATTTGAACC        840

CTAATAAAAC CAAACGTTGG GGCTACTCCC TTAACTTCAT GGGATATGTA ATTGGAAGTT        900

GGGGTACTTT ACCACAGGAA CATATTGTAT TAAAACTCAA GCAATGTTTT CGAAAACTGC        960

CTGTAAATAG ACCTATTGAT TGGAAAGTAT GTCAAAGAAT TGTGGGTCTT TTGGGCTTTG       1020

CTGCCCCTTT TACACAATGT GGCTATCCTG CCTTGATGCC TTTGTATGCA TGTATACAAT       1080

CTAAGCAGGC TTTCACTTTC TCGCCAACTT ATAAGGCCTT TCTGTGTCAA CAATACCTGC       1140

ACCTTTACCC CGTTGCCCGG CAACGGTCAG GTCTCTGCCA AGTGTTTGCT GACGCAACCC       1200

CCACTGGATG GGGCTTGGCC ATAGGCCATC GGCGCATGCG TGGAACCTTT GTGGTTCCTC       1260

TGCCGATCCA TACTGCGGAA CTCCTAGCAG CTTGTTTTGC TCGCGACCGG TCTGGAGCAA       1320

AACTTATCGG GACTGACAAC TCGGTTGTCC TCTCTCGGAA ATACACCTCC TTCCCATGGC       1380

TGCTCGGGTG TGCTGCCAAC TGGATCCTGC GCGGGACGTC CTTTGTCTAC GTCCCGTCGG       1440

CGCTGAATCC CGCGGACGAC CCGTCTCGGG GCCGTTGGG CCTCTACCGT CCCTTGCTTT       1500

CTCTGCCGTT CCAGCCGACC ACGGGGCGCA CCTCTCTTTA CGCGGTCTCC CCGTCTGTGC       1560

CTTCTCATCT GCCGGACCGT GTGCACTTCG CTTCACCTCT GCACGTCGCA TGGAGACCAC       1620

CGTGAACGGC CACCAGGTCT TGCCCAAGCT CTTACATAAG AGGACTCTTG GACTCTCAGC       1680

AATGTCAACA ACCGACCTTG AGGCATACTT CAAAGACTGT TTGTTTAAAG ACTGGGAGGA       1740

GTTGGGGGAG GAGATTAGGT TAAAGGTCTT TGTACTAGGA GGCTGTAGGC ATAAATTGGT       1800

CTGTTCACCA GCACCATGCA ACTTTTTCAC CTCTGCCTAA TCATCTCATG TTCATGTCCT       1860

ACTGTTCAAG CCTCCAAGCT GTGCCTTGGG TGGCTTTGGG GCATGGACAT TGACCCGTAT       1920

AAAGAATTTG GAGCTTCTGT GGAGTTACTC TCTTTTTTGC CTTCTGACTT CTTTCCTTCT       1980

ATTCGAGATC TCCTCGACAC CGCCTCTGCT CTGTATCGGG AGGCCTTAGA GTCTCCGGAA       2040

CATTGTTCAC CTCACCATAC AGCACTCAGG CAAGCTATTC TGTGTTGGGG TGAGTTGATG       2100

AATTTGGCCA CCTGGGTGGG AAGTAATTTG GAAGACCCAG CATCCAGGGA ATTAGTAGTC       2160

AGCTATGTCA ATGTTAATAT GGGCCTAAAA ATCAGACAAC TATTGTGGTT TCATATTTCC       2220

TGTCTTACTT TTGGAAGAGA AACTGTTCTT GAGTATTTGG TGTCTTTTGG AGTGTGGATT       2280

CGCACTCCTC CCGCTTACAG ACCACCAAAT GCCCCTATCT TATCAACACT TCCGGAAACT       2340

ACTGTTGTTA GACGACGAGG CAGGTCCCCT AGAAGAAGAA CTCCCTCGCC TCGCAGACGA       2400

AGGTCTCAAT CGCCGCGTCG CAGAAGATCT CAATCTCGGG AATCTCAATG TTAGTATCCC       2460

TTGGACTCAT AAGGTGGGAA ACTTTACTGG GCTTTATTCT TCTACTGTAC CTGTCCTTAA       2520

TCCTGAGTCC CAAACTCCCT CCTTTCCTAA CATTCATTTA CAGGAGGACA TTATTAATAG       2580

ATGTCAACAA TATGTGGGCC CTCTTACAGT TAATGAAAAA AGGAGATTAA AATTAATTAT       2640

GCCTGCTAGG TTCTATCCTA ACCTTACCAA ATATTTGCCC TTGGATAAAG GCATTAAACC       2700

TTATTATCCT GAACATGCAG TTAATCATTA CTTCAAAACT AGGCATTATT TACATACTCT       2760

GTGGAAGGCT GGCATTCTAT ATAAAAGAGA AACTACACGC AGCGCTTCAT TTTGTGGGTC       2820
```

```
ACCATATTCT TGGGAACAAG AGCTACGGCA TGGGAGGTTG GTCTTCCAAA CCTCGACAAG    2880

GCATGGGGAC GAATCTTTCT GTTCCCAATC CTCTGGGATT CTTTCCCGAT CACCAGTTGG    2940

ACCCTGCGTT CGGAGCCAAC TCAAACAATC CAGATTGGGA CTTCAACCCC AACAAGGATC    3000

ACTGGCCAGA GGCAATCAAG GTAGGAGCGG GAGACTTCGG GCCAGGGTTC ACCCCACCAC    3060

ACGGCGGTCT TTTGGGGTGG AGCCCTCAGG CTCAGGGCAT ATTGACAACA GTGCCAGCAG    3120

CGCCTCCTCC TGTTTCCACC AATCGGCAGT CAGGAAGACA GCCTACTCCC ATCTCTCCAG    3180

CTCTAAGAGA CAGTCATCCT CAGGCCATGC AGTGG                               3215

(2) INFORMATION FOR SEQ ID NO: 291:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 291:

AACTCCACAA CATTCCACCA AGCTCTGCTA GATCCCAGAG TGAGGGGCCT ATATTTTCCT      60

GCTGGTGGCT CCAGTTCCGG AACAGTAAAC CCTGTTCCGA CTACTGCCTC ACCCATATCG     120

TCAATCTTCT CGAGGACTGG GGACCCTGCA CCGAACATGG AGAGCACAAC ATCAGGATTC     180

CTAGGACCCC TGCTCGTGTT ACAGGCGGGG TTTTTCTTGT TGACAAGAAT CCTCACAATA     240

CCACAGAGTC TAGACTCGTG GTGGACTTCT CTCAATTTTC TAGGGGAGC ACCCACGTGT      300

CCTGGCCAAA ATTCGCAGTC CCCAACCTCC AATCACTCAC CAACCTCTTG TCCTCCAATT     360

TGTCCTGGCT ATCGCTGGAT GTGTCTGCGG CGTTTTATCA TATTCCTCTT CATCCTGCTG     420

CTATGCCTCA TCTTCTTGTT GGTTCTTCTG GACTACCAAG GTATGTTGCC CGTTTGTCCT     480

CTACTTCCAG GAACATCAAC TACCAGCACG GGACCATGCA AGACCTGCAC GATTCCTGCT     540

CAAGGAACCT CTATGTTTCC CTCTTGTTGG TGTACAAAAC CTTCGGACGG AAACTGCACT     600

TGTATTCCCA TCCCATCATC CTGGGCTTTC GCAAGATTCC TATGGGAGTG GCCCTCAGTC     660

CGTTTCTCCT GGCTCAGTTT ACTAGTGCCA TTTGTTCAGT GGTTCGCAGG GCTTTCCCCC     720

ACTGTTTGGC TTTCAGTTAT ATGGATGATG TGGTATTGGG GGCCAAGTCT GTACAACATC     780

TTGAGTCCCT TTTTACCTCT ATTACCAATT TTCTTTTGTC TTTGGGTATA CATTTGAACC     840

CTAATAAAAC CAAACGTTGG GGCTACTCCC TTAACTTCAT GGGATATGTA ATTGGAAGTT     900

GGGGTACTTT ACCACAGGAA CATATTGTAT TAAAACTCAA GCAATGTTTT CGGAAACTGC     960

CTGTAAATAG ACCTATTGAT TGGAAAGTAT GTCAAAGAAT TGTGGGTCTT TTGGGCTTTG    1020

CTGCCCCTTT TACACAATGT GGCTATCCTG CCTTGATGCC TTTATATGCA TGTATACAAT    1080

CTAAGCAGGC TTTCACTTTC TCGCCAACTT ATAAGGCCTT TCTGTGTCAA CAATACCTGC    1140

ACCTTTACCC CGTTGCCCGG CAACGGTCAG GTCTCTGCCA AGTGTTTGGT GACGCAACCC    1200

CCACTGGATG GGGCTTGGCC ATAGGCCATC GGCGCATGCG TGGAACCTTT GTGGCTCCTC    1260

TGCCGATCCA TACTGCGGAA CTCCTAGCAG CTTGTTTTGC TCGCAGCCGG TCTGGAGCAA    1320

AACTTATCGG GACTGACAAC TCTGTTGTCC TCTCTCGGAA ATACACCTCC TTCCCATGGC    1380

TGCTCGGGTG TGCTGCCAAC TGGATCCTGC GCGGGACGTC CTTTGTCTAC GTCCCGTCGG    1440
```

```
CGCTGAATCC CGCGGACGAC CCGTCTCGGG GCCGTTTGGG CCTCTACCGT CCCCTTCTTC      1500

ATCTGCCGTT CCAGCCGACC ACGGGGCGCA CCTCTCTTTA CGCGGTCTCC CCGTCTGTGC      1560

CTTCTCATCT GCCGGTCCGT GTGCACTTCG CTTCACCTCT GCACGTCGCA TGGAGACCAC      1620

CGTGAACGCC CACCAGGTCT TGCCTAAGCT CTTACATAAG AGGACTCTTG GACTCTCAGC      1680

AATGTCAACG ACCGACCTTG AGGCATACTT CAAAGACTGT TTGTTTAAAG ACTGGGAGGA      1740

GTTGGGGGAG GAGATTAGGT TAAAGGTCTT TGTACTAGGA GGCTGTAGGC ATAAATTGGT      1800

CTGTTCACCA GCACCATGCA ACTTTTTCAC CTCTGCCTAA TCATCTCATG TTCATGTCCT      1860

ACTGTTCAAG CCTCCAAGCT GTGCCTTGGG TGGCTTTGGG GCATGGACAT TGACCCGTAT      1920

AAAGAATTTG GAGCTTCTGT GGAGTTACTC TCTTTTTTGC CTTCTGACTT CTTTCCTTCT      1980

ATTCGAGATC TCCTCGACAC CGCCTCTGCT CTGTATCGGG AGGCCTTAGA GTCTCCGGAA      2040

CATTGTTCAC CTCACCATAC AGCACTCAGG CAAGCTATCC TGTGTTGGGG TGAGTTGATG      2100

AATTTGGCCA CCTGGGTGGG AAGTAATTTG GAAGACCCAG CATCCAGGGA ATTAGTAGTC      2160

AGCTATGTCA ATGTTAATAT GGGCCTAAAA ATCAGACAAC TATTGTGGTT TCACATTTCC      2220

TGTCTTACTT TTGGAAGAGA AACTGTTCTT GAGTATTTGG TGTCTTTTGG AGTGTGGACT      2280

CGCACTCCTC CCGCTTACAG ACCACCAAAT GCCCCTATCT TATCAACACT TCCGAAACT       2340

ACTGTTGTTA GACGACGAGG CAGGTCCCCT AGAAGAAGAA CTCCCTCGCC TCGCAGACGA      2400

AGGTCTCAAT CGCCGCGTCG CAGAAGATCT CAATCTCGGG AATCTCAATG TTAGTATCCC      2460

TTGGACTCAT AAGGTGGGAA ACTTTACTGG GCTTTATTCT TCTACTGTAC CTGTCTTTAA      2520

TCCTGAGTGC CAAACTCCCT CCTTTCCTAA CATTCATTTA CAAGAGGATA TTATTAATAG      2580

ATGTCAACAA TATGTGGGCC CTCTTACAGT TAATGAAAAA AGGAGATTAA AATTAATTAT      2640

GCCTGCTAGG TTCTATCCTA ACCTTACCAA ATATTTGCCC TTGGATAAAG GCATTAAACC      2700

TTATTATCCT GAACATGCAG TTAATCATTA CTTCAAAACT AGGCATTATT TACATACGCT      2760

GTGGAAGGCT GGCATTCTAT ATAAAAGAGA AACTACACGC AGCGCTTCAT TTTGTGGGTC      2820

ACCATATTCT TGGGAACAAG AGCTACAGCA TGGGAGGTTG GTCTTCCAAA CCTCGACAAG      2880

GCATGGGGAC GAATCTTTCT GTTCCCAATC CTCTGGGATT CTTTCCCGAT CACCAGTTGG      2940

ACCCTGCGTT CGGAGCCAAC TCAAACAATC CAGATTGGGA CTTCAACCCC AACAAGGATC      3000

ACTGGCCAGA CGGAATCAAG GTAGGAGCGG GAGACTTCGG GCCAGGGTTC ACCCCACCAC      3060

ACGGCGGTCT TTTGGGGTGG AGCCCTCAGG CTCAGGGCAT CTTGACAACA GTGCCAGCAG      3120

CTCCTCCTCC TGCCTCCACC AATCGGCAGT CAGGAAGACA GCCTACTCCC ATCTCTCCAC      3180

CTCTAAGAGA CAGTCATCCT CAGGCCATGC AGTGG                                3215
```

(2) INFORMATION FOR SEQ ID NO: 292:

(i) SEQUENCE CHARACTERISTICS:
    (A) LENGTH: 3215 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 292:

```
AACTCCACAA CATTCCACCA AGCTCTGCTA GATCCCAGAG TGAGGGGCCT ATATTTTCCT        60
```

-continued

```
GCTGGTGGCT CCAGTTCCGG AACAGTAAAC CCTGTTCCGA CTACTGCCTC ACCCATATCG    120

TCAATCTTCT CGAGGACTGG GGACCCTGCA CCGAACATGG AGAGCACAAC ATCAGGATTC    180

CTAGGACCCC TGCTCGTGTT ACAGGCGGGG TTTTTCTTGT TGACAAGAAT CCTCACAATA    240

CCACAGAGTC TAGACTCGTG GTGGACTTCT CTCAATTTTC TAGGGGGAGC ACCCACGTGT    300

CCTGGCCAAA ATTCGCAGTC CCCAACCTCC AATCACTCAC CAACCTCTTG TCCTCCAACT    360

TGTCCTGGCT ATCGCTGGAT GTGTCTGCGG CGTTTTATCA TATTCCTCTT CATCCTGCTG    420

CTATGCCTCA TCTTCTTGTT GGTTCTTCTG GACTACCAAG GTATGTTGCC CGTTTGTCCT    480

CTACTTCCAG GAACATCAAC TACCAGCACG GGACCATGCA GAACCTGCAC GATTCCTGCT    540

CAAGGAACCT CTATGTTTCC CTCTTGTTGC TGTACAAAAC CTTCGGACGG AAACTGCACT    600

TGTATTCCCA TCCCATCATC CTGGGCTTTC GCAAGATTCC TATGGGAGTG GCCTCAGTC    660

CGTTTCTCCT GGCTCAGTTT ACTAGTGCCA TTTGTTCAGT GGTTCGTAGG GCTTTCCCCC    720

ACTGTTTGGC TTTCAGCTAT ATGGATGATG TGGTATTGGG GGCCAAGTCT GTACAACATC    780

TTGAGTCCCT TTTTACCTCT ATTACCAATT TTCTTTTGTC TTTGGGTATA CATTTGAACC    840

CTAATAAAAC CAAACGTTGG GGCTACTCCC TTAACTTCAT GGGATATGTA ATTGGAAGTT    900

GGGGTACTTT ACCGCAGGAA CATATTGTAC AAAAACTCAA GCAATGTTTT CGAAAATTGC    960

CTGTAAATAG ACCTATTGAT TGGAAAGTAT GTCAAAGAAT TGTGGGTCTT TTGGGCTTTG   1020

CTGCCCCTTT TACACAATGT GGCTATCCTG CCTTGATGCC TTTATATGCA TGTATACAAT   1080

CTAAGCAGGC TTTCACTTTC TCGCCAACTT ACAAGGCCTT TCTGTGTAAA CAATATCTAA   1140

ACCTTTACCC CGTTGCCCGG CAACGGTCAG GTCTCTGCCA AGTGTTTGCT GACGCAACCC   1200

CCACGGGTTG GGGCTTGGCC ATAGGCCATC GGCGCATGCG TGGAACCTTT GTGGCTCCTC   1260

TGCCGATCCA TACTGCGGAA CTCCTAGCAG CTTGTTTTGC TCGCAGCCGG TCTGGAGCGA   1320

AACTTATCGG AACCGACAAC TCAGTTGTCC TCTCTCGGAA ATACACCTCC TTTCCATGGC   1380

TGCTAGGCTG TGCTGCCAAC TGGATCCTGC GCGGGACGTC CTTTGTCTAC GTCCCGTCGG   1440

CGCTGAATCC CGCGGACGAC CCGTCTCGGG GCCGTTTGGG CCTCTACCGT CCCCTTCTTC   1500

ATCTGCCGTT CCGGCCGACC ACGGGGCGCA CCTCTCTTTA CGCGGTCTCC CCGTCTGTGC   1560

CTTCTCATCT GCCGGACCGT GTGCACTTCG CTTCACCTCT GCACGTAGCA TGGAGACCAC   1620

CGTGAACGCC CACCAGGTCT TGCCCAAGGT CTTACACAAG AGGACTCTTG GACTCTCAGC   1680

AATGTCAACG ACCGACCTTG AGGCATACTT CAAAGACTGT TTGTTTAAAG ACTGGGAGGA   1740

GTTGGGGGAG GAGATTAGGT TAAAGGTCTT TGTACTAGGA GGCTGTAGGC ATAAATTGGT   1800

CTGTTCACCA GCACCATGCA ACTTTTTCCC CTCTGCCTAA TCATCTCATG TTCATGTCCT   1860

ACTGTTCAAG CCTCCAAGCT GTGCCTTGGG TGGCTTTGGG GCATGGACAT TGACCCGTAT   1920

AAAGAATTTG GAGCTTCTGT GGAGTTACTC TCTTTTTTGC CTTCTGACTT CTTTCCTTCT   1980

ATTCGAGATC TCCTCGACAC CGCCTCTGCT CTGTATCGGG AGGCCTTAGA GTCTCCGGAA   2040

CATTGTTCAC CTCACCATAC AGCACTCAGG CAAGCTATTC TGTGTTGGGG TGAGTTGATG   2100

AATCTGGCCA CCTGGGTGGG AAGTAATTTG GAAGACCCAG CATCCAGGGA ATTAGTAGTC   2160

AGCTATGTCA ATGTTAATAT GGGCCTAAAA ATTAGACAAC TATTGTGGTT TCACATTTCC   2220

TGCCTTACTT TTGGAAGAGA AACTGTCCTT GAGTATTTGG TGTCTTTTGG AGTGTGGATT   2280

CGCACTCCTC CCGCTTACAG ACCACCAAAT GCCCCTATCT TATCAACACT TCCGAAACT    2340

ACTGTTGTTA GACGACGAGG CAGGTCCCCT AGAAGAAGAA CTCCCTCGCC TCGCAGACGA   2400

AGGTCTCAAT CGCCGCGTCG CAGAAGATCT CAATCTCGGG AATCTCAATG TTAGTATCCC   2460
```

```
TTGGACTCAT AAGGTGGGAA ACTTTACTGG GCTTTATTCT TCTACTGTAC CTGTCTTTAA    2520

TCCTGATTGG AAAACTCCCT CCTTTCCTCA CATTCATTTA CAGGAGGACA TTATTAATAG    2580

ATGTCAACAA TATGTGGGCC CTCTGACAGT TAATGAAAAA AGGAGATTAA AATTAATTAT    2640

GCCTGCTAGG TTCTATCCTA ACCTTACCAA ATATTTGCCC TTGGACAAAG GCATTAAACC    2700

GTATTATCCT GAATATGCAG TTAATCATTA CTTCAAAACT AGGCATTATT TACATACTCT    2760

GTGGAAGGCT GGCATTCTAT ATAAGAGAGA AACTACACGC AGCGCCTCAT TTTGTGGGTC    2820

ACCATATTCT TGGGAACAAG AGCTACAGCA TGGGAGGTTG GTCTTCCAAA CCTCGACAAG    2880

GCATGGGGAC GAATCTTTCT GTTCCCAATC CTCTGGGATT CTTTCCCGAT CACCAGTTGG    2940

ACCCTGCGTT CGGAGCCAAC TCAAACAATC CAGATTGGGA CTTCAACCCC AACAAGGATC    3000

ACTGGCCAGA GGCAAATCAG GTAGGAGCGG GAGCATTTGG TCCAGGGTTC ACCCCACCAC    3060

ACGGAGGCCT TTTGGGGTGG AGCCCTCAGG CTCAGGGCAT ATTGACAACA CTGCCAGCAG    3120

CACCTCCTCC TGCCTCCACC AATCGGCAGT CAGGAAGACA GCCTACTCCC ATCTCTCCAC    3180

CTCTAAGAGA CAGTCATCCT CAGGCCATGC AGTGG                              3215

(2) INFORMATION FOR SEQ ID NO: 293:

(i) SEQUENCE CHARACTERISTICS:
        (A) LENGTH: 3188 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 293:

AATTCCACAA CATTCCACCA AGCTCTGCTA GATCCCAGAG TGAGGGGCCT ATATTTTCCT      60

GCTGGTGGCT CCAGTTCCGG AACAGTAAAC CCTGTTCCGA CTACTGCCTC ACCCATATCG     120

TCAATCTTCT CGAGGACTGG GGACCCTGCA CCGAACATGG AGAACACAAC ATCAGGATTC     180

CTAGGACCCC TGCTCGTGTT ACAGGCGGGG TTTTTCTTGT TGACAAGAAT CCTCACAATA     240

CCACAGAGTC TAGACTCGTG GTGGACTTCT CTCAATTTTC TAGGGGAGC ACCCACGTGT      300

CCTGGCCAAA ATTCGCAGTC CCCAACCTCC AATCACTCAC CAACCTCTTG TCCTCCAATT     360

TGTCCTGGCT ATCGCTGGAT GTGTCTGCGG CGTTTTATCA TATTCCTCTT CATCCTGCTG     420

CTATGCCTCA TCTTCTTGTT GGTTCTTCTG GACTACCAAG GTATGTTGCC CGTTTGTCCT     480

CTACTTCCAG GAACATCAAC CACCAGCACG GGGCCATGCA AGACCTGCAC GATTCCTGCT     540

CAAGGAACCT CTATGTTTCC CTCTTGTTGC TGTACAAAAC CTTCGGACGG AAACTGCACT     600

TGTATTCCCA TCCCATCATC CTGGGCTTTC GCAAGATTCC TATGGGAGTG GCCTCAGTC      660

CGTTTCTCCT GGCTCAGTTT ACTAGTGCCA TTTGTTCAGT GGTTCGTAGG GCTTTCCCCC     720

ACTGTTTGGC TTTCAGTTAT ATGGATGATG TGGTATTGGG GGCCAAGTCT GTACAACATC     780

TTGAGTCCCT TTTTACCTCT ATTACCAATT TTCTTTTGTC TTTGGGTATA CATTTAAACC     840

CTAATAAAAC CAAACGTTGG GGCTACTCCC TTAACTTCAT GGGATATGTA ATTGGAAGTT     900

GGGGTACTTT ACCGCAGGAA CATATTGTAC TAAAACTCAA GCAATGTTTT CGAAAATTGC     960

CTGTAAATAG CCCTATTGAT TGGAAAGTAT GTCAAAGAAT TGTGGGTCTT TTGGGCTTTG    1020

CTGCCCCTTT TACACAATGC GGCTATCCTG CCTTGATGCC TTTATATGCA TGTATACAAT    1080
```

```
CTAAGCAGGC TTTCACTTTC TCGCCAACTT ATAAGGCCTT TCTGTGTAAA CAATATCTGA      1140

ACCTTTACCC CGTTGCCCGG CAACGGTCAG GTCTCTGCCA AGTGTTTGCT GACGCAACCC      1200

CCACTGGATG GGGCTTGGCC ATAGGCCATC GGCGCATGCG TGGAACCTTT GTGGCTCCTC      1260

TGCCGATCCA TACTGCGGAA CTCCTAGCAG CTTGTTTTGC TCGCAGCCGG TCTGGAGCGA      1320

AACTTATCGG AACCGACAAC TCTGTTGTCC TCTCTCGGAA ATACACCTCC TTTCCATGGC      1380

TGCTAGGGTG TGCTGCCAAC TGGATCCTGC GCGGGACGTC CTTTGTCTAC GTCCCGTCGG      1440

CGCTGAATCC CGCGGACGAC CCGTCTCGGG GCCGTTTGGG GCTCTACCGT CCCCTTCTTG      1500

TTCTGCCGTT CCGGCCGACC ACGGGGCGCA CCTCTCTTTA CGCGGTCTCC CCGTCTGTGC      1560

CTTCTCATCT GCCGGACCGT GTGCACTTCG CTTCACCTCT GCACGTCGCA TGGAGACCAC      1620

CGTGAACGCC CACCAGGTCT TGCCCAAGGT CTTACATAAG AGGACTCTTG GACTCTCAGC      1680

CATGTCAACG ACCGACCTTG AGGCATACTT CAAAGACTGT GTGTTTAAAG ACTGGGAGGA      1740

GTTGGGGGAG GAGATTAGGT TAAAGGTCTT TGTACTAGGA GGCTGTAGGC ATAACTTTTT      1800

CACCTCTGCC TAATCATCTC ATGTTCATGT CCTACTGTTC AAGCCTCCAA GCTGTGCCTT      1860

GGGTGGCTTT GGGGCATGGA CATTGACCCG TATAAAGAAT TTGGAGCATC TGTGGAGTTA      1920

CTCTCTTTTT TGCCTTCTGA CTTCTTTCCG TCTATTCGAG ATCTCCTTGA CACCGCCTCT      1980

GCTCTGTATC GGGAGGCCTT AGAGTCTCCG GAACATTGTT CACCTCACCA TACAGCACTC      2040

AGGCAAGCTA TTCTGTGTTG GGGTGAGTTA ATGAATCTGG CCACCTGGGT GGGAAGTAAT      2100

TTGGAAGACC CAGCATCCAG GGAATTAGTA GTCAGCTATG TCAATGTTAA TATGGGCCTA      2160

AAAATCAGAC AACTATTGTG GTTTCACATT TCCTGCCTTA CTTTTGGAAG AGAAACTGTT      2220

TTGGAGTATT TGGTATCTTT TGGAGTGTGG ATTCGCACTC CTCCCGCTTA CAGACCACCA      2280

AATGCCCCTA TCTTATCAAC ACTTCCGGAA ACTACTGTTG TTAGACGACG AGGCAGGTCC      2340

CCTAGAAGAA GAACTCCCTC GCCTCGCAGA CGAAGGTCTC AATCGCCGCG TCGCAGAAGA      2400

TCTCAATCTC GGGAATCTCA ATGTTAGTAT CCCTTGGACT CATAAGGTGG GAAACTTTAC      2460

TGGGCTTTAT TCTTCTACTG TACCTGTCTT TAATCCCGAG TGGCAAACTC CCTCCTTTCC      2520

TCACATTCAT TTACAGGAGG ACATTATTAA TAGATGTCAA CAATATGTGG GCCCTCTTAC      2580

GGTTAATGAA AAAAGGAGAT TAAAATTAAT TATGCCTGCT AGGTTCTATC CTAACCTTAC      2640

TAAATATTTG CCCTTAGACA AAGGCATTAA ACCGTATTAT CCTGAACATG CAGTTAATCA      2700

TTACTTCAAA ACTAGGCATT ATTTACATAC TCTGTGGAAG GCTGGCATTC TATATAAGAG      2760

AGAAACTACA CGCAGCGCCT CATTTTGTGG GTCACCATAT TCTTGGGAAC AAGAGCTACA      2820

GCATGGGAGG TTGGTCTTCC AAACCTCGAC AAGGCATGGG GACGAATCTT TCTGTTCCCA      2880

ATCCTCTGGG ATTCTTTCCC GATCACCAGT TGGACCCTGC GTTCGGAGCC AACTCAAACA      2940

ATCCAGATTG GGACTTCAAC CCCAACAAGG ATCAATGGCC AGAGGCAAAT CAGGTAGGAG      3000

CGGGAGCATT CGGGCCAGGG TTCACCCCAC CACACGGCGG TCTTTTGGGG TGGAGCCCTC      3060

AGGCTCAGGG CATATTGACA ACAGTGCCAG CAGCACCTCC TCCTGCCTCC ACCAATCGGC      3120

AGTCAGGAAG ACAGCCTACT CCCATCTCTC CACCTCTAAG AGACAGTCAT CCTCAGGCCA      3180

TGCAGTGG                                                              3188
```

(2) INFORMATION FOR SEQ ID NO: 294:

(i) SEQUENCE CHARACTERISTICS:
        (A) LENGTH: 3214 base pairs
        (B) TYPE: nucleic acid

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 294:

AACTCCACAA CATTCCACCA AGCTCTGCTA GACCCCAGAG TGAGGGGCCT ATACTTTCCT      60

GCTGGTGGCT CCAGTTCCGG AACAGTAAAC CCTGTTCCGA CTACTGCCTC ACCCATATCG     120

TCAATCTCCT CGAGGACTGG GGACCCTGCA CCGAACATGG AGAACACAAC ATCAGGATTC     180

CTAGGACCCC TGCTCGTGTT ACAGGCGGGG TTTTTCTTGT TGACAAGAAT CCTCACAATA     240

CCACAGAGTC TAGACTCGTG GTGGACTTCT CTCAATTTTC TAGGGGAGC ACCCACGTGT      300

CCTGGCCAAA ATTCGCAGTC CCCAACCTCC AATCACTCAC CAACCTCTTG TCCTCCAATT     360

TGTCCTGGCT ATCGCTGGAT GTGTCTGCGG CGTTTTATCA TATTCCTCTT CATCCTGCTG     420

CTATGCCTCA TCTTCTTGTT GGTTCTTCTG GACTACCAAG GTATGTTGCC CGTTTGTCCT     480

CTACTTCCAG GAACATCAAC TACCAGCACG GGACCATGCA AGACCTGCAC GATTCCTGCT     540

CAAGGAACCT CTATGTTTCC CTCTTGTTGC TGTACAAAAC CTTCGGACGG AAACTGCACT     600

TGTATTCCCA TCCCATCATC CTGGGCTTTC GCAAGATTCC TATGGGAGGG GGCCTCAGTC     660

CGTTTCTCCT GGCTCAGTTT ACTAGTGCCA TTTGTTCAGT GGTTCGTAGG GCTTTCCCCC     720

ACTGTTTGGC TTTCAGTTAT ATGGATGATG TGGTATTGGG GGCCAAGTCT GTACAACATC     780

TTGAGTCCCT TTTTACCTCT ATTACCAATT TTCTTTTGTC TTTGGGTATA CATTTAAACC     840

CTAATAAAAC CAAACGTTGG GGCTACTCCC TTAACTTCAT GGGATATGTA ATTGGATGTT     900

GGGGTACTTT ACCGCAAGAA CATATTGTAC TAAAAATCAA GCAATGTTTT CGAAAACTGC     960

CTGTAAATAG ACCTATTGAT TGGAAAGTAT GTCAGAGACT TGTGGGTCTT TTGGGCTTTG    1020

CTGCCCCTTT TACACAATGT GGCTATCCTG CCTTAATGCC TTTATATGCA TGTATACAAT    1080

CTAAGCAGGC TTTCACTTTC TCGCCAACTT ACAAGGCCTT TCTGTGTAAA CAATATCTCC    1140

ACCTTTACCC CGTTGCCCGG CAACGGTCAG GTCTCTGCCA AGTGTTTGCT GACGCAACCC    1200

CCACTGGATG GGGCTTGGCT ATCGGCCATA GCCGCATGCG CGGACCTTTG TGGCTCCTAA    1260

GCCGATCCAT ACTGCGGAAC TCCTAGCAGC TTGTTTTGCT CGCAGGCGGT CTGGAGCGAA    1320

ACTTATCGGC ACCGACAACT CTGTTGTCCT CTCTCGGAAA TACACCTCCT TTCCATGGCT    1380

GCTAGGGTGT GCTGCCAACT GGATCCTGCG CGGGACGTCC TTTGTCTACG TCCCGTCGGC    1440

GCTGAATCCC GCGGACGACC CGTCTCGGGG CCGTTTGGGA CTCTACCGTC CCCTTCTTCA    1500

TCTGCCGTTC CGGCCGACCA CGGGGCGCAC CTCTCTTTAC GCGGTCTTTT TGTCTGTGCC    1560

TTCTCATCTG CCGGTCCGTG TGCACTTCGC TTCACCTCTG CACGTCGCAT GGAGACCACC    1620

GTGAACGCCC ACCAGGTCTT GCCCAAGGTC TTACATAAGA GGACTCTTGG ACTCTCAGCG    1680

ATGTCAACGA CCGACCTTGA GGCATACTTC AAAGACTGTT TGTTTAAGGA CTGGGAGGAG    1740

TTGGGGGAGG AGATTAGGTT AAAGGTCTTT GTACTAGGAG GCTGTAGGCA TAAATTGGTC    1800

TGTTCACCAG CACCATGCAA CTTTTTCACC TCTGCCTAAT CATCTCATGT TCATGTCCTA    1860

CTGTTCAAGC CTCCAAGCTG TGCCTTGGGT GGCTTTGGGG CATGGACATT GACCCGTATA    1920

AAGAATTTGG AGCTTCTGTG GAGTTACTCT CTTTTTTGCC TTCTGACTTC TTTCCTTCTA    1980

TTCGAGATCT CCTCGACACC GCCTCAGCTC TATATCGGGA GGCCTTAGAG TCTCCGGAAC    2040
```

-continued

```
ATTGTTCTCC TCATCATACA GCACTCAGGC AAGCTATTCT GTGTTGGGGT GAGTTGATGA    2100
ATCTGGCCAC CTGGGTGGGA AGTAATTTGG AAGACCCAGC ATCCAGGGAA TTAGTAGTCA    2160
GCTATGTCAA TGTTAATATG GGCCTAAAAA TCAGACAACT ACTGTGGTTT CACATTTCCT    2220
GTCTTACTTT TGGAAGAGAA ACTGTTCTTG AGTATTTGGT GTCTTTTGGA GTGTGGATTC    2280
GCACTCCTCC TGCTTACAGA CCACCAAATG CCCCTATCTT ATCAACACTT CCGGAAACTA    2340
CTGTTGTTAG ACGACGAGGC AGGTCCCCTA GAAGAAGAAC TCCCTCGCCT CGCAGACGAA    2400
GGTCTCAATC GCCGCGTCGC AGAAGATCTC AATCTCGGGA ATCTCAATGT TAGTATCCAT    2460
TGGACTCATA AGGTGGGAAA CTTTACTGGG CTTTATTCTT CTACTGTACC TGTCTTTAAT    2520
CCTGAGTGGC AAACTCCCTC CTTTCCTCAC ATTCATTTAC AGGAGGACAT TATTAATAGA    2580
TGTCAACAAT ATGTGGGCCC TCTTACAGTT AATGAAAAAA GGAGATTAAA ATTAATTATG    2640
CCTGCTAGGT TCTATCCTAA CCTTACCAAA TATTTGCCAT GGACAAAGG CATTAAACCA     2700
TATTATCCTG AACATGCAGT TAATCATTAC TTCAAAACTA GGCATTATTT ACATACTCTG    2760
TGGAAGGCGG GCATTCTATA TAAGAGAAA ACTACACGCA GTGCCTCATT CTGTGGGTCA     2820
CCATATTCTT GGGAACAAGA GCTACAGCAT GGGAGGTTGG TCTTCCAAAC CTCGACAAGG    2880
CATGGGGACG AATCTTTCTG TTCCCAATCC TCTGGGATTC TTTCCCGATC ACCAGTTGGA    2940
CCCTGCGTTC GGAGCCAACT CACACAATCC CGATTGGGAC TTCAACCCCA ACAAGGATCA    3000
TTGGCCAGAG GCAAATCAGG TAGGAGCGGG AGCATTCGGG CCAGGGTTCA CCCCACCACA    3060
CGGCGGTCTT TTGGGGTGGA GCCCGCAGGC TCAGGGCGTA TTGACAACCG TGCCAGTAGC    3120
ACCTCCTCCT GCCTCCACCA ATCGGCAGTC AGGAAGACAG CCTACTCCCA TCTCTCCACC    3180
TCTAAGAGAC AGTCATCCTC AGGCCATGCA GTGG                                3214
```

(2) INFORMATION FOR SEQ ID NO: 295:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 295:

```
AACTCCACAA CATTCCACCA AGCTCTGCTA GACCCCAGAG TGAGGGGCCT ATACTTTCCT      60
GCTGGTGGCT CCAGTTCCGG AACAGTAAAC CCTGTTCCGA CTACTGCCTC ACCCATATCG     120
TCAATCTTCT CGAGGACTGG GGACCCTGCA CCGAACATGG AGAACACAAC ATCAGGATTC     180
CTAGGACCCC TGCTCGTGTT ACAGGCGGGG TTTTTCTTGT TGACAAGAAT CCTCACAATA     240
CCACAGAGTC TACACTCGTG GTGGACTTCT CTCAATTTTC TAGGGCAGC ACCCACGTGT      300
CTTGGCCAAA ATTCGCAGTC CCCAACCTCC AATCACTCAC CAACCTCTTG TCCTCCAATT     360
TGTCCTGGTT ATCGTTGGAT GTGTCTGCGG CGTTTTATCA TATTCCTCTT CATCCTGCTG     420
CTATGCCTCA TCTTCTTGTT GGTTCTTCTG GACTACCAAG GTATGTTGTC TGTTTGTCCT     480
CTACTTCCAA GAACATCAAC TACCAGCACG GGACCATGCA AGACCTGCAC GATTCCTGCT     540
CAAGGAACCT CTATGTTTCC CTCTTCTTGC TGTACAAAAC CTTCGGACGG AAACTGCACT     600
TGTATTCCCA TCCCATCATC TTGGGCTTTC GCAAGATTCC TATGGGAGTG GGCCTCAGTC     660
```

```
                                                   -continued

CGTTTCTCCT GGCTCAGTTT ACTAGTGCCA TTTGTTCAGT GGTTCGTAGG GCTTTCCCCC    720

ACTGTTTGGC TTTCAGTTAT ATGGATGATG TGGTATTGGG GGCCAAGTCT GTACAACATC    780

TTGAGTCCCT TTTTACCTCT ATTACCAATT TTCTTTTGTC TTTGGGTATA CATTTGAACC    840

CCAATAAAAC CAAACGTTGG GGCTATTCCC TTAATTTCAT GGGATATGTA ATTGGATGTT    900

GGGGTACTTT ACCGCAAGAA CATATTGTAC TAAAAATCAA GCAATGTTTT CGAAAACTGC    960

CTGTAAATAG ACCTATTGAT TGGAAAGTAT GTCAGAGAAT TGTGGGTCTT TTGGGCTTTG   1020

CTGCCCCTTT TACACAATGT GGCTATCCTG CCTTGATGCC TTTATATGCA TGTATACAAT   1080

CTAAGCAAGC TTTCACTTTC TCGCCAACTT ACAAGGCCTT TCTGTGTAAA CAATATCTGA   1140

ACCTTTACCC CGTTGCCCGG CAACGGTCAG GTCTCTGCCA AGTGTTTGCT GACGCAACCC   1200

CCACTGGATG GGGCTTGGCT ATTGGCCATC GCCGCATGCG TGGAACCTTT GTGGCTCCTC   1260

TGCCGATCCA TACTGCGGAA CTCCTGGCAG CCTGTTTTGC TCGCAGCCGG TCTGGAGCAA   1320

AACTTATCGG AACCGACAAC TCTGTTGTCC TCTCTCGGAA ATACACCTCC TTTCCATGGC   1380

TGCTCGGGTG TGCTGCCAAC TGGATCCTGC GCGGGACGTC CTTTGTCTAC GTCCCGTCGG   1440

CGCTGAATCC CGCGGACGAC CCGTCTCGGG GCCGTTTGGG CCTCTATCGT CCCCTTCTTC   1500

ATCTACCGTT CCGGCCGACC ACGGGGCGCA CCTCTCTTTA CGCGGTCTCC CCGTCTGTGC   1560

CTTCTCATCT GCCGGACCGT GTGCACTTCC CTTCACCTCT GCACGTCGCA TGGAGACCAC   1620

CGTGAACGCC CACCAGGTCT TGCCCAAGGT CTTACATAAG AGCACTCTTG GACTCTCAGC   1680

AATGTCAACG ACCGACCTTG AGGCATACTT CAAAGACTGT TTGTTTAAGG ACTGGGAGGA   1740

GTTGGGGGAG GAGATTAGGT TAAAGGTCTT TGTACTGGGA GGCTGTAGGC ATAAATTGGT   1800

CTGTTCACCA GCACCATGCA ACTTTTTCAC CTCTGCCTAA TCATCTCATG TTCATGTCCT   1860

ACTGTTCAAG CCTCCAAGCT GTGCCTTGGG TGGCTTTGGG GCATGGACAT TGACCCGTAT   1920

AAAGAATTTG GAGCTTCTGT GGAGTTACTC TCTTTTTTGC CTTCTGACTT CTTTCCTTCT   1980

ATTCGAGATC TCCTCGACAC CGCCTCAGCT CTGTATCGGG AGGCCTTAGA GTCTCCGGAA   2040

CATTGCTCAC CTCACCATAC CGCACTCAGG CAAGCTATTC TGTGTTGGCG TGAGTTGATG   2100

AATCTGGCCA CCTGGGTGGG AAGTAATTTG GAAGACCCAG CATCCAGGGA ATTAGTAGTC   2160

AGCTATGTCA ATGTTAATAT CGGCCTAAAA ATCAGACAAC TACTGTGGTT TCACATTTCC   2220

TGTCTTACTT TTGGAAGAGA AACTGTTCTT GAGTATTTGG TGTCTTTTGG AGTGTGGATT   2280

CGCACTCCTC CTGCTTACAG ACCACCAAAT GCCCCTATCT TATCAACACT TCCGGAAACT   2340

ACTGTTGTTA GACGACGAGG CAGGTCCCCT AGAAGAAGAA CTCCCTCGCC TCGCAGACGA   2400

AGGTCTCAAT CGCCGCGTCG CAGAAGATCT CAATCTCGGG AATCTCAATG TTAGTATCCC   2460

TTGGACTCAT AAGGTGGGAA ACTTTACTGG GCTTTATTCT TCTACTGTAC CTATCTTTAA   2520

TCCTGAGTGG CAAACTCCCT CCTTTCCTCA CATTCATTTA CAGGAGGACA TTATTAATAG   2580

ATGTCAACAA TATGTGGGCC CTCTTACAGT TAATGAAAAA AGGAGATTAA AGTTAATTAT   2640

GCCTGCTAGG TTCTATCCTA ACCTTACCAA ATATCTGCCC TTGGACAAAG GCATTAAACC   2700

ATATTATCCT GAACATGCAG TTAATCATTA CTTCAAAACT AGGCATTATT TACATACTCT   2760

GTGGAAGGCG GGCATTCTAT ATAAGAGAGA AACTACGCGC AGCGCCTCAT TTTGTGGGTC   2820

ACCATATTCT TGGGAACAAG AGCTACAGCA TGGGAGGTTG GTCTTCCAAA CCTCGACAAG   2880

GCATGGGGAC GAATCTTTCT GTTCCCAATC CTCTGGGATT CTTTCCCGAT CACCAGTTGG   2940

ACCCTGCGTT CGGAGCCAAC TCAAACAATC CAGATTGGGA CTTCAACCCC AACAAGGAAC   3000

ACTGGCCAGA GGCAAATCAG GTAGGAGCGG GAGCATTCGG GCCAGGGTTC ACCCCACCAC   3060
```

```
ACGGCGGTCT TTTGGGGTGG AGCCCTCAGG CTCAGGGCAT ATTGACAACA GTGCCAGTAG     3120

CACCTCCTCC TGCCTCCACC AATCGGCAGT CAGGAAGACA GCCTACTCCC ATCTCTCCAC     3180

CTCTAAGAGA CAGTCATCCT CAGGCCATGC AGTGG                                3215
```

(2) INFORMATION FOR SEQ ID NO: 296:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 296:

```
AACTCCACAA CATTCCACCA AGCTGTGCTA GATCCCAGAG TGAGGGGCCT ATATCTTCCT       60

GCTGGTGGCT CCAGTTCCGG AACAGTGAAC CCTGTTCCGA CTACTGCCTC ACCCATATCG      120

TCAATCTTCT CGAGGACTGG GGACCCTGCA CCGAACATGG AGAACACAAC ATCAGGATTC      180

CTAGGACCCC TGCTCGTGTT ACAGGCGGGG TTTTTCTTGT TGACAAGAAT CCTCACAATA      240

CCACAGAGTC TAGACTCGTG GTGGACTTCT CTCAATTTTC TAGGGGGAGC ACCCACGTGT      300

CCTGGCCCAA ATTCGCAGTC CCCAACCTCC AATCACTCAC CAACCTCTTG TCCTCCAATT      360

TGTCCTGGCT ATCGCTGGAT GTGTCTGCGG CGTTTTATCA TATTCCTCTT CATCCTGCTG      420

CTATGCCTCA TCTTCTTGTT GGTTCTTCTG GACTACCAAG GTATGTTGCC CGTTTGTCCT      480

CTACTTCCAG GAACATCAAC TACCAGCACG GGACCATGCA AGACCTGCAC GATTCCTGCT      540

CAAGGAACCT CTATGTTTCC CTCCTGTTGC TGTACAAAAC CTTCGGACGG AAACTGCACT      600

TGTATTCCCA TCCCATCATC CTGGGCTTTC GCAAGATTCC TATGGGAGTG GGCCTCAGTC      660

CGTTTCTCCT GGCTCAGTTT ACTAGTGCCA TTTGTTCAGT GGTTCGTAGG GCTTTCCCCC      720

ACTGTTTGGC TTTCAGTTAT ATGGATGATG TGGTATTGGG GGCCAAGTCT GTACAACATC      780

TTGAGTCCCT TTTTACCTCT ATTACCAATT TTCTTTTGTC TTTGGGTATA CATTTGAACC      840

CTCATAAAAC CAAACGTTGG GGCTACTCCC TTAACTTCAT GGGATATGTA ATTGGAAGTT      900

GGGGTACTTT ACCACAGGAA CATATTGTAC TAAAAATCAA GCAATGTTTT CGGAAGCTGC      960

CTGTAAATAG ACCTATTGAT TGGAAAGTAT GTCAAAGGAT TGTGGGTCTT TTGGGCTTTG     1020

CTGCCCCTTT TACACAATGT GGCTATCCTG CCTTGATGCC TTTATATGCA TGTATACAAT     1080

CTAAGCAGGC TTTCACTTTC TCGCCAACTT ACAAGGCCTT TCTGTGTAAA CAATATCTGC     1140

ACCTTTACCC CGTTGCCCGG CAACGGTCAG GTCTCTGCCA AGTGTTTGCT GACGCAACCC     1200

CCACTGGATG GGGCTTGGCC ATTGGCCAAT CGGGCATGCG TGGAACCTTT GTGGCTCCTC     1260

TGCCGATCCA TACTGCGGAA CTCCTAGCAG CTTGTTTTGC TCGCAGCCGG TCTGGAGCGA     1320

AACTTATCGG GACTGACAAC TCTGTTGTCC TCTCTCGGAA ATACACCTCC TTCCCATGGC     1380

TGCTCGGGTG TGCTGCCAAC TGGATCCTGC GCGGGACGTC CTTTGTCTAC GTCCCGTCGG     1440

CGCTGAATCC CGCGGACGAC CCGTCTCGGG GCCGTTTGGG CCTCTACCGT CCCCTTCTTC     1500

ATCTGCCGTT CCGGCCGACC ACGGGGCGCG CCTCTCTTTA CGCGGTCTCC CCGTCTGTGC     1560

CTTCTCATCT GCCGGTCCGT GTGCACTTCG CTTCACCTCT GCACGTCGCA TGGAGACCAC     1620

CGTGAACGCC CACCAGGTCT TGCCCAAGGT CTTACATAAG AGGACTCTTG GACTCTCAGC     1680
```

```
GATGTCAACG ACCGACCTTG AGGCATATTT CAAAGACTGT TGTTTAAAG  ACTGGGAGGA   1740

GTTGGGGGAG GAGATTAGGT TAATGGTCTT TGTACTAGGA GGCTGTAGGC ATAAATTGGT   1800

CTGTTCACCA GCACCATGCA ACTTTTTCAC CTCTGCCTAA TCATCTCCTG TTCATGTCCT   1860

ACTGTTCAAG CCTCCAAGCT GTGCCTTGGG TGGCTTAGGG GCATGGACAT TGACACGTCT   1920

AAAGAATTTG GAGCTTCTGT GGAGTTACTC TCTTTTTTGC CTTCTGACTT CTTTCCTTCT   1980

ATTCGAGATC TCCTCGACAC CGCCTTTGCT CTGCATCGGG AGGCCTTAGA GTCTCCGGAA   2040

CATTGTTCAC CTCACCATAC AGCACTCAGG CAAGCTATTG TGTGTTGGGG TGAGTTGAGT   2100

AATCTGGCCA CCTGGGTGGG AAGTAATTTG GAAGACCCAG CATCCAGGGA ATTGGTAGTC   2160

AGCTATGTCA ATGTTAATAT GGGCCTAAAA ATCAGACAAC TATTGTGGTT TCACATTTCC   2220

TGTCTTACTT TTGGAAGAGA AACGGTTCTT GAGTATTTGG TATCTGTTGG AGTGTGGATT   2280

CGCACTCCTC AAGCCTACAG ACCACCAAAT GCCCCTATCT TATCAACACT TCCGAAAACT   2340

ACTGTTGTTA GACGACGAGG CAGGTCCCCT AGAAGAAGAA CTCCCTCGCC TCGCAGACGA   2400

AGGTCTAAAT CGCCGCGTCG CAGAAGATCT CAATCTCGGG AATCTCAATG TTAGTATCCC   2460

TTGGACTCAT AAGGTGGGAA ACTTTACTGG TCTCTATTCT TCTACTGTAC CTGTCTTTAA   2520

TCCTGAGTGG CAAACTCCCT CCTTTCCTAA TATTCATTTA CAGGAGGATA TTATTAATAG   2580

ATGTCAACAA TATGTAGGCC CTCTTACAGT TAATGAAAAA AGGAGATTAA AATTAATTAT   2640

GCCTGCTAGG TTCTATCCTA ACCTTACCAA ATATTTGCCC TTGGATAAAG GTATTAAACC   2700

TTATTATCCT GAACATGCAG TTAATCATTA TTTCAAAACT AGGCATTATT TACATACTCT   2760

GTGGAAGGCT GGCATTCTAT ATAAGAGAGA AACTACACGT AGTGCCTCAT TTTGTGGGTC   2820

ACCATATTCT TGGGAACAAG AGCTACAGCA TGGGAGGTTG GTCTTCCAAA CCTCGACAAG   2880

GCATGGGGAC GAATCTTTCT GTTCCCAATC CTCTGGGATT CTTTCCCGAT CACCAGTTGG   2940

ACCCTGCATT CGGAGCCAAC TCAAACAATC CAGATTGGGA CTTCAACCCC AACAAGGATC   3000

ATTGGCCAGA GGCAAATCAG GTAGGAGCGG GAGCATTTGG GCCAGGGTTC ACTCCACCAC   3060

ACGGCGGTCT TTTGGGGTGG AGCCCTCAGG CTCAGGGCAT ATTGACAACA GTGCCAGCAG   3120

CGCCTCCTCC TGCCTCTACC AATCGGCAGT CAGGAAGACA GCCTACTCCC ATCTCTCCAC   3180

CTCTAAGAGA CAGTCATCCT CAGGCCATGC AGTGG                             3215

(2) INFORMATION FOR SEQ ID NO: 297:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 297:

AACTCCACAA CATTCCACCA AGCTGTGCTA GATCCCAGAG TGAGGGGCCT ATATCTTCCT     60

GCTGGTGGCT CCAGTTCCGG AACAGTGAAC CCTGTTCCGA CTACTGCCTC ACCCATATCG    120

TCAATCTTCT CGAGGACTGG GGACCCTGCA CCGAACATGG AGAACACAAC ATCAGGATTC    180

CTAGGACCCC TGCTCGTGTT ACAGGCGGGG TTTTTCTTGT TGACAAGAAT CCTCACAATA    240

CCACAGAGTC TAGACTCGTG GTGGACTTCT CTCAATTTTC TAGGGGAGC  ACCCACGTGT    300
```

-continued

```
CCTGGCCCAA ATTCGCAGTC CCCAACCTCC AATCACTCAC CAACCTCTTG TCCTCCAATT     360

TGTCCTGGCT ATCGCTGGAT GTGTCTGCGG CGTTTTATCA TATTCCTCTT CATCCTGCTG     420

CTATGCCTCA TCTTCTTGTT GGTTCTTCTG GACTACCAAG GTATGTTGCC CGTTTGTCCT     480

CTACTTCCAG GAACATCAAC TACCAGCACG GGACCATGCA AGACCTGCAC GATTCCTGCT     540

CAAGGAACCT CTATGTTTCC CTCCTGTTGC TGTACAAAAC CTTCGGACGG AAACTGCACT     600

TGTATTCCCA TCCCATCATC CTGGGCTTTC GCAAGATTCC TATGGGAGTG GGCCTCAGTC     660

CGTTTCTCCT GGCTCAGTTT ACTAGTGCCA TTTGTTCAGT GGTTCGTAGG GCTTTCCCCC     720

ACTGTTTGGC TTTCAGTTAT ATGGATGATG TGGTATTGGG GGCCAAGTCT GTACAACATC     780

TTGAGTCCCT TTTTACCTCT ATTACCAATT TTCTTTTGTC TTTGGGTATA CATTTGAACC     840

CTCATAAAAC CAAACGTTGG GGCTACTCCC TTAACTTCAT GGGATATGTA ATTGGAAGTT     900

GGGGTACTTT ACCACAGGAA CATATTGTAC TAAAAATCAA GCAATGTTTT CGGAAGCTGC     960

CTGTAAATAG ACCTATTGAT TGGAAAGTAT GTCAAAGGAT TGTGGGTCTT TTGGGCTTTG    1020

CTGCCCCTTT TACACAATGT GGCTATCCTG CCTTGATGCC TTTATATGCA TGTATACAAT    1080

CTAAGCAGGC TTTCACTTTC TCGCCAACTT ACAAGGCCTT TCTGTGTAAA CAATATCTGC    1140

ACCTTTACCC CGTTGCCCGG CAACGGTCAG GTCTCTGCCA AGTGTTTGCT GACGCAACCC    1200

CCACTGGATG GGGCTTGGCC ATTGGCCAAT CGGGCATGCG TGGAACCTTT GTGGCTCCTC    1260

TGCCGATCCA TACTGCGGAA CTCCTAGCAG CTTGTTTTGC TCGCAGCCGG TCTGGAGCGA    1320

AACTTATCGG GACTGACAAC TCTGTTGTCC TCTCTCGGAA ATACACCTCC TTCCCATGGC    1380

TGCTCGGGTG TGCTGCCAAC TGGATCCTGC GCGGGACGTC CTTTGTCTAC GTCCCGTCGG    1440

CGCTGAATCC CGCGGACGAC CCGTCTCGGG GCCGTTTGGG CCTCTACCGT CCCCTTCTTC    1500

ATCTGCCGTT CCGGCCGACC ACGGGGCGCG CCTCTCTTTA CGCGGTCTCC CCGTCTGTGC    1560

CTTCTCATCT GCCGGTCCGT GTGCACTTCG CTTCACCTCT GCACGTCGCA TGGAGACCAC    1620

CGTGAACGCC CACCAGGTCT TGCCCAAGGT CTTACATAAG AGGACTCTTG GACTCTCAGC    1680

GATGTCAACG ACCGACCTTG AGGCATATTT CAAAGACTGT TTGTTTAAAG ACTGGGAGGA    1740

GTTGGGGGAG GAGATTAGGT TAATGGTCTT TGTACTAGGA GGCTGTAGGC ATAAATTGGT    1800

CTGTTCACCA GCACCATGCA ACTTTTTCAC CTCTGCCTAA TCATCTCCTG TTCATGTCCT    1860

ACTGTTCAAG CCTCCAAGCT GTGCCTTGGG TGGCTTAGGG GCATGGACAT TGACACGTAT    1920

AAAGAATTTG GAGCTTCTGT GGAGTTACTC TCTTTTTTGC CTTCTGACTT CTTTCCTTCT    1980

ATTCGAGATC TCCTCGACAC CGCCTTTGCT CTGCATCGGG AGGCCTTAGA GTCTCCGGAA    2040

CATTGTTCAC CTCACCATAC AGCACTCAGG CAAGCTATTG TGTGTTGGGG TGAGTTGATG    2100

AATCTGGCCA CCTGGGTGGG AAGTAATTTG GAAGACCCAG CATCCAGGGA ATTGGTAGTC    2160

AGCTATGTCA ATGTTAATAT GGGCCTAAAA ATCAGACAAC TATTGTGGTT TCACATTTCC    2220

TGTCTTACTT TTGGAAGAGA AACGGTTCTT GAGTATTTGG TATCTGTTGG AGTGTGGATT    2280

CGCACTCCTC AAGCCTACAG ACCACCAAAT GCCCCTATCT TATCAACACT TCCGGAAACT    2340

ACTGTTGTTA GACGACGAGG CAGGTCCCCT AGAAGAAGAA CTCCCTCGCC TCGCAGACGA    2400

AGGTCTAAAT CGCGCGCGTCG CAGAAGATCT CAATCTCGGG AATCTCAATG TTAGTATCCC    2460

TTGGACTCAT AAGGTGGGAA ACTTTACTGG TCTCTATTCT TCTACTGTAC CTGTCTTTAA    2520

TCCTGAGTGG CAAACTCCCT CCTTTCCTAA TATTCATTTA CAGGAGGATA TTATTAATAG    2580

ATGTCAACAA TATGTAGGCC CTCTTACAGT TAATGAAAAA AGGAGATTAA AATTAATTAT    2640
```

| | |
|---|---|
| GCCTGCTAGG TTCTATCCTA ACCTTACCAA ATATTTGCCC TTGGATAAAG GTATTAAACC | 2700 |
| TTATTATCCT GAACATGCAG TTAATCATTA TTTCAAAACT AGGCATTATT TACATACTCT | 2760 |
| GTGGAAGGCT GGCATTCTAT ATAAGAGAGA AACTACACGT AGTGCCTCAT TTTGTGGGTC | 2820 |
| ACCATATTCT TGGGAACAAG AGCTACAGCA TGGGAGGTTG GTCTTCCAAA CCTCGACAAG | 2880 |
| GCATGGGGAC GAATCTTTCT GTTCCCAATC CTCTGGGATT CTTTCCCGAT CACCAGTTGG | 2940 |
| ACCCTGCATT CGGAGCCAAC TCAAACAATC CAGATTGGGA CTTCAACCCC AACAAGGATC | 3000 |
| ATTGGCCAGA GGCAAATCAG GTAGGAGCGG GAGCATTTGG GCCAGGGTTC ACTCCACCAC | 3060 |
| ACGGCGGTCT TTTGGGGTGG AGCCCTCAGG CTCAGGGCAT ATTGACAACA GTGCCAGCAG | 3120 |
| CGCCTCCTCC TGCCTCTACC AATCGGCAGT CAGGAAGACA GCCTACTCCC ATCTCTCCAC | 3180 |
| CTCTAAGAGA CAGTCATCCT CAGGCCATGC AGTGG | 3215 |

(2) INFORMATION FOR SEQ ID NO: 298:

(i) SEQUENCE CHARACTERISTICS:
        (A) LENGTH: 3212 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 298:

| | |
|---|---|
| AACTCCACCA CATTCCACCA AGCTCTGCTA GATCCCAGAG TGAGGGGCCT ATATTTTCCT | 60 |
| GCTGGTGGCT CCAGTTCCGG AACAGTAAAC CCTGTTCCGA CTACTGCCTC ACCCATATCG | 120 |
| TCAATCTTCT CGAGGACTGG GGACCCTGCG CCGAACATGG AGAACACAAC ATCAGGATTC | 180 |
| CTAGGACCCC TGCTCGTGTT ACAGGCGGGG TTTTTCTTGT TGACAAGAAT CCTCACAATA | 240 |
| CCACAGAGTC TAGACTCGTG GACTTCTCTC AATTTTCTAG GGGGAGCACC CACGTGTCCT | 300 |
| GGCCAAAATT CGCAGTCCCC AACCTCCAAT CACTCACCAA CCTCTTGTCC TCCAATTTGT | 360 |
| CCTGGCTATC GCTGGATGTG TCTGCGGCGT TTTATCATAT TCCTCTTCAT CCTGCTGCTA | 420 |
| TGCCTCATCT TCTTGTTGGC TCTTCTGGAC TACCAAGGTA TGTTGCCCGT TGTCCTCTA | 480 |
| CTTCCAGGAA CATCAACTAC CAGCACGGGA CCATGCAAGA CCTGCACGAT TCCTGCTCAA | 540 |
| GGAACCTCTA TGTTTCCCTC TTGTTGCTGT ACAAAACCTT CGGACGGAAA TTGCACTTGT | 600 |
| ATTCCCATCC CGTCATCTTG GGCTTTCGCA AGATTCCTAT GGGAGTGGGC CTCAGTCCGT | 660 |
| TTCTCCTGGC TCAGTTTACT AGTGCCATTT GTTCAGTGGT TCGCAGGGCT TTCCCCCACT | 720 |
| GTTTGGCTTT CAGTTATATG GATGATGTGG TATTGGGGGC CAAGTCTGTA CAACATCTTG | 780 |
| AGTCCCTTTA TACCTCTATT ACCAATTTTC TTGTGTCTTT GGGTATACAT TTGAACCCTA | 840 |
| ATAAAACCAA ACGTTGGGGC TACTCCCTTA ACTTCATGGG ATATGTAATT GGAAGTTGGG | 900 |
| GTACGTTACC ACAGGAACAT ATTGTACAAA AAATCAAGCA ATGTTTTCGG AAACTGCCTG | 960 |
| TAAATAGACC TATTGATTGG AAAGTATGTC AAAGAATTGT GGGTCTTTTG GCTTTGCTG | 1020 |
| CCCCTTTTAC ACAATGTGGT TATCCTGCCT TGATGCCTTT ATATGCATGT ATACAAGCTA | 1080 |
| AGCAGGCTTT TACTTTCTCG TCAACTTACA AGGCCTTTCT GTGTAAACAA TATCTGCACC | 1140 |
| TTTACCCCGT TGCCCGGCAA CGGTCAGGTC TCTGCCAAGT GTTTGCTGAC GCAACCCCCA | 1200 |
| CTGGATGGGG CTTGGCCATA GGCCATCGGC GCATGCGTGG AACCTTTGTG GCTCCTCTGC | 1260 |

-continued

| | |
|---|---|
| CGATCCATAC TGCGGAACTC CTAGCAGCTT GTTTTGCTCG CAGCCGGTCT GGAGCGAAAC | 1320 |
| TTATCGGGAC TGACAACTCT GTTGTCCTCT CTCGGAAATA CACCTCCTTC CCATGGCTGC | 1380 |
| TCGGATGTGC TGCCAACTGG ATCCTGCGCG GGACGTCCTT TGTCTACGTC CCGTCGGCGC | 1440 |
| TGAATCCCGC GGACGACCCG TCTCGGGGTC GTTTGGGCCT CTACCGTCCC CTTCTTCATT | 1500 |
| TGCCGTTCCG GCCGACCACG GGGCGCACCT CTCTTTACGC GGTCTCCCCG TCTGTGCCTT | 1560 |
| CTCATCTGCC GGACCGTGTG CACTTCGCTT CACCTCTGCA CGTCGCATGG AGACCACCGT | 1620 |
| GAACGCCCAT CAGGTGTTGC CCAAGGTCTT ATATAAGAGG ACTCTTGGAC TTTCAGCAAT | 1680 |
| GTCAACGACC GACCTTGAGG CATACTTCAA AGACTGTTTG TTTAAGGACT GGGAGGAGTT | 1740 |
| GGGGGAGGAA CTTAGGTTAA TGATCTTTGT ACTAGGAGGC TGTAGGCATA AATTGGTCTG | 1800 |
| TTCACCAGCA CCATGCAACT TTTTCACCTC TGCCTAATCA TCTCTTGTTC ATGTCCTATG | 1860 |
| GTTCAAGCCT CCAAGCTGTG CCTTGGGTGG CTTTAGGACA TGGACATTGA CCCATATAAA | 1920 |
| GAATTTGGAG CTTCTGTGGA GTTACTCTCT TTTTTGCCTT CTGACTTCTT TCCTTCTATT | 1980 |
| CGAGATCTCC TCGACACCGC CTCTGCTCTG TATCGGGAGG CCCTAGAGTC TCCGGAGCAT | 2040 |
| TGTACACCTC ACCATACAGC ACTCAGGCAA GCTATTCTGT GTTGGGGTGA GTTGATGAAC | 2100 |
| CTGGCCACCT GGGTGGGAAG TAATTTGGAA GATCCAACAT CCAGGGAAGC AGTAGTCAGC | 2160 |
| TATGTCAATG TTAATATGGG CCTAAAACTC AGACAACTAT TGTGGTTTCA CATTTCCTGT | 2220 |
| CTTACTTTTG GAAGAGATAC TGTTCTTGAG TATTTGGTGT CTTTTGGAGT GTGGATTCGC | 2280 |
| ACTCCTACCG CTTACAGACC ACCAAATGCC CCTATCTTAT CAACACTTCC GGAAACTACT | 2340 |
| GTTGTTAGAC GACGAGGCAG GTCCCCTAGA AGAAGAACTC CCTCGCCTCG CAGACGAAGG | 2400 |
| TCTCAATCGC CGCGTCGCAG AAGATCTCAA TCTCGGGAAC CTCAATGTTA ATGTCCCTTG | 2460 |
| GACTCATAAG GTGGGAAACT TTACAGGACT TTACTCTTCT ACTGTACCTG TCTTTAATCC | 2520 |
| TGAGTGGCAA ACTCCCTCCT TTCCTAACAT TCATTTACAG GAGGACATTA TTGATAGATG | 2580 |
| TCAACAATAT GTGGGCCCTC TTACAGTTAA TGAAAAAAGG AGATTAAAAT TAATTATGCC | 2640 |
| TGCTAGGTTT TATCCAAACC TTACCAAATA TTTGCCCTTG GATAAAGGCA TTAAACCTTA | 2700 |
| TTATCCTGAA CATGCAGTTA ATCATTACTT TCAAACTAGG CATTATTTAC ATACTCTGTG | 2760 |
| GAAGGCTGGC ATTCTATATA AGAGAGAAAC TACCCGCAGC GCTTCATTTT GTGGGTCACC | 2820 |
| ATATTCTTGG GAACAAGAGC TACAGCATGG GAGGTTGGTC TTCCAAACCT CGACAAGGCA | 2880 |
| TGGGACGAA TCTTTCTGTT CCCAATCCTC TGGGATTCTT TCCCGATCAC CAGTTGGACC | 2940 |
| CTGCGTTCGG AGCCAACTCA AACAATCCAG ATTGGGACTT CAACCCCAAC AAGGATCATT | 3000 |
| GGCCAGAGGC CAATCAGGTA GGAGTGGGAG CATTCGGGCC AGGGTTCACC CCACCACACG | 3060 |
| GCGGTCTTTT GGGGTGGAGC CCTCAGGCTC AGGGCATATT GACAACAGTG CCAGCAGCGC | 3120 |
| CTCCTCCTGC CTCTACCAAT CGGCAGTCAG GAAGACAGCC AACTCCCATC TCTCCACCTC | 3180 |
| TAAGAGACAG TCATCCTCAG GCCATGCAGT GG | 3212 |

(2) INFORMATION FOR SEQ ID NO: 299:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 299:

```
AACTCCACAA CATTCCAACA AGCTCTGCAG GATCCCAGAG TCAGGGTCCT TTATTTTCCT          60
GCTGGTGGCT CCAGTTCCGG AACAGTAAAC CCTGTTCCGA CTACTGCCTC TCTCATTTCG         120
TCAATCTTCT CGAGGATTGG GGACCCTGTA ACGAACATGG AGAACACAAC ATCAGGATTC         180
CTAGGACCCC TGCTCGTGTT ACAGGCGGGG TTTTTCTTGT TGACAAAAAT CCTCACAATA         240
CCACAGAGTC TAGACTCGTG GTGGACTTCT CTCAATTTTC TAGGGGAGC ACCCGTGTGT          300
CCTGGCCAAA ATTCGCAGTC CCCAACCTCC AATCACTCAC CAACCTCTTG TCCTCCAATT         360
TGTCCTGGCT ATCGCTGGAT GTGTCTGCGG CGTTTTATCA TCTTCCTCTT CATCCTGCTG         420
CTATGCCTCA TCTTCTTGTT GGTTCTTCTG GACTACCAAG GTATGTTGCC CGTTTGTCCT         480
CTACTTCCAG GAACATCAAC TACCAGCACG GGACCATGCA AGACCTGCAC GATTCCTGCT         540
CAAGGAACCT CTATGTTTCC CTCATGTTGC TGTACAAAAC CTTCGGACGG AAACTGCACT         600
TGTATTCCCA TCCCATCATC CTGGGCTTTC GTAAGATTCC TATGGGAGTG GCCTCAGTC          660
CGTTTCTCCT GGCTCAGTTT ACTAGCGCCA TTTGTTCAGT GGTTCGTAGG GCTTTCCCCC         720
ACTGTTTGGC TTTCAGTTAT ATGGATGATG TGGTATTGGG GGCCAAGTCT GTACAACATC         780
TTGAGTCCCT TTATACCTCT ATTACCAATT TTCTTTTGTC TTTGGGTATA CATTTAAACC         840
CTAATAAAAC CAAAAGATGG GGCTATTCCC TTAACTTCAT GGGCTATGTA ATTGGAAGTT         900
GGGGTACCTT ACCACAAGAA CATATTGTAC TAAAAATCAC ACAATGTTTT CGAAAACTTC         960
CTGTTAATAG GCCTATTGAT TGGAAAGTGT GTCAAAGAAT TGTGGGTCTT TTGGGCTTTG        1020
CTGCCCCTTT TACACAATGT GGGTATCCTG CCTTAATGCC CTTGTATGCC TGTATTCAAG        1080
CTAAGCAGGC TTTCACTTTC TCGCCAACTT ATAAGGCCTT TCTGTGTAAA CAATATCTGA        1140
ACCTTTACCC CGTTGCCCGG CAACGGTCTG GTCTTTGCCA AGTGTTTGCT GACGCAACCC        1200
CCACTGGCTG GGGCTTGGCC ATGGGCCATC AGCGCATGCG TGGAACCTTT GTGGCTCCTC        1260
TGCCGATCCA TACTGCGGAA CTCCTAGCGG CTTGTTTTGC TCGCAGCCGG TCTGGAGCAA        1320
ACATTATCGG AACCGACAAC TCTGTCGTCC TCTCTCGGAA ATACACATCC TTTCCATGGC        1380
TGCTCGGGTG TGCTGCCAAC TGGATCCTAC GCGGGACGTC CTTTGTTTAC GTCCCGTCGG        1440
CGCTGAATCC CGCGGACGAC CCGTCTCGCG GCCGTTTGGG GCTCTACCGT CCCCTTCTTT        1500
GTCTGCGGTT CCGGCCAACC ACGGGCGCA CCTCTCTTTA CGCGGTCTCC CCGTCTGTGC         1560
CTTCTCATCT GCCGGACCGT GTGCACTTCG CTTCACCTCT GCACGTCGCA TGGAAACCAC        1620
CGTGAACGCC CACATGGTCT TGCCCAAGGT CTTGCATAAG AGAACTCTTG GACTCTCAGC        1680
AATGTCAACG ACCGACCTTG AGGCATATTT CAAAGACTGT GTGTTCAAAG ACTGGGAGGA        1740
GTTGGGGGAG GAGGTTAGAT TAAAGGTCTT TGTACTAGGA GGCTGTAGGC ATAAATTGGT        1800
CTGCGCACCA GCACCATGCA ACTTTTTCAC CTCTGCCTAA TCATCTCATG TTCATGTCCT        1860
ACTGTTCAAG CCTCCAAGCT GTGCCTTGGG TGGCTTGGG GCATGGACAT TGACCCTTAT         1920
AAAGAATTTG GAGCTTCTGT GGAGTTACTC TCTTTTTTGC CTTCTGATTT CTTTCCATCT        1980
ATTCGAGACC TCCTCGACAC CGCCTCAGCT CTGTATCGGG AGGCCTTAGA GTCTCCGGAG        2040
CATTGTTCAC CTCACCATAC AGCACTCAGG CAAGCTGTTC TGTGTTGGGG TGAGTTAATG        2100
AATCTGGCTA CCTGGGTGGG AAGTAATTTG GAAGACCCAG CATCAAGAGA ATTGGTAGTC        2160
AGTTATGTCA ATGTTAATAT GGGCCTAAAA ATCAGGCAAC TGTTGTGGTT TCATATTTCC        2220
TGTCTTACTT TTGGAAGAGA AACTGTTCTT GAGTACTTGG TGTCCTTTGG AGTGTGGATT        2280
```

```
CGCACTCCTC CCGCTTACAG ACCACCAAAT GCCCCTATCT TATCAACACT TCCGGAAACT    2340

ACTGTTGTTA GACGAAGAGG CAGGTCCCCT AGAAGAAGAA CTCCCTCGCC TCGCAGACGA    2400

AGGTCTCAAT CGCCGCGTCG CAGAAGATCT CAATCTCGGG AATCCCAATG TTAGTATCCC    2460

TTGGACTCAT AAGGTGGGAA ACTTTACTGG GCTTTATTCT TCTACTGTAC CTGTCTTTAA    2520

TCCTGAATGG CAAACTCCCT CTTTTCCTGA CATTCATTTG CAGGAGGACA TTATTAATAG    2580

ATGTCAACAA TATGTGGGCC CTCTTACAGT TAATGAAAAA AGAAGATTAA AATTAATTAT    2640

GCCTGCTAGG TTTTATCCTA ACCTTACTAA ATATTTGCCC TTAGACAAAG GCATTAAACC    2700

TTATTATCCA GAACAGACAG TTAATCATTA CTTCAAAACT AGGCATTATT TGCATACTCT    2760

GTGGAAGGCT GGTAGTCTAT ATAAGAGAGA AACTACACGC AGCGCCTCAT TTTGTGGGTC    2820

ACCATATTCT TGGGAACAAG AGCTACAGCA TGGGAGGTTG GTCTTCAAAA CCTCGGAAAG    2880

GCATGGGGAC GAATCTTTCG GTACCCAATC CTCTGGGATT CTTTCCCGAT CACCAGTTGG    2940

ACCCTGCGTT CGGAGCCAAC TCAAACAATC CCGATTGGGA CTTCAACCCC AACAAGGATC    3000

ACTGGCCAGA GGCAAATCAG GTAGGAGCGG GAGCATTCGG GCCAGGGTTC ACCCCACCAC    3060

ACGGAGGTCT TTTGGGGTGG AGCCCTCAGG CCCAGGGCAT ATTGACAACA GTGCCAGCAG    3120

CTCCTCCTTC TGCCTCCACC AATCGGCAGT CAGGAAGACA GCCTACGCCC ATCTCTCCAC    3180

CTCTAAGAGA CAGTCATCCT CAGGCCATGC AGTGG                               3215

(2) INFORMATION FOR SEQ ID NO: 300:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 300:

AACTCCACAA CATTCCAACA AGCTCTGCTA GATCCCAGAG TGAGGGGCCT ATATTTTCCT      60

GCTGGTGGCT CCAGTTCCGG AACAGTAAAC CCTGTTCCGA CTACTGCCTC TCTCATTTCG     120

TCAATCTTCT CGAGGACTGG GGACCCTGTA ACGAACATGG AGAACACAAC ATCAGGATTC     180

CTAGGACCCC TGCTCGTGTT ACAGGCGGGG TTTTTCTTGT TGACAAGAAT CCTCACAATA     240

CCACAGAGTC TAGACTCGGG GTGGACTTCT CTCAATTTTC TAGGGGAAGC ACCAAGGTGT     300

CCTGGCCAAA ATTCGCAGTC CCCAACCTCC AATCACTCAC CAACCTCTTG TCCTCCAATT     360

TGTCCTGGCT ATCGCTGGAT GTGTCTGCGG CGTTTTATCA TCTTCCTCTT CATCCTGCTG     420

CTATGCCTCA TCTTCTTGTT GGTTCTTCTG GACTACCAAG GTATGTTGCC CGTTTGTCCT     480

CTACTTCCAG GAACATCAAC TACCAGCACG GGACCATGCA AGACCTGCAC GATTCCTGCT     540

CAAGGAACCT CTATGTTTCC CTCATGTTGC TGTACAAAAC CTTCGGACGG AAACTGCACT     600

TGTATTCCCA TCCCATCATC CTGGGCTTTC GTAAGATTCC TATGGGAGTG GCCTCAGTT     660

CGTTTCTCCT GGCTCAGTTT ACTAGCGCCA TTTGTTCAGT GGTTCGTAGG GCTTTCCCCC     720

ACTGTTTGGC TTTCAGTTAT ATGGATGATG TGGTATTGGG GGCCAAGTCT GTACAACATC     780

TTGAGTCCCT TTATACCTCT ATTACCAATT TTCTTTTGTC TTTGGGTATA CATTTGAACC     840

CTAATAAGAC CAAAAGATGG GGCTATTCCC TTAACTTCAT GGGCTATGTA ATTGGAAGTT     900
```

```
GGGGTACCTT ACCACAAGAA CATATTGTAC TAAAAATCAA ACAATGTTTT CGAAAACTTC      960

CTGTAAATAG GCCTATTGAT TGGAAGGTCT GCCAAAGAAT TGTGGGTCTT TTGGGATTTG     1020

CTGCCCCTTT TACACAATGT GGATATCCTG CCTTAATGCC TTTGTATGCA TGTATTCAAG     1080

CTAAGCAAGC TTTCACTTTT TCGTCAACTT ACAAAGCCTT TCTGTGTAAA CAATATCTGA     1140

ACCTTTACCC CGTTGCCCGG CAACGGTCTG GTCTCTGCCA AGTGTTTGCT GACGCAACCC     1200

CCACTGGCTG GGGCTTGGCC ATTGGCAATC AGCGCATGCG TGGAACCTTT GTGGCTCCTC     1260

TGCCGATCCA TACTGCGGAA CTCCTAGCAG CTTGTTTTGC TCGCAGCCGG TCTGGAGCAA     1320

AACTTATCGG AACTGACAAC TCTGTCGTCC TCTCTCGCAA ATACACATCC TTTCCATGGG     1380

TGCTCGGCTG TGCTGCCAAC TGGATCCTAC GAGGGACGTC CTTTGTTTAC GTCCCGTCGG     1440

CGCTGAATCC CGCGGACGAC CCGTCTCGGG GCCGTTTGGG GATCTACCGT CCCCTTCTTC     1500

GTCTGCGGTT CCGGCCAACC ACGGGGCGCA CCTCTCTTTA CGCGGTCTCC CCGTCTGTGC     1560

CTTCTCATCT GCCGGACCGT GTGCACTTCG CTTCACCTCT GCACGTCGCA TGGAGACCAC     1620

CGTGAACGCC CACATGGTAT TGCCCAAGGT CTTGCATAAG AGGACTCTTG GACTCTCAGC     1680

GATGTCAACG ACCGACCTTG AGGCATACTT CAAAGACTGT GTATTTAAAG ACTGGGAGGA     1740

GTTGGGGGAG GAGATTAGAT TAAAGGTCTT TGTACTAGGA GGCTGTAGGC ATAAATTGGT     1800

CTGCGCACCA GCACCATGCA ACTTTTTCAC CTCTGCCTAA TCATCTCATG TTCATGTCCT     1860

ACTGTTCAAG CCTCCAAGCT GTGCCTTGGG TGGCTTGGG GCATGGACAT TGACCCTTAT     1920

AAAGAATTTG GAGCTTCTGT GGAGTTACTC TCTTTTTTGC CTTCTGATTT CTTTCCATCT     1980

ATTCGAGACC TCCTCGACAC CGCCTCAGCT CTGTATCGGG AGGCCTTAGA GTCTCCGGAA     2040

CATTGTTCAC CTCACCATAC AGCACTCAGG CAAGCTGTTC TGTGTTGGGG TGAGTTAATG     2100

AATCTGGCTA CCTGGGTGGG AAGTAATTTG GAAGACCCAG CATCCAGGGA ATTAGTGGTC     2160

AGTTATGTCA ACATTAATAT GGGCCTAAAA ATCAGACAAC TATTGTGGTT TCACATTTCC     2220

TGTCTTACTT TTGGAAGAGA AACTGTTCTT GAGTATTTGG TGTCTTTTGG AGTGTGGATT     2280

CGCACTCCTC CCGCTTACAG ACCACCAAAT GCCCCTATCT TATCAACACT TCCGGAAACT     2340

ACTGTTGTTA GACGTCGAGG CAGGTCCCCT AGAAGAAGAA CTCCCTCGCC TCGCAGACGA     2400

AGGTCTCAAT CACCGCGTCG CAGAAGATCT CAATCTCGGG AATCCCAATG TTAGTATCCC     2460

TTGGACTCAT AAGGTGGGAA ACTTACTGG GCTTTATTCT TCTACTGTAC CTGTCTTTAA      2520

TCCTGAATGG CAAACTCCCT CTTTTCCTGA CATTCATTTG CAGGAGGACA TTATTAATAG     2580

ATGTCAACAA TATGTGGGCC CTCTTACAGT TAATGAAAAA AGAAGATTAA AATTAATTAT     2640

GCCTGCTAGG TTTTATCCTA ACCTTACCAA ATATTTGCCC TTAGATAAAG GCATTAAACC     2700

TTATTATCCT GAACATGCAG TTAATCATTA CTTCAAAACA AGGCATTATT TACATACTCT     2760

GTGGAAGGCT GGCATCTTAT ATAAAAGAGA AACTACACGC AGTGCCTCAT TTTGTGGGTC     2820

ACCATATTCT TGGGAACAAG AGCTACAGCA TGGGAGGTTG GTCTTCCAAA CCTCGGAAAG     2880

GCATGGGGAC GAATCTTTCT GTTCCCAATC CTCTGGGATT CTTTCCCGAT CACCAGTTGG     2940

ACCCTGCATT CGGAGCCAAC TCAAACAATC CAGATTGGGA CTTCAACCCC AACAAGGATC     3000

AATGGCCAGA GGCAAATCAG GTAGGAGCGG GAGCATTCGG GCCAGGGTTC ACCCCACCAC     3060

ACGGAGGTCT TTTGGGGTGG AGCCCTCAGG CACAAGGCAT ATTGACAACA CTGCCAGCAG     3120

CTCCTCCTCC TGCCTCCACC AATCGGCAGT CAGGAAGACA GCCTACGCCC ATCTCTCCAC     3180

CTCTAAGAGA CAGTCATCCT CAGGCCATGC AGTGG                                3215
```

(2) INFORMATION FOR SEQ ID NO: 301:

(i) SEQUENCE CHARACTERISTICS:
        (A) LENGTH: 3161 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 301:

```
AATTCCACAA CCTTCCACCA AACTCTACAA GATCCCCCTG CTGGTGGCTC CAGTTCAGGA      60

ACAGTAAACC CTGTTCCGAC TACTGTCTCT CACATATCGT CAATCTTCAC GAGGATTGGA     120

GACCCTGCAC TGAACATGGA GAACATCACA TCAGGATTCC TAGGACCCCT GCTCGTGTTG     180

CAGGCGGGGT TTTTCTTGTT GACAAGAATC CTCACAATAC CGCAGAGTCT AGACTCGTGA     240

TGGACTTCTC TCAATTTTCT AGGGGGAACT ACCGTGTGTC TTGGCCAAAA TTCGCAGTCG     300

CCAACCTCCA ATCACTCACC AACCTCCTGT CCTCCAACTT GTCCTGGTTA TCGCTGGATC     360

TGTCTGCGGC GTTTTATCAT CTTCCTCTTC ATCCTGCTGC TATGCCTCAT CTTCTTGTTG     420

GTTCTTCTGG ACTATCAAGG TATGTTGCCC GTTTGTCCTC TAATTCCAGG ATCTTCAACG     480

ACCAGCACGG GACCATGCAG GACCTGCACG ACTCCTGCTC AAGGCAACTC TATGTATCCC     540

TCCTGTTGCT GTACCAAACC TTCGGACGGA AATTGCACCT GTATTCCCAT CCCATCATCT     600

TGGGCTTTCG GAAAATTCCT ATGGGAGTGG GCCTCAGCCC GTTTCTCCTG GCTCAGTTTA     660

CTAGTGCCAT TTGTTCAGTG GTTCGTAGGG CTTTCCCCCA CTGTTTGGCT TTCAGTTATA     720

TGGATGATGT GGTATTGGGG GCCAAGTCTG TACAGCATCT TGAGTCCCTT TTTACCGCTG     780

TTACCAATTT TCTTTTGTCT TTGGGCATAC ATTTAAACCC TAACAAAACA AAAGATGGG     840

GTTACTCTTT ACACTTCATG GGCTATGTCA TTGGATGTTA TGGGTCATTG CCACAAGATC     900

ACATCAGACA GAAAATCAAA GAATGTTTTA GAAAACTTCC TGTTAACAGG CCTATTGATT     960

GGAAAGGCTG TCAACGAATT GTGGGTTTAT TGGGTTTTGC TGCCCCTTTT ACACAATGTG    1020

GTTATCCTGC GTTGATGCCT TTGTATGCAT GTATTCAATC TAAGCAGGCT TTCACTTTCT    1080

CGCCAACTTA CAAGGCCTTT CTGTGTAAAC AATACCTGAA CCTTTACCCC GTTGCCCGGC    1140

AACGGCCAGG TCTGTGCCAA GTGTTTGCTG ACGCAACCCC CACTGGCTGG GGCTTGGTCA    1200

TGGGCCATCA GCGCATGCGT GGAACCTTTC GGGCTCCTCT GCCGATCCAT ACTGCGGAAC    1260

TCCTAGCCGC TTGTTTTGCT CGCAGCAGGT CTGGAGCAAA CATTCTCGGG ACGGATAACT    1320

TTGTTGTCCT ATCCCGCAAA TATACATCGT TTCCATGGCT GCTAGGCTGT GCTGCCAACT    1380

GGATCCTGAG CGGGACGTCC TTCGTTTACG TCCCGTCGGC GCTGAATCCA GCGGACGACC    1440

CTTCTCGGGG CCGCTTGGGA CTCTCTCGTC CCCTTCTCCG TCTGCCGTTT CGTCCGACCA    1500

CGGGGCGCAC CTCTCTTTAC GCGGACTCCC CGTCTGTGCC TTCTCATCTG CCGGACCGTG    1560

TGCACTTCGC TTCACCTCTG CACGTCGCAT GGAGACCACC GTGAACGCCC ACCAATTCTT    1620

GCCCAAGGTC TTACATAAGA GGACTCTTGG ACTCTCAGCA ATGTCAACGA CCGACCTTGA    1680

GGCATACTTC AAAGACTGTT TGTTTAAAGA GTGGGAGGAG TTGGGGGAGG AGATTAGATT    1740

AAAGTTGTTT GTATTAGGAG GCTGTAGGCA TAAATTGGTC TGCGCACCAG CACCATGCAA    1800

CTTTTTCACC TCTGCCTAAT CATCTCTTGT TCATGTCCTA CTGTTCAAGC CTCCAAGCTG    1860
```

-continued

```
TGCCTTGGGT GGCTTTAGGA CATGGACATT GATCCTTATA AAGAATTTGG AGCTTCTATG    1920

GAGTTGCTCT CGTTTTTGCC TTCTGACTTC TATCCTTCAG TACGAGATCT TCTAGATACC    1980

GCCTCAGCTC TATATCGGGA AGCCTTAGAG TCTCCTGAGC ATTGTACACC TCATCATACT    2040

GCACTCAGGC AAGCAATTCT TTGCTGGGGG GAATTAATGA CTCTAGCCAC CTGGGTGGGT    2100

GGTAATTTGC AAGATCCAAC ATCCAGGGAC CTAGTAGTCA GTTATGTTAA CACTAATATG    2160

GGCCTAAAGT TCAGGCAACT ATTGTGGTTT CACGTTCTT  GTCTCACTTT TGGAAGAGAA    2220

ACAGTCGTAG AGTATTTGGT GTCTTTTGGA GTGTGGATTC GCACTCCTCA AGCTTATAGA    2280

CCACCAAATG CCCCTATCTT ATCAACACTT CCGGAGACTT GTGTTGTTAG ACGACGAGGC    2340

AGGTCCCCTA GAAGAAGAAC TCCCTCGCCT CGCAGACGAA GGTCTCAATC GCCGCGTCGC    2400

AGAAGATCTC AATCTCGGGA ATCTCAATGT TAGTATTCCT TGGACTCATA AGGTGGGAAA    2460

CTTTACGGGG CTTTATTCTT CTACTGTTCC TGTCTTTAAC CCTCATTGGA AAACACCCTC    2520

TTTTCCTAAT ATACATTTAC ACCAAGACAT TATCAAAAAA TGTGAACAAT TTGTAGGCCC    2580

ACTCACAGTC AATGAGAAAA GAAGACTGCA ATTGATTATG CCTGTCAGGT TTTATCCAAT    2640

GGTTACCAAA TATTTGCCAT TGGATAAGGG TATTAAACCG TATTATCCAG AACATCTAGT    2700

TAATCATTAC TTCCAAACCA GACATTATTT ACACACTCTA TGGAAGGCGG GTGTATTATA    2760

TAAGAGAGAA ACAACACATA GCGCCTCATT TTGTGGATCA CCATATTCTT GGGAACAAGA    2820

GATACAGCAT GGGGCAGAAT CTTTCCACCA GCAATCCTCT GGGATTCTTT CCCGACCACC    2880

AGTTGGATCC AGCCTTCAGA GCAAACACCG CAAATCCAGA TTGGGACTTC AATCCCAACA    2940

AGGACACCTG GCCAGACGCC AACAAGGTAG GAGCTGGAGC ATTCGGGCTG GGACTCACCC    3000

CACCGCACGG AGGCCTTTTG GGGTGGAGCC CTCAGGCTCA GGGCATACTA CAGACCGTGC    3060

CAGCAAATCC GCCTCCTGCC TCTACCAATC GCCAGACAGG AAGGCAGCCT ACCCCTCTGT    3120

CTCCACCTTT GAGAGACACT CATCCTCAGG CCATGCAGTG G                        3161
```

(2) INFORMATION FOR SEQ ID NO: 302:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 302:

```
AACTCCACAA CCTTCCACCA AACTCTGCAA GATCCCAGAG TGAGAGGCCT GTATTTCCCT      60

GCTGGTGGCT CCAGTTCAGG AACAGTAAAC CCTGTTCCGA CTACTGCCTC TCACTTATCG    120

TCAATCTTCT CGAGGATTGG GGACCCTGCG CTGAACATGG AGAACATCAC ATCAGGATTC    180

CTAGGACCCC TTCTCGTGTT ACAGGCGGGG TTTTTCTTGT TGACAAGAAT CCTCACAATA    240

CCGCAGAGTC TAGACTCGTG GTGGACTTCT CTCAATTTTC TAGGGGAAC  TACCGTGTGT    300

CTTGGCCAAA ATTCGCAGTC CCCAACCTCC AATCACTCAC CAACCTCCTG TCCTCCAACT    360

TGTCCTGGTT ATCGCTGGAT GTGTCTGCGG CGTTTTATCA TCTTCCTCTT CATCCTGCTG    420

CTATGCCTCA TCTTCTTGTT GGTTCTTCTG GACTATCAAG GTATGTTGCC CGTTTGTCCT    480

CTAATTCCAG GATCCTCAAC CACCAGCACG GGACCATGCC GAACCTGCAC GACTCCTGCT    540
```

-continued

```
CAAGGAACCT CTATGTATCC CTCCTGTTGC TGTACCAAAC CTTCGGACGG AAATTGCACC      600

TGTATTCCCA TCCCATCATC CTGGGCTTTC GGAAAATTCC TATGGGAGTG GGCCTCAGCC      660

CGTTTCTCCT GGCTCAGTTT ACTAGTGCCA TTTGTTCAGT GGTTCGTAGG GCTTTCCCCC      720

ACTGTTTGGC TTTCAGTTAT ATGGATGATG TGGTATTGGG GGCCAAGTCT GTACAGCATC      780

TTGAGTCCCT TTTTACCGCT GTTACCAATT TTCTTTTGTC TTTGGGTATA CATTTAAACC      840

CTAACAAAAC AAAGAGATGG GGTTACTCTC TAAATTTTAT GGGCTATGTC ATTGGATGTT      900

ATGGGTCCTT GCCACAAGAA CACATCATAC AAAAAATCAA AGAATGTTTT AGAAAACTTC      960

CTGTTAACAG GCCTATTGAT TGGAAAGTAT GTCAACGAAT TGTGGGTCTT TTGGGTTTTG     1020

CTGCCCCTTT TACTCAATGT GGTTATCCTG CTTTAATGCC CTTGTATGCA TGTATTCAAT     1080

CTAAGCAGGC TTTCACTTTC TCGCCAACTT ACAAGGCCTT TCTGTGTAAA CAATACCTGA     1140

ACCTTTACCC CGTTGCCGGG CAACGGCCAG GTCTATGCCA AGTGTTTGCT GACGCAACCC     1200

CCACTGGCTG GGGCTTGGCT ATGGGCCATC AGCGCATGCG TGGAACCTTT TCGGCTCCTC     1260

TGCCGATCCA TACTGCGGAA CTCCTAGCCG CTTGTTTTGC TCGCAGCAGG TCTGGAGCAA     1320

ACATTATCGG GACTGATAAC TCTGTTGTCC TCTCCCGCAA ATATACATCG TTTCCATGGC     1380

TGCTAGGCTG TGCTGCCAAC TGGATCCTGC GCGGGACGTC CTTTGTTTAC GTCCCGTCGG     1440

CGCTGAATCC CGCGGACGAC CCGTCTCGGG GTCGCTTGGG ACTCTCTCGT CCCCTTCTCC     1500

GTCTGCCGTT CCGACCGACC ACGGGGCGCA CCTCTCTTTA CGCGGACTCC CCGTCTGTGC     1560

CTTCTCATCT GCCTGACCTT GTGCACTTCG CTTCACCTCT GCACGTCGCA TGGAGACCAC     1620

CGTGAACGCC CACCAAATAT TGCCCAAGGT CTTACATAAG AGGACTCTTG GACTCTCTGC     1680

AATGTCAACG ACCGACCTTG AGGCATACTT CAAAGACTGT TTGTTTAAAG ACTGGGAGGA     1740

GTTGGGGGAG GAGATTAGAT TAAAGGTCTT TGTACTAGGA GGCTGTAGGC ATAAATTGGT     1800

CTGCGCACCA GCACCATGCA ACTTTTTCAC CTCTGCCTAA TCATCTCTTG TTCATGTCCT     1860

ACTGTTCAAG CCTCCAAGCT GTGCCTTGGG TGGCTTTGGG GCATGGACAT TGACCCTTGA     1920

AAAGAATTTG GAGCTACCGT GGAGTTACTC TCGTTTTTGC CTTCTGACTT CTTTCCTTCA     1980

GTACGAGATC TTCTAGATAC CGCCTCAGCT CTGTATCGGG ATGCCTTAGA GTCTCCTGAG     2040

CATTGTTCAC CTCACCATAC TGCACTCAGG CAAGCAATTC TTTGCTGGGG GAACTAATG     2100

ACTCTAGCTA CCTGGGTGGG TGTTAATTTG GAAGATCCAG CATCTAGGGA CCTAGTAGTC     2160

AGTTATGTCA ACACTAATAT GGGCCTAAAG TTCAGACAAC TCTTGTGGTT TCACATTTCT     2220

TGTCTCATTT TTGGAAGAGA AACAGTTATA GAGTATTTGG TGTCTTTCGG AGTGTGGATT     2280

CGCACTCCTC CAGCTTATAG ACCACCAAAT GCCCCTATCC TATCAACACT TCCGGAGACT     2340

ACTGTTGTTA GACGACGAGG CAGGTCCCCT AGAAGAAGAA CTCCCTCGCC TCGCAGACGA     2400

AGGTCTCAAT CGCCGCGTCG CAGAAGATCT CAATCTCGGG AATCTCAATG TTAGTATTCC     2460

TTGGACTCAT AAGGTGGGGA ATTTTACTGG GCTTTATTCT TCTACTGTAC CTGTCTTTAA     2520

TCCTCATTGG AAAACACCAT CTTTTCCTAA TATACATTTA CACCAAGACA TTATCAAAAA     2580

ATGTGAACAG TTTGTAGGCC CACTCACAGT TAATGAGAAA GAAGATTGC AATTGATCAT     2640

GCCTGCTAGG TTTTATCCAA AGGTTACCAA ATATTTACCA TTGGATAAGG GTATTAAACC     2700

TTATTATCCA GAACATCTAG TTAATCATTA CTTCCAAACT AGACACTATT TACACACTCT     2760

ATGGAAGGCG GGTATATTAT ATAAGAGAGA ACAACACAT AGCGCCTCAT TTTGTGGGTC     2820

ACCATATTCT TGGGAACAAG ATCTACAGCA TGGGGCAGAA TCTTTCCACC AGCAATCCTC     2880

TGGGATTCTT TCCCGACCAC CAGTTGGATC CAGCCTTCAG AGCAAACACC GCAAATCCAG     2940
```

| | | |
|---|---|---|
| ATTGGGACTT CAATCCCAAC AAGGACACCT GGCCAGACGC CAACAAGGTA GGAGCTGGAG | 3000 | |
| CATTCGGGCT GGGTTTCACC CCACCGCACG GAGGCCTTTT GGGGTGGAGC CCTCAGGCTC | 3060 | |
| AGGGCATACT ACAAACTTTG CCAGCAAATC CGCCTCCTGC CTCCACCAAT CGCCAGTCAG | 3120 | |
| GAAGGCAGCC TACCCCTCTG TCTCCACCTT TGAGAAACAC TCATCCTCAG GCCATGCAGT | 3180 | |
| GG | 3182 | |

(2) INFORMATION FOR SEQ ID NO: 303:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 303:

| | |
|---|---|
| AACTCCACAA CTTTCCACCA AACTCTGCAA GATCCCAGAG TGAGAGGCCT ATATTTCCCT | 60 |
| GCTGGTGGCT CCAGTTCAGG AACAGTAAAC CCTGTTCCGA CTACTGCCTC TCCCTTATCG | 120 |
| TCAATCTTCT CGAGGATTGG GGACCCTGTG ACGAATATGG AGAACATCAC ATCAGGATTC | 180 |
| CTAGGACCCC TGCTCGTGTT ACAGGCGGGG TTTTTCTTGT TGACAAGAAT CCTCACAATA | 240 |
| CCGCAGAGTC TAGACTCGTG GTGGACTTCT CTCAATTTTC GAGGGGGAAC TACCGTGTGT | 300 |
| CTTGGCCAAA ATTCGCAGTC CCCAACCTCC AATCACTCAC CAACCTCCTG TCCTCCAACT | 360 |
| TGTCCTGGTT ATCGCTGGAT GTGTCTGCGG GGTTTTATCA TCTTCCTCTT CATCCTGCTG | 420 |
| CTATGCCTCA TCTTCTTGTT GGTTCTTCTG GAGTATCAAG GTATGTTGCA CGTTTGTCCT | 480 |
| CTAATTCCAG GAACAACAAC AACCAGTACG GGACCATGCA AAACCTGCAC GACTCCTGCT | 540 |
| CAAGGCAACT CTATGTTTCC CTCATGTTGC TGTACCAAAA CTTCGGATGG AAATTGCACC | 600 |
| TGTATTCCCA TCCCATCGTC TTGGGCTTTC GCAAAATACC TATGGGAGTG GCCTCAGTC | 660 |
| CGTTTCTCTT GGCTCAGTTT ACTAGTGCCA TTTGTTCAGT GGTTCGTAGG GCTTTCCCCC | 720 |
| ACTGTTTGGC TTTCAGCTAT ATGGATGATG TGGTATTGGG GGCCAAGTCT GTACAGCATC | 780 |
| TTGAGTCCCT TTTTACCGCT GTTACCAATT TTCTTTTGTC TTTGGGTATA CATTTAAACC | 840 |
| CTAACAAAAC AAAGAGATGG GGTTACTCTT TACATTTCAT GGGCTATGTC ATTGGATGTT | 900 |
| ATGGGTCCTT GCCACAAGAA CACATCATAC AAAAAATCAA AGAATGTTTT AGAAAAGTTC | 960 |
| CTGTTAACAG GCCTATTGAT TGGAAAGTAT GTCAACGAAT TGTGGGTCTT TTAGGTTTTG | 1020 |
| CTGCCCCTTT CACACAATGT GGTTATCCTG CTTTAATGCC CTTGTATGCT TGTATTCAAT | 1080 |
| TTAAGCAGGC TTTCACTTTC TCGCCAACTT ACAAGGCCTT TCTGTGTAAA CAATACCTGA | 1140 |
| ACCTTTACCC CGTTGCCCGG CAACGGCCAG GTCTATGCCA AGTGTTTGCT GACGCAACCC | 1200 |
| CCACTGGCTG GGGCTTGGGT ATGGGCCATC AGCGCATGCG TGGAACCTTT TCGGCTCCTC | 1260 |
| TGCCGATCCA TACTGCGGAA CTCCTAGCCG CCTGTTTTGC TCGCAGCAGG TCTGGAGCAA | 1320 |
| ACATTCTCGG GACGGATAAC TCTGTTGTTC TCTCCCGCAA ATATACATCG TTTCCATGGC | 1380 |
| TGCTAGGCTG TGCTGCCAAC TGGATCCTGC GCGGGACGTC CTTTGTTTAC GTCCCGTCGG | 1440 |
| CGCTGAATCC CGCGGACGAC CCTTCTCGGG GCCGCTTGGG ACTCTCTCGT CCCCTTCTCT | 1500 |
| GTCTGCCGTT TCGACCGACC ACGGGGCGCA CCTCTCTTTA CGCGGACTCC CCGTCTGTGC | 1560 |

```
CTTCTCATCT GCCGGACCGT GTGCACTTCG CTTCACCTCT GCACGTCGCA TGGAGACCAC      1620

CGTGAACGCC CATCAGATCC TGCCCAAGGT CTTACATAAG AGGACTCTTG GACTCCCAGC      1680

AATGTCAACG ACCGACCTTG AGGCCTACTT CAAAGACTGT GTGTTTAAGG ACTGGGAGGA      1740

GCTGGGGGAG GAGATTAGGT TAAAGGTCTT TGTATTAGGA GGCTGTAGGC ATAAATTGGT      1800

CTGCGCACCA GCACCATGCA ACTTTTTCAC CTCTGCCTAA TCATCTCTTG TACATGTCCC      1860

ACTGTTCAAG CCTCCAAGCT GTGCCTTGGG TGGCTTTGGG GCATGGACAT TGACCCTTAT      1920

AAAGAATTTG GAGCTACTGT GGAGTTACTC TCGTTTTTGC CTTCTGACTT CTTTCCTTCC      1980

GTACGAGATC TCCTAGACAC CGCCTCAGCT CTGTATCGGG AAGCCTTAGA GTCTCCTGAG      2040

CATTGTTCAC CTCACCATAC TGCACTCAGG CAAGCAATTC TTTGCTGGGG GGAACTAATG      2100

ACTCTAGCTA CCTGGGTGGG TGTTAATTTG GAAGATCCAG CATCTAGAGA CCTAGTAGTC      2160

AGTTATGTCA ACACTAATAT GGGCTTAAAG TTCAGGCAAC TCTTGTGGTT TCACATTTCT      2220

TGTCTCACTT TTGGAAGAGA AACAGTTATA GAGTATTTGG TGGCTTTCGG AGTGTGGATT      2280

CGCACTCCTC CAGCTTATAG ACCACCAAAT GCCCCTATCC TATCAACACT TCCGGAGACT      2340

ACTGTTGTTA GACGACGAGG CAGGTCCCCT AGAAGAAGAA CTCCCTCGCC TCGCAGACGA      2400

AGGTCTCAAT CGCCGCGTCG CAGAAGATCT CAATCTCGGG AATCTCAATG TTAGTATTCC      2460

TTGGACTCAT AAGGTGGGAA ACTTTACGGG GTTTTATTCT TCTACTGTTC CTGTCTTTAA      2520

CCCTCATTGG GAAACCCCCT CTTTTCCTAA TATACATTTA CACCAAGACA TTATCAAAAA      2580

ATGTGAACAG TTTGTAGGCC CACTCACAGT TAATGAGAAA AGAAGATTGC AATTGATTAT      2640

GCCTGCTAGG TTTTATCCAA AGGTTACCAA ATATTTACCA TTGGATAAGG GTATTAAACC      2700

TTATTATCCA GAACATCTAG TTAATCATTA CTTCCAAACT AGACACTATT TACACACTCT      2760

ATGGAAGGCG GGTATATTAT ATAAGAGAGA ACAACACAT AGCGCCTCAT TTTGTGGGTC      2820

ACCATATTCT TGGGAACAAG ATCTACAGCA TGGGGCAGAA TCTATCCACC AGCAATCCTC      2880

TGGGATTCTT TCCCGACCAC CAGTTGGATC CAGCCTCCAG AGCAAACACC GCAAATCCAG      2940

ATTGGGACTT CAATCCCAAC AAGGACACCT GGCCAGACGC CAACAAGGAT GGAGCTGGAG      3000

CATTCGGGCT GGGACTCACC CCACCGCACG GAGGCCTTTT GGGGTGGAGC CCTCAGGCTC      3060

AGGGCATACT ACACACCGTG CCAGCAAATC CGCCTCCTGC CTCTACCAAT CGCCAGACAG      3120

GAAGGCAACC TACCCCTCTG TCTCCACCTT TGAGAGACAC TCATCCTCAG GCCGTGCAGT      3180

GG                                                                    3182

(2) INFORMATION FOR SEQ ID NO: 304:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 304:

AACTCCACAA CCTTCCACCA AACTCTGCAA GATCCCAGAG TGAGAGGCCT GTATTTCCCT        60

GCTGGTGGCT CCAGTTCAGG AACAGTAAAC CCTGTTCTGA CTACTGCCTC TCCCTTATCG       120

TCAATCTCCG CGAGGACTGG GGACCCTGCA CTGAACATGG AGAACATCAC ATCAGGATTG       180
```

```
CTAGGACCCC TGCTCGTGTT ACAGGCGGGG TTTTTCTTGT TGACAAGAAT CCTCACAATA    240
CCGCAGAGTC TAGACTCGTG GTGGACTTCT CTCAATTTTC TAGGGGGAAC TACCGTGTGT    300
CTTGGCCAAA ATTCGCAGTC CCCAACCTCC AATCACTCAC CAACCTCTTG TCCTCCAACT    360
TGTCCTGGTT ATCGCTGGAT GTGTCTGCGG CGTTTTATCA TCTTCCTCTT CATCCTGCTG    420
CTATGCCTCA TCTTCTTGTT GGTTCTTCTG GACTATCAAG GTATGTTGCC CGTTTGTCCT    480
CTAATTCCAG GATCTTCAAC AACCAGCACG GGACCATGCA GAACCTGCAC GACTCCTGCT    540
CAAGGAACCT CTATGTATCC CTCCTGTTGC TGTACCAAAC CTTCGGACGG AAATTGCACC    600
TGTATTCCCA TCCCATCATC TTGGGCTTTC GGAAAATTCC TATGGGAGTG GGCCTCAGCC    660
CGTTTCTCCT GGCTCAGTTT ACTAGTGCCA TTTGTTCAGT GGTTCGTAGG GCTTTCCCCC    720
ACTGTTTGGC TTTCAGTTAT ATGGATGATG TGGTATTGGG GGCCAAGTCT GTACAGCATC    780
TTGAGTCCCT TTTTACCGCT GTTACCAATT TTCTTTTGTC TCTGGGTATA CATTTAAACC    840
CTAACAAAAC AAAAAGATGG GGTTATTCCC TAAACTTCAT GGGTTACATA ATTGGAAGTT    900
GGGGAACGTT GCCACAAGAT CATATTGTAC AAAAGATCAA AGAATGTTTT AGAAAACTTC    960
CTGTTAACAG GCCTATTGAT TGGAAAGTAT GGCAACGAAT TGTGGGTCTT TTGGGCTTTG   1020
CTGCTCCATT TACACAATGT GGATATCCTG CCTTAATGCC TTTGTATGCC TGTATACAAG   1080
CTAAACAGGC TTTCACTTTC TCGCCAACTT ACAAGGCCTT TCTAAGTAAA CAGTACATGA   1140
ACCTTTACCC CGTTGCTCGG CAACGGCCTG GTCTGTGCCA AGTGTTTGCT GACGCAACCC   1200
CCACTGGCTG GGGCTTGGCA ATAGGCAATC AGCGCATGCG TGGAACCATT GTGGCTCCTC   1260
TGCCGATCCA TACTGCGGAA CTCCTAGCCG CTTGTTTTGC TCGCAGCCGG TCTGGGGCAA   1320
AGCTCATCGG AACTGACAAT TCTGTTGTCC TCTCGCGGAA ATATACATCG TTTCCATGGC   1380
TGCTAGGTTG TACTGCCAAC TGGATCCTTC GCGGGACGTC CTTTGTTTAC GTCCCGTCGG   1440
CGCTGAATCC CGCGGACGAC CCTTCTCGGG GCCGCTTGGG ACTCTCTCGT CCCCTTCTCC   1500
GTCTGCCGTT CCAGCCGACC ACGGGGCGCA CCTCTCTTTA CGCGGTCTCC CCGTCTGTGC   1560
CTTCTCATCT GCCGGTCCGT GTGCACTTCG CTTCACCTCT GCACATTGCA TGGAGACCAC   1620
CGTGAACGCC CATCAGATTA TGCCCAAGGT TTTACATAAG AGGACTCTTG GACTCCCAGC   1680
AATGTCAACG ACCGACCTTG AGGCCTACTT CAAAGACTGT GTGTTTAAGG ACTGGGAGGA   1740
GCTGGGGGAG GAGATTAGGT TAAAGGTCTT TGTATTAGGA GGCTGTAGGC ATAAATTGGT   1800
CTGCGCACCA GCACCATGCA ACTTTTTCAC CTCTGCCTAA TCATCTCTTG TTCATGTCCT   1860
ACTGTTCAAG CCTCCAAGCT GTGCCTTGGG TGGCTTTAGG GCATGGACAT TGACCCTTAT   1920
AAACAATTTG GAGCTACTGT GGAGTTACTC CCGTATTTGC CTTCTGACTT CTTTCTCTAC   1980
GTACGAGATC TCCTAGATAC CGCCTCAGCT CTGTATCGGG AAGCCTTAGA GTCTCCTGAG   2040
CATTGTTCAC CTCACCATAC TGCACTCAGG CAAGCAATTC TTTGCTGGGG GGAACTAATG   2100
ACTCTAGCTA CCTGGGTGGG TGTTAATTTG GAAGATCCAG CATCTAGAGA CTTAGTAGCT   2160
AGTTATGTCA ACACTAATAT GGGCCTAAAG TTCAGGCAAC TCTTGTGGTT TCACATTTCT   2220
TGTCTCACTT TTGGAAGAGA AACAGTTATA GAGTATTTGG TGTCTTTCGG AGTGTGGATT   2280
CGCACTCCTC CAGCTTATAG ACCACCAAAT GCCCCTATCC TATCAACACT TCCGGAGACT   2340
ACTGTTGTTA CACGACGAGG CAGGTCCCCT AGAAGAAGAA CTCCCTCGCC TGCCAGACCA   2400
AGGTCTCAAT CGCCGCGTCG CAGAAGATCT CAATCTCGGG AATCTCAATG TTAGTATTCC   2460
TTGGACTCAT AAGGTGGGGA ACTTTACGGG GCTTTATTCT TCTACTGTTC CTGTCTTTAA   2520
```

-continued

| | |
|---|---|
| TCCTCATTGG AAAACACCTT CTTTTCCTAA TATACATTTA CACCAAGACA TTATCAAAAA | 2580 |
| ATGTGAACAA TTTGTAGGCC CACTCACAGT CAATGAGAAA AGAAGACTGC AATTGATTAT | 2640 |
| GCCTGCTAGG TTTTATCCAA ATGTCACCAA ATATTTGCCA TTGGATAAGG GTATTAAACC | 2700 |
| TTATTATCCA GAGCATCTAG TTAATCATTA CTTCCAAACC AGACATTATT TACACACTCT | 2760 |
| ATGGAAGGCG GGTATATTAT ATAAGAGAGA AACAACACAT AGCGCCTCAT TTTGTGGGTC | 2820 |
| ACCATATTCT TGGGAACAAG AGCTACAGCA TGGGGCAGAA TCTTTCCACC AGCAATCCTC | 2880 |
| TGGGATTCTT TCCCGACCAC CAGTTGGATC CAGCCTTCAG AGCAAACACC GCAAATCCAG | 2940 |
| ATTGGGACTT CAATCCCAAC AAGGACACCT GGCCAGACGC CAACAAGGTA GGAGCTGGAG | 3000 |
| CATTCGGGCT GGGTTTCACC CCACCGCACG GAGGTCTTTT GGGGTGGAGC CCTCAGGCTC | 3060 |
| AGGGCATACT ACATACCGTG CCAGCAAATC CGCCTCCTGC CTCTACCAAT CGCCAGTCAG | 3120 |
| GAAGGCAGCC TACCCCTCTG TCTCCACCTT TGAGAAACAC TCATCCTCAG GCCATGCAGT | 3180 |
| GG | 3182 |

(2) INFORMATION FOR SEQ ID NO: 305:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 305:

| | |
|---|---|
| AACTCCACAA CCTTCCACCA AACTCTGCAA GATCCAAGAG TGAGAGGCCT GTATTTCCCT | 60 |
| GCTGGTGGCT CCAGTTCAGG AACAGTAAAC CCTGTTCTGA CTACTGCCTC TCCCTTATCG | 120 |
| TCAATCTCCG CGAGGACTGG GGACCCTGTG ACGATCATGG AGAACATCAC ATCAGGATTC | 180 |
| CTAGGACCCC TGCTCGTGTT AGAGGCGGGG TTTTTCTTGT TGACAAGAAT CCTCACAATA | 240 |
| CCGCAGAGTC TAGACTCGTG GTGGACTTCT CTCAATTTTC TAGGGGGAAC TACCGTGTGT | 300 |
| CTTGGCCAAA ATTCGCAGTC CCCAACCTCC CATCACTCAC CAACCTCCTG TCCTCCAATT | 360 |
| TGTCCTGGTT ATCGCTGGAT GTGTCTGCGG CGTTTTATCA TATTCCTCTT CATCCTGCTG | 420 |
| CTATGCCTCA TCTTCTTGTT GGTTCTTCTG GACTATCAAG GTATGTTGCC CGTTTGTCCT | 480 |
| CTAATTCCAG GTACTTCAAC AACCAGCACG GGACCATGCA GAACCTGCAC GACTCCTGCT | 540 |
| CAAGGAACCT CTATGTATCC CTCCTGTTGC TGTACCAAAC CTTCGGACGG AAATTGCACC | 600 |
| TGTATTCCCA TCCCATCATC TTGGGCTTTC GGAAAATTCC TATGGCAGTG GGCCTCAGC6 | 60 |
| CGTTTCTCCT GGCTCAGTTT ACTAGTGCCA TTTGTTCAGT GGTTCGTAGG GCTTTCCCCC | 720 |
| ACTGTTTGGG TTTCAGCTAT ATGGATGATG TGGTATTGGG GGCCAAGTCT GTACAGCATC | 780 |
| GTGAGTCCCT TTATACCGCT GTTACCAATT TTCTTTTGTC TCTGGGTATA CATTTAAACC | 840 |
| CTAACAAAAC AAAAAGATGG GGTTATTCCC TAAACTTCAT GGGTTACATA ATTGGAAGTT | 900 |
| GGGGAACGTT GCCACAGGAT CATATTGTAC AAAAGATCAA ACACTGTTTT AGAAAACTTT | 960 |
| CTGTTAACAG GCCTATTGAT TGGAAAGTAT GGCAACGAAT TGTGGGTCTT TTGGGTTTTG | 1020 |
| CTGCTCCATT TACACAATGT GGTTATCCTG CCTTAATGCC TTTGTATGCC TGTATACAAG | 1080 |
| CTAAACAGGC TTTCACTTTC TCGCCAACTT ACAAGGCCTT TCTAAGTAAA CAGTACATGA | 1140 |

-continued

```
ACCTTTACCC CGTTGCTCGG CAACGGCCTG GTCTGTGCCA AGTGTTTGCT GACGCAACCC    1200

CCACTGGCTG GGGCTTGGCA TAGGGCCATC AGCGCATGCG TGGAACCTTT GAGGCTCCTC    1260

TGCCGATCCA TACTGCGGAA CTCCTAGCCG CTTGTTTTGC TCGCAGCAGG TCTGGAGCAA    1320

ACATTATCGG GACTGATAAC TCTGTTGTCC TATCGCGGAA ATATACATCG TTTCCATGGC    1380

TGCTAGGTTG TACTGCCAAC TGGATCCTTC GCGGGACGTC CTTTGTTTAC GTCCCGTCGG    1440

CGCTGAATCC CGCGGACGAC CCCTCTCGGG GCCGCTTGGG ACTCTCTCGT CCCCTTCTCC    1500

GTCTGCCGTT CCAGCCGACC ACGGGGCGCA CCTCTCTTTA CGCGGTCTCA CCGTCTGTGC    1560

CTTCTCATCT GCCGGTCCGT GTGCACTTCG CTTCACCTCT GCACGTCGCA TGGAGACCAC    1620

CGTGAACGCC CATCAAAGTC TGCCCAAGGT CTTACATAAG AGGACTCTTG GACTCCCAGC    1680

AATGTCAACG ACCGACCTTG AGGCCTACTT CAAAGACTGT GTGTTTAAGG ACTGGGAGGA    1740

GCTGGGGGAG GAGATTAGGT TAAAGGTCTT TGTATTAGGA GGCTGTAGGC ATAAATTGGT    1800

CTGCGCACCA GCACCATGCA ACTTTTTCAC CTCTGCCTAA TCATCTCTTG TTCATGTCCC    1860

ACTGTTCAAG CCTCCAAGCT GTGCCTTGGG TGGCTTTGGG GCATGGACAT TGACCCTTAT    1920

AAAGAATTTG GAGCTACTGT GGAGTTACTC TCGTTTTTGC CTTCTGACTT CTTTCCTTCC    1980

GTAAGAGATC TCCTAGACAC CGCCTCAGCT CTGTATCGAG AAGCCTTAGA GTCTCCTGAG    2040

CATTGCTCAC CTCACCATAC TGCACTCAGG CAAGCCATTC TCTGCTGGGG GGAACTGATG    2100

ACTCTAGCAT CCTGGGTGGG TGATAATTTG GAAGATCCAG CGTCTAGGGA CCTAGTAGTC    2160

AGTTATGTTA ACACTAATAT GGGCCTAAAG ATCAGGCAAC TATTGTGGTT TCATATATCT    2220

TGCCTTACTT TTGGAAGAGA GACTGTACTT GAATATTTGG TCTCTTTCGG AGTGTGGATT    2280

CGCACTCCTC CAGCCTATAG ACCACCAAAT GCCCCTATCT TATCAACACT TCCGGAAACT    2340

ACTGTTGTTA GACGACGGGA CAGGTCCCCT AGAAGAAGAA CTCCCTCGCC TCGCAGACGA    2400

AGGTCTCAAT CGCCGCGTCG CAGAAGATCT CAATCTCGGG AATCTCAATG TTAGTATTCC    2460

TTGGACTCAT AAGGTGGGGA ACTTTACTGG GCTTTATTCT TCTACTGTAC CTGTCTTTAA    2520

TCCTCATTGG AAAACACCAT CTTTTCCTAA TATACATTTA CACCAAGACA TTATCAAAAA    2580

ATGTGAACAG TTTGTAGGCC CACTCACAGT TAATGAGAAA AGAAGATTGC AATTGATTAT    2640

GCCTGCTAGG TTTTATCCAA AGGTTACCAA ATATTTACCA TTGGATAAGG GTATTAAACC    2700

TTATTATCCA GAACATCTAG TTAATCATTA CTTCCAAACT AGACACTATT TACACACTCT    2760

ATGGAAGGCG GGTATATTAT ATAAGAGAGA ACAACACAT AGCGCCTCAT TTTGTGGGTC    2820

ACCATATTCT TGGGAACAAG ATCTACAGCA TGGGGCAGAA TCTATCCACC AGCAATCCTC    2880

TGGGATTCTT TCCCGACCAC CAGTTGGATC CAGCCTTCAG AGCAAACACC GCAAATCCAG    2940

ATTGGGACTT CAATCCCAAC AAGGACACCT GGCCAGACGC CAACAAGGTA GGAGCTGGAG    3000

CATTCGGGCT GGGTTTCACC CCACCGCACG GAGGCCTTTT GGGGTGGAGC CCTCAGGCTC    3060

AGGGCATACT ACAAACTTTG CCAGCAAATC CGCCTCCTGC CTCCACCAAT CGCCAGTCAG    3120

GAAGGCAGCC TACCCCTCTG TCTCCACCTT TGAGAAACAC TCATCCTCAG GCCATGCAGT    3180

GG                                                                  3182
```

(2) INFORMATION FOR SEQ ID NO: 306:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 306:

| | | | | | |
|---|---|---|---|---|---|
| AACTCCACAA | CCTTCCACCA | AACTCTGCAA | GATCCCAGAG | TGAGAGGCCT | GTATCTCCCT | 60 |
| GCTGGTGGCT | CCAGTTCAGG | AACAGTAAAC | CCTGTTCCGA | CTACTGTCTC | TCCCATATCG | 120 |
| TCAATCTTCT | CGAGGATTGG | GGACCCTGCG | CTGAACATGG | AGAACATCAC | ATCAGGATTC | 180 |
| CTAGGACCCC | TGCTCGTGTT | ACAGGCGGGG | TTTTTCTTGT | TGACAAAAAT | CCTCACAATA | 240 |
| CCGAAGAGTC | TAGACTCGTG | GTGGACTTCT | CTCAATTTTC | TAGGGGGAAC | CACCGTGTGT | 300 |
| CTTGGCCAAA | ATTCGCAGTC | CCCAACCTCC | AATCACTCAC | CAACCTCCTG | TCCTCCAACT | 360 |
| TGTCCTGGTT | ATCGCTGGAT | GTGTCTGCGG | CGTTTTATCA | TCTTCCTCTT | CATCCTGCTG | 420 |
| CTATGCCTCA | TCTTCTTGTT | GGTTCTTCTG | GACTATCAAG | GTATGTTGCC | CGTTTGTCCT | 480 |
| CTGATTCCAG | GATCTTCAAC | CACCAGCACG | GGACCATGCA | GAACCTGCAC | GACTCCTGCT | 540 |
| CAAGGAACCT | CTATGTATCC | CTCCTGTTGC | TGTACCAAAC | CTTCGGACGG | AAATTGCACC | 600 |
| TGTATTCCCA | TCCCATCATC | CTGGGCTTTC | GGAAAATTCC | TATGGGAGTG | GGCCTCAGCC | 660 |
| CGTTTCTCCT | GGCTCAGTTT | ACTAGTGCCA | TTTGTTCAGT | GGTTCGTAGG | GCTTTCCCCC | 720 |
| ACTGTTTGGC | TTTTAGTTAT | ATGGATGATG | TGGTATTGGG | GGCCAAAACT | GTTCACCATC | 780 |
| TTGAGTCCCT | TTTTACCGCT | GTTACCAATT | TTCTTTTGTC | TTTGGGTATA | CATCTAAACC | 840 |
| CTAACAAAAC | AAAAAGATGG | GGTTACTCTT | TACATTTTAT | GGGCTATGTC | ATTGGATGTT | 900 |
| ATGGGTCTTT | GCCACAAGAT | CACATCATAC | AGAAAATCAA | AGAATGTTTT | AGAAAACTTC | 960 |
| CTGTTAACAG | GCCTATTGAT | TGGAAAGTCT | GTCAACGTAT | TGTGGGTCTT | TTGGGATTTG | 1020 |
| CTGCTCCTTT | TACACAATGT | GGTTATCCTG | CTTTAATGCC | CTTGTATGCA | TGTATTCAAT | 1080 |
| CTAAGCAGGC | TTTCACTTTC | TCGCCAACTT | ACAAGGCCTT | TCTGTGTAAA | CAATACCTGA | 1140 |
| ACCTTTACCC | CGTTGCCCGG | CAACGCCCAG | GTCTGTGCCA | AGTGTTTGCT | GACGCAACCC | 1200 |
| CCACTGGCTG | GGGCTTGGTC | ATGGGCCATC | AGCGCATGCG | TGGAACCTTT | CAGGCTCCTC | 1260 |
| TGCCGATCCA | TACTGCGGAA | CTCCTAGCCG | CTTGTTTTGC | TCGCAGCCGG | TCTGGAGCAA | 1320 |
| ACATTCTCGG | GACGGATAAC | TCTGTTGTTC | TCTCCCGCAA | ATATACGTCG | TTTCCATGGC | 1380 |
| TGCTAGGCTG | TGCTGCCAAC | TGGATCCTGC | GCGGGACGTC | CTTTGTTTAC | GTCCCGTCGG | 1440 |
| CGCTGAATCC | CGCGGACGAC | CCTTCTCGGG | GCCGCTTGGG | ACTCTCTCGT | CCCCTTCTCC | 1500 |
| GTCTGCCGTT | TCGACCGACC | ACGGGGCGCA | CCTCTCTTTA | CGCGGACTCC | CCGTCTGTGC | 1560 |
| CTTCTCATCT | GCCGGACCGT | GTGCACTTCG | CTTCACCTCT | GCACGTCGCA | TGGAGACCAC | 1620 |
| CGTGAACGCC | CACCAATTCT | TGCCCAAGGT | CTTACATAAG | AGGACTCTTG | GACTCTCTGT | 1680 |
| AATGTCAACG | ACCGACCTTG | AGGCATACTT | CAAAGACTGT | TGTTTAAGG | ACTGGGAGGA | 1740 |
| GTCGGGGAG | GAGATTAGAT | TAATGATCTT | TGTACTAGGA | GGCTGTAGGC | ATAAATTGGT | 1800 |
| CTGCGCACCA | GCACCATGCA | ACTTTTTCAC | CTCTGCCTAA | TCATCTCTTG | TTCATGTCCT | 1860 |
| ACTGTTCAAG | CCTCCAAGCT | GTGCCTTGGG | TGGCTTTAGG | ACATGGACAT | TGATCCTTAT | 1920 |
| AAAGAATTTG | GAGCTACTGT | GGAGTTACTC | TCGTTTCTGC | CTTCTGACTT | CTTTCCTTCA | 1980 |
| GTACGAGATC | TTCTAGATAC | CGCCTCAGCT | CTATATCGGG | AAGCCTTAGA | ATCTCCTGAG | 2040 |
| CATTGTTCAC | CTCACCATAC | TGCACTCAGG | CAAGCAATTC | TCTGCTGGGG | GGATCTAATA | 2100 |
| ACTCTATCCA | CCTGGGTGGG | TGGTAATTTG | GAAGATCCAA | CATCTAGGGA | CCTAGTAGTC | 2160 |

| | | |
|---|---|---|
| AGTTATGTTA ACACTAATAT GGGCCTAAAG TTCAGGCAAC TATTGTGGTT TCACATTTCT | 2220 |
| TGTCTCACTT TTGGAAGAGA AACGGTCATA GAGTATTTGG TGTCTTTTGG AGTGTGGATT | 2280 |
| CGCACTCCTC CAGCTTATAG ACCACCAAAT GCCCCTATCT TATCAACACT TCCGGAGACT | 2340 |
| ACTGTTGTTA GACGACGAGG CAGGTCCCCT AGAAGAAGAA CTCCCTCGCC TCGCAGACGA | 2400 |
| AGGTCTCAAT CGCCACGTCG CAGAAGAACT CAATCTCGGG AATCTCAATG TTAGTATTCC | 2460 |
| CTGGACTCAT AAGGTGGGAA ACTTTACGGG GCTTTATTCT TCTACTGTTC CTGTCTTTAA | 2520 |
| CCCTCATTGG AAAACACCCT CTTTTCCTAA TATACATTTA CACCAAGACA TTATCAAAAA | 2580 |
| ATGTGAACAA TTTGTAGGCC CACTCACAGT CAATGAGAAA AGAAGACTGC AATTGATTAT | 2640 |
| GCCTGCTAGG TTTTATCCAA AGGTTACCAA ATATTTGCCA TTGGATAAGG GTATTAAACC | 2700 |
| TTATTATCCA GAACATCTAG TTAATCATTA CTTCCAAACC AGACATTATT TACACACTCT | 2760 |
| ATGGAAGGCG GGTGTATTAT ATAAGAGAGA AACTACACAT AGCGCCTCAT TTTGTGGGTC | 2820 |
| ACCATATTCC TGGGAACAAG AGCTACAGCA TGGGGCAGAA TCTTTCCACC AGCAATCCTC | 2880 |
| TGGGATTCTT TCCCGACCAC CAGTTGGATC CAGCCTTCAG AGCAAACACT GCAAATCCAG | 2940 |
| ATTGGGACTT CAATCCCAAC AAGGACTCCT GGCCAGACGC CAACAAGGTA GGAGCTGGAG | 3000 |
| CATTCGGGCT GGGATTCACC CCACCGCACG GAGGCCTTTT GGGGTGGAGC CCTCAGGCTC | 3060 |
| AGGGCATACT ACAAACCTTG CCAGCAAATC CGCCTCCTGC CTCCACCAAT CGCCAGTCAG | 3120 |
| GAAGGCAACC TACCCTCTG TCTCCACCTT TGAGAAACAC TCATCCTCAG GCCATGCAGT | 3180 |
| GG | 3182 |

(2) INFORMATION FOR SEQ ID NO: 307:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 307:

| | | |
|---|---|---|
| AACTCCACAA CCTTCCACCA AACTCTGCAA GATCCCAGAG TGAGAGGCCT GTATTTCCCT | 60 |
| GCTGGTGGCT CCAGTTCAGG AACAGTAAAC CCTGTTCCGA CTACTGTCTC TCCCATATCG | 120 |
| TCAATCTTCT CGAGGATTGG GGACCCTGCG CTGAACATGG AGAACATCAC ATCAGGATTC | 180 |
| CTAGGACCCC TGCTCGTGTT ACAGGCGGGG TTTTTCTTGT TGACAAGAAT CCTCACAATA | 240 |
| CCGCAGAGTC TAGACTCGTG GTGGACTTCT CTCAATTTTC TAGGGGAAC TACCGTGTGT | 300 |
| CTTGGCCAAA ATTCGCAGTC CCCAACCTCC AATCACTCAC CAACCTCCTG TCCTCCAACT | 360 |
| TGTCCTGGTT ATCGCTGGAT GTGTCTGCGG CGTTTTATCA TCTTCCTCTT CATCCTGCTG | 420 |
| CTATGCCTCA TCTTCTTGTT GGTTCTTCTG GACTATCAAG GTATGTTGCC CGTTTGTCCT | 480 |
| CTAATTCCAG GATCTTCAAC TACCAGCACG GGACCATGCA GAACCTGCAC GACTCCTGCT | 540 |
| CAAGGAACCT CTATGTATCC CTCCTGTTGC TGTACCAAAC CTTCGGACGG AAATTGCACC | 600 |
| TGTATTCCCA TCCCATCATC CTGGGCTTTC GGAAAATTCC TATGGGAGTG GGCCTCAGCC | 660 |
| CGTTTCTCCT GGCTCAGTTT ACTAGTGCCA TTTGTTCAGT GGTTCGTAGG GCTTTCCCCC | 720 |
| ACTGTTTGGC TTTCAGTTAT ATGGATGATG TGGTATTGGG GGCCAAGTCT GTACAGCATC | 780 |

```
TTGAGTCCCT TTTTACCGCT GTTACCAATT TTCTTCTGTC TTTGGGTATA CATTTAAACC    840
CTAACAAAAC AAAAAGATGG GGTTACTCTT TACATTTCAT GGGCTATGTC ATTGGATGTT    900
ATGGGTCATT GCCACAAGAT CACATCATAC AGAAAATCAA AGAATGCTTT AGAAAACTTC    960
CTGTTAACAG GCCTATTGAT TGGAAAGTCT GTCAACGTAT TGTGGGTCTT TTGGGTTTTG   1020
CTGCCCCTTT TACACAATGT GGTTATCCTG CTTTAATGCC TTTGTATGCA TGTATTCAGT   1080
CGAAGCAGGC TTTTACTTTC TCGCCAACTT ACAAGGCCTT TCTGTGTAAA CAATACCTGA   1140
ACCTTTACCC CGTTGCCCGG CAACGGCCAG GTCTGTGCCA AGTGTTTGCT GACGCAACCC   1200
CCACTGGCTG GGGCTTGGTC ATGGGCCATC AGCGCATGCG TGGAACCTTT CTGGCTCGTC   1260
TGCCGATCCA TACTGCGGAA CTCCTAGCCG CTTGTTTTGC TCGCAGCAGG TCTGGAGCAA   1320
ACATTCTCGG GACGGATAAC TCTGTTGTTC TCTCCCGCAA ATATACATCG TATCCATGGC   1380
TGCTAGGCTG TGCTGCCAAC TGGATCCTGC GCGGACGTC CTTTGTTTAC GTCCCGTCGG    1440
CGCTGAATCC CGCGGACGAC CCTTCTCGGG GTCGCTTGGG ACTCTCTCGT CCCCTTCTCC   1500
GTCTGCCGTT TCGACCGACC ACGGGGCGCA CCTCTCTTTA CGCGGACTCC CCGTCTGTGC   1560
CTTCTCATCT GCCGGACCGT GTGCACTTCG CTTCACCTCT GCACGTCGCA TGGAGACCAC   1620
CGTGAAAGCC CAACCATTCT TGCCCAAGGT CTTACATAAG AGGACTCTTG GACTCTCTGT   1680
AATGTCAACG ACCGACCTTG AGGCATACTT CAAAGACTGT TTGTTTAAAG ACTGGGAGGA   1740
GTTGGGGGAG GAGATTAGAT TAAAGGTCTT TGTATTAGGA GGCTGTAGGC ATAAATTGGT   1800
CTGCGCACCA GCACCATGCA ACTTTTTCAC CTCTGCCTAA TCATCTCTTG TTCATGTCCT   1860
ACTGTTCAAG CCTCCAAGCT GTGCCTTGGG TGGCTTTGGG GCATGGACAT TGATCCTTAT   1920
AAAGAATTTG GAGCTACTGT GGAGTTACTC TCGTTTTTGC CTTCTGACTT CTTTCCTTCA   1980
GTACGAGATC TTCTAGATAA CGCCTCAGCT CTGTATCGGG AAGCCTTAGA GTCTCCTGAG   2040
CATTGTTCAC CTCACCATAC TGCACTCAGG CAAGCAATAC TGTGCTGGGG GAACTAATC    2100
ACTCTAGCTA CCTGGGTGGG TGGTAATTTG GAAGATCCAA TATCCAGGGA CCTAGTAGCT   2160
AGTTATGTCA ACACTAATAT GGGCCTAAAA TTCAGGCAAC TATTGTGGTT TCACATTTCT   2220
TGTCTCACTT TTGGAAGAGA AACAGTTATA GAGTATTTGG TGTCTTTTGG AGTGTGGATT   2280
CGCACTCCTC CAGCTTATAG ACCACCAAAT GCCCCTATCT TATCAACACT TCCGGAGACT   2340
ACTGTTGTTA GACGACGAGG CAGGTCCCCT AGAAGAAGAA CTCCCTCGCC TCGCAGACGA   2400
AGGTCTCAAT CGCCGCGTCG CAGAAGATCT CAATCTCGGG AATCTCAATG TTAGTATTCC   2460
TTGGACTCAT AAGGTGGGAA ACTTTACGGG GCTTTATTCT TCTACTGTAC CTGTCTTTAA   2520
CCCTCATTGG AAAACACCCT CTTTTCCTAA TATACATTTA CACCAAGACA TTATCAAAAA   2580
ATGTGAACAA TTTGTAGGCC CACTCACAGT CAATGAGAAA AGAAGACTGC AATTGATTAT   2640
GCCAGCTAGG TTTTATCCAA ATGTTACCAA ATATTTGCCA TTGGATAAGG GTATTAAACC   2700
TTATTATCCA GAATATTTAG TTAATCATTA CTTCCAAACT AGACATTATT TACACACTCT   2760
ATGGAAGGCG GGTATATTAT ACAAGAGAGA AACTACACAT AGCGCCTCAT TTTGTGGGTC   2820
ACCATATTCT TGGGAACAAG AGCTACAGCA TGGGGCAGAA TCTTTCCACC AGCAATCCTC   2880
TGGGATTCTT TCCCGACCAC CAGTTGGATC CAGCCTTCAG AGCAAACACC GCAAATCCAG   2940
ATTGGGACTT CAATCCCAAC AAGGACACCT GGCCAGACGC CAACAAGGTA GGAGCTGGAG   3000
CATTCGGGCT GGGATTCACC CCACCACACG GAGGCCTTTT GGGGTGGAGC CCTCAGGCTC   3060
AGGGCATACT AGAAACGTTG CCAGCAAATC CGCCTCCTGC CTCTACCAAT CGCCAGTCAG   3120
```

| | |
|---|---|
| GAAGGCAGCC TACCCCGCTG TCTCCACCTT TGAGAAACAC TCATCCTCAG GCCATGCAGT | 3180 |
| GG | 3182 |

(2) INFORMATION FOR SEQ ID NO: 308:

(i) SEQUENCE CHARACTERISTICS:
        (A) LENGTH: 3182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 308:

| | |
|---|---|
| AACTCCACAA CTTTCCACCA AACTCTGCAA GATCCCAGGG TGAGAGGCCT GTATTTCCCT | 60 |
| GCTGGTGGCT CCAGTTCAGG AACAGTAAAC CCTGTTCCGA CTACTGCCTC TCCCATATCG | 120 |
| TCAATCTTCT CGAGGATTGG GGACCCTGCA CTGAACATGG AGAACATCAC ATCAGGATTC | 180 |
| CTAGGACCCC TGCTCGTGTT ACAGGCGGGG TTTTTCTTGT TGACAAGAAT CCTCACAATA | 240 |
| CCGCAGAGTC TAGACTCGTG GTGGACTTCT CTCAATTTTC TAGGGGGAAC CACCGTGTGT | 300 |
| CTTGGCCAAA ATTCGCAGTC CCCAACCTCC AATCACTCAC CAACCTCCTG TCCTCCAACT | 360 |
| TGTCCTGGTT ATCGCTGGAT GTGTCTGCGG CGTTTTATCA TCTTCCTCTT CATCCTGCTT | 420 |
| CTATGCCTCA TCTTCTTGTT GGTTCTACTG GACTATCAAG GTATGTTGCC CGTGTGTCCT | 480 |
| CTAATTCCAG GATCTTCAAC CACCAGCGCG GGACCATGCA GAACCTGCAC GACTACTGCT | 540 |
| CAAGGAACCT CTATGTATCC CTCCTGTTGC TGTACCAAAC CTTCGGACGG AAATTGCACC | 600 |
| TGTATTCCCA TCCCATCATC CTGGGCTTTC GGAAAATTCC TATGGGAGTG GGCCTCAGCC | 660 |
| CGTTTCTCCT GGCTCAGTTT ACTAGTGCCA TTTGTTCAGT GGTTCGTAGG GCTTTCCCCC | 720 |
| ACTGTTTGGC TTTCAGTTAT ATGGATGATG TGGTATTGGG GGCCAAGTCT GTACAGCATC | 780 |
| TTGAGTCCCT TTTTACCGCT GTTACCAATT TTCTTTTGTC TTTGGGTATA CATTTAAACC | 840 |
| CTAACAAAAC TAAGAGATGG GGTTACTCTT TACATTTCAT GGGCTATGTC ATTGGAAGTT | 900 |
| ATGGGTCATT GCCACAAGAT CACATCATAC AGAAAATCAA AGAATGTTTT AGAAAACTTC | 960 |
| CTATTAACAG GCCTATTGAT TGGAAAGTCT GTCAACGTAT TGTGGGTCTT TTGGGTTTTG | 1020 |
| CTGCCCCTTT TACACAATGT GGTTATCCTG CTTTAATGCC CTTGTATGCC TGTATTCAAT | 1080 |
| CTAAACAGGC TTTCACTTTC TCGCCAACTT ACAAGGCCTT TCTGTGTAAA CAATACCTAG | 1140 |
| ACCTTTACCC CGTTGCTAGG CAACGGCCAG GTCTGTGCCA AGTGTTTGCT GACGCAACCC | 1200 |
| CCACTGGCTG GGGCTTGGTC ATGGGCCATC AGCGCATGCG TGGAACCTTT CTGGCTCCTC | 1260 |
| TGCCGATCCA TACTGCGGAA CTCCTAGCCG CTTGTTTTGC TCGCAGCAGG TCTGGAGCAA | 1320 |
| ACATTCTCGG GACGGATAAC TCTGTTGTTC TCTCCCGCAA ATATACATCG TTTCCATGGC | 1380 |
| TGCTAGGCTG TGCTGCCAAC TGGATCCTGC GCGGACGTC CTTTGTTTAC GTCCCGTCGG | 1440 |
| CGCTGAATCC CGCGGACGAC CCTTCTCGGG GCCGCTTGGG GATCTTTCGT CCCCTTCTCC | 1500 |
| GTCTGCCGTT CCGTCCGACC ACGGGGCGCA CCTCTCTTTA CGCGGACTCC CCGTCTGTGC | 1560 |
| CTTCTCATCT GCCGGTCCGT GTGCACTTCG CTTCACCTCT GCACGTCGCA TGGAGACCAC | 1620 |
| CGTGAACGCC CACCACTTCT TGCCCAAGGT CTTACATAAG AGGACTCTTG GACTCTCAGC | 1680 |
| AATGTCAACG ACCGACCTTG AGGCATACTT CAAAGACTGT TTGTTTAAGG ACTGGGAGGA | 1740 |

```
GTTGGGGGAG GAGATTAGAT TAAAGGTCTT TGTACTAGGA GGCTGTAGGC ATAAATTGGT    1800

CTGCGCACCA GCACCATGCA ACTTTTTCAC CTCTGCCTAA TCATCTCTTG TTCATGTCCT    1860

ACTGTTCAAG CCTCCAAGCT GTGCCTTGGG TGGCTTTGGG GCATGGACAT TGACCCTTAT    1920

AAAGAATTTG GAGCTACTGT GGAGTTACTC TCATTTTTGC CTTCTGACTT TTTTCCTTCG    1980

GTACGAGATC TTCTAGATAC CGCCTCAGCT CTGTATCGGG ATGCCTTAGA GTCTCCTGAG    2040

CATTGTTCAC CTCACCATAC TGCACTCAGG CAAGCAATTC TTTGCTGGGG GAACTAATG     2100

ACTCTAGCTA CCTGGGTGGG TGTTAATTTG GAAGATCCAG CATCTAGGGA CCTAGTAGTC    2160

AGTTATGTCA ACACTAATAT GGGCCTAAAG TTCAGGCAAC TATTGTGGTT TCACATTTTT    2220

TGTCTCACTT TTGGAAGAGA AACAGTCATA GAGTATTTGG TGTCTTTCGG AGTGTGGATT    2280

CGCACTCCTC CAGCTTATAG ACCACCAAAT GCCCCTATCT TATCAACACT TCCGGAAACT    2340

ACTGTTGTTA GACGACGAGG CAGGTCCCCT AGAAGAAGAA CTCCCTCGCC TCGCAGACGA    2400

AGATCTCAAT CGCCGCGTCG CAGAAGATCT CAATCTCGGG AATCTCAATG TTAGTATTCC    2460

TTGGACTCAT AAAGTGGGTA ACTTTACGGG GCTTTATTCC TCTACTGTAC CTGTCTTTAA    2520

CCCTCATTGG AAAACACCCT CTTTTCCTAA TATACATCTA CACCAAGACA TTATCAAAAA    2580

ATGTGAACAA TTTGTAGGCC CACTCACAGT AAATGAGAAA CGAAGACTGC AATTAATTAT    2640

GCCTGCTAGG TTTTATCCAA ATGTTACTAA ATATTTGCCA TTAGATAAGG GTATTAAACC    2700

TTATTATCCG GAACATTTAG TTAATCATTA CTTCCAAACC AGACATTATT TACACACTCT    2760

ATGGAAGGCG GGTATATTAT ATAAGAGGGA ACAACACGT AGCGCCTCAT TTTGTGGGTC     2820

ACCATATTCT TGGGAACAAG AGCTACAGCA TGGGGCAGAA TCTTTCCACC AGCAATCCTC    2880

TGGGATTCTT TCCCGACCAC CAGTTGGATC CAGCCTTCAG AGCAAACACC GCAAATCCAG    2940

ATTGGGACTT CAATCCCAAC AAGGACACCT GGCCAGACGC CAACAAGGTA GGAGCTGGAG    3000

CATTCGGGCT GGGATTCACC CCACCGCACG GAGGCCTTTT GGGGTGGAGC CCTCAGGCTC    3060

AGGGCATAAT ACAAACCTTG CCAGCAAATC CGCCTCCTGC ATCTACCAAT CGCCAGTCAG    3120

GAAGGCAGCC TACCCCGCTG TCTCCACCTT TGAGAAACAC TCATCCTCAG GCCATGCAGT    3180

GG                                                                  3182

(2) INFORMATION FOR SEQ ID NO: 309:

(i) SEQUENCE CHARACTERISTICS:
        (A) LENGTH: 3212 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 309:

AACTCCACAA CATTTCATCA AGCTCTGCAG GATCCCAGAG TAAGAGGCCT GTATTTTCCT      60

GCTGGTGGCT CCAGTTCCGG AACAGTGAAC CCTGTTCCGA CTACTGCCTC ACTCATCTCG     120

TCAATCTTCT CGAGGATTGG GGACCCTGCA CCGAACATGG AAAGCATCAC ATCAGGATTA     180

CTAGGACCCC TGCTCGTGTT ACAGGCGGGG TTTTTCTTGT TGACAAAAAT CCTCACAATA     240

CCGCAGAGTC TAGACTCGTG GTGGACTTCT CTCAATTTTC TAGGGGGAGC TCCCGTGTGT     300

CTTGGCCAAA ATTCGCAGTC CCCAACCTCC AATCACTCAC CAACCTCTTG TCCTCCAATT     360
```

-continued

```
TGTCCTGGCT ATCGCTGGAT GTGTCTGCGG CGTTTTATCA TCTTCCTCTT CATCCTGCTG    420

CTATGCCTCA TCTTCTTGTT GGTTCTTCTG GACTATCAAG GTATGTTGCC CGTTTGTCCT    480

CTAATTCCAG GATCATCAAC CACCAGCACG GGACCCTGCC GAACCTGCAT GACTCTTGCT    540

CAAGGAACCT CTATGTTTCC CTCATGTTGC TGTTCAAAAC CTTCGGACGG AAATTGCACT    600

TGTATTCCCA TCCCATCATC ATGGGCTTTC GGAAAATTCC TATGGGAGTG GGCCTCAGCC    660

CGTTTCTCCT GGCTCAGTTT ACTAGTGCCA TTTGTTCAGT GGTTCGCCGG GCTTTCCCCC    720

ACTGTCTGGC TTTCAGTTAT ATGGATGATG TGGTATTGGG GGCCAAGTCT GTACGACATC    780

TTGAGTCCCT TTATACCTCT GTTACCAATT TTCTTTTGTC TTTGGGTATA CATTTAAATC    840

CCAACAAAAC AAAAAGATGG GGATATTCCC TAAATTTCAT GGGTTATGTA ATTGGAAGTT    900

GGGGGTCATT ACCACAGGAA CACATCATAC AAAAAATCAA ACACTGTTTT GGAAAACTCC    960

CTGTTAACCG GCCTATTGAT TGGAAAGTAT GTCAAGGAAT GTGGGTCTT TTGGGCTTTG    1020

CTGCCCCTTT TACACAATGT GGGTATCCTG CTTTAATGCC TCTGTATACG TGTATTCAAT    1080

CTAAGCAGGC TTTCACTTTC TCGCCAACTT ACAAGGCCTT TCTGTGTAAA CAATACCTGA    1140

ACCTTTACCC CGTTGCCCGG CAACGGCCAG GTCTGTGCCA AGTGTTTGCT GATGCAACCC    1200

CCACTGGCTG GGGCTTGGCC ATAGGCATTC AGCGCATGCG CGGAACCTTT GTGGCTCCTC    1260

TGCCGATCCA TACTGCGGAA CTCCTAGCCG CTTGTTTTGC TCGCAGCAGG TCTGGAGCAA    1320

AACTTATCGG GACCGATAAT TCTGTCGTTC TCTCCCGGAA ATATACATCC TTTCCATGGC    1380

TGCTAGGCTG TGCTGCCAAC TGGATCCTGC GAGGGACGTC CTTTGTCTAC GTCCCGTCAG    1440

CGCTGAATCC TGCGGACGAC CCGTCTCGGG GTCGCTTGGG GATCTTTCGT CCCCTTCTCC    1500

GTCTGCGGTT CCGGCCGACC ACGGGGCGCA CCTCTCTTTA CGCGGTCTCC CCGTCTGTGC    1560

CTTCTCATCT GCCGGACCGT GTGCACTTCG CTTCACCTCT GCACGTCGCA TGGAGACCAC    1620

CGTGAACGCC CACCAAATCT TGCCCAAGGT CTTACATAAG AGGACTCTTG GACTCTCTGC    1680

AATGTCAACG ACCGACCTTG AGGCATACTT CAAAGACTGT TTGTTTAAAG ACTGGGAGGA    1740

GTTGGGGGAG GAGATTAGAT TAAAGGTCTT TGTACTAGGA GGCTGTAGGC ATAAATTGGT    1800

CTGCGCACCA GCACCATGCA ACTTTTTCAC CTCTGCCTAA TCATCTCTTG TTCATGTCCT    1860

ACTGTTCAAG CCTCCAAGCT GTGCCTTGGG TGGCTTTGGG GCATGGACAT TGACCCTTAT    1920

AAAGAATTTG GAGCTACTGT GGAGTTACTC TCGTTTTTGC CTTCTGACTT CTTTCCTTCA    1980

GTAAGAGATC TTCTAGATAC CGCCTCAGCT CTGTATCGGG ATGCCTTAGA ATCTCCTGAA    2040

CATTGTTCAC CGCACCACAC TGCACTCAGG CAAGCCATTC TTTGCTGGGG GAACTAATG    2100

ACTCTAGCTA CCTGGGTGGG TGTAAATTTG AAGATCCAG CATCCAGGGA CCTAGTAGTC    2160

AGTTATGTCA ATACTAATAT GGGCCTAAAG TTCAGGCAAT TATTGTGGTT TCACATTTCT    2220

TGTCTCACTT TTGGAAGAGA AACCGTCATA GAGTATTTGG TGTCTTTTGG AGTGTGGATT    2280

CGCACTCCTC CAGCTTATAG ACCACCAAAT GCCCCTATCT TATCAACACT TCCGGAGAAT    2340

ACTGTTGTTA GACGAAGAGG CAGGTCCCCT AGAAGAAGAA CTCCCTCGCC TCGCAGACGA    2400

AGATCTCAAT CGCCGCGTCG CAGAAGATCT CAATCTCCAG CTTCCCAATG TTAGTATTCC    2460

TTGGACTCAT AAGGTGGGAA ATTTTACGGG GCTCTACTCT TCTACTATTC CTGTCTTTAA    2520

TCCTAACTGG AAAACTCCAT CTTTTCCTGA TATTCATTTG CACCAGGACA TTATTAACAA    2580

ATGTGAACAA TTTGTAGGTC CTCTAACAGT AAATGAAAAA CGAAGATTAA ACTTAGTCAT    2640

GCCTGCTAGA TTTTTTCCCA TCTCTACAAA ATATTTGCCC CTAGAGAAAG GTATAAAACC    2700

TTATTATCCA GATAATGTAG TTAATCATTA CTTCCAAACC AGACACTATT TACATACCCT    2760
```

| | |
|---|---|
| ATGGAAGGCT GGGCATCTAT ATAAAAGAGA AACTACACGT AGCGCCTCAT TTTGTGGGTC | 2820 |
| ACCATATTCT TGGGAACAAG AGCTACATCA TGGGGCTTTC TTGGACGGTC CCTCTCGAAT | 2880 |
| GGGGGAAGAA TATTTCCACC ACCAATCCTC TGGGATTTTT TCCCGACCAC CAGTTGGATC | 2940 |
| CAGCATTCAG AGCAAACACC AGAAATCCAG ATTGGGACCA CAATCCCAAC AAAGACCACT | 3000 |
| GGACGGAAGC CAACAAGGTA GGAGTGGGAG CCTTCGGGCC GGGGTTCACT CCCCCACACG | 3060 |
| GAGGCCTTTT GGGGTGGAGC CCTCAGGCTC AAGGCATGCT AAAAACATTG CCAGCAGACC | 3120 |
| CGCCTCCTGC CTCCACCAAT CGGCAGTCAG GAAGGCAGCC TACCCCAATC ACTCCACCTT | 3180 |
| TGAGAGACAC TCATCCTCAG GCCATGCAGT GG | 3212 |

(2) INFORMATION FOR SEQ ID NO: 310:

(i) SEQUENCE CHARACTERISTICS:
        (A) LENGTH: 3212 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 310:

| | |
|---|---|
| AATTCCACAA CATTCCACCA AGCTCTGCAG GATCCCAGAG TAAGAGGCCT GTATTTTCCT | 60 |
| GCTGGTGGCT CCAGTTCCGG AACAGTGAAC CCTGTTCCGA CTACTGCCTC ACTCATCTCG | 120 |
| TCAATCTTCT CGAGGATTGG GGACCCTGCA CCGAACATGG AAAGCATCAC ATCAGGATTC | 180 |
| CTAGGACCCC TGCTCGTGTT ACAGGCGGGG TTTTTCTTGT TGACAAAAAT CCTCACAATA | 240 |
| CCGCAGAGTC TAGACTCGTG GTGGACTTCT CTCAATTTTC TAGGGGGAGC TCCCGTGTGT | 300 |
| CTTGGCCAAA ATTCGCAGTC CCCAACCTCC AGTCACTCAC CAACCTCTTG TCCTCCAATT | 360 |
| TGTCCTGGCT ATCGCTGGAT GTGTCTGCGG CGTTTTATCA TCTTCCTCTT CATCCTGCTG | 420 |
| CTATGCCTCA TCTTCTTGTT GGTTCTTCTG GACTATCAAG GTATGTTGCC CGTTTGTCCT | 480 |
| CTAATTCCAG GATCATCAAC CACCAGTACG GGACCCTGCC GAACCTGCAC GACTCTTGCT | 540 |
| CAAGGAACCT CTATGTTTCC CTCATGTTGC TGTTCAAAAC CTTCGGACGG AAATTGCACT | 600 |
| TGTATTCCCA TCCCATCATC ATGGGCTTTC GGAAAATTCC TATGGGAGTG GGCCTCAGCC | 660 |
| CGTTTCTCCT GGCTCAGTTT ACTAGTGCCA TTTGTTCAGT GGTTCGCCGG GCTTTCCCCC | 720 |
| ACTGTCTGGC TTTCAGTTAT ATGGATGATG TGGTATTGGG GGCCAAGTCT GTACAACATC | 780 |
| TTGAGTCCCT TTATACCGCT GTTACCAATT TTCTTTTGTC TTTGGGTATA CATTTAAATC | 840 |
| CCAACAAAAC AAAAAGATGG GGCTATTCCC TTAATTTCAT GGGTTATGTA ATTGGAAGTT | 900 |
| GGGGCTCATT ACCACAGGAA CACATCATAC AAAAAATCAA AGACTGTTTT AGAAAACTCC | 960 |
| CTGTTAACCG GCCTATTGAT TGGAAAGTAT GTCAAAGAAT TGTGGGTCTT TTGGGCTTTG | 1020 |
| CTGCCCCCTT TACACAATGT GGATATCCTG CTTTAATGCC TCTGTATGCA TGTACTCAAT | 1080 |
| CTAAGCAGGC TTTCACTTTC TCGCCAACTT ACAAGGCCTT TCTGTGTAAA CAATACCTGA | 1140 |
| ACCTTTACCC CGTTGCCCGG CAACGGCCAG GTCTGTGCCA AGTGTTTGCT GATGCAACCC | 1200 |
| CCACTGGCTG GGGCTTGGCC ATAGGCATTC AGCGCATGCG CGGAACCTTT GTGGCTCCTC | 1260 |
| TGCCGATCCA TACTGCGGAA CTCCTAGCCG CTTGTTTTGC TCGCAGCAGG TCTGGAGCAA | 1320 |
| AACTTATCGG GACCGATAAT TCTGTCGTTC TCTCCCGGAA GTATACATCC TTTCCATGGC | 1380 |

```
TGCTAGGCTG TGCTGCCAAC TGGATCCTGC GAGGGACGTC CTTTGTCTAC GTCCCGTCAG    1440

CGCTGAATCC TGCGGACGAC CCGTCTCGGG GTCGCTTGGG GATCTATCGT CCCCTTCTCC    1500

GTCTGCCGTT CCAGCCGACC ACGGGGCGCA CCTCTCTTTA CGCGGTCTCC CCGTCTGTTC    1560

CTTCTCATCT GCCGGACCGT GTGCACTTCG CTTCACCTCT GCACGTCGCA TGGAGACCAC    1620

CGTGAACGCC CACCAAATAT TGCCCAAGGT CTTACATAAG AGGACTCTTG GACTCTCTGC    1680

AATGTCAACG ACCGACCTTG AGGCATACTT CAAAGACTGT TTGTTTAAAG ACTGGGAGGA    1740

GTCGGGGGAG GAGATTAGAT TAAAGGTCTT TGTACTAGGA GGCTGTAGGC ATAAATTGGT    1800

CTGCGCACCA GCACCATGCA ACTTTTTCAC CTCTGCCTAA TCATCTCTTG TTCATGTCCT    1860

ACTGTTCAAG CCTCCAAGCT GTGCCTTGGG TGGCTTTGGG GCATGGACAT TGACCCTTAT    1920

AAAGAATTTG GAGCTACTGT GGAGTTACTC TCGTTTTTGC CTTCTGACTT CTTTCCTTCA    1980

GTAAGAGATC TTCTAGATAC CGCCTCAGCT CTGTATCGGG ATGCCTTAGA GTCTCCTGAG    2040

CATTGTTCAC CTCACCACAC TGCACTCAGG CAAGCCATTC TTTGCTGGGG AGAACTAATG    2100

ACTCTAGCTA CCTGGGTGGG TGTAAATTTG GAAGATCCAG CATCCAGGGA CCTAGTAGTC    2160

AGTTATGTCA ATACTAATAT GGGCCTAAAG TTCAGGCAAT TATTGTGGTT TCACATTTCT    2220

TGTCTCACTT TTGGAAGAGA AACCGTCATA GAGTATTTGG TGTCTTTTGG AGTGTGGATT    2280

CGCACTCCTC CAGCTTATAG ACCACCAAAT GCCCCTATCT TATCAACACT TCCGGAGAAT    2340

ACTGTTGTTA GACGAAGAGG CAGGTCCCCT AGAAGAAGAA CTCCCTCGCC TCGCAGACGA    2400

AGATCTCAAT CGCCGCGTCG CAGAAGATCT CAATCTCCAG CTTCCCAATG TTAGTATTCC    2460

TTGGACTCAT AAGGTGGGAA ATTTTACGGG GCTTTACTCT TCTACTATAC CTGTCTTTAA    2520

TCCTAACTGG AAAACTCCAT CTTTTCCTGA TATTCATTTG CACCAGGACA TTATTAACAA    2580

ATGTGAACAA TTTGTAGGTC CTCTAACTGT AAATGAAAAA CGAAGATTAA ACTTAGTCAT    2640

GCCTGCTAGA TTTTTTCCCA TCTCTACGAA ATATTTGCCC CTAGAGAAAG GTATAAAACC    2700

TTATTATCCA GATAATGTAG TTAATCATTA CTTCCAAACC AGACACTATT TACATACCCT    2760

ATGGAAGGCG GGCATCTTAT ATAAAAGAGA AACTACACGT AGCGCCTCAT TTTGTGGGTC    2820

ACCTTATTCT TGGGAACAAG AGCTACATCA TGGGGCTTTC TTGGACGGTC CCTCTCGAAT    2880

GGGGGAAGAA TATTTCCACC ACCAATCCTC TGGGATTTTT TCCCGACCAC CAGTTGGATC    2940

CAGCATTCAG AGCAAACACC AGAAATCCAG ATTGGGACCA CAATCCCAAC AAAGACCACT    3000

GGACAGAAGC CAACAAGGTA GGAGTGGGAG CATTCGGGCC TGGGTTCACT CCCCCACACG    3060

GAGGCCTTTT GGGGTGGAGC CCTCAGGCTC AAGGCATGCT AAAAACATTG CCAGCAGATC    3120

CGCCTCCTGC CTCCACCAAT CGGCAGTCAG GAAGGCAGCC TACCCCAATC ACTCCACCTT    3180

TGAGAGACAC TCATCCTCAG GCCATGCAGT GG                                  3212
```

(2) INFORMATION FOR SEQ ID NO: 311:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 311:

```
AACTCAACTC ACTTCCACCA AGCTCTGTTG GATCCCAGGG TAAGGGCACT GTATTTTCCT      60
GCTGGTGGCT CCAGTTCAGG AACACAGAAC CCTGCTCCGA CTATTGCCTC TCTCACATCA     120
TCAATCTCCT CGAAGACTGG GGGCCCTGCT ATGAACATGG AGAACATCAC ATCAGGACTC     180
CTAGGACCCC TGCGCGTGTT ACAGGCGGTG TGTTTCTTGT TGACAAAAAT CCTCACAATA     240
CCACAGAGTC TAGACTCGTG GTGGACTTCT CTCAATTTTC TAGGGGGACT ACCCAGGTGT     300
CCTGGCCAAA ATTCGCAGTC CCCAACCTCC AATCACTTAC CAACCTCCTG TCCTCCAACT     360
TGTCCTGGCT ATCGTTGGAT GTGTCTGCGG CGTTTTATCA TCTTCCTCTT CATCCTGCTG     420
CTATGCCTCA TCTTCTTGTT GGTTCTTCTG GACTACCAAG GTATGTTGCC CGTTTGTCCT     480
CTACTTCCAG GATCCACGAC CACCAGCACG GGACCATGCA AAACCTGCAC AGCTCTTGCT     540
CAAGGAACCT CTATGTTTCC CTCCTGTTGC TGTTCCAAAC CCTCGGACGG AAACTGCACC     600
TGTATTCCCA TCCCATCATC TTGGGCTTTA GGAAAATACC TATGGGAGTG GGCCTCAGCC     660
CGTTTCTCCT GGCTCAGTTT ACTAGTGCAA TTTGTTCAGT GGTGCGTAGG GCTTTCCCCC     720
ACTGTCTGGC TTTTAGTTAT ATGGATGATC TGGTATTGGG GGCCAAATCT GTGCAGCATC     780
TTGAGTCCCT TTATACCGCT GTTACCAATT TTCTGTTATC TGTGGGTATC CATTTAAATA     840
CTGCTAAAAC AAAAAGATGG GGTTACAACC TACATTTCAT GGGTTATGTT ATTGGTAGTT     900
GGGGAACGTT ACCCCAAGAT CATATTGTAC ACAAAATCAA AGATTGTTTT CGAAAAGTTC     960
CTGTAAATCG CCCAATTGAT TGGAAAGTTT GTCAAAGTAT TGTGGGTCTT TTGGGCTTTG    1020
CGGCCCCTTT TACCCAATGT GGTTATCCTG CTCTCATGCC TTTGTATGCC TGTATTACTG    1080
CTAAACAGGC TTTTGTCTTC TCGCCAACTT ACAAGGCCTT TCTGTGTAAA CAATACATGA    1140
ACCTTTACCC CGTTGCTCGG CAACGGCCAG GCCTGTGCCA AGTGTTTGCT GACGCAACCC    1200
CCACTGGCTG GGGCTTGGCC ATAGGCCATC AGCGCATGCG TGGAACCTTT GTGGCTCCTC    1260
TGCCGATCCA TACTGCGGAA CTCCTTGCAG CTTGCTTCGC TCGCAGCCGG TCTGGAGCAA    1320
TCCTCATCGG CACAGACAAT TCTGTCGTCC TCTCTCGGAA GTATACATCC TTTCCATGGC    1380
TGCTCGGTTG TGCTGCCAAC TGGATCCTGC GCGGGACGTC CTTTGTTTAC GTCCCGTCGG    1440
CGCTGAATCC AGCGGACGAA CCCTCCCGGG GTCGCTTGGG GCTGTACCGC CCCCTTCTTC    1500
GTCTGCCGTT CCAGCCGACA ACGGGTCGCA CCTCTCTTTA CGCGGACTCC CCGTCTGTTC    1560
CTTCTCATCT GCCGGACCGT GTGCACTTCG CTTCACCTCT GCACGTCGCA TGGAGACCAC    1620
CGTGAACGCC CCCTGGAGTT TGCCAACAGT CTTACATAAG AGGACTCTTG GACTTTCAGG    1680
ACGGTCAATG ACCTGGATCG AAGACTACAT CAAAGACTGT GTATTTAAGG ACTGGGAGAG    1740
GCTGGGGGAG GAGATCAGGT TAAAGGTCTT TGTACTAGGA GGCTGTAGGC ATAAATTGGT    1800
CTGTTCACCA GCACCATGCA ACTTTTTCAC CTCTGCCTAA TCATCTCTTG TTCATGTCCC    1860
ACTGTTCAAG CCTCCAAGCT GTGCCTTGGG TGGCTTTGGG GCATGGACAT TGACCCTTAT    1920
AAAGAATTTG GAGCTTCTGT GGAATTGTTC TCTTTTTTGG CTTCTGACTT CTTTCCGTCT    1980
GTTCGGGACC TCCTCGACAC CGCCTCAGCC CTGTACCGGG ATGCCTTAGA GTCACCGGAA    2040
CATTGCACCC CCAATCATAC CGCTCTCAGG CAAGCTATTT TGTGCTGGGG TGAGTTAATG    2100
ACTTTGGCTT CCTGGGTGGG TAATAATTTG GAAGACCCTG CAGCTAGGGA TTTAGTAGTT    2160
AATTATGTCA ACACTAATAT GGGCTTAAAG ATTAGACAAC TATTGTGGTT TCACATCTCC    2220
TGTCTTACTT TTGGAAGAGA AACAGTTCTT GAGTATTTGG TGTCCTTTGG AGTGTGGATT    2280
CGCACTCCAC CTGCTTATAG ACCACCAAAT GCCCCTATCC TATCCACACT TCCGGAAACT    2340
```

```
ACTGTTGTTA GACGACGAGG CAGGTCCCCT AGAAGAAGAA CTCCCTCGCC TCGCCGACGA    2400

AGGTCTCAAT CGCCGCGTCG CAGAAGATCT CAATCTCCAG CTTCCCAATG TTAGTATTCC    2460

TTGGACTCAT AAGGTGGGAA ATTTTACGGG GCTCTACTCT TCTACTGTAC CTGCTTTCAA    2520

TCCTAACTGG TTAACTCCTT CTTTTCCTGA TATTCATTTA CATCAGGATA TGATATCTAA    2580

ATGTGAACAA TTTGTAGGCC CGCTCACTAA AAATGAATTG AGAAGATTAA AATTGGTCAT    2640

GCCAGCTAGA TTTTATCCTA AGCATACCAA ATATTTCCTA TTGGAGAAAG GGATTAAACC    2700

CTATTATCCA GATCAGGCAG TTAATCATTA TTTTCAAACC AGACATTATT TGCATACTTC    2760

ATGGAAGGCG GGAATTCTAT ATAAGAGAGA AACCACACGT AGCGCCTCAT TTTGTGGGGG    2820

ACAATATTCC TGGGAACAAG AGCTACAGCA TGGGAGCACC TCTCTCAACG ACAAGAAGGG    2880

GCATGGGACA GAATCTTTCT GTGCCCAATC CACTGGGCTT CTTGCCAGAC CATCAGCTGG    2940

ATCCGCTATT CAGAGCAAAT TCCAGCAGTC CCGACTGGGA CTTCAACACA AACAAGGACA    3000

GTTGGCCAAT GGCAAACAAG GTAGGAGTGG GAGGCTACGG TCCAGGGTTC ACACCCCAC    3060

ACGGTGGCCT GCTGGGGTGG AGCCCTCAGG CACAGGGTGT TTTAACAACC TTGCCAGCAC    3120

ATCCGCCTCC TGCTTCCACC AATCGGCTGT CCGGGAGGAA GCCAACCCAA GTCTCTCCAC    3180

CTCTAAGAGA CACACATCCT CAGGCCATGC AGTGG                              3215

(2) INFORMATION FOR SEQ ID NO: 312:

(i) SEQUENCE CHARACTERISTICS:
        (A) LENGTH: 3215 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 312:

AACTCAACTC ACTTCCACCA GGCTCTGTTG GATCCGAGGG TAAGGGCACT GTATTTTCCT      60

GCTGGTGGCT CCAGTTCAGG CACGCAGAAC CCTGCTCCGA CTATTGCCTC TCTCACATCA     120

TCAATCTCCT CGAAGACTGG GGGCCCTGCT ATGAACATGG ACAACATCAC ATCAGGACTC     180

CTAGGACCCC TGCTCGTGTT ACAGGCGGTG TGTTTCTTGT TGACAAAAAT CCTCACAATA     240

CCACAGAGTC TAGACTCGTG GTGGACTTCT CTCAATTTTC TAGGGGGACT ACCCGGGTGT     300

CCTGGCCAAA ATTCGCAGTC CCCAACCTCC AATCACTTAC CAACCTCCTG TCCTCCAACT     360

TGTCCTGGCT ATCGTTGGAT GTGTCTGCGG CGTTTTATCA TCTTCCTCTT CATCCTGCTG     420

CTATGCCTCA TCTTCTTGTT GGTTCTTCTG GACTATCAAG GTATGTTGCC CGTTTGTCCT     480

CTAATTCCAG GATCTACGAC CACCAGCACG GGACCATGCA AAACCTGCAC AACTCTTGCT     540

CAAGGAACCT CTATGTTTCC CTCCTGTTGC TGTTCCAAAC CCTCGGACGG AAACTGCACC     600

TGTATTCCCA TCCCATCATC TTGGGCTTTA GGAAAATACC TATGGGAGTG GGCCTCAGCC     660

CGTTTCTCCT GGCTCAGTTT ACTAGTGCAA TTTGTTCAGT GGTGCGTAGG GCTTTCCCCC     720

ACTGTCTGGC TTTTAGTTAT ATGGATGATC TGGTATTGGG AGCCAAATCT GTGCAGCATC     780

TTGAGTCCCT TTATACCGCT GTTACCAATT TTCTGTTATC TGTGGGTATC CATTTGAATA     840

CCTCTAAAAC AAAAAGATGG GGTTACAATT TACATTTCAT GGGTTATGTC ATTGGCAGTT     900

GGGGAGCATT ACCCCAAGAT CATATTGTAC ACAAAATCAA AGAATGTTTT CGAAAAGTTC     960
```

-continued

```
CTGTAAATCG TCCAATTGAC TGGAAAGTTT GTCAACGTAT TGTGGGACTT TTGGGCTTTG    1020
CTGCTCCTTT TACCCAATGT GGTTATCCTG CTCTCATGCC TCTGTATAAC TGTATCACTG    1080
CGAAACAGGC TTTTGTCTTT TCGCCAACTT ACAAGGCCTT TCTCTGTAAA CAGTACATGA    1140
ACCTTTACCC CGTTGCTCGG CAACGGCCAG GCCTGTGCCA AGTGTTTGCT GACGCAACCC    1200
CCACTGGTTG GGGCTTGGCC ATTGGCCATC AGCGCATGCG TGGAACCTTT GTGGCTCCTC    1260
TGCCGATCCA TACTGCGGAA CTCCTTGCAG CTTGCTTCGC TCGCAGCCGG TCTGGAGCAA    1320
TCCTCATCGG CACAGACAAT TCTGTCGTCC TCTCCCGGAA GTATACATCC TTTCCATGGC    1380
TGCTCGGATG TGCTGCCAAC TGGATCCTGC GCGGGACGTC CTTTGTTTAC GTCCCGTCGG    1440
CGCTGAATCC AGCGGACGAA CCCTCCCGGG GCCGCTTGGG GCTCTACCGC CCTCTTCTGC    1500
GTCTGCCGTT CCAGCCGACC ACGGGTCGCA CCTCTCTTTA CGCGGACTCC CCGTCTGTTC    1560
CTTCTCATCT GCCGGTCCGT GTGCACTTCG CTTCACCTCT GCACGTCGCA TGGAGACCAC    1620
CGTGAACGCC CCCTGGAGTT TGCCAACAGT CTTACATAAG AGGACTATTG GACTTTCAGG    1680
ACGGTCAATG ACCTGGATCG AAGAATACAT CAAAGACTGT GTATTTAAAG ACTGGGAGGA    1740
GCTGGGGGAG GAGATCAGGT TAAAGGTCTT TGTACTAGGA GGCTGTAGGC ATAAATTGGT    1800
CTGCGCACCA GCACCATGCA ACTTTTTCAC CTCTGCCTAA TCATCTCTTG TTTATGTCCC    1860
ACTGTTCAAG CCTCCAAGCT GTGCCTTGGG TGGCTTTGGG GCATGGACAT TGACCCTTAT    1920
AAAGAATTTG GAGCTTCTGT GGAATTGTTC TCTTTTTTGC CTTCTGACTT CTTTCCGTCA    1980
ATCCGAGACC TTCTCGACAC CGCCTCAGCT CTGTATCGGG ATGCGTTAGA GTCACCGGAA    2040
CATTGCACCC CCAATCATAC CGCTCTCAGG CAAGCTATTT TGTGTTGGGG TGAATTAATG    2100
ACTTTGGCTT CCTGGGTGGG CAATAATTTG GAGGACCCTG CAGCCAGGGA TTTAGTAGTT    2160
AACTATGTTA ACACTAATAT GGGCTTAAAG ATTAGACAAC TATTGTGGTT TCACATTTCC    2220
TGCCTTACTT TTGAAGAGA AACAGTTCTT GAGTATTTGG TGTCCTTTGG AGTGTGGATT    2280
CGCACTCCTC CAGCTTATAG ACCACCAAAT GCCCCTATCC TATCCACACT TCCGGAAACT    2340
ACTGTTGTTA GACGACGAGG CAGGTCCCCT AGAAGAAGAA CTCCCTCGCC TCGCAGACGA    2400
AGGTCTCAAT CGCCGCGTCG CAGAAGATCT CAATCTCCAG CTTCCCAATG TTAGTATTCC    2460
TTGGACTCAT AAGGTGGGAA ATTTTACGGG GCTCTACTCT TCTACTGTAC CTGCTTTCAA    2520
TCCTCACTGG TTAACTCCTT CTTTTCCTGA TATTCATTTG CATCAAGACC TGATATCTAA    2580
ATGTGAACAA TTTGTAGGCC CACTTACCAA AAATGAATTG AGAAGGTTGA AATTGATTAT    2640
GCCAGCCAGA TTCTTTCCTA AACTTACTAA ATATTTCCCT CTGGAGAAAG ACATTAAACC    2700
TTATTATCCA GAGCATGCAG TTAATCATTA TTTTCAAACC AGACATTATT TGCATACTTT    2760
ATGGAAGGCG GGAATTTTAT ATAAGAGAGA ATCCACACGT AGCGCCTCAT TTTGTGGGTC    2820
ACCATATTCT TGGGAACAAG AGCTACAGCA TGGGAGCACC TCTCTCAACG ACAAGAAGGG    2880
GCATGGGACA GAATCTCTCT GTGCCCAATC CACTGGGATT CTTTCCAGAC CATCAACTGG    2940
ATCCTCTTTT CAGAGCAAAT TCCAGCAGTC CCGATTGGGA CTTCAACAAA ACAAGGACA    3000
CTTGGCCAAT GGCAAACAAG GTAGGAGTGG GAGGTTACGG TCCAGGGTTC ACACCCCAC    3060
ACGGTGGCCT GTTGGGGTGG AGCCCTCAGG CACAAGGTGT TCTAACAACC TTGCCAGCAG    3120
ATCCGCCTCC TGCCTCCACC AATCGGCTGT CCGGGAGGAA GCCAACCCCA GTCTCTCCAC    3180
CTCTAAGAGA CACACATCCA CAGGCAATGC AGTGG                              3215
```

(2) INFORMATION FOR SEQ ID NO: 313:

(i) SEQUENCE CHARACTERISTICS:
    (A) LENGTH: 3215 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 313:

```
AACTCAACCC AGTTCCACCA AGCTCTGTTG GATCCCAGGG TAAGGGCTCT GTACTTCCCT      60
GCTGGTGGCT CCAGTTCAGG GACACAGAAC CCTGCTCCGA CTATTGCCTC TCTCACATCA     120
TCAATCTTCT CGAAGACTGG GGGCCCTGCT ATGAACATGG ACAACATTAC ATCAGGACTC     180
CTAGGACCCC TGCTCGTGTT ACAGGCGGTG TGTTTCTTGT TGACAAAAAT CCTCACAATA     240
CCACAGAGTC TAGACTCGTG GTGGACTTCT CTCAATTTTC TAGGGGGACT ACCCGGGTGT     300
CCTGGCCAAA ATTCGCAGTC CCCAACCTCC AATCACTTAC CAACCTCCTG TCCTCCAACT     360
TGTCCTGGCT ATCGTTGGAT GTGTCTGCGG CGTTTTATCA TCTTCCTCTT CATCCTGCTG     420
CTATGCCTCA TCTTCTTGTT GGTTCTTCTG GACTATCAAG GTATGTTGCC CGTTTGTCCT     480
CTACTTCCAG GATCCACGAC CACCAGCACG GGACCCTGCA AAACCTGCAC AACTCTTGCA     540
CAAGGAACCT CTATGTTTCC CTCCTGTTGC TGTTCCAAAC CCTCGGACGG AAACTGCACT     600
TGTATTCCCA TCCCATCATC CTGGGCTTTA GGAAAATACC TATGGGAGTG GGCCTCAGCC     660
CGTTTCTCCT GGCTCAGTTT ACTAGTGCAA TTTGTTCAGT GGTGCGTCGG GCTTTCCCCC     720
ACTGTTTGGC TTTTAGTTAT ATGGATGATC TGGTATTGGG GGCCAAATCT GTGCAGCATC     780
TTGAGTCCCT TTATACCGCT GTTACCAATT TTCTGTTATC TGTGGGTATC CATTTAAATA     840
CCTCTAAAAC AAAAAGATGG GGTTACTCCC TACATTTTAT GGGTTATGTC ATTGGTAGTT     900
GGGATCATT ACCCCAAGAT CACATTGTAC ACAAAATCAA GGAATGCTTT CGAAAACTGGC     960
CTGTAAATCG TCCAATTGAT TGGAAAGTTT GTCAACGCAT AGTGGGTCTT TTGGGCTTTG    1020
CTGCCCCTTT CACCCAATGC GGTTATCCTG CTCTCATGCC TCTGTATGCC TGTATTACTG    1080
CTAAACAGGC TTTTGTCTTC TCGCCAACCT ACAAGGCCTT TCTGTGTAAA CAATACATGA    1140
ACCTTTACCC GGTTGCTCGG CAACGGCCAG GCCTGTGCCA AGTGTTTGCT GACGCAACCC    1200
CCACTGGTTG GGGCTTGGCC ATTGGCCATC AGCGCATGCG TGGAACCTTT GTGGCTCCTC    1260
TGCCGATCCA TACTGCGGAA CTCCTAGCAG CTTGTTTCGC TCGCAGCAGG TCTGGAGCGA    1320
CTCTCATCGG CACGGACAAT TCTGTTGTCC TCTCTAGGAA GTACACCTCC TTTCCATGGC    1380
TGCTCGGATG TGCTGCAAAC TGGATCCTGC GCGGGACGTC CTTTGTTTAC GTCCCATCGG    1440
CGCTGAATCC CGCGGACGAC CCCTCCCGGG GCCGCTTGGG GCTGTACCGC CCTCTTCTCC    1500
GTCTGCCGTT CCAGCCGACG ACGGGTCGCA CCTCTCTTTA CGCGGACTCC CCGTCTGTTC    1560
CTTCTCATCT GCCGGACCGT GTGCACTTCG CTTCACCTCT GCACGTCGCA TGGAGACCAC    1620
CGTGAACGCC CCCTGGAGTT TGCCAACAGT CTTACATAAG CGGACTCTTG GACTTTCAGG    1680
ATGGTCAATG ACCTGGATCG AAGAATACAT CAAAGACTGT GTATTTAAGG ACTGGGAGGA    1740
GTTGGGGGAG GAGATTAGGT TAAAGGTCTT TGTATTAGGA GGCTGTAGGC ATAAATTGGT    1800
CTGTTCACCA GCACCATGCA ACTTTTTCAC CTCTGCCTAA TCATCTTTTG TTCATGTCCC    1860
ACTGTTCAAG CCTCCAAGCT GTGCCTTGGG TGGCTTTGGG GCATGGACAT TGACCCTTAT    1920
AAAGAATTTG GAGCTTCTGT GGAGTTACTC TCGTTTTTGC CTTCTGATTT CTTCCCATCG    1980
```

-continued

```
GTTCGGGACC TACTCGACAC CGCTTCAGCT CTTTACCGGG ATGCTTTAGA GTCACCTGAA    2040

CATTGCACTC CCAACCATAC TGCTCTCAGG CAAGCTATTT TGTGTTGGGG TGAGTTAATG    2100

ACTTTGGCTT CCTGGGTGGG CAATAATTTG GAGGACCCTG CAGCTAGGGA TTTAGTAGTT    2160

AACTATGTTA ACACTAACAT GGGCCTAAAA ATTAGACAAC TGTTGTGGTT TCACATTTCC    2220

TGCCTTACTT TTGGAAGAGA AACAGTTCTA GAGTATTTGG TGTCCTTTGG AGTGTGGATT    2280

CGCACTCCTC CTGCTTACAG ACCACCAAAT GCCCCTATCC TATCCACACT TCCGGAAACT    2340

ACTGTTGTTA GACGACGAGG CAGGTCCCCT AGAAGAAGAA CTCCCTCGCC TCGCAGACGA    2400

AGATCTCAAT CGCCGCGTCG CCGCAGATCT CAATCTCCAG CTTCCCAATG TTAGTATTCC    2460

TTGGACTCAT AAGGTGGGAA ACTTTACGGG GCTTTACTCT TCTACTGTGC CTGCTTTTAA    2520

TCCTAACTGG TCCACTCCTT CTTTTCCTGA TATTCATTTG CATCAAGACC TGATTTCTAA    2580

ATGTGAACAA TTTGTAGGCC CACTTACTAA AAATGAATTA CGAAGATTAA AATTGGTTAT    2640

GCCAGCTAGA TTTTATCCTA AGGTTACCAA ATATTTTCCC ATGGATAAAG GCATCAAACC    2700

CTATTATCCT GAGCATGCAG TTAATCATTA CTTTAAAACC AGACATTATT TGCATACTTT    2760

ATGGAAGGCG GGAATTTTAT ATAAGAGAGA ATCCACACGT AGCGCCTCAT TTTGTGGGTC    2820

ACCATATTCC TGGGAACAAG AGCTACAGCA TGGGAGCACC TCTCTCAACG ACACGAAGAG    2880

GCATGGGACA GAATCTCTCT GTGCCCAATC CTCTGGGATT CTTTCCAGAC CATCAGCTGG    2940

ATCCGCTATT CAGAGCAAAT TCCAGCAGTC CCGACTGGGA CTTCAACACA AACAAGGACA    3000

GTTGGCCAAT GGCAAACAAG GTAGGAGTGG GAGGCTACGG TCCAGGGTTC ACACCCCCAC    3060

ACGGTGGCCT GCTGGGGTGG AGCCCTCAAG CACAAGGTGT GTTAACAACC TTGCCAGCAG    3120

ATCCGCCTCC TGCTTCCACC AATCGGCGGT CCGGGAGAAA GCCAACCCCA GTCTCTCCAC    3180

CTCTAAGAGA CACACATCCA CAGGCAATGC AGTGG                                3215
```